(12) United States Patent
Afshar et al.

(10) Patent No.: US 12,723,230 B2
(45) Date of Patent: Sep. 1, 2026

(54) SYSTEMS AND METHODS FOR AUTOMATED CELL CULTURING

(71) Applicant: MYTOS BIO LIMITED, London (GB)

(72) Inventors: Ali Afshar, London (GB); James Cunningham, London (GB); Henry Miskin, Stroud (GB); Xian Weng Jiang, London (GB); Ignacio Willats, London (GB); Sina Atashpazgargari, London (GB); Benedict Greenberg, London (GB)

(73) Assignee: Mytos Bio Limited, London (GB)

( * ) Notice: Subject to any disclaimer, the term of this patent is extended or adjusted under 35 U.S.C. 154(b) by 943 days.

(21) Appl. No.: 17/800,071

(22) PCT Filed: Feb. 18, 2021

(86) PCT No.: PCT/EP2021/054027

§ 371 (c)(1),
(2) Date: Aug. 16, 2022

(87) PCT Pub. No.: WO2021/165397

PCT Pub. Date: Aug. 26, 2021

(65) Prior Publication Data

US 2023/0087656 A1 Mar. 23, 2023

Related U.S. Application Data

(60) Provisional application No. 62/978,012, filed on Feb. 18, 2020.

(51) Int. Cl.

*C12M 1/36* (2006.01)
*C12M 1/00* (2006.01)

(Continued)

(52) U.S. Cl.

CPC ............ *C12M 41/48* (2013.01); *C12M 23/40* (2013.01); *C12M 23/42* (2013.01); *C12M 27/16* (2013.01);

(Continued)

(58) Field of Classification Search

None

See application file for complete search history.

(56) References Cited

U.S. PATENT DOCUMENTS 4,146,364 A 3/1979 McCormick
5,372,425 A * 12/1994 Tannenbaum .......... B01F 31/22 366/208

(Continued)

FOREIGN PATENT DOCUMENTS

AU 2011218747 A1 9/2011
CN 107083328 A 8/2017

(Continued)

OTHER PUBLICATIONS

Translation of DE-102016108464-B3, Bertiller Marco, Sep. 14, 2017 (Year: 2017).*

(Continued)

*Primary Examiner* — Henry H Nguyen
(74) *Attorney, Agent, or Firm* — Mills IP Law, PLLC

(57) ABSTRACT

Systems and methods for automated cell culturing are disclosed. In some embodiments, one or more cell culture vessels are fluidly connected with one or more multiport valves and one or more fluid pumps. The fluid pumps may pump various fluids into and out of the cell culture vessels as necessary to support cell growth, routed by the one or more multiport valves. In some embodiments, one or more components may be removable from other components so that some components may be prepared and sterilized independently prior to usage.

10 Claims, 115 Drawing Sheets

(51) Int. Cl.
*C12M 1/26* (2006.01)
*C12M 1/34* (2006.01)
*C12M 3/00* (2006.01)
*C12M 3/06* (2006.01)

(52) U.S. Cl.
CPC ............ *C12M 33/07* (2013.01); *C12M 41/36* (2013.01); *C12M 41/42* (2013.01)

(56) References Cited

U.S. PATENT DOCUMENTS

| | | | |
|---|---|---|---|
| 6,399,375 | B2 | 6/2002 | Vajta |
| 8,383,395 | B2 | 2/2013 | Hata et al. |
| 8,445,261 | B2 | 5/2013 | Greenberger et al. |
| 8,445,266 | B2 | 5/2013 | Kiyota et al. |
| 8,785,173 | B2 | 7/2014 | Thompson et al. |
| 8,808,643 | B1 | 8/2014 | Benner et al. |
| 9,695,393 | B2 | 7/2017 | Nankervis et al. |
| 9,783,768 | B2 | 10/2017 | Larcher et al. |
| 9,983,222 | B2 | 5/2018 | Peltier |
| 10,119,970 | B2 | 11/2018 | Miltenyi et al. |
| 10,858,621 | B2 | 12/2020 | Kawarai et al. |
| 10,988,726 | B2 | 4/2021 | Afshar et al. |
| 11,579,063 | B2 | 2/2023 | Ikehata et al. |
| 2005/0051723 | A1 | 3/2005 | Neagle et al. |
| 2005/0095705 | A1 | 5/2005 | Kadan et al. |
| 2006/0035368 | A1 * | 2/2006 | Malinge ................. C12M 41/14 435/286.2 |
| 2006/0275888 | A1 | 12/2006 | Hibino et al. |
| 2008/0248552 | A1 | 10/2008 | Castillo Fernandez |
| 2011/0207209 | A1 | 8/2011 | Hammons et al. |
| 2011/0217767 | A1 * | 9/2011 | Niazi ...................... C12N 1/20 435/243 |
| 2011/0287534 | A1 | 11/2011 | Rowley et al. |
| 2013/0038727 | A1 | 2/2013 | Clark |
| 2013/0203106 | A1 | 8/2013 | Shvets et al. |
| 2016/0017271 | A1 | 1/2016 | Nozaki et al. |
| 2016/0152936 | A1 | 6/2016 | Bargh et al. |
| 2016/0178490 | A1 | 6/2016 | Civel et al. |
| 2017/0037357 | A1 | 2/2017 | Cattaruzzi et al. |
| 2017/0145373 | A1 | 5/2017 | Lianides et al. |
| 2017/0204359 | A1 | 7/2017 | Ando et al. |
| 2017/0342365 | A1 | 11/2017 | Nozaki et al. |
| 2018/0127695 | A1 | 5/2018 | Nam et al. |
| 2018/0171296 | A1 | 6/2018 | Murthy et al. |
| 2018/0179483 | A1 | 6/2018 | Amino et al. |
| 2018/0251723 | A1 | 9/2018 | Murthy et al. |
| 2019/0284519 | A1 | 9/2019 | Kaffka et al. |
| 2021/0238532 | A1 | 8/2021 | Afshar et al. |
| 2025/0002835 | A1 | 1/2025 | Afshar et al. |

FOREIGN PATENT DOCUMENTS

| | | | | |
|---|---|---|---|---|
| CN | 107287119 | A | 10/2017 | |
| DE | 102011054363 | A1 | 4/2013 | |
| DE | 102016108464 | B3 * | 9/2017 | ............. B01F 31/22 |
| EP | 1944359 | A1 | 7/2008 | |
| JP | H04179471 | | 6/1992 | |
| JP | U3141686 | | 5/2008 | |
| JP | 2018-050550 | | 4/2018 | |
| WO | WO2006/122089 | A2 | 11/2006 | |
| WO | WO2018/005521 | A2 | 1/2018 | |
| WO | WO2019/155032 | A1 | 8/2019 | |
| WO | WO2020/038874 | | 2/2020 | |

OTHER PUBLICATIONS

Okano Guangfu Shenyang, “tissue engineering” Liaoning Science and Technology Press, Apr. 30, 2016, pp. 46-49—non-English.

Office Action for JP Application No. 2021-505715, mailed Jun. 2, 2023 (with English translation).

Office Action for U.S. Appl. No. 17/238,644, mailed Oct. 6, 2023.

Final Office Action for JP Application No. 2021-505715, mailed Dec. 1, 2023 (with English translation).

Office Action for CN Application No. 201980054549.X, mailed Dec. 9, 2023 (with English translation).

Office Action for JP Application No. 2022-549594, mailed Apr. 2, 2025 (with English translation).

Corning, Life Sciences, “Corning® Reusable Gas and Media Handling Fitting with Dual Inlets (1 long, 1 short tube) for Angled Sidearm Flasks,” [online] [retrieved on Aug. 15, 2019] Retrieved from the Internet <URL: https://ecatalog.corning.com/life-sciences/b2c/US/en/Cell-Culture/Cell-Culture-Vessels/Flasks%2C-Culture/Corning%C2%AE-Reusable-Gas-and-Media-Handling-Fitting-with-Dual-Inlets-%281-long%2C-1-short-tube%29-for-Angled-Sidearm-Flasks/p/gasOrMediaHandlingFittingsAngledSidearmFlasksCombinationStyle> (undated), 1 page.

Thermofisher Scientific, “Cell Culture Flasks/Tissue Culture Flasks,” [online] [retrieved on Aug. 15, 2019] Retrieved from the Internet <URL: https://www.thermofisher.com/us/en/home/life-science/cell-culture/cell-culture-plastics/cell-culture-flasks.html> (undated), 4 pages.

Office Action for U.S. Appl. No. 16/543,369, mailed Jun. 17, 2020.

Final Office Action for U.S. Appl. No. 16/543,369, mailed Jan. 7, 2021.

International Application No. PCT/EP2019/072115, Invitation to Pay Additional Fees and, Where Applicable, Protest Fee, mailed Nov. 28, 2019.

International Application No. PCT/EP2019/072115, International Search Report and Written Opinion mailed Jan. 23, 2020.

International Application No. PCT/EP2021/054027, Invitation to Pay Additional Fees and, Where Applicable, Protest Fee mailed Jun. 1, 2021.

International Application No. PCT/EP2021/054027, International Search Report and Written Opinion mailed Jul. 29, 2021.

Office Action for JP Application No. 2022-549594, mailed Sep. 29, 2025 (with English machine translation).

Office Action for Chinese Application No. 202180028924.0, mailed Sep. 18, 2025 (with English translation).

Second Office Action for Chinese Application No. 202180028924.0, mailed Mar. 7, 2026 (with English translation).

* cited by examiner 200
223
225a
225b
225c
225d
225e
225f
225g
201
202
203
204
205
206
207
208
209
210
211
212
213
215
217
219
221
237
235
227
233
229
231

Figure 20:
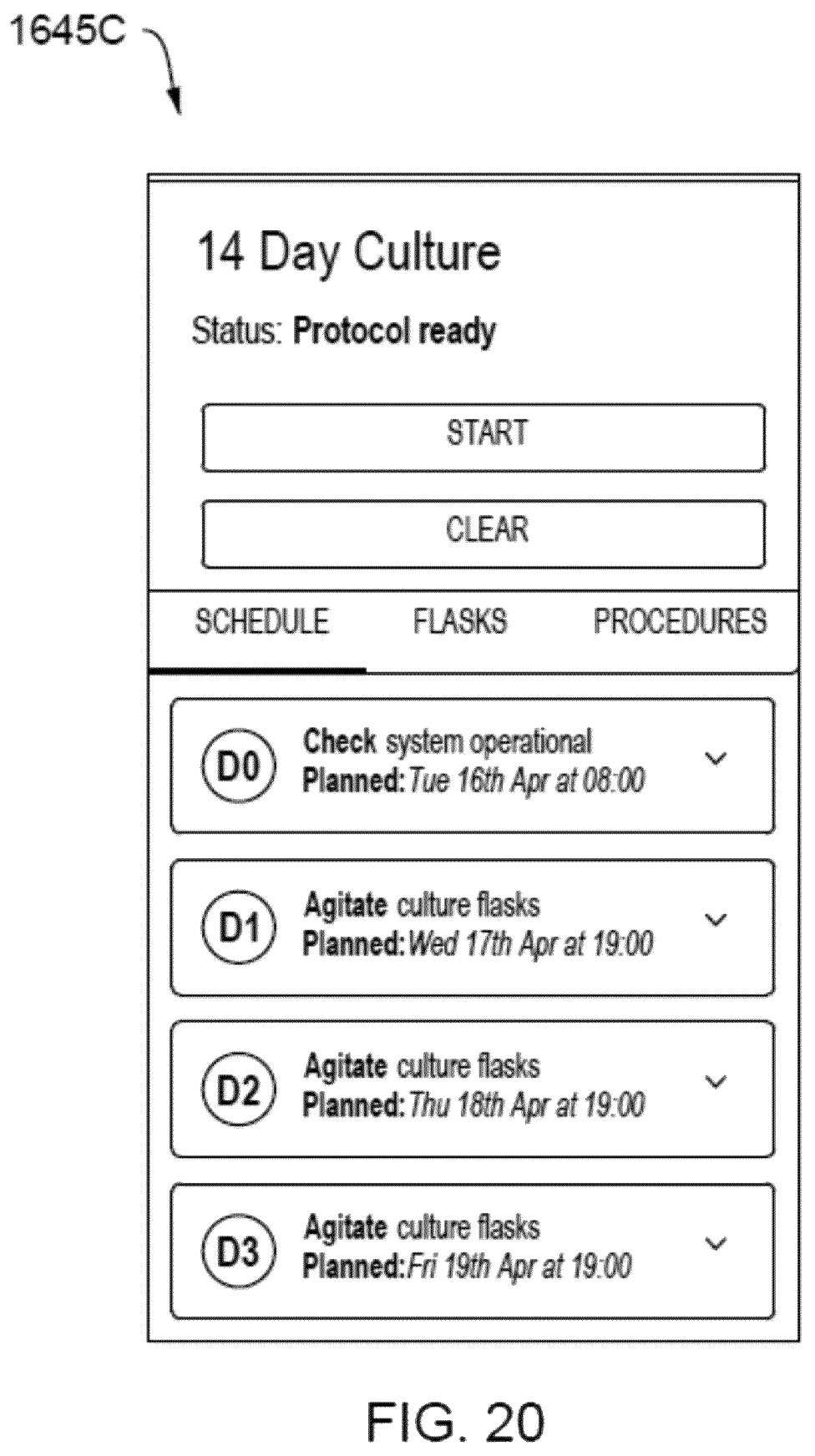

1645C

14 Day Culture

Status: Protocol ready

START

CLEAR

SCHEDULE FLASKS PROCEDURES

D0 Check system operational
Planned: *Tue 16th Apr at 08:00*

D1 Agitate culture flasks
Planned: *Wed 17th Apr at 19:00*

D2 Agitate culture flasks
Planned: *Thu 18th Apr at 19:00*

D3 Agitate culture flasks
Planned: *Fri 19th Apr at 19:00*

| Vessel | Type | Volume | Location |
|---|---|---|---|
| Fresh media (F) | GL45 | 250ml | Fridge |
| Fresh holding | Falcon | 50ml | Incubator |
| Pump holding | Falcon | 50ml | Incubator |
| PBS | Falcon | 50ml | Incubator/Room temp location |
| Trypsin | Falcon | 15ml | Incubator/Room temp location |
| Harvest | Falcon | 50ml | Incubator |
| Waste | GL45 | 250ml | Room temp location |

FIG. 60

TABLE 2

Cell passaging example (maintenance of adherent culture)

| Purpose of step | Source | Destination | Fluid | Flask 1 state after step | Flask 2 state after step |
|---|---|---|---|---|---|
| | | | | Spent media + attached cells | Empty |
| Remove spent media | Flask 1 | Waste | Spent media | Attached cells | Empty |
| Wash off old media | PBS | Flask 1 | PBS | PBS + attached cells | Empty |
| Remove PBS | Flask 1 | Waste | PBS | Attached cells | Empty |
| Add enzyme | Trypsin | Flask 1 | Trypsin solution | Trypsin solution + attached cells | Empty |
| Incubation time for enzyme | N/A | N/A | N/A | Trypsin solution + detached cells | Empty |
| Quench enzyme | Fresh holding | Flask 1 | Fresh media | Trypsin + fresh media + detached cells solution | Empty |
| Reduce total number of cells by pumping some to waste | Flask 1 | Waste | Trypsin + fresh media + detached cells solution | Trypsin + fresh media + detached cells solution | Empty |
| Move cells to new flask | Flask 1 | Flask 2 | Trypsin + fresh media + detached cells solution | Empty and not usable | Trypsin + fresh media + detached cells solution |

FIG. 61A

TABLE 2 - CONTINUED

| | | | | | |
|---|---|---|---|---|---|
| Top up fresh holding with media from fridge | Fresh | Fresh holding | Fresh media | Empty and not usable | Trypsin + fresh media + detached cells solution |
| Incubation time for media in fresh holding to warm up | N/A | N/A | N/A | Empty and not usable | Trypsin + fresh media + detached cells solution |
| Incubation time for cells to attach | N/A | N/A | N/A | Empty and not usable | Trypsin + fresh media solution + attached cells |
| Remove remaining trypsin | Flask 2 | Waste | Trypsin + media solution | Empty and not usable | Attached cells |
| Add fresh media | Fresh holding | Flask 2 | Fresh media | Empty and not usable | Fresh media + attached cells |

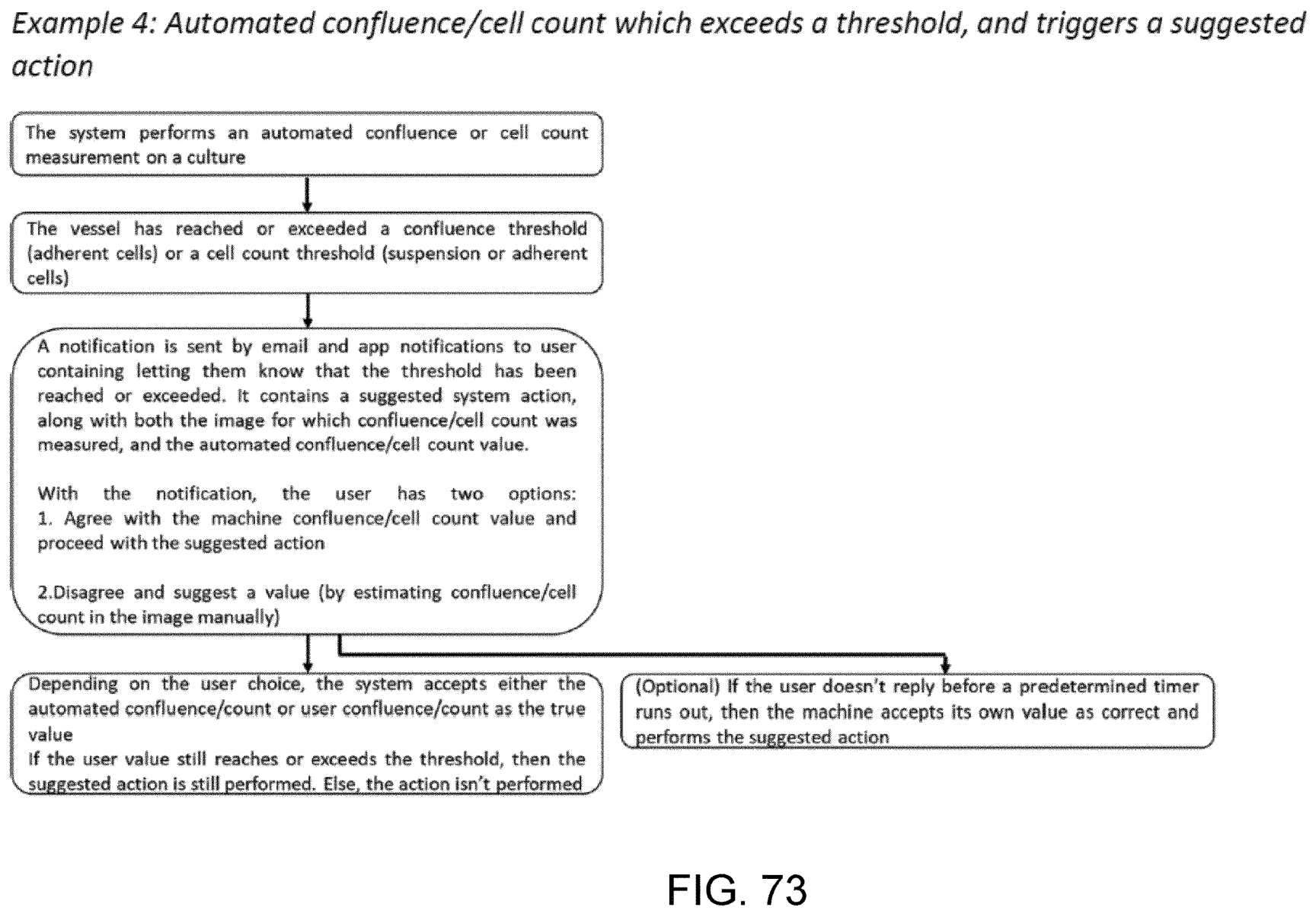

*Example 4: Automated confluence/cell count which exceeds a threshold, and triggers a suggested action*

The system performs an automated confluence or cell count measurement on a culture The vessel has reached or exceeded a confluence threshold (adherent cells) or a cell count threshold (suspension or adherent cells)

A notification is sent by email and app notifications to user containing letting them know that the threshold has been reached or exceeded. It contains a suggested system action, along with both the image for which confluence/cell count was measured, and the automated confluence/cell count value.

With the notification, the user has two options:
1. Agree with the machine confluence/cell count value and proceed with the suggested action 2.Disagree and suggest a value (by estimating confluence/cell count in the image manually)

Depending on the user choice, the system accepts either the automated confluence/count or user confluence/count as the true value
If the user value still reaches or exceeds the threshold, then the suggested action is still performed. Else, the action isn't performed (Optional) If the user doesn't reply before a predetermined timer runs out, then the machine accepts its own value as correct and performs the suggested action

FIG. 73

Images taken during removal of selective differentiated cells

SYSTEMS AND METHODS FOR AUTOMATED CELL CULTURING

CROSS-REFERENCE TO RELATED APPLICATIONS

This application is a U.S. national stage filing under 35 U.S.C. § 371 of International Application No. PCT/EP2021/054027, entitled "Systems and Methods for Automated Cell Culturing," filed Feb. 18, 2021, which claims priority to and the benefit of U.S. Provisional Patent Application No. 62/978,012, entitled "Systems and Methods for Automated Cell Culturing," filed Feb. 18, 2020, each of which is incorporated herein by reference in its entirety. This application is also related to U.S. patent application Ser. No. 16/543,369, entitled "Systems and Methods for Automated Cell Culturing," filed Aug. 16, 2019 (U.S. Pat. No. 10,988,726), which claims priority to U.S. Provisional Application No. 62/719,652 entitled "Automated Cell Culture," filed Aug. 19, 2018, each of the disclosures of which is incorporated herein by reference in its entirety.

FIELD OF INVENTION

This specification generally relates to systems and methods for culturing cells.

BACKGROUND

Cells may be grown, or cultured, under controlled conditions in a laboratory or industrial setting for various purposes. Typically, cells are grown in an enclosed vessel and covered with a solution referred to as a cell culture medium that provides essential nutrients and other supplements to help the cells grow. Examples of vessels used in cell culture include flat circular dishes such as Petri dishes or laboratory flasks. As cells grow and multiply they consume the nutrients in the cell culture medium and produce waste byproducts. For this reason, the cell culture medium must be periodically changed so that the cells continue to flourish. In addition, cell cultures may be expanded by transferring a portion of a cells to new vessels, providing additional volume or area within which the cells can grow. This process of transferring a portion of cells to new vessels may be referred to as passaging or subculturing. Additionally, cells can be removed from the vessel in preparation for their use. The process of separating cells from the vessel they are grown in may be referred to as harvesting.

Cell cultures usually proliferate following a standard growth pattern. The first phase of growth after the culture is seeded is the lag phase, which is a period of slow growth when the cells are adapting to the culture environment. The lag phase is followed by the logarithmic phase in which cells proliferate exponentially and consume nutrients in the growth medium. As a cell culture reaches the capacity of the environment by either consuming all the nutrients in the growth medium or occupying all of the space available, growth slows, and cells enter a stationary or plateau phase in which the proliferation is greatly reduced or ceases entirely. Known cell culture procedures often include passaging the cells prior to entering this stationary phase to optimize growth.

Generally, adherent cells are harder to grow than suspension cells. Adherent cells grow attached to a surface, such as the bottom of a culture flask or dish. The amount of cells in the flask is normally measured as the percentage of the growth surface covered by cells, referred to as percentage confluency. Adherent cells have to be detached from the surface before they can be removed from a vessel. Cells may be detached by one of several methods, including mechanically scraping or using enzymes such as trypsin to cleave adhesion to the vessel surface. The detached cells are then resuspended in fresh growth medium and allowed to settle back onto a growth surface. These additional steps increase the likelihood of cell damage or contamination.

Additionally, the dissociation reagents used to facilitate detachment of adherent cells can also be harmful to the cells, and thus should be fully removed before the cells are placed back into the fresh growth medium. These processes of removing spent medium from cell culture vessels, adding fresh medium, detaching adherent cells, and transferring cells from one vessel to another are typically carried out by laborious manual procedures. For example, known cell culturing methods often include repeated operations that involve moving the cells (within the cell culture vessels) between various workstations and/or opening the cell culture vessels to move fluids into and out of the vessels. Specifically, known methods include first loading the cells and cell culture medium into the vessels in an aseptic environment (e.g., a laminar flow hood). After being prepared, the cell culture vessels are closed (to minimize contamination) and moved to an incubator to facilitate growth. The cell culture containers are often manually monitored to determine the appropriate time to change the cell culture medium, as well as periodically manually monitoring to inspect parameters such as, for example, confluence and cell morphology, by removing the vessels from the incubator and imaging under a microscope. These manual monitoring steps usually require travelling to the lab just to check on the cultures and determine whether other operations need to be performed. When it is time to change the cell culture medium, the cell culture vessels are then moved from the incubator to an aseptic environment, opened (or otherwise connected to a source of waste and fresh cell culture medium), and the fluids are transferred to and/or from the cell culture vessels. The vessels are also moved and/or opened to complete other operations, such as cell passaging or cell harvesting.

Such known procedures are inefficient, costly, and susceptible to contamination. For example, repeatedly opening the cell culture system and moving the cell culture vessels between lab stations potentially exposes the cells to contamination. Additionally, every operation that is manually performed is expensive and also susceptible to contamination (or cell damage) due to the operator not following proper procedures. Further, determining when to change medium or when to passage cells is typically done according to a predetermined schedule, which may not be optimal. Adhering to set schedules can result in additional (and potentially unnecessary) use of a laminar flow hood (the operation of which can consume large amounts of energy and can therefore be costly). Adhering to set schedules can also result in reduced efficiency for cell growth (e.g., if the cell growth reaches the plateau phase before the cell culture medium is exchanged).

Some known systems and methods for culturing adherent cells are for use in various applications, such as drug development and cell therapy. Different cell types can require different levels of environmental control, such as induced pluripotent stem cells (iPSC), which can be very difficult to culture. In addition, known systems for monitoring cell health do not take into account details of iPSC, such as morphology indicating undesired differentiation. Known systems also do not efficiently allow for passaging of adherent cells. Many known systems use centrifuge systems and require that cells be removed from the culture system to separate cells from dissociation reagents; thus the cells are not maintained in a closed system.

As noted above, many existing cell culture systems are designed to grow a large batch of one type of cell, usually so that those cells can then be used as "factories" to produce a desired biological product, such as, for example, a protein. Typically, only the product is kept (and not the cells). This use case where cells make product for the user is called "bioprocessing," and such known systems are often referred to as bioreactors. Because the product of interest is the produced biological product and not the cell, such known systems often use (or are seeded with) any suitable robust cell that can be easily grown and that can produce the desired product. In many cases, the easiest type of cell to grow is chosen as the factory ("producer"), and such cells are often grown in suspension. Known bioreactor systems are large, and used for a single type of cell (to produce large amounts of a product). Such systems are not suitable for cell culturing for development or therapy, where smaller quantities of several different type of cells are desired.

It may be desirable, however, to obtain cells to be used for testing drugs or for other therapeutic purposes. In other words, in certain situations, the cell (and not the products produced by the cell) is actually the desired product for experiments. Many known bioreactors, however, are not suitable for culturing cells that are to be used as the end product. Specifically, when cells are grown for drug testing, the cells are subject to different requirements distinct from the requirements and capabilities of known bioprocessing systems. First, there is a need to grow the most realistic cells as possible (i.e., cells that are associated with the drugs, therapeutic regimen, or condition that is addressed by the drug). Said another way, the cells are chosen based on their applicability for the desired testing, and not based on simply their ability to produce a product. Usually, cells used for drug testing do not grow in suspension, but instead stick to a surface as they grow (i.e., adherent cells). Processing of adherent cells introduces technological challenges in their culture. Second, there is need to produce small batches of a lot of different types of cells growing simultaneously, such that cells of different types are always ready for testing. Known existing machines may not be configured for this type of cell harvesting.

A challenge that arises is designing a system with tolerable setup time, considering all fluidics typically get thrown away with each batch. With bioprocessing, the batch is typically so large that long setup time is tolerable. With a use case to grow multiple different types of cell at the same time for testing, there are a lot of small batches to handle (at least one for each cell type), so setup time needs to be very fast. Known systems require long-setup time and can include extensive post-use cleaning. Elaborate setup of tubing into valve heads can increase set-up time. Thus, a need exists for cell culturing systems that can provide for efficient and fast setup time.

Moreover, many known cell culture systems (e.g., bioreactors) cannot accommodate growing different types of cells within a single system. For example, certain test methods can involve the use of multiple different cell types. Because known systems generally include a single reservoir to accommodate one type of cell (e.g., to be used as a factory), they are not suitable for including multiple different types of cells. In addition, many known cell culture systems do not have the ability to passage cells from one vessel to another when a culture becomes confluent, thus requiring that operators manually intervene regularly to switch the consumable on the system each time the culture becomes confluent.

It is important for cells to be distributed evenly on the surface of a culture plate for effective culturing. It is especially important for stem cell culturing because if not evenly distributed, the cells can undergo undesired differentiation during culture. Many known systems and methods for cell culturing manually shake the cell culture vessel after cells are input into the vessel. Such a method is of shaking is not repeatable, not always effective and cells can begin to adhere to a nutrient layer on the surface, thus post-seeding shaking is not always affective.

Cell counting is also an important aspect of cell culture. Known methods for cell counting are laborious and require that cells be removed from the cell culture system and placed into an external counting device. More specifically, cell sample is removed from a culture tray and put into a separate cartridge outside of the incubator. This process increases the likelihood of contamination by accessing a closed system. In addition, known counting systems rely on having a homogenous mixture of cells. If settling or inconsistencies exists by manually removing a cell sample and placing it into a counting cartridge, then results may not be accurate. Further, the counted sample needs to be discarded as waste. Thus, a system and method are needed for accurately counting cells within a closed system.

Stem cell cultures are prone to issues related with undesired differentiation. In many instances, upon detection of the undesired stem cell behavior, the entire container is discarded and the culture must be started again. There are some known methods to selectively remove the desired cells to avoid discarding entire culture, but these methods are generally manual, labor intensive and require opening the system to manually separate desired cells from undesired cells/surface. Thus, a system and method are needed for removing the desired cells while avoiding these issues.

Additional challenges can arise when the cell to be cultured is a stem cell. Specifically, culturing of pluripotent stem cells can be challenging because even minor changes in the environment can produce unintended differentiation of the stem cells. Known cell culture systems often do not maintain the desired control over the environment to maintain the pluripotency of stem cells. For example, difference in cell density and non-uniform seeding of cells in a cell culture container can result in a greater likelihood that induced pluripotent stem cells (iPSC) will undergo undesired spontaneous differentiation. Thus, known methods of seeding stem cells generally include manually moving the cell container after the cells have been loaded to facilitate a more homogenous mixture of stem cells before they settle and become attached to the surface. Such methods, however, are inconsistent and do not reliably produced the desired spatial uniformity. Specifically, such manual methods are subject significant differences depending on the lab technician and procedures followed. Additionally, because the movement (or gentle shaking) is performed after the cells are loaded (and the container is closed), the lapse in time can result in portions of the seeded cells settling before the movement is commenced. Thus, a need exists for improved systems and methods for seeding stem cells.

As another example, known cell culture methods include periodically counting the cells. Known systems and methods for cell counting often involve opening the cell culture environment, removing a portion of the cells, and counting, via an external cell counting system, the cells. Because the counted cells have been handled through multiple steps and are subject to contamination or damage, they are generally discarded. Thus, a need exists for improved methods of cell counting to ensure that a homogenous mixture of cells is counted within the closed system. Moreover, a need exists for improved cell counting methods and systems in which the counted cells can be recovered for continued use.

Known cell culturing systems generally use a centrifuge process to wash cells or to remove spent media and/or reagents. Such known methods often include removing the cell sample from the culture system and completing the filtering/washing operations via centrifuge. Such methods can expose the cells to potential contamination and damage. Thus a need exists for improved systems and methods for filtering and/or washing cells.

A need also exists for cell culturing systems that improve the efficiency and limit potential contamination during cell culturing. Specifically, a need exists for systems and methods for automating the cell culture procedures, for maintaining the cell culture system in a closed aseptic environment during the culturing, and for allowing efficient set-up and use. A need also exists for an automated cell culturing system that can optionally operate with existing off-the-shelf cell culturing vessels.

SUMMARY

According to one implementation, this specification describes systems and methods for automatically culturing cells. Automated cell culture systems disclosed herein enable scientists to accelerate their research and development by automating manual cell culture. Systems and methods disclosed in various embodiments may provide for automated cell growth media replenishment, automated passaging of cells, and/or automated cell culture analysis. These automated cell culture systems and methods may increase efficiency and decrease error compared to manual cell culture operations. Furthermore, these embodiments increase the quantity and quality of data points on cell culture available to scientists via integrated automated analysis mechanisms.

An automated cell culture system according to an embodiment includes a housing with a valve actuator and a fluid pump disposed within the housing. The automated cell culture system also includes a removable tray configured to removably mate to the housing. A plurality of cell culture vessel brackets attached to the removable tray are configured to hold a respective plurality of cell culture vessels, where each cell culture vessel is capped with an aseptic lid. A selector valve is configured to couple to the valve actuator of the housing when the removable tray is mated with the housing. A plurality of media sources may be provided that are, in some embodiments, external to the housing and removable tray. The selector valve is configured to fluidly connect a master port to a selected one of a plurality of selectable ports, where the master port of the selector valve is fluidly connected to the fluid pump, and each of the plurality of cell culture vessels and media sources are directly fluidly connected to a respective one of the plurality of selectable ports of the selector valve. In some embodiments, the plurality of cell culture vessels and their aseptic lids, the selector valve, and the fluid connections therebetween form a first aseptically sealed system attached to the removable tray.

In some embodiments, a method of cell line maintenance using an automated cell culture system includes transmitting a command to a movable imaging system of an automated cell culture system to image the cells within a selected vessel of the automated cell culture system; receiving from the imaging system an image of the cells within the selected vessel; based on the image of the cells within the selected vessel, measuring a cell passaging criterion; comparing the cell passaging criterion to a threshold cell passaging criterion; based on the comparing, determining to initiate passaging of the cells within the selected vessel to a subculture vessel. The method of cell line maintenance also includes passaging a configured portion of the cells of the selected vessel to the subculture vessel; and transmitting a notification that the automated cell culture system has passaged the configured portion of cells of the selected vessel to the subculture vessel. Other embodiments of this aspect include corresponding computer systems, apparatus, and computer programs recorded on one or more computer storage devices, each configured to perform the actions of the methods.

The details of one or more implementations of the subject matter described in this specification are set forth in the accompanying drawings and the description below. Other potential features, aspects, and advantages of the subject matter will become apparent from the description, the drawings, and the claims.

BRIEF DESCRIPTION OF THE DRAWINGS

FIGS. 18-20 are each an example screenshot showing various GUI elements produced in connection with operation of the electronic control system.

FIG. 60 is a table illustrating the contents shown in FIG. 59.

FIGS. 61A-61B include a table illustrating an example of a cell passaging procedure.

FIGS. 70-73 each illustrate a different example of a software workflow and decision loop.

DETAILED DESCRIPTION

Figure 1A:
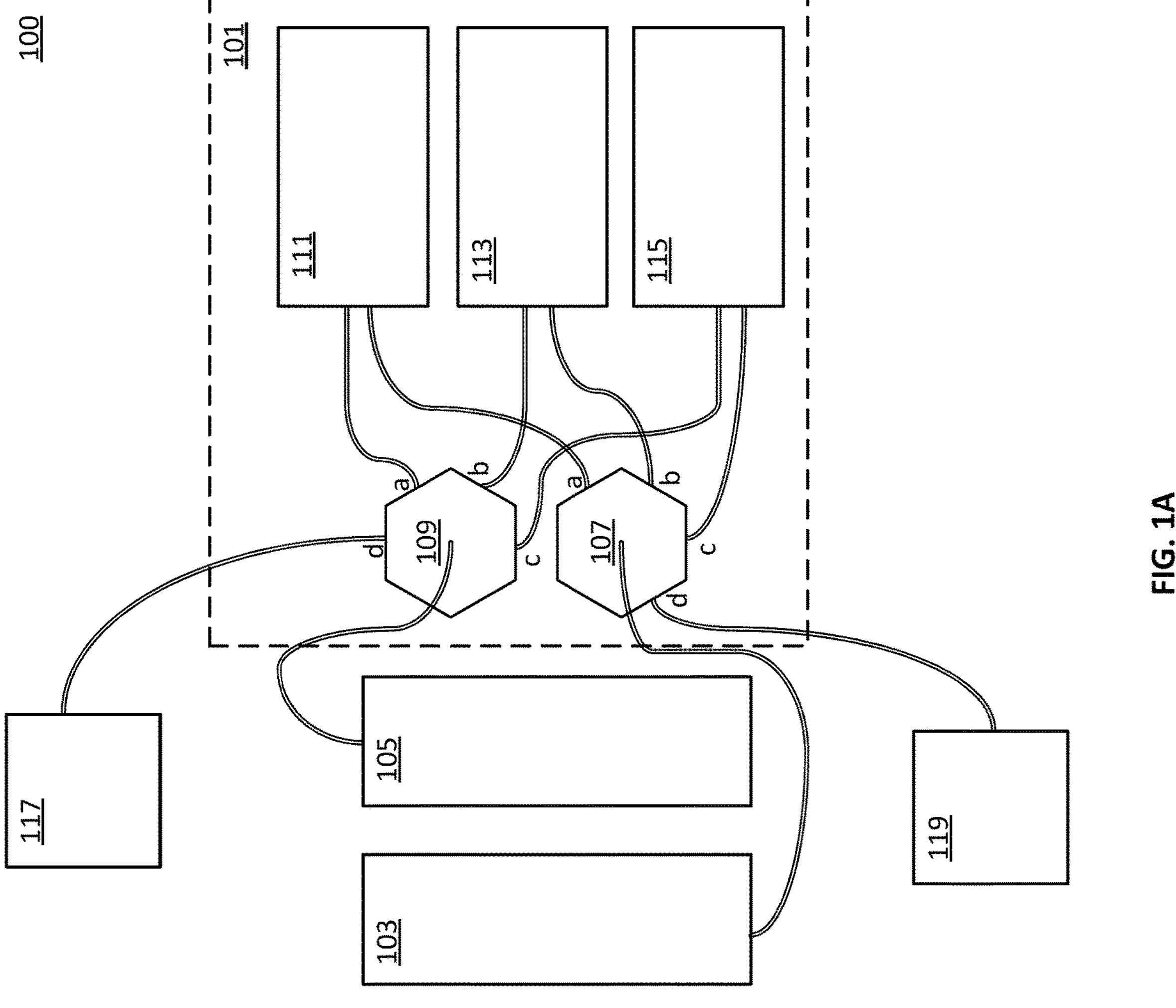
FIG. 1A illustrates a schematic view of an automated cell culture system according to an embodiment.

As described herein, in some embodiments, cell culturing systems and methods are configured to obtain cells to be used to test drugs on, such that the cell is actually a required reagent for experiments. When cells are grown to test drugs on for this purpose, the cells are typically adherent cells. Further, it is desirable for such cell culturing to produce small batches of a lot of different types of cells growing simultaneously, such that cells of different types are always ready for testing. In addition, as growing simultaneous batches of different types of cells means each batch needs to be setup individually, fast per-batch setup times are key when automating this process. The various embodiments of a consumable tray assembly and base unit described herein are configured for this type of cell harvesting and provide for reduced set up time.

In some embodiments described herein, the cell culturing system or groups of systems are designed to maintain in culture or to expand (make many more of) different types of cells simultaneously, while aiming to maximize hands-off time for the operators (i.e., maximizing the stretches of time when a user does not have to physically touch the system, such as to change consumables. For example, in some embodiments described herein, an imaging device (e.g., microscope) is integrated within the system to provide for remote-monitoring without having to physically remove the cell culture containers from the system.

In some embodiments described herein, a consumable tray assembly is provided that contains empty cell culture containers into which the system passages cells when the current container becomes confluent (adherent cells). As described herein, in some embodiments, a cell culture system can fully remove dissociation reagent from a cell culture container. In some embodiments, a cell culturing system can harvest cells at a requested density. In some embodiments, a cell culturing system described herein can rescue stem cell cultures where the cells start to unintentionally differentiate, by detaching only the undifferentiated cells and moving them to a new vessel.

In some embodiments described herein, a cell culturing system can grow cells to test batches of manufactured advanced therapy medical products (ATMPs). Usually when a batch of edited cells for cell therapy are manufactured, or a batch of virus to use for gene therapies are manufactured, manual cell culture procedures are performed on a small sample to show that the batch is safe for use and will work in the patient. For cell therapies, this can involve manually culturing a sample of cells for a period of time to show they will behave as intended in the patient. The systems described herein enable hands-off cell culture capabilities (i.e., limited manual interaction by an operator) combined with monitoring, and thus are well suited for culturing cells for ATMPs. For virus batches, this testing can involve transfecting cells with virus, and then manually growing those cells over many passages, and checking at the final passage that there is no virus, to prove the virus has no ability to replicate. The systems and methods described herein are also well-suited for such manipulation of virus batches.

In some embodiments, an apparatus includes a tray configured to be removably coupled within an instrument. The tray includes an alignment portion configured to matingly engage with a corresponding alignment portion of the instrument. The tray defines a sensor opening and includes a shoulder surrounding at least a portion of the sensor opening. The apparatus includes a container having a top surface and a bottom surface. The top surface and the bottom surface each have a transparent portion. The container coupled to the tray such that an edge of the bottom surface is supported by the shoulder and the transparent portion of the bottom surface is aligned with the sensor opening. A mounting bracket is coupled to the tray and coupled to an edge of the top surface of the container to secure the container to the tray. A valve assembly is fluidically coupled to the container and a fluid pump. The valve assembly is removably coupled to the tray. The valve assembly and the fluid pump are each configured to be actuated to cause transfer of a fluid into or out of the container.

In some embodiments, an apparatus includes a tray configured to be removably coupled within a cell culture instrument. A first container is coupled to the tray and is configured to receive a cell sample therein. A second container is also coupled to the tray. The apparatus includes a first tangential flow filter assembly having an inlet port, a first outlet port, and a second outlet port, and a second tangential flow filter assembly having an inlet port, a first outlet port, and a second outlet port. The second outlet port of the first tangential flow filter assembly fluidically coupled to the inlet port of the second tangential flow filter assembly. The apparatus further includes a fluid pump assembly, and a valve assembly operably coupled to the first container, the second container, the inlet port of the first tangential flow filter assembly, and the fluid pump assembly. The valve assembly and the fluid pump assembly are each configured to be actuated by the cell culture instrument to cause: A) transfer of the cell sample from the first container into the inlet port of the first tangential flow filter assembly, B) transfer of a first volume of retentate from the cell sample from the first outlet port of the first tangential flow filter assembly to the second container, and C) transfer of a first volume of permeate from the second outlet port of the first tangential flow filter assembly to the inlet port of the second tangential flow filter assembly.

In some embodiments, an apparatus includes a base unit having a lower housing, a support plate, a first portion of a cell sensor assembly movably coupled within the lower housing. The support plate is configured to be removably coupled to a cell culture tray assembly. The cell culture tray assembly has a tray and a container coupled to the tray. The tray defines a sensor opening and a portion of the container is transparent and coupled to the tray to provide optical access of contents of the container via the sensor opening and transparent portion of the container. The apparatus includes an upper unit having an upper housing and a second portion of the cell sensor assembly coupled within the upper housing. The upper unit movably coupled to the base unit and configured to be moved between an opened position and a closed position. The support plate being accessible when the upper unit is in the opened configuration. The support plate being at least partially enclosed when the upper unit is in the closed configuration. An electronic control system coupled within at least one of the lower housing or the upper housing, the electronic control system configured to control movement of at least the first portion of the cell sensor assembly to align the first portion of the cell sensor assembly with the container.

In some embodiments, an apparatus includes a base unit having a lower housing, a support plate, and an agitator assembly disposed within the lower housing. The support plate is configured to be removably coupled to a cell culture tray assembly. The cell culture tray assembly having a tray and a container coupled to the tray. An upper unit having an upper housing is movably coupled to the base unit and configured to be moved between an opened position and a closed position. The support plate being accessible when the upper unit is in the opened configuration. The support plate being at least partially enclosed when the upper unit is in the closed configuration. An agitator assembly is disposed within the lower housing of the base unit and operatively coupled to the support plate via a plurality of coupling elements at attachment locations disposed about a perimeter of the support plate. At least one of the plurality of coupling elements configured to maintain a position of the support plate in a first direction. At least another one of the plurality of coupling elements configured to maintain a position of the support plate in a second direction different than the first direction. The agitator assembly configured to move the support plate when actuated to agitate the cell culture tray assembly when coupled to the support plate. An electronic control system is coupled within at least one of the lower housing or the upper housing and is configured to control actuation of the agitator assembly.

In some embodiments, a method includes removing a cell culture tray assembly from an outer protective wrap. The cell culture tray assembly includes a tray, a container coupled to the tray, a pump, and a valve assembly removably coupled to the tray, the tray including an alignment portion and the container is aseptically coupled to the pump and the valve assembly to form a closed system. The valve assembly and the fluid pump are each configured to be actuated to cause transfer of a fluid into or out of the container. The cell culture tray assembly is coupled to an instrument by engaging the alignment portion of the tray with a corresponding alignment portion of the instrument, the instrument including a valve actuator and a pump actuator. The valve assembly is removed from the tray and is coupled to the valve actuator of the instrument while the container, the pump, and the valve assembly remain coupled within the closed system. The pump is coupled to the pump actuator of the instrument while the container, the pump, and the valve assembly remain coupled within the closed system. One or more cell culture operations is performed on a cell sample within the container coupled to the tray by actuating at least one of the valve assembly and the pump.

In some embodiments, a method of seeding a cell sample into a cell culture container includes coupling a cell culture tray assembly to a support plate of an instrument. The cell culture tray assembly includes a tray and the cell culture container is coupled to the tray, a pump, and a valve assembly removably coupled to the tray. The cell culture container is aseptically coupled to the pump and the valve assembly to form a closed system. The valve assembly and the fluid pump are each configured to be actuated to cause transfer of a fluid into or out of the cell culture container. The instrument includes the support plate, a valve actuator, a pump actuator, and an agitator assembly. The agitator assembly is configured to agitate the support plate. A seeding container is coupled within the closed system to the container, the pump, and the valve assembly. The seeding container contains the cell sample. At least one of the pump or the valve assembly is actuated to convey a portion of the cell sample from the seeding container to the cell culture container to seed the cell culture container with the cell sample. The agitator assembly is actuated to agitate the support plate and the cell culture tray assembly while the portion of the cell sample is being conveyed from the seeding container into the cell culture container.

In some embodiments, a method is provided for counting cells within a cell culture system including a tray, a cell culture container coupled to the tray, a holding container, a counting chip coupled to the tray, and a pump. Each of the cell culture container, the holding container, the counting chip, and the pump are aseptically coupled together to form a closed system. The method includes actuating the pump to convey a cell sample from the cell culture container to the holding container. The cell sample is mixed within the holding container by further actuating the pump to convey a volume of air to the holding container. After the mixing, conveying the cell sample from the holding container into the counting chip. The cell sample is analyzed within the counting chip to produce a cell signal associated with an amount of cells within the cell sample.

In some embodiments, a method of selectively removing cells within a cell culture system is provided. The cell culture system includes a tray assembly and an instrument. The tray assembly includes a tray, a cell culture container coupled to the tray, a reagent container, a holding container, and a pump. Each of the cell culture container, the reagent container, the holding container, and the pump are aseptically coupled together to form a closed system. The instrument includes a support plate to which the tray is removably coupled, a pump actuator, an agitator assembly configured to agitate the support plate, and a cell sensor. The method includes actuating the pump to convey a dissociation reagent from the reagent container to the cell culture container. The agitator assembly is actuated to agitate the support plate and the tray assembly to facilitate dissociation of a first portion of cells within the cell culture container. A sensor output is received from the cell sensor. The sensor output is associated with a cell sample within the cell culture container. Based on the sensor output, a cell signal associated with at least one of a status of dissociation of the first portion of cells within the cell culture container or a second portion of cells within the cell culture container is produced. The pump is actuating based on the cell signal to convey the first portion of cells from the cell culture container to a holding container.

In some embodiments, a method of processing cells within a cell culture system is provided. The cell culture system includes a tray assembly and an instrument. The tray assembly includes a tray, a first container coupled to the tray, a second container coupled to the tray, a tangential flow filtration assembly, and a pump. Each of the first container, the second container, the tangential flow filtration assembly, and the pump are aseptically coupled together to form a closed system. The instrument includes a support plate to which the tray is removably coupled, a pump actuator, and a cell sensor. The method includes receiving a sensor output from the cell sensor. The sensor output is associated with a cell sample within the first container. Based on the sensor output, a cell signal associated with a status of cells within the first container is produced. The pump is actuated to convey the cell sample from the first container into the tangential flow filtration assembly to produce a permeate output and a retentate output. One of the permeate output or the retentate output is conveyed to the second container.

In some embodiments, an apparatus includes a tray, a first lid, a second lid, and a multiport valve. The tray is configured to be removably coupled to a housing of a base unit. The tray has a first coupler configured to couple a first container to the tray and a second coupler configured to couple a second container to the tray. The first lid is configured to be coupled to the first container and includes a first liquid exchange port and a first gas exchange port. The second lid is configured to be coupled to the second container and includes a second liquid exchange port and a second gas exchange port. The multiport valve coupled to the tray and including a master port and a set of selectable ports. The multiport valve is configured to engage a valve actuator of the base unit and be coupled to a fluid pump coupled to the base unit. A first selectable port of the set of selectable ports is aseptically coupled to the first liquid exchange port of the first lid. A second selectable port of the set of selectable ports aseptically coupled to the second liquid exchange port of the second lid.

In some embodiments, the first coupler maintains the first container in a fixed position on the tray and the second coupler maintains the second container in a fixed position on the tray during operation of the apparatus. In some embodiments, the first container is a cell culture container configured to receive a cell sample and the second container is one of a waste container, a reagent container, or a cell harvest container. In some embodiments, the first coupler is configured to removably couple the cell culture container to the tray. In some embodiments, the cell culture container and the tray each include a transparent portion. The first coupler is configured to couple the cell culture container to the tray such that the transparent portion of the cell culture container is aligned with the transparent portion of the tray.

In some embodiments, the multiport valve and the fluid pump are configured to transfer fluid between the first container and the second container in a closed, aseptic system. In some embodiments, the multiport valve is removably coupled to the tray and is also configured to be removably coupled to a valve actuator of the base unit. In some embodiments, the pump includes a pump actuator and a pump body defining a pumping chamber. The pump body is configured to be coupled to the master port of the multiport valve.

In some embodiments, the tray is configured to engage an agitator coupled to the base unit. The agitator is configured to agitate the tray when actuated.

In some embodiments, the apparatus includes a counting chip coupled to the tray and coupled to a third selectable port of the multiport valve. The counting chip is configured to receive a portion of a cell sample mixture from the first container at periodic time intervals.

In some embodiments, the tray, the first lid, the second lid, and the multiport valve are enclosed within a wrap. In some embodiments, the tray, the first lid, the second lid, and the multiport valve are sterilized within the wrap.

In some embodiments, a base unit of a cell culturing system includes a housing, a pump actuator, and a valve actuator. The housing defines (or includes) a receiving portion configured to removably receive a cell culture tray assembly. The cell culture tray assembly includes a tray, a first lid coupled to the tray that can be removably coupled to a first container, and a second lid coupled to the tray that can be removably coupled to a second container. The first lid and the second lid each include a liquid exchange port and a gas exchange port. The cell culture tray also includes a multiport valve coupled to the tray and including a master port and a set of selectable ports. The pump actuator is coupled to the housing and configured to be operatively coupled to a fluid pump coupled to the master port of the multiport valve. The valve actuator is coupled to the housing and is configured to be coupled to the multiport valve when the cell culture tray assembly is coupled to the receiving portion of the housing. The valve actuator and the pump actuator are collectively configured to selectively move a fluid into and out of the first container coupled to the first lid and into and out of the second container coupled to the second lid.

In some embodiments, the multiport valve is configured to be removed from the tray and coupled to the valve actuator while a first port of the multiport valve is aseptically coupled to the first lid and a second port of the multiport valve is aseptically coupled to the second lid. In some embodiments, the valve actuator includes a keyed drive member configured to matingly engage the multiport valve.

In some embodiments, the fluid pump is aseptically coupled to the master port of the multiport valve via a length of tubing. In some embodiments, the fluid pump is any one of a piston pump, a peristaltic pump, or a vane pump.

In some embodiments, the base unit further includes an agitator coupled to the housing and configured to engage the cell culture tray assembly when the cell culture assembly is coupled to the housing. The agitator is configured to agitate the cell culture tray assembly when actuated. In some embodiments, the receiving portion of the housing includes a support plate coupled to the agitator. The support plate includes a surface to which the cell culture tray assembly can be removably coupled.

In some embodiments, the base unit further includes (or is coupled to) an electronic (or computer) control system configured to control movement of the fluid into and out of the first container coupled to the first lid and into and out of the second container coupled to the second lid. In some embodiments, the base unit includes a sensor movably coupled to the housing and configured to produce a cell signal associated with a quantity of cells within the first container. In some embodiments, sensor is an imaging device coupled to the housing and configured to image the contents within the first container such that at least one of a confluence or a density of the cells within the first container can be determined. In some embodiments, the sensor is configured to monitor a color of the contents of the first container. The first container can contain a color-based pH indicator such that a pH of the contents of the first container can be determined.

In some embodiments, a base unit of a cell culturing system includes a housing, a pump actuator, a valve actuator, and an electronic control system. The housing defines a receiving portion configured to removably receive a cell culture tray assembly. The cell culture tray assembly includes a tray, a first lid coupled to the tray that can be removably coupled to a first container, and a second lid coupled to the tray that can be removably coupled to a second container. The cell culture tray also includes a multiport valve coupled to the tray and including a master port and a set of selectable ports. The pump actuator is coupled to the housing and configured to be operatively coupled to a fluid pump. The valve actuator is coupled to the housing and is configured to be coupled to the multiport valve when the cell culture tray assembly is coupled to the receiving portion of the housing. The valve actuator and the pump actuator are collectively configured to selectively move a fluid into and out of the first container coupled to the first lid and into and out of the second container coupled to the second lid. The electronic control system includes a cell sensor, a cell sensor module, and an actuator module. The cell sensor is configured to produce an output associated with the contents within the first container. The cell sensor module is implemented in at least one of a memory or a processing device of the electronic control system and produces a cell signal associated with a quantity of cells within the first container based on the output of the cell sensor. The actuator module is implemented in at least one of the memory or the processing device and receives the cell signal and produces, based on the cell signal, at least one of a valve control signal or a pump signal to cause movement of cells out of the first container.

In some embodiments, the actuator module is configured to control movement of a first volume of fluid out of the first container and into a waste container, and movement of a second volume of fluid out of a reagent container and into the first container. In some embodiments, the actuator module is configured to control movement of a volume of an enzyme into the first container to facilitate cell dissociation of adherent cells within the first container.

In some embodiments, the apparatus includes an agitator coupled to the housing and configured to engage the tray assembly when the tray assembly is coupled to the receiving portion. The agitator is configured to agitate the tray assembly. The actuator module of the electronic control system is configured to control the actuation of the agitator (e.g., when to agitate and the time period of the agitation).

In some embodiments, the cell sensor is movably coupled to the housing. The sensor module is configured to control movement of the cell sensor relative to the housing such that the cell sensor can be aligned with the first container.

In some embodiments, the base unit includes a valve sensor configured to produce a valve position signal associated with a rotation position of the valve actuator. The valve position signal indicates a selection of one of the selectable ports of the multiport valve. The actuator module is configured to produce the valve control signal based in part on the valve position signal. In some embodiments, the base unit includes a pump sensor configured to produce a pump signal associated with a position of the pump actuator during operation. The actuator module is configured to produce the pump control signal based in part on the pump signal.

In some embodiments, the electronic control system further includes a radio configured to electronically communicate with a computing device. The radio is configured to send to the computing device a wireless signal associated with a measurement associated with a quantity of cells within the first container.

In some embodiments, a base unit of a cell culturing system includes a housing, a pump actuator, a valve actuator, and an electronic control system. The housing defines a receiving portion configured to removably receive a cell culture tray assembly. The cell culture tray assembly includes a tray, a first cell culture container, a second cell culture container, a reagent container, a waste container, and a multiport valve. The multiport valve includes a master port and a set of selectable ports. A first selectable port is coupled to the first cell culture container, a second selectable port is coupled to the second cell culture container, a third selectable port is coupled to the reagent container, and a fourth selectable port is coupled to the waste container. The pump actuator is coupled to the housing and configured to be operatively coupled to a fluid pump coupled to the master port of the multiport valve. The valve actuator is coupled to the housing and is configured to be coupled to the multiport valve. The electronic control system is operably coupled to the valve actuator and the pump actuator. The electronic control system includes an actuator module implemented in at least one of a memory or a processing device, and that is configured to produce a series of valve control signals and pump control signals. Specifically, the actuator module can produce a first valve control signal to cause the valve actuator to actuate the multiport valve and a first pump control signal to cause the pump actuator to actuate the fluid pump to move a cell culture media from the first cell culture container to the waste container. The actuator module can produce a second valve control signal to cause the valve actuator to actuate the multiport valve and a second pump control signal to cause the pump actuator to actuate the fluid pump to move a reagent from the reagent container to the first cell culture container. The actuator module can produce a third valve control signal to cause the valve actuator to actuate the multiport valve and a third pump control signal to cause the pump actuator to actuate the fluid pump to move a plurality of cells from the first cell culture container to the second cell culture container.

In some embodiments, the electronic control system includes a cell sensor module implemented in at least one of the memory or the processing device. The cell sensor module receives an output from a cell sensor and produces a cell signal indicating a dissociation of cells within the first cell culture container. The actuator module is configured to produce at least one of the third valve control signal or the third pump control signal in response to the cell signal. In some embodiments, the cell sensor is microscope and the output from the microscope is an image. The cell sensor module is configured to produce the cell signal indicating the dissociation of cells based on the image. In some embodiments, the cell sensor module is configured to produce an alignment signal to move the cell sensor into alignment with the first cell culture container.

In some embodiments, the base unit includes an agitator coupled to the housing and configured to engage the tray assembly. The agitator is configured to agitate the tray assembly. The actuator module of the electronic control system is configured to produce an agitator signal to cause agitation of the tray assembly.

In some embodiments, a computer-implemented method includes receiving at an electronic control system of a cell culture assembly, a sensor output from a sensor of the cell culture assembly. The cell culture assembly includes a disposable cell culture tray assembly couplable to a reusable base unit. The cell culture tray assembly includes a tray, a first lid coupled to a first container, a second lid coupled to a second container, and a multiport valve coupled to the tray. The multiport valve includes a plurality of selectable ports and a master port coupled to a fluid pump. At least one of the first container or the second container contains a plurality of cells. A cell signal associated with a quantity of the plurality of cells within one of the first container and the second container is produced based on the sensor output. Based on the cell signal, at least one of a valve control signal to actuate the multiport valve or a pump control signal actuate the fluid pump is produced at the electronic control system to initiate flow of fluid out of at least one of the first container or the second container.

In some embodiments, the sensor is a part of an optical measurement assembly configured to move the sensor, and the method further includes sending a position signal to the optical measurement assembly to move the sensor into a measurement position relative to at least one of the first container or the second container. In some embodiments, the cell sensor is microscope and the sensor output from the microscope is an image. The electronic control system can produce the cell signal indicating a dissociation of cells within the first container or the second container based on the image.

In some embodiments, the base unit includes an agitator operably coupled to the tray of the tray assembly. The method optionally includes sending from the electronic control system to the agitator an agitator signal to actuate agitation of the tray assembly to maintain cells within at least one of the first container or the second container in suspension. In some embodiments, the method includes sending, after the sending an agitator signal, at least one of an actuator signal or a pump signal to cause flow of a fluid mixture out of one of the first container and the second container and into a counting chip fluidically coupled to the one of the first container and the second container.

In some embodiments, a computer-implemented method can control fluid movement within a cell culture assembly that includes a disposable cell culture tray assembly coupled to a reusable base unit. The method includes producing, via an actuator module of an electronic control system of the cell culture assembly, a first valve control signal and a first pump control signal. The first valve control signal causes a valve actuator of the base unit to actuate a multiport valve to fluidically couple a first selectable port of the multiport valve to a master port of the multiport valve. The master port is fluidically coupled to a fluid pump and each selectable port is fluidically coupled to one of a first cell culture container, a second cell culture container, a reagent container, or a waste container. The first pump control signal causes a pump actuator of the base unit to actuate the fluid pump to move a cell culture media from the first cell culture container to the waste container. A second valve control signal is produced causing the valve actuator to actuate the multiport valve to fluidically couple a second selectable port to the master port and a second pump control signal causing the pump actuator to actuate the fluid pump to move a reagent from the reagent container to the first cell culture container. A third valve control signal is produced causing the valve actuator to actuate the multiport valve to fluidically couple a third selectable port to the master port and a third pump control signal causing the pump actuator to actuate the fluid pump to move a plurality of cells from the first cell culture container to the second cell culture container.

In some embodiments, the method includes producing, via the actuator module, a fourth valve control signal causing the valve actuator to actuate the multiport valve to fluidically couple a fourth selectable port to the master port and a fourth pump control signal causing the pump actuator to actuate the fluid pump to move a wash media from a wash container into any one of the multiport valve, a holding volume, or a tube coupled to the multiport valve, or a cell culture vessel.

In some embodiments, the base unit includes a cell sensor and the method includes receiving an output from the cell sensor. A cell signal is produced indicating a dissociation of cells within the first cell culture container. The actuator module produces at least one of the third valve control signal or the third pump control signal in response to the cell signal. In some embodiments, the method includes producing an alignment signal to move the cell sensor into alignment with the first cell culture container.

In some embodiments, a computer-implemented method can control fluid movement within a cell culture assembly based on measured or calculated values of the amount of fluid within one or more containers. The cell culture assembly includes a disposable cell culture tray assembly coupled to a reusable base unit. The method includes producing, via an actuator module of an electronic control system of the cell culture assembly, a first valve control signal and a first pump control signal. The first valve control signal causes a valve actuator of the base unit to actuate a multiport valve to fluidically couple a first selectable port of the multiport valve to a master port of the multiport valve. The master port is fluidically coupled to a fluid pump. Each selectable port is fluidically coupled to one of a cell culture container, a second cell culture container, or a cell culture media container. The first pump control signal causes a pump actuator of the base unit to actuate the fluid pump to move a first volume of cell culture media from the cell culture media container to the first cell culture container. A volume of fluid within the first cell culture container is determined. The method includes producing, via the actuator module when the volume of fluid is below a threshold volume, a second valve control signal and a second pump control signal. The second valve control signal causes the valve actuator to actuate the valve or otherwise maintain the fluidic coupling of the first selectable port and the master port of the multiport valve. The second pump control signal causes the pump actuator of the base unit to actuate the fluid pump to move a second volume of cell culture media from the cell culture media container to the first cell culture container. The method includes producing via the actuator module when the volume of fluid is above the threshold volume, a third valve control signal and a third pump control signal. The third valve control signal causes the valve actuator to actuate the multiport valve to fluidically couple a second selectable port of the plurality of selectable ports to the master port of the multiport valve. The third pump control signal causes the pump actuator of the base unit to actuate the fluid pump to move a plurality of cells from the first cell culture container to the second cell culture container.

In some embodiments, a method includes removing a cell culture tray assembly from an outer protective wrap. The tray assembly includes a tray, a first lid, a second lid, and a multiport valve. The first lid is coupled to the tray and configured to be removably coupled to a first container. The first lid includes a first liquid exchange port and a first gas exchange port. The second lid is coupled to the tray and configured to be removably coupled to a second container. The second lid includes a second liquid exchange port and a second gas exchange port. The multiport valve is coupled to the tray and includes a master port and a plurality of selectable ports. A first selectable port of the plurality of selectable ports is aseptically coupled to the first liquid exchange port of the first lid, and a second selectable port of the plurality of selectable ports is aseptically coupled to the second liquid exchange port of the second lid. At least one cell is added to a first container through an opening of the first container. The first lid is secured to the first container to close the opening. The tray assembly is couple to a base unit. A valve actuator of the base unit is engaged with the multiport valve of the tray assembly after coupling the tray assembly or simultaneous with coupling the tray assembly to the base unit. A fluid pump is coupled to a pump actuator of the base unit.

In some embodiments, the method includes, after coupling the tray assembly and coupling a fluid pump, moving the base unit with the tray assembly coupled thereto to an incubation environment. In some embodiments, the method includes removing the multiport valve from the tray assembly and coupling the multiport valve to the base unit such that that the valve actuator of the base unit matingly engages the multiport valve. In some embodiments, removing the multiport valve is performed while the first selectable port of the multiport valve is aseptically coupled to the first lid and the second selectable port of the multiport valve is aseptically coupled to the second lid. In some embodiments, the removing, adding, and securing are done in an aseptic environment. In some embodiments, before securing the first lid to the first container, a volume of reagent and at least one cell are added to the first container. In some embodiments, after securing the first lid to the first container, the first container is coupled to a coupler of the tray assembly. In some embodiments, the method further includes coupling the fluid pump to a port of the multiport valve via tubing. In some embodiments, coupling the fluid pump to the multiport valve includes coupling a master port of the multiport valve to the fluid pump via the tubing.

The term "about" when used in connection with a referenced numeric indication means the referenced numeric indication plus or minus up to 10% of that referenced numeric indication. For example, "about 100" means from 90 to 110. The term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10% of the stated geometric construction, numerical value, and/or range.

As used herein, the term "reagent" includes any substance that is used in connection with any of the reactions described herein. For example, a reagent can include a buffer, an enzyme, a cell culture medium, a wash solution, or the like. A reagent can include a mixture of one or more constituents. A reagent can include such constituents regardless of their state of matter (e.g., solid, liquid or gas). Moreover, a reagent can include the multiple constituents that can be included in a substance in a mixed state, in an unmixed state and/or in a partially mixed state. A reagent can include both active constituents and inert constituents. Accordingly, as used herein, a reagent can include non-active and/or inert constituents such as, water, colorant or the like.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method)

FIG. 1A illustrates a schematic view of an automated cell culture system according to an embodiment. This example automated cell culture system 100 has three cell culture vessels 111, 113, and 115. These vessels may be laboratory flasks or dishes, for example. The cell culture vessels hold cell cultures, growth medium, and any other additives or reagents associated with cell culture. The cell cultures within the vessels maybe any kind of adherent or suspension cell cultures.

Fluid pumps 103 and 105 pump are one-port fluid pumps that contain an internal fluid reservoir. An example of a one-port fluid pump is a syringe mated to a syringe driver. A syringe fluid pump may draw fluid into its internal reservoir through creating suction in the reservoir by pulling out the syringe's plunger. Similarly, the syringe pump may push fluid out of the reservoir by pushing the plunger back in to the syringe. In other embodiments, one or both of fluid pumps 103, 105 may comprise a bi-directional in-line pump with a separate reservoir. The bi-directional pump may be, for example, a peristaltic pump or impeller-based fluid pump that is capable of pumping fluid in two directions along a fluid channel. A bi-directional in-line pump may be mated to a dedicated reservoir on one end and the other end used as an input and output port with behavior similar to the syringe pump. The dedicated reservoir mated to the pump may be flexible and sealed, e.g., a bag or pouch, such that air pockets do not form in the reservoir when fluid is pumped out of it.

Fluid pumps 103 and 105 are each respectively fluidly connected to multiport valves 107 and 109. Multiport valves 107 and 109 have one master port and a plurality of selectable ports. The multiport valves may selectively fluidly connect the master port to one of the selectable ports at a time. If the master port of a multiport valve is connected to a selected port, other selectable ports are sealed off and not fluidly connected to the master port. When a master port of a multiport valve is fluidly connected to a selectable port, fluid may flow in either direction through the valve. That is, fluid may flow into the multiport valve through the master port and out through the selected port, or fluid may flow in the opposite direction, flowing into the multiport valve through the selected port and out through the master port. In some embodiments, the multiport valve may be a mechanical valve apparatus, and in other embodiments the multiport valve may be comprised of microfluidic chip components.

Fluid pumps 103 and 105, multiport valves 107 and 109, and cell culture vessels 111, 113, and 115 are all fluidly interconnected by fluid channels. In an embodiment, the fluid channels are comprised of flexible tubing. In other embodiments, some or all of the fluid channels may be rigid tubing, or channels in a substrate. In the illustrated example in FIG. 1A, fluid pump 103 is fluidly connected to the master port of multiport valve 107 by flexible tubing. Multiport port 107 has several selectable ports, 107*a-d*. Selectable port 107*a* is fluidly connected to cell culture vessel 111, selectable port 107*b* is fluidly connected to cell culture vessel 113, and selectable port 107*c* is fluidly connected to cell culture vessel 115. Selectable port 107*d* is fluidly connected to container 119. Container 119 may be any kind of fluid container for either supply fluid to the automated cell culture system or receiving fluid from the automated cell culture system. For example, container 119 may be a waste container for receiving waste product from the automated cell culture system. In another example, container 119 may contain fresh cell culture media to supply cell culture vessels with fresh media.

Fluid pump 105, multiport valve 109, and container 117 are configured similar to fluid pump 103, multiport valve 107, and container 119. Multiport port 109 has several selectable ports, 109*a-d*. Selectable port 109*a* is fluidly connected to cell culture vessel 111, selectable port 109*b* is fluidly connected to cell culture vessel 113, and selectable port 109*c* is fluidly connected to cell culture vessel 115. Selectable port 109*d* is fluidly connected to container 117.

In operation, the combination of fluid pumps, multiport valves, containers, and cell culture vessels in the example illustrated in FIG. 1A may be used to transfer liquids to and from the cell culture vessels and the containers. In some embodiments, a first fluid pump 103 is used for adding media to cell culture vessels from container 119 and a second fluid pump 105 is used for removing media from cell culture vessels to container 117. In another embodiment, a single fluid pump is used for both adding and removing from cell culture vessels and containers. In some embodiments, the components of group 101 including cell culture vessels 111, 113, 115 and multiport valves 107 and 109 may be separable from fluid pumps 103 and 105 and containers 117 and 119. The fluid connections between components in group 101 may be established independently in a first stage of assembly, and then the additional components connected at a later stage. The components of group 101 may be independently sterilized or processed in the first stage, and then introduced to the remainder of components in the second stage. The fluid connections between components of group 101 and other components may be made with aseptic connections so that contaminants are not introduced to the sterilized components of group 101. Cell culture vessels 111, 113, 115 may be connected to the valves 107 and 109 using tubing and aseptic connections, such that the vessels can be aseptically disconnected from the system when the cells in the vessels are to be removed for usage or analysis.

Figure 1B:
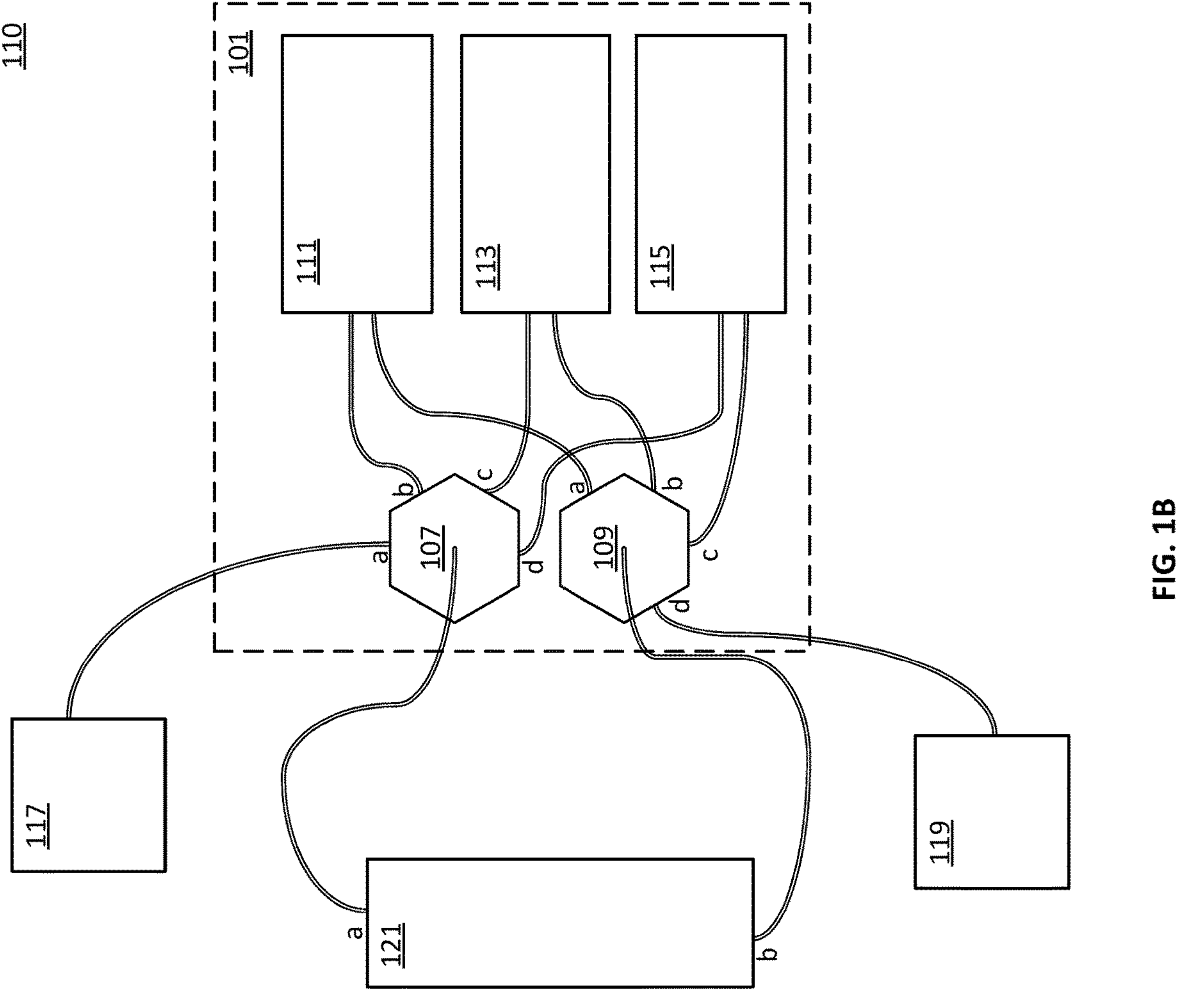
FIG. 1B illustrates a schematic view of an automated cell culture system according to an embodiment.

FIG. 1B illustrates a schematic view of an automated cell culture system according to an embodiment. Automated cell culture system 110 includes one bi-directional fluid pump 121. In this embodiment, cell culture vessels 111, 113, 115, multiport valves 107 and 109, and containers 117 and 119 are the same as described in connection with FIG. 1A. In FIG. 1B, fluid pump 121 is a two-port fluid pump such as a peristaltic pump. A first port 121*a* of two-port fluid pump 121 is fluidly connected to the master port of multiport valve

107, and a second port 121*b* of fluid pump 121 is fluidly connected to the master port of multiport valve 109. The fluid pump 121 is capable of pumping fluid in two directions. In a first mode of operation, fluid pump 121 pumps fluid from port 121*a* to port 121*b*, and in a second mode of operation fluid pump 121 pumps fluid from port 121*b* to port 121*a*.

Figure 2:
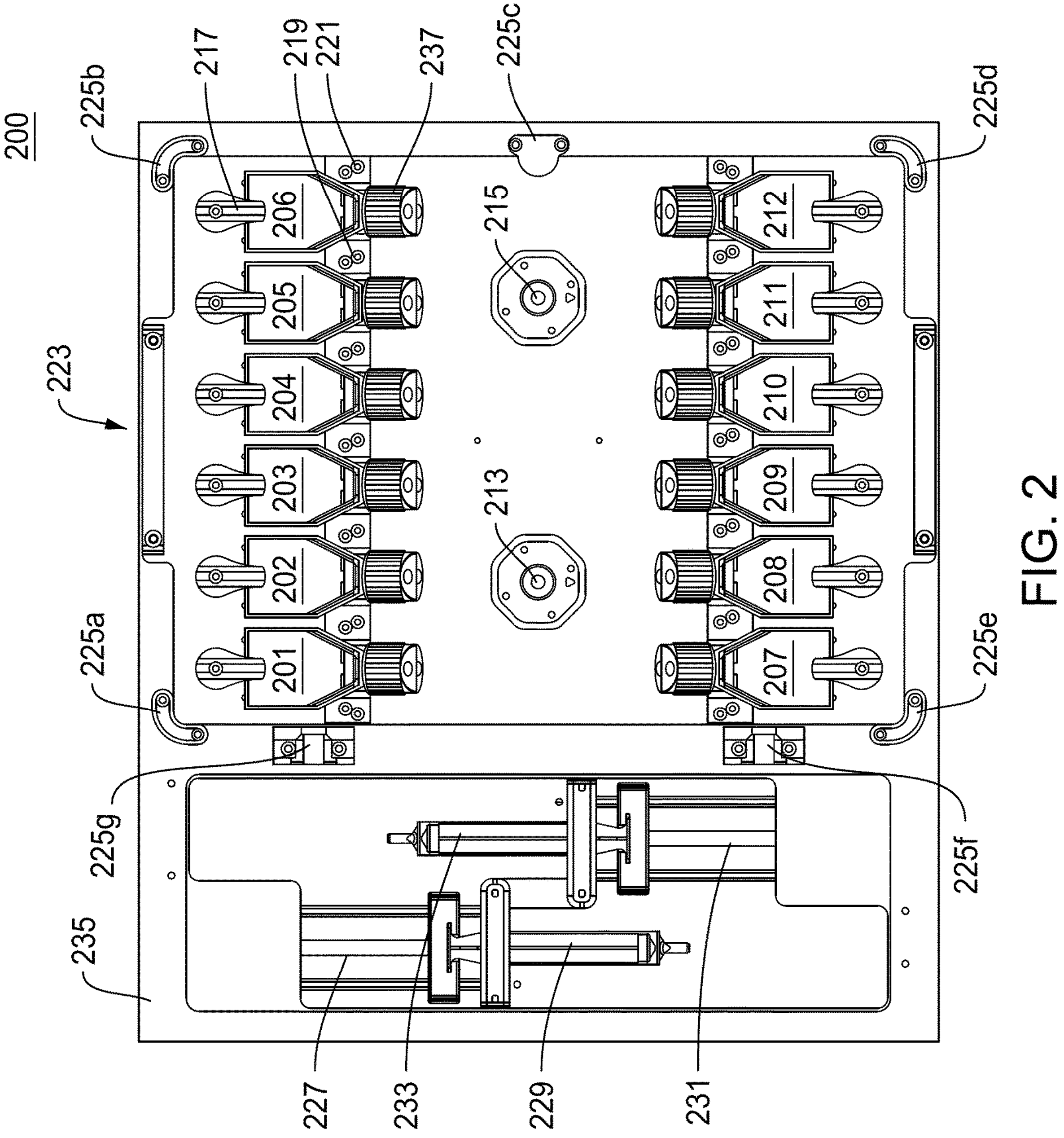
FIG. 2 illustrates a top view of an automated cell culture system according to an embodiment.

FIG. 2 illustrates a top view of an automated cell culture system according to an embodiment. Automated cell culture system 200 has two fluid pumps, two multiport valves, and 12 cell culture vessels. No fluid connections are included in the illustrated example for clarity, however it is to be understood that at least some of the various components of an automated cell culture system would be fluidly connected when in use. Removable tray 223 contains cell culture vessels 201-212 and multiport valves 213 and 215. Each cell culture vessel is capped by an aseptic lid such as aseptic lid 237 which caps cell culture vessel 206. Each cell culture vessel is removably affixed to removable tray 223 by brackets such as brackets 217, 219, and 221 which hold cell culture vessel 206. Removable tray 223 is removably inserted into base housing 235, and guided in by way of guides 225*a*-*f*. Base housing 235 contains two syringe-style fluid pumps. A first fluid pump is comprised of syringe 229 and syringe actuator 227. Syringe actuator 227 pushes and pulls on the plunger of syringe 229, effecting fluid flow into and out of the syringe. In an embodiment, syringe actuator is a linear actuator, however any other method of pushing and pulling a syringe plunger may be used. A second pump is comprised of syringe 233 and syringe actuator 231.

Figure 3A:
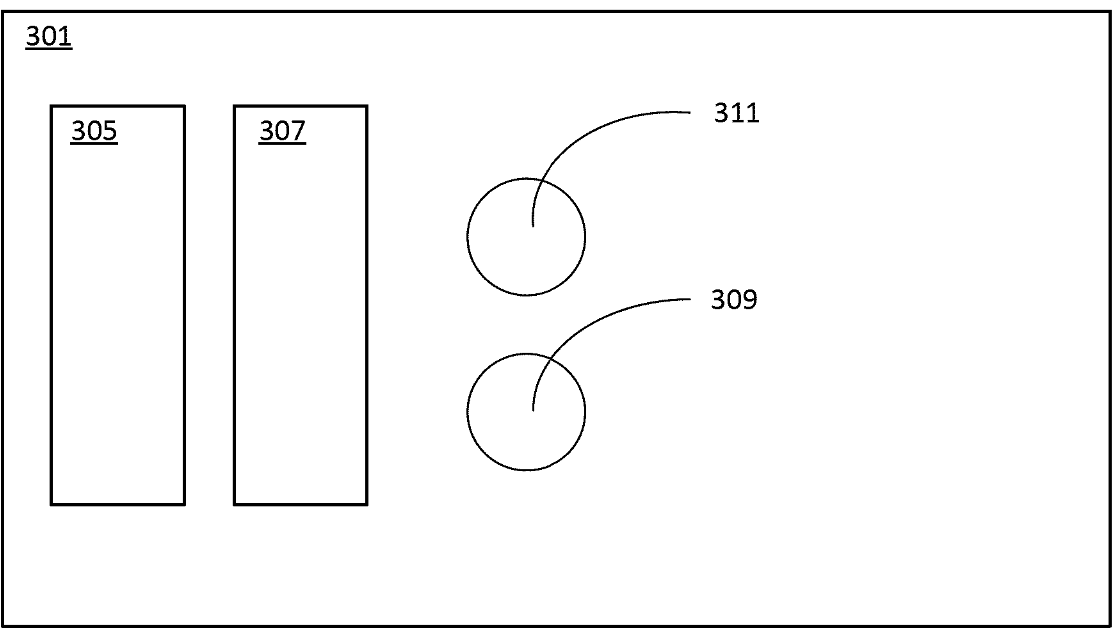
FIG. 3A illustrates a top-down view of a base housing of an automated cell culture system according to an embodiment.

FIG. 3A illustrates a top-down view of a base housing of an automated cell culture system according to an embodiment. The illustrated example base housing 301 contains fluid pumps 305 and 307 and multiport valve actuators 309 and 311. Base housing 301 also includes a controller which controls actuation of fluid pumps, multiport valves, and any other systems such as automated cell counter systems, hemocytometers, imaging systems, microscopes, or other measurement or analysis systems to facilitate automated cell growth. The controller may include one or more processors configured to execute instructions contained on one or more memory systems to control the automated cell culture system and other corresponding systems. In addition, the controller may include one or more network interfaces through which various notifications or data transfers may be sent or received.

Figure 3B:
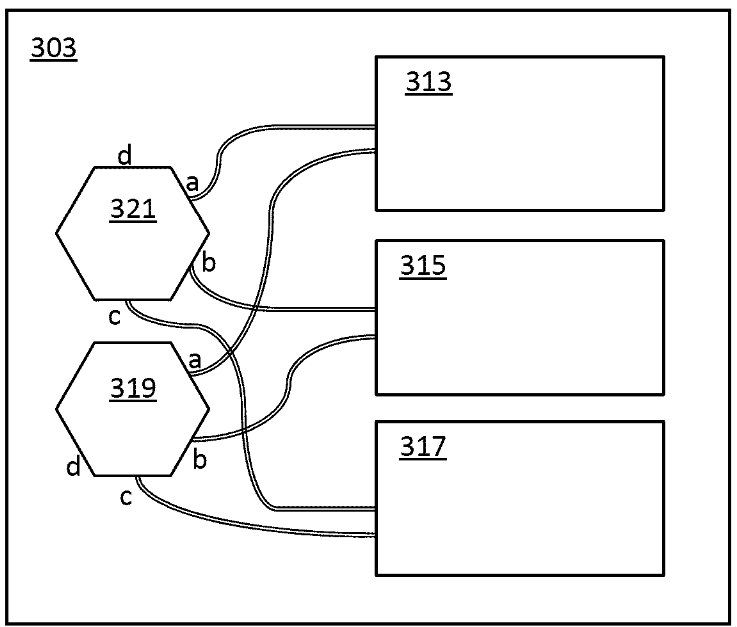
FIG. 3B illustrates a removable tray assembly of an automated cell culture system according to an embodiment.

FIG. 3B illustrates a removable tray assembly of an automated cell culture system according to an embodiment. Removable tray assembly 303 is configured to mate to base housing 301. When removable tray assembly 303 is placed on top of base housing 301, multiport valve actuators 309 and 311 mechanically couple with multiport valves 319 and 321, respectively. For example, in an embodiment, multiport valve actuator 309 rotates an internal member of multiport valve 319 to align a master port of multiport valve 319 with one of the selectable ports 319*a*-*d*. Multiport valves 319 and 321 and cell culture vessels 313, 315, and 317 are carried on removable tray 303. When base housing 301 and removable tray 303 are combined, fluid pumps 305 and 307 may be fluidly connected to the master ports of multiport valves 319 and 321.

In some embodiments, base housing 301 may also include an agitator configured to agitate the removable tray assembly 303 in relation to the base housing. This agitator may agitate the tray in a rocking motion, vibrating motion, circular swirling motion, or other motions useful in cell culturing. In some embodiments, individual cell culture vessels may be independently agitated by independent agitators displaced between the cell culture vessel and the removable tray. Independent agitators may be used in applications where it would be disadvantageous to agitate all cell culture vessels of a tray when only a subset of cell culture vessels require agitation. In some embodiments, independent agitators may be integrated into a bracket or brackets used to affix cell culture vessels to the removable tray. In some embodiments, agitators may have active components disposed within the base housing that mechanically mate to passive components on the removable tray, similar to how multiport valves on the removable tray may mechanically couple to actuators in the base housing.

In use, removable tray 303 may be configured with any number or configuration of multiport valves, cell culture vessels, and fluid tubing as required separate from base housing 301. The removable tray 303 and its associated components may then be sealed and sterilized before being introduced to base housing 301. In some embodiments, the cell culture vessels may be added to the tray 303 in a sterile environment after sterilization of the tray 303. The base housing 301 may remain stationary, and any electromechanically components such as valve actuators and pump mechanisms disposed within the base housing need not be subject to transport or sterilization procedures as the components of the base housing are not in fluid contact with the sterile system on the removable tray 303. If a syringe-style fluid pump is used, a sterile syringe may be placed in the syringe actuator for use, such that the syringe actuator is not in contact with any fluids in the sterile system. Similarly, a peristaltic pump may use a sterile portion of tubing such that the stationary components associated with the base housing do not come in fluid contact with the sterile system.

Figure 4:
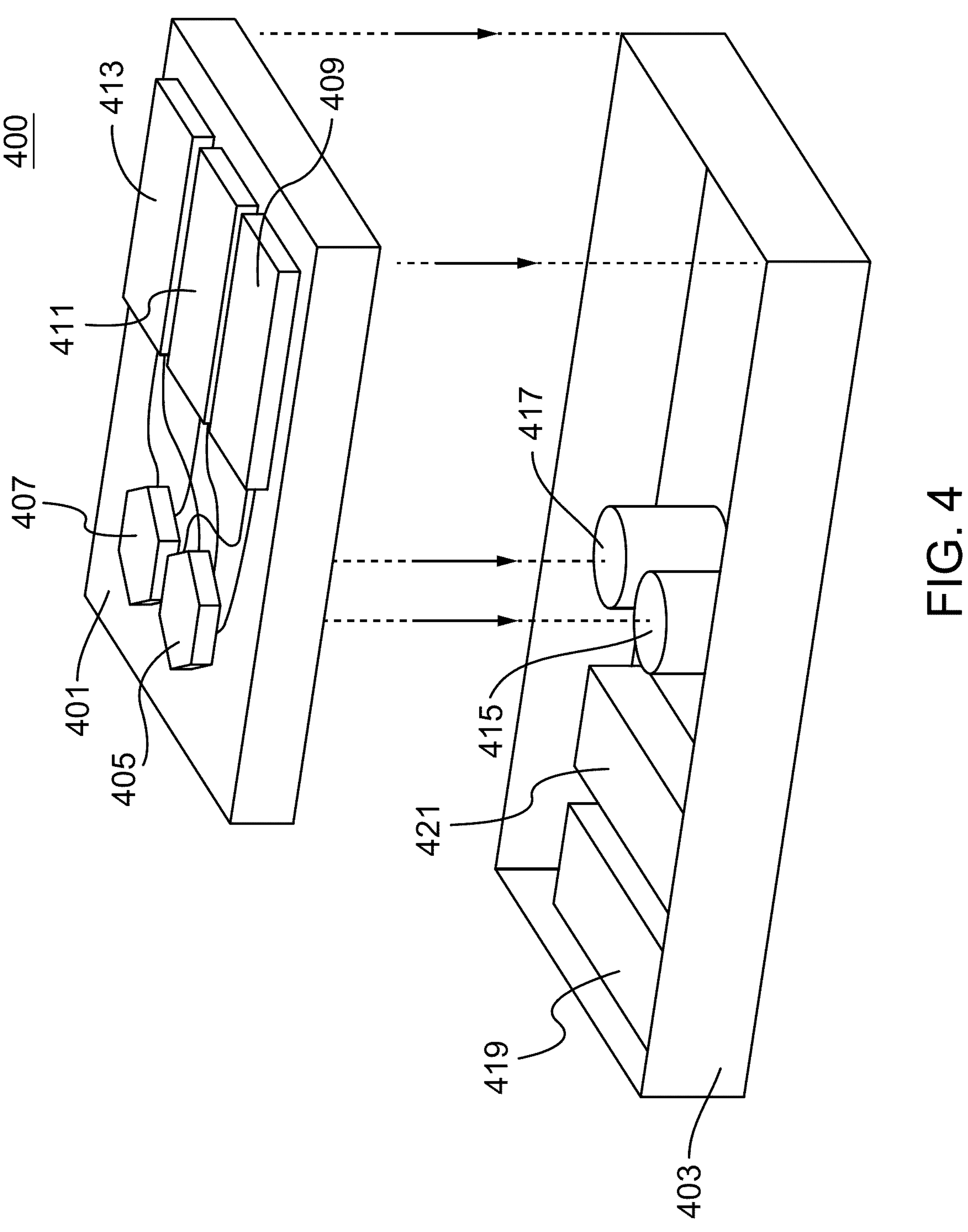
FIG. 4 illustrates an example removable tray of an automated cell culture system being mated to an example base housing according to an embodiment.

FIG. 4 illustrates an example removable tray of an automated cell culture system being mated to an example base housing according to an embodiment. As illustrated in this example, automated cell culture system 400 includes removable tray 401 and base housing 403. Removable tray 401 contains multiport valves 405 and 407 and cell culture vessels 409, 411, and 413. Removable tray 401 is lowered down onto base housing 403 where multiport valve actuators 415 and 417 align with multiport valves 405 and 407, respectively. Once removable tray 401 is lowered down onto base housing 403, multiport valve actuators 415 and 417 mechanically couple with multiport valves 405 and 407. After the two parts are joined, fluid pumps 419 and 421 are fluidly connected, such as by a manual connection step, to multiport valves 405 and 407 on-board the removable tray.

Figure 5:
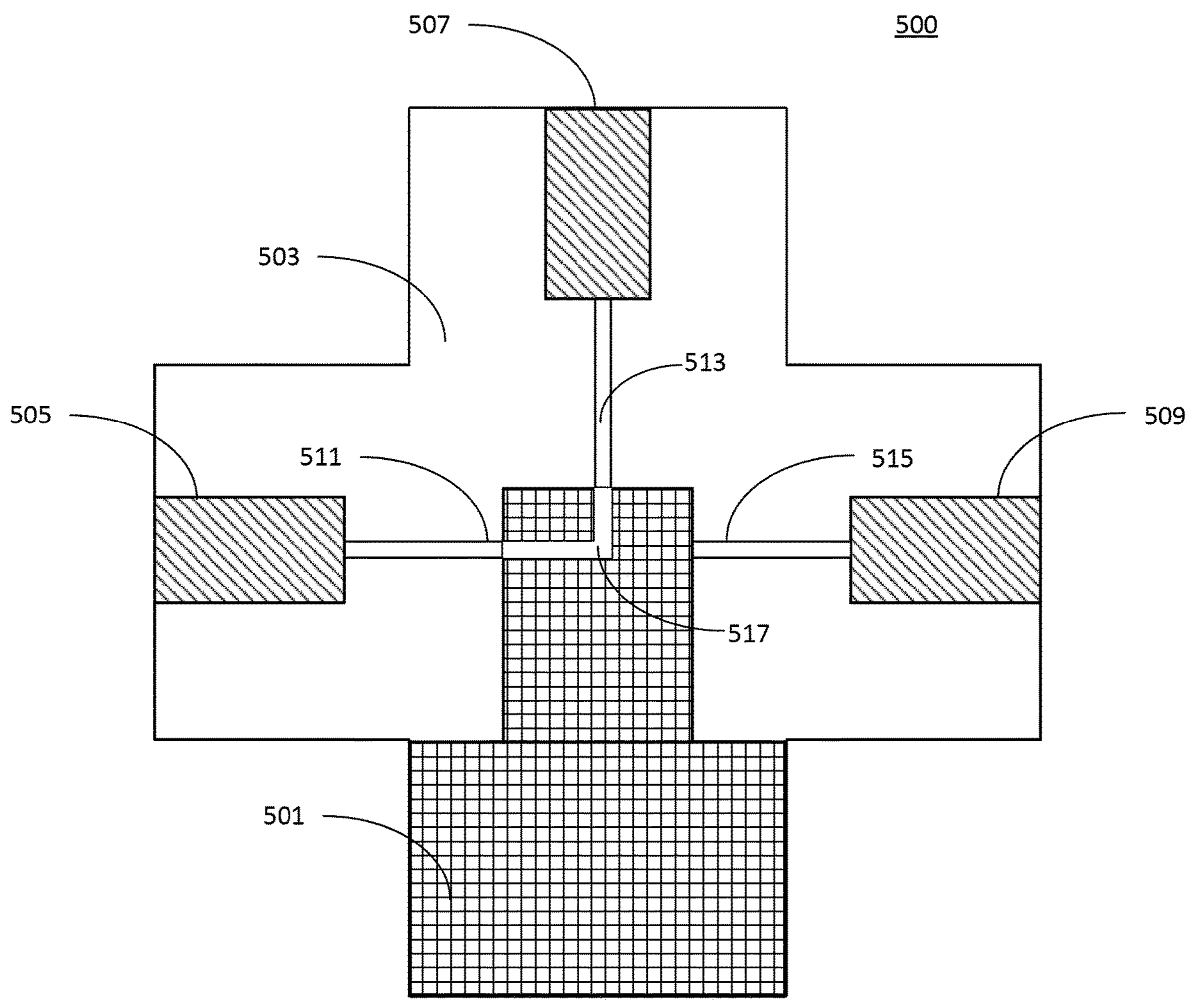
FIG. 5 illustrates a cross-sectional view of an example multiport valve according to an embodiment.

FIG. 5 illustrates a cross-sectional view of an example multiport valve according to an embodiment. In this embodiment, a multiport valve 500 comprises a valve body 503 having master port 507 on a top side and a plurality of selectable ports 505 and 509 dispersed around its circumference. Two selectable ports are illustrated in this cross-sectional view; however, it is to be understood that various embodiments of multiport valves may include any number of selectable ports.

Valve body 503 has a cylindrical cavity on its underside to which rotatable cylindrical valve rotor 501 is inserted. Within rotatable cylindrical valve rotor 501 is a fluid channel 517 which fluidly connected an axial master port of rotatable cylindrical valve rotor 501 to a radial master port of rotatable cylindrical valve rotor 501. Within valve body 503 is a fluid channel 513 which fluidly connects master port 507 to fluid channel 517 of rotatable cylindrical valve rotor 501. The connection between fluid channel 513 and fluid channel 517 remains constant as rotatable cylindrical valve rotor 501 rotates because both fluid channels are centered on the axis of rotation of rotatable cylindrical valve rotor 501 within the cylindrical cavity of valve body 503.

In the state illustrated in FIG. 5, rotatable cylindrical valve rotor 501 is rotated such that fluid channel 511 is aligned with fluid channel 517. Thus, a fluid circuit is established from master port 507 to selectable port 505 through fluid channel 513, fluid channel 517, and fluid channel 511. In this illustrated state, fluid channel 515 and, in turn, selectable port 509, is sealed off by the presence of a solid portion of rotatable cylindrical valve rotor 501. In operation, rotatable cylindrical valve rotor 501 may rotate to establish a fluid pathway from master port 507 to selectable port 509 while sealing off selectable port 505 and fluid channel 511.

Multiport valve 500 may be made of any appropriate material, and valve body 503 and valve rotor 501 may be made of the same or different materials. Examples of materials that may be used include plastics, TFE-based materials such as polytetrafluoroethylene PTFE, metals, rubbers, or similar materials. In some embodiments, the valve body 503 and valve rotor 501 may be machined to fit with very close tolerances so that a fluid-tight seal is created between the two components. In some embodiments, additional gaskets, bearings, seals, and/or flanges may be incorporated into multiport valve 500 to provide for a fluid-tight connection between valve body 503 and valve rotor 501.

Figure 6A:
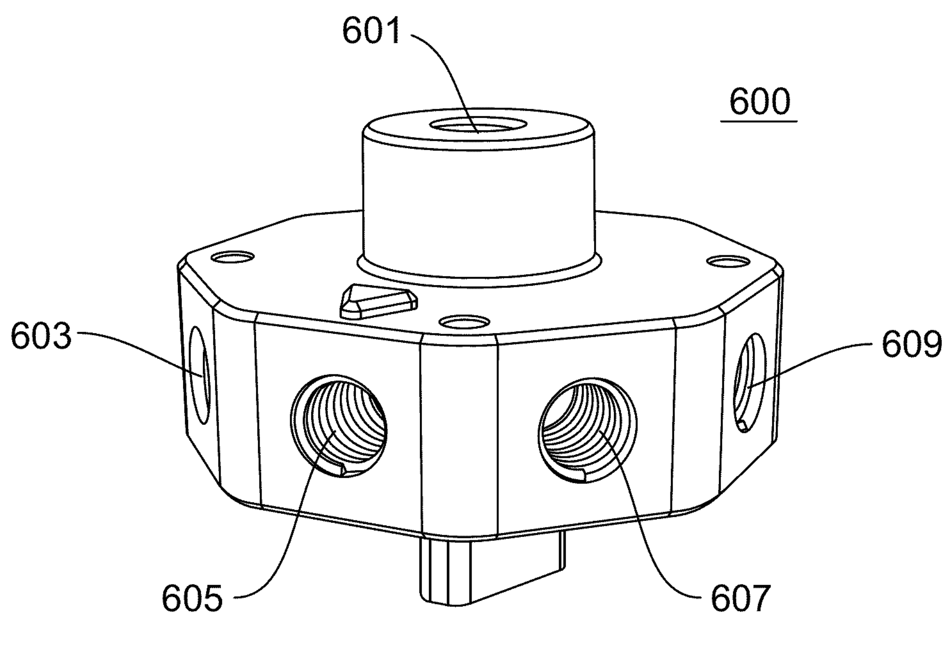
FIG. 6A illustrates an example multiport valve according to an embodiment.
Figure 6B:
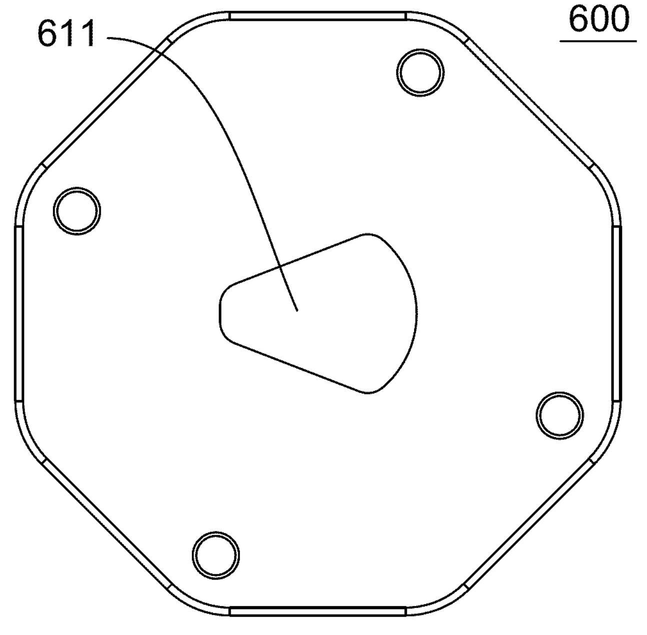
FIG. 6B illustrates a bottom view of an example multiport valve.

FIG. 6A illustrates an example an example multiport valve according to an embodiment. In this example, multiport valve 600 has an axial port 601 and eight selectable ports, of which four (ports 603, 605, 607, and 609) are viewable in the perspective view of FIG. 6A. FIG. 6B illustrates a bottom view of multiport valve 600 showing a mechanical coupler 611 which is configured to mechanically couple to a multiport valve actuator. A corresponding multiport valve actuator has a cavity shaped to accept mechanical coupler 611 and transfer rotational mechanical energy to the multiport valve 600.

Figure 7:
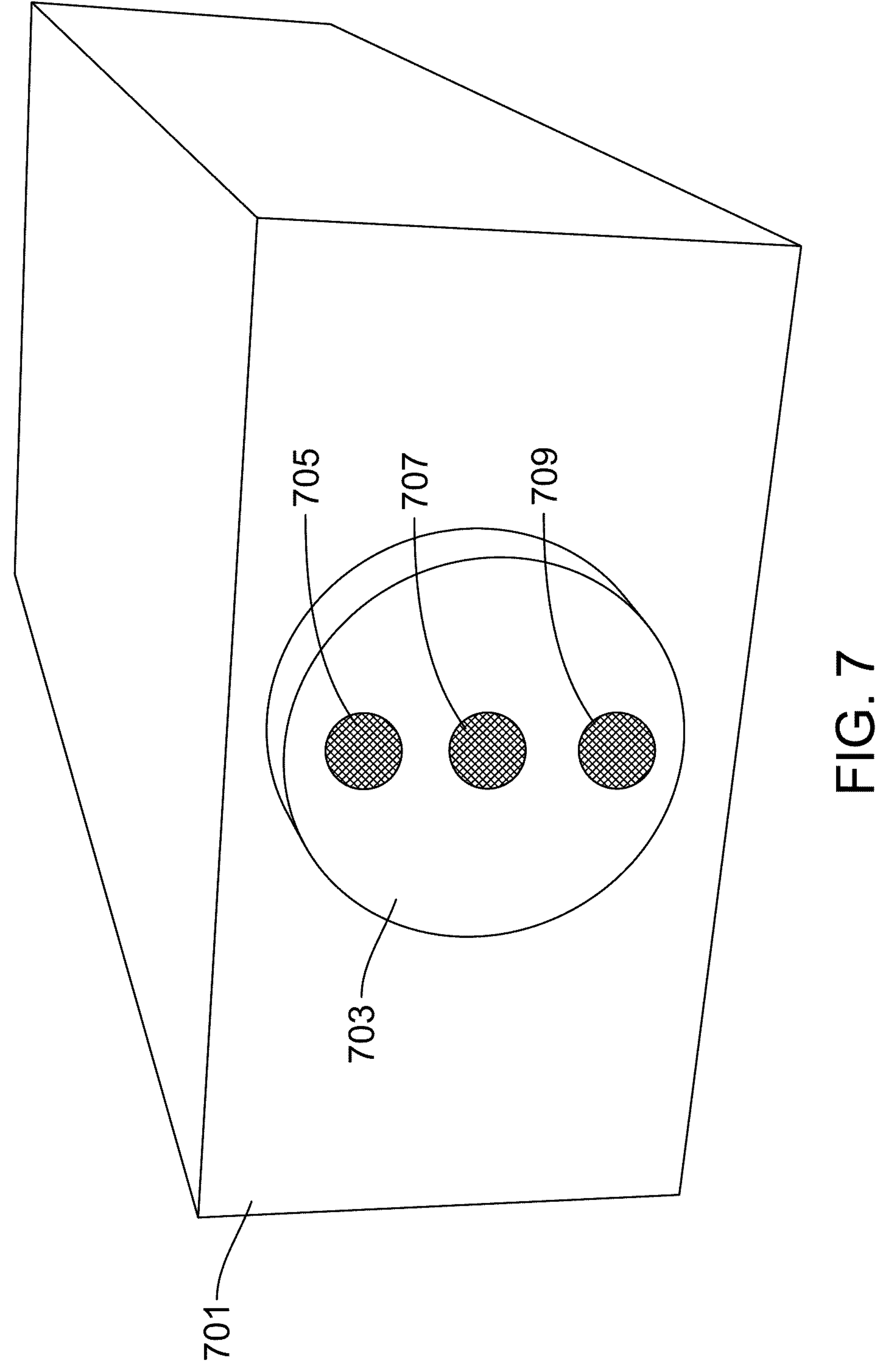
FIG. 7 illustrates a cell culture vessel lid according to an embodiment.

FIG. 7 illustrates an aseptic cell culture vessel lid according to an embodiment. In this example embodiment, cell culture vessel lid 703 is affixed to cell culture vessel 701. In this example embodiment, cell culture vessel lid 703 has three ports 705, 707, and 709. In this example, the three ports are vertically aligned. If the cell culture vessel 701 is filled with liquid such as cell growth media, tubing entered via the lowest port 709 may be submerged in the liquid such that the liquid may be siphoned out via port 709 using the tubing. Tubing entering via the middle port, port 707, may be placed so that the tubing is not in liquid contact with the contents of the cell culture vessel, so that additional liquid may be added to the cell growth vessel without contaminating the fluid path to port 707. Port 705 may be configured to allow gas exchange in and out of the cell growth vessel 701. In some embodiments, port 705 includes a filter for filtering gas on the way into the flask to sterilize the gas. In some applications, the automated cell culture system may be placed in an incubation chamber to regulate the environment in proximity to the cell culture vessel. The incubation chamber may be integrated with the automated cell culture system base housing in some embodiments. In one embodiment, characteristics of the environment to be regulated include gas mix, temperature, and humidity levels. In one embodiment, the incubation chamber modulates gas mix, temperature and humidity levels depending on the cell line to be grown. In some embodiments, port 705 may be attached to an environmental regulation device that manages the temperature, humidity, oxygenation, gas mix, and other such parameters of the gaseous environment within the cell culture vessel. Aseptic lids may be created to fit any cell culture vessel, such that any culture vessel used for manual cell culture can be integrated with the system.

Figure 8:
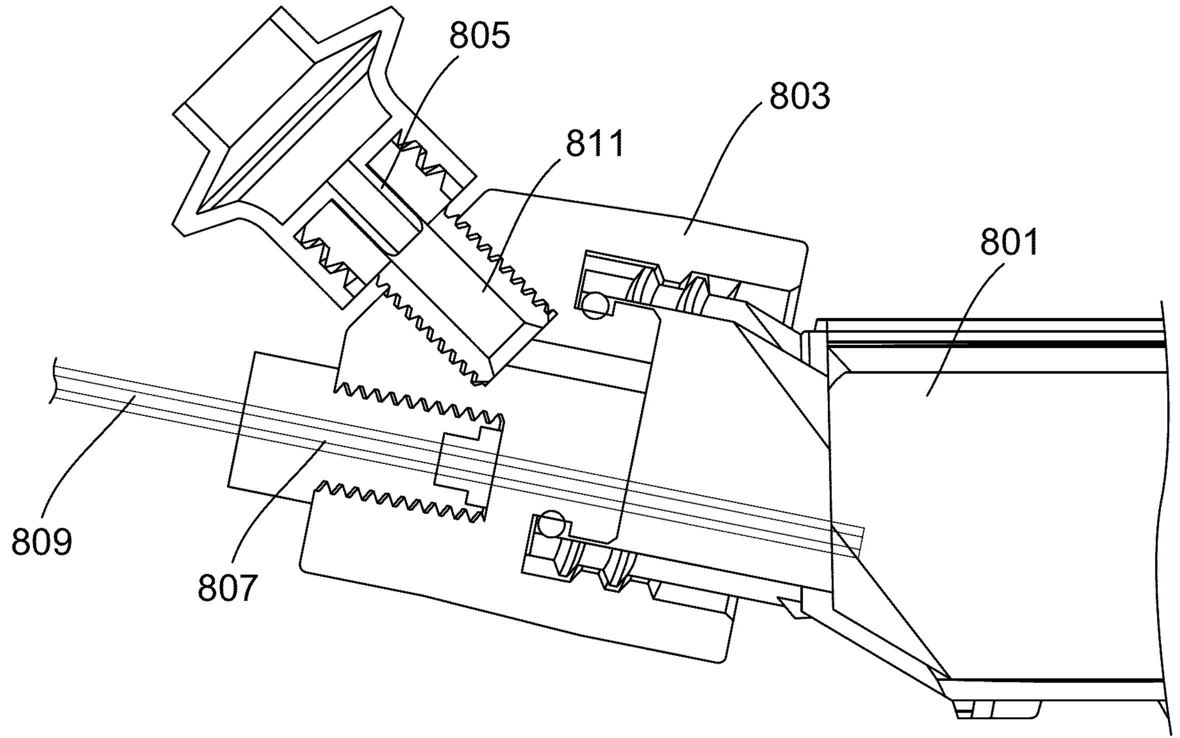
FIG. 8 illustrates a cross-sectional view of a cell culture vessel lid according to an embodiment.

FIG. 8 illustrates a cross-sectional view of a cell culture vessel lid according to an embodiment. Cell culture vessel lid 803 is screwed onto the mouth of cell culture vessel 801 such that the threads of cell culture vessel lid 803 engage with the threads of the mouth of cell culture vessel 801. In this example embodiment, cell culture lid 803 has a liquid port 807 and a gas port 811. A liquid channel 809 is threadedly engaged with liquid port 807. A gas filter 805 is threadedly engaged with gas port 811. Gas filter 805 may allow gas exchange in and out of the cell culture vessel while blocking any microbes or pathogens from entering the cell culture vessel from the outside. In an embodiment, gas filter 805 is a 0.22 micron filter.

Figure 9:
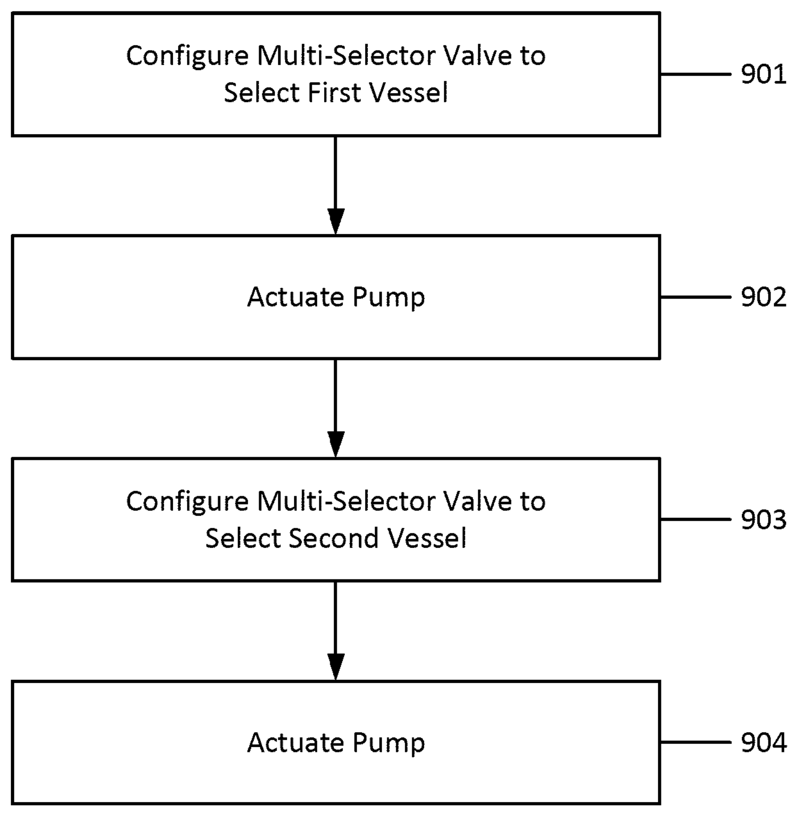
FIG. 9 illustrates the steps of a method for transferring liquid from a first vessel to a second vessel using an automated cell culture system with a single-port pump according to an embodiment.

FIG. 9 illustrates the steps of a method for transferring liquid from a first vessel to a second vessel using an automated cell culture system with a single-port pump according to an embodiment. In this example, an automated cell culture system has a single-port pump such as a syringe-type pump as discussed above, or a two-port pump with a holding vessel attached to one port. This method may be used to transfer liquid from any vessel to another vessel. For example, the first vessel may be a cell culture vessel, and the second vessel may be a waste container. In another example, the first vessel may be a container of fresh cell growth media and the second container may be a cell culture vessel.

In FIG. 9, at step 901, a multiport valve with a master port either connected to a single-port pump or connected to a two-port pump with a holding vessel, is configured to select a selectable port in fluid communication with a first vessel. At step 902, the single-port pump is actuated so that fluid is drawn out of the first vessel and into the reservoir of the single-port pump, or similarly the two-port pump is actuated so that fluid is drawn into the holding vessel. Next, at step 903, the multiport valve is configured to select a selectable port in fluid communication with a second vessel. Then, at step 904, the fluid is pumped out of the reservoir of the single-port pump, or similarly pumped out of the holding vessel by the two-port pump, through the configured multiport valve, and into the second vessel.

Figure 10:
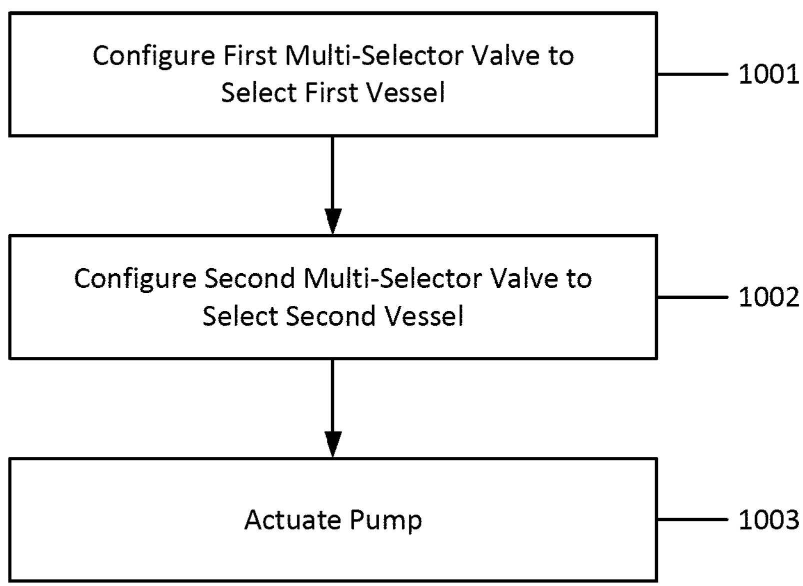
FIG. 10 illustrates the steps of a method for transferring liquid from a first vessel to a second vessel using an automated cell culture system with a two-port pump according to an embodiment.

Some embodiments of an automated cell culture system may use two-port pumps with a multiport valve fluidly connected to each port. A two-port pump may be unidirectional or bidirectional. The two-port pump does not need to transfer liquid into a holding reservoir like a single-port pump but may pump directly from one vessel to another. FIG. 10 illustrates the steps of a method for transferring liquid from a first vessel to a second vessel using an automated cell culture system with a two-port pump according to an embodiment. In this example, a first port of the two-port pump is fluidly connected to the master port of a first multiport valve, and the second port of the two-port pump is fluidly connected to the master port of a second multiport valve. At step 1001, the first multiport valve is configured to select a selectable port in fluid communication with a first vessel. At step 1002, the second multiport valve is configured to select a selectable port in fluid communication with a second vessel. Finally, at step 1003, the two-port pump as actuated to pump in the direction of the first port to the second port, such that liquid from the first vessel is pumped into the second vessel.

For any embodiments disclosed herein, a simple reference to pumping from a first vessel to a second vessel may refer in the alternative to the appropriate method depending on whether an automated cell culturing system is configured with a one-port pump or a two-port pump. Some embodiments of an automated cell culture system may also combine two-port and single port pumps in one system, such that one step of pumping may use one type of pump and another step of pumping may use a different type of pump.

In some embodiments, media from different sources may be fed to the cells, depending on an observed condition of the cells, for example if signs of differentiation are observed for stem cells. In an embodiment, a first step of a method is observing a condition of the cells, such as signs of differentiation in stem cells. The first step may be performed by a microscope, camera, or other measurement device. A second step of the method is selecting an appropriate source of media based on the condition of the cells. A third step of the method is actuating the one-port pump or two-port pump system to transfer media from the selected source of media to a vessel containing the cells.

In some embodiments, an automated cell culture system includes a microscope that may be moved to image the contents of any cell culture vessel of the automated cell culture system. In some examples, the microscope may be mounted on a mechanical system that is capable of moving the microscope to the cell culture vessels such as a 2-dimensional or 3-dimensional gantry mechanism or a hinged robotic arm mechanism. In some embodiments, the microscope may remain stationary while the automated cell culture system is moved to position individual cell culture vessels in view of the stationary microscope. In some embodiments, the microscope and moving assembly may be contained within the base housing of an automated cell culture system, such that the cell culture vessels may be imaged from their bottom side. In such embodiments, the removable tray holding the cell culture vessels may have transparent windows or cutouts underneath the cell culture vessels to allow a microscope to image the cells contained therein. In some embodiments, an adjustable and controllable light source is placed on the opposite side of the cell culture vessel as the microscope to provide a light source for the microscope. For example, a light source may be mounted on mechanical system that is capable of moving the light source to any cell culture vessel as necessary, similar to the microscope. In some embodiments, a stationary light source may be placed on one side of the automated cell culture system such that each cell culture vessel is sufficiently illuminated.

The automated cell culture system may include other imaging devices as well. For example, the automated cell culture system may include one or more cameras or pairs of LEDs and light sensors to image the contents of cell culture vessels. This type of imager may be useful to measure and monitor macro-level visual properties of the cell culture vessels. For example, a color camera, or pairs of LEDs and light sensors, may be useful for monitoring the color of the contents of a cell culture vessel containing a color-based pH indicator such as phenol red from which the pH of the contents of the cell culture vessel may be determined. In an embodiment, each cell culture vessel bracket may include a camera to image the contents of a cell culture vessel. In another embodiment, a single camera may be mechanically movable to each cell culture vessel, in the same or a similar way as a microscope may be moved, to image each cell culture vessel. In an embodiment, an LED and light sensor may be mechanically movable to each cell culture vessel, in the same or a similar way as a microscope may be moved, to monitor the color of a cell culture vessel.

In some example implementations, one or more off-tray devices may be interfaced with the automated cell culture system. For example, an automated cell counter machine may be fluidly connected to a selectable port of a multiport valve such that samples of the contents of cell culture vessels may be transported to the automated cell counter machine. In some embodiments, the automated cell counter machine may be controlled by the controller such that the entire process of counting cells with the automated cell counter machine is automated by the automated cell culture system. By way of further example, a cell counting chamber may be fluidly connected to a selectable port of a multiport valve such that samples of the contents of cell culture vessels may be transported to the cell counting chamber. A microscope may image the cell counting chamber to count the cells in the cell counting chamber. By way of further example, an external chamber may be fluidly connected to a selectable port of a multiport valve such that samples of the contents of cell culture vessels may be transported to the external chamber. An LED and light sensor may be used to measure the cloudiness of solution in the external chamber. By way of further example, in order to take a sample of cells, a sampling vessel may be aseptically connected to a port on a multiport valve such that samples of the contents of cell culture vessels may be transported to the vessel, and then the vessel can be aseptically disconnected and the cells taken away.

Various support methods or procedures may be necessary for some operations of an automated cell culture system. For example, a fluid line or pump may need to be primed prior to pumping a liquid through the line. As an example, the fluid line from a bottle of new growth media to a multiport valve may need to be primed prior to pumping new growth media to cell culture vessels. To do this, a small amount of new growth media may be pumped from the new growth media bottle to a waste bottle to ensure that the line is free of air pockets.

Similarly, a line, pump, or valve may need to be cleaned or flushed periodically to remove contaminants. This may be accomplished by pumping a wash fluid through the line, pump, or valve for a period of time or until the line, pump, or valve is sufficiently flushed.

Figure 11:
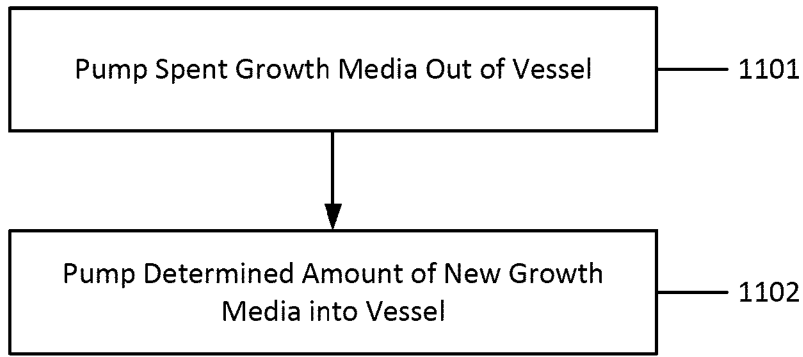
FIG. 11 illustrates the steps of a method for replacing cell culture media during adherent cell line maintenance.

FIG. 11 illustrates the steps of a method for adherent cell line maintenance. At step 1101, the spent cell culture growth media in a vessel is pumped out of the vessel and into a waste container. At step 1102, a determined amount of new cell culture growth media is pumped into the vessel.

Figure 12A:
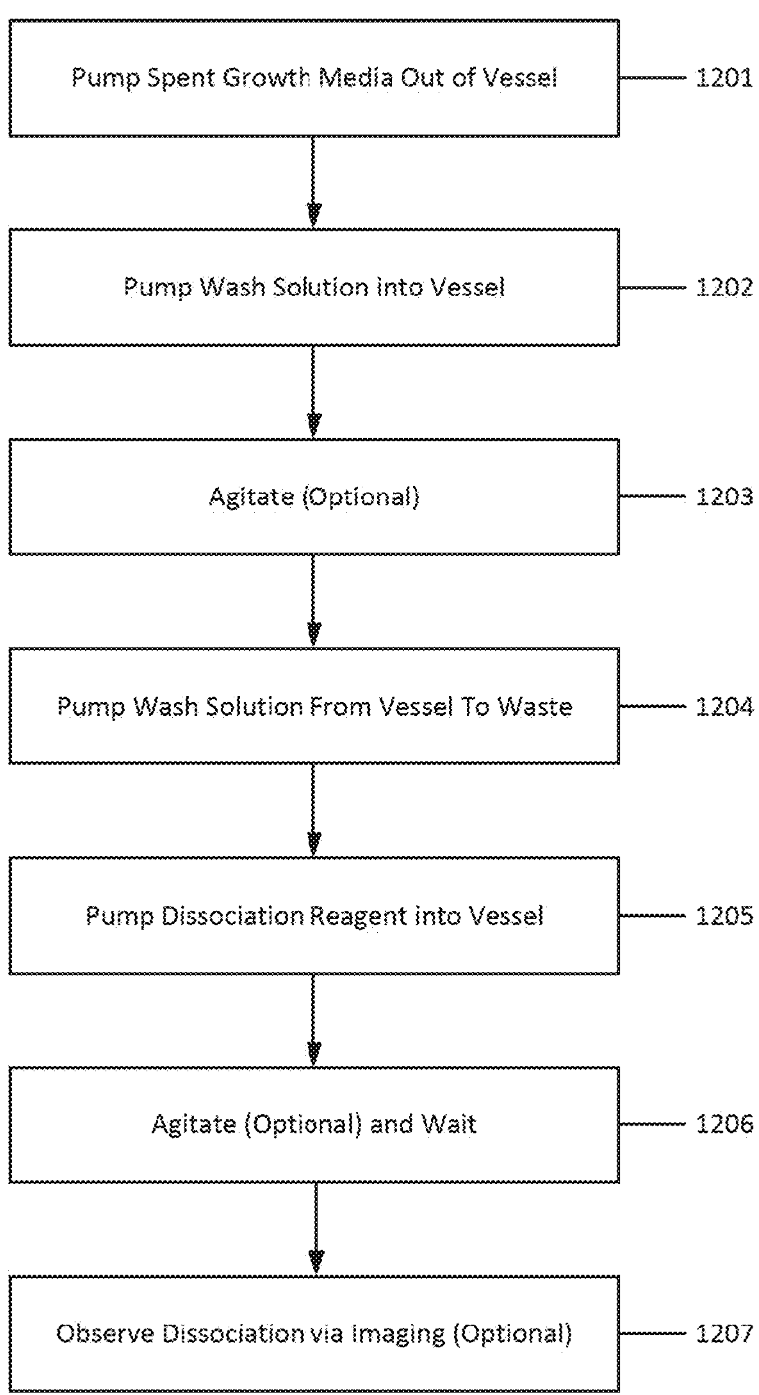
FIGS. 12A and 12B illustrate the steps of a method for adherent cell line maintenance or expansion with passaging to a new cell culture vessel.
Figure 12B:
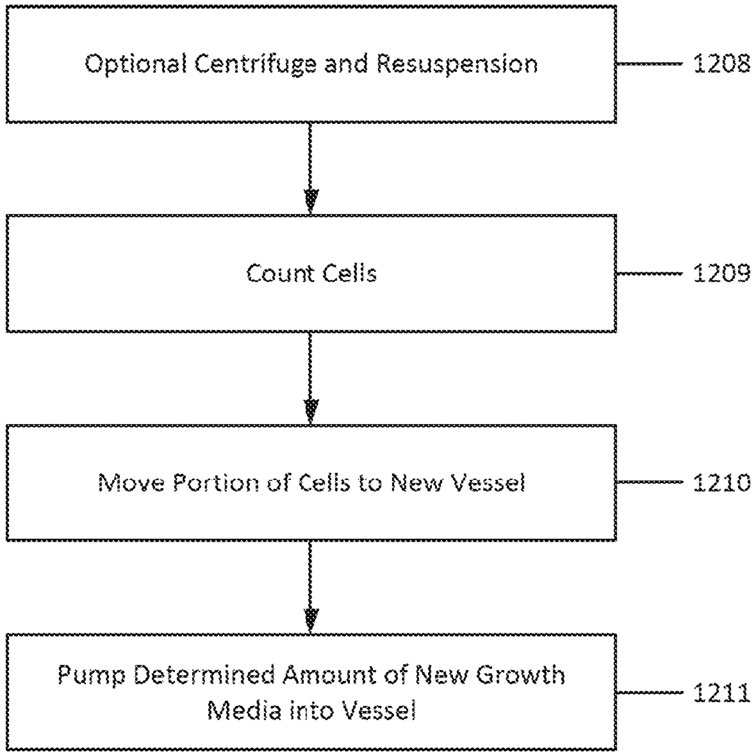

FIGS. 12A and 12B illustrate the steps of a method for adherent cell line maintenance or expansion with passaging to a new cell culture vessel. In contrast to the method discussed in connection with FIG. 11, here the adherent cells of a cell culture vessel are transferred to a new vessel. At step 1201, the cell culture growth media in a vessel is pumped out of the vessel and into a waste container. Then, at step 1202, a wash solution is pumped into the vessel and at step 1203 the vessel may optionally be agitated. Next, the wash solution is pumped out of the vessel and into a waste container in step 1204.

At step 1205, a dissociation reagent is pumped into the vessel. An example of a dissociation reagent is trypsin. The dissociation reagent is used to resuspend cells adherent to the cell culture vessel walls. Depending on the cells being cultured and the dissociation reagent used, the cell culture vessel may be gently agitated to assist in separating the adherent cells from the cell culture vessel walls. The automated cell culture system then waits a configurable amount of time at step 1206 depending on the cells being cultured and the dissociation reagent used. In an alternative embodiment, the automated cell culture system dynamically monitors the dissociation of the cells from the vessel with a microscope to determine when the amount of dissociation reaches a threshold value. The vessel may optionally be agitated during the waiting in step 1206. At step 1207, optionally, the cells are imaged to observe the detachment of the adherent cells. If the cells are not sufficiently detached, the automated cell culture system may wait an additional amount of time. Once the adherent cells are sufficiently detached from the walls of the cell culture vessel, a dissociation reagent inhibitor or neutralizer may be pumped into the cell culture vessel to stop the dissociation reagent action. At step 1208, the contents of the cell culture vessel may optionally be removed from the automated cell culture system and spun inside a centrifuge to separate the cells from the liquid contents of the cell culture vessel, and then resuspended. The cells may be counted at step 1209 to determine the total number of cells or cell density and the percent viability. At step 1210, a portion of the cells are transferred to a new cell culture vessel. Then, at step 1211, a determined amount of new growth media is pumped into the new vessel. If the automated cell culture system is configured to only maintain the cell line, the original cell culture vessel may be detached from the system and discarded, such that only the new vessel remains in the system growing cells. If the automated cell culture system is configured for expansion of the cell line, the original vessel may be retained, and a proportional amount of new growth media added to it such that both the original and the new cell culture vessel remain in the system growing cells. While described in the context of using a single new vessel, it is to be understood that this process may be expanded to any number of vessels such that a single original vessel may be split between any number of new vessels.

Figure 13:
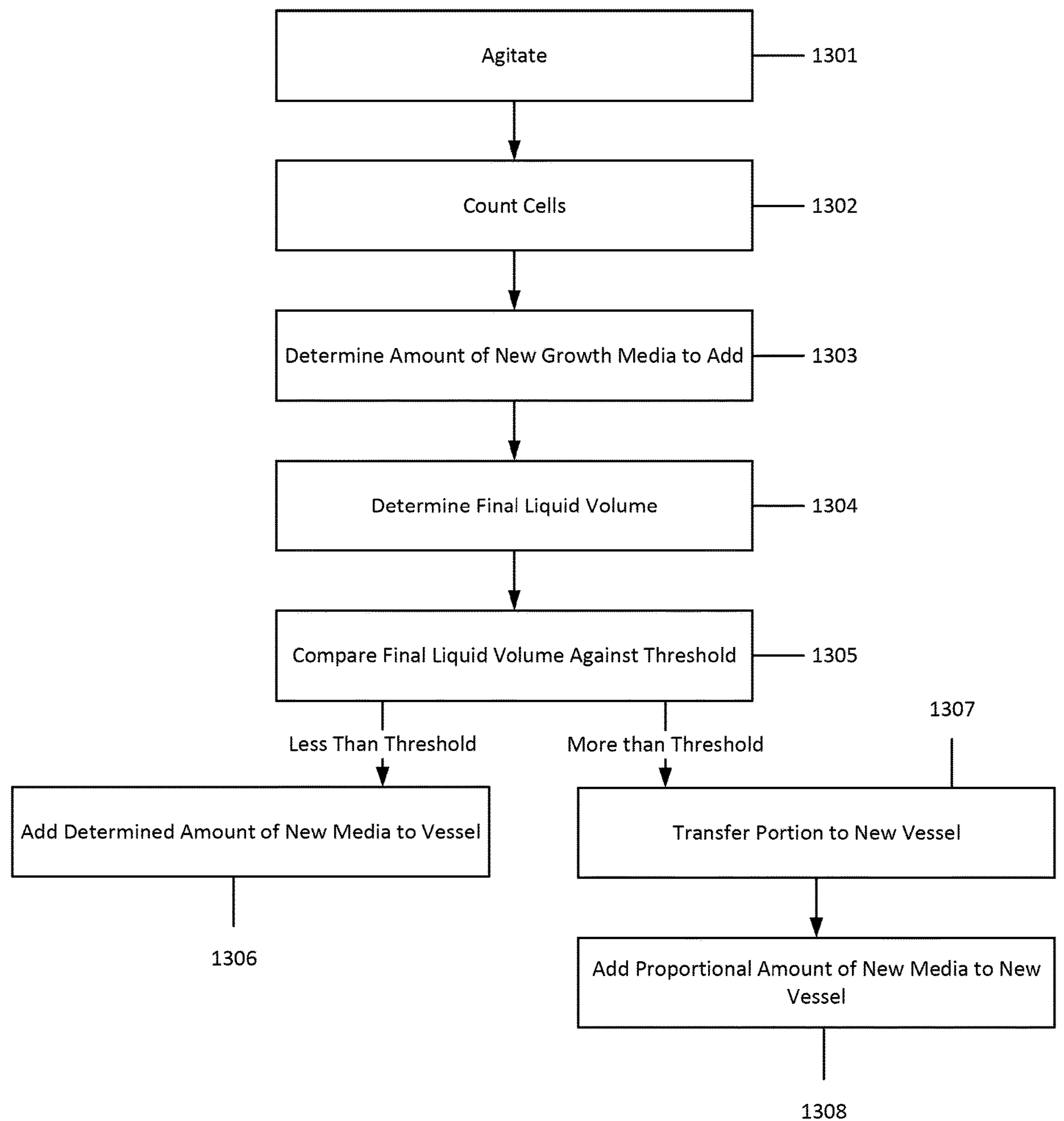
FIG. 13 illustrates the steps of a method for suspension cell line maintenance with optional passaging.

FIG. 13 illustrates the steps of a method for suspension cell line maintenance with optional passaging. At step 1301, a cell culture vessel may be agitated gently to evenly distribute the cells within the growth media in the vessel. Next, at step 1302, the cells within the vessel are counted and at step 1303 an optimal amount of new growth media is determined based on the cell count or the cell density. At step 1304, a final liquid volume of the cell culture vessel after adding the determined amount of new growth media is determined. Every time a procedure adds liquid to a cell culture vessel, the amount of liquid added is recorded and tallied by a controller. In this way, the controller maintains a current value for the amount of liquid in each cell culture vessel. At step 1305, the estimated final fluid volume of the cell culture vessel is compared against a configured maximum volume for the particular cell culture vessel being used. For example, the total volume of a vessel cannot exceed the total capacity of the vessel. In some embodiments, the threshold maximum volume may be significantly lower than the total volume of the vessel. If the estimated final fluid volume is lower than the configured threshold, at step 1306 the determined amount of new media is added to the vessel. If the estimated final fluid volume is greater than the configured threshold, the automated cell culture system may divide the contents of the cell culture vessel into two or more cell culture vessels to accommodate the estimated final fluid volume. In this example method, the contents of the cell culture vessel, referred to now as the first cell culture vessel, will be split between the first cell culture vessel and an additional second cell culture vessel. At step 1307, a portion of the contents of the first cell culture vessel may be transferred to the second cell culture vessel. The proportion of the contents of the first and second cell culture vessels is recorded by a controller. Then, at step 1308, a proportional amount of new cell culture growth media is added to each of the first and second cell culture vessels in proportion to the amount of the final liquid volume each contains. For example, if the fluid contents of the first cell culture vessel are evenly divided between the first cell culture vessel and the second cell culture vessel, new media will be similarly equally divided between the first and second cell culture vessels.

Figure 14:
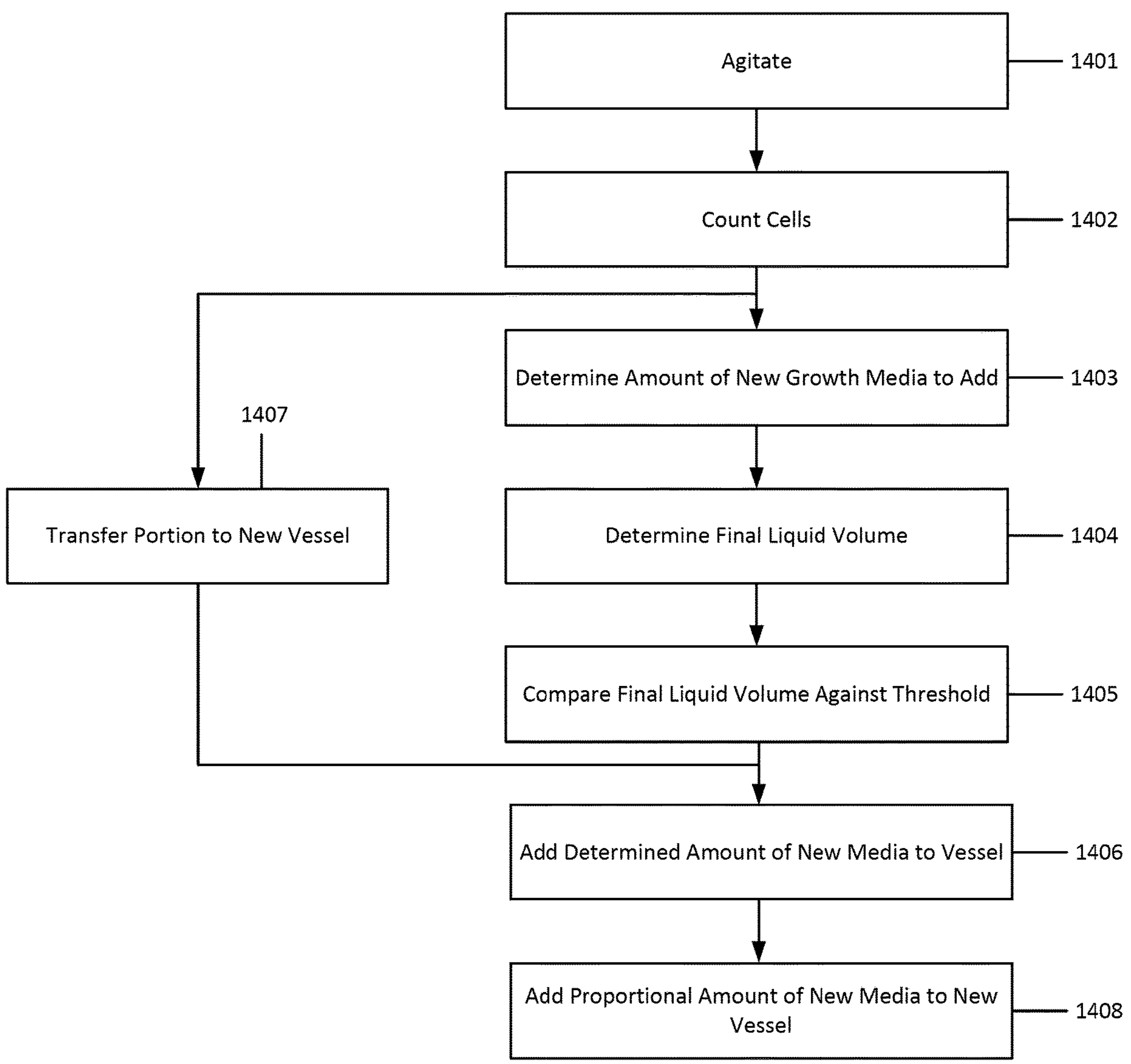
FIG. 14 illustrates the steps of a method for suspension cell line expansion.

FIG. 14 illustrates the steps of a method for suspension cell line expansion. The method for suspension cell line expansion mirrors that of suspension cell line maintenance, however at step 1407, the contents of the vessel may be transferred to new cell culture vessels even if the total volume remains below the total volume threshold for the cell culture vessel. That is, cells may be transferred to new cell culture vessels when appropriate for encouraging growth of cells rather than only in response to running out of volume in the cell culture vessels.

Figure 15:
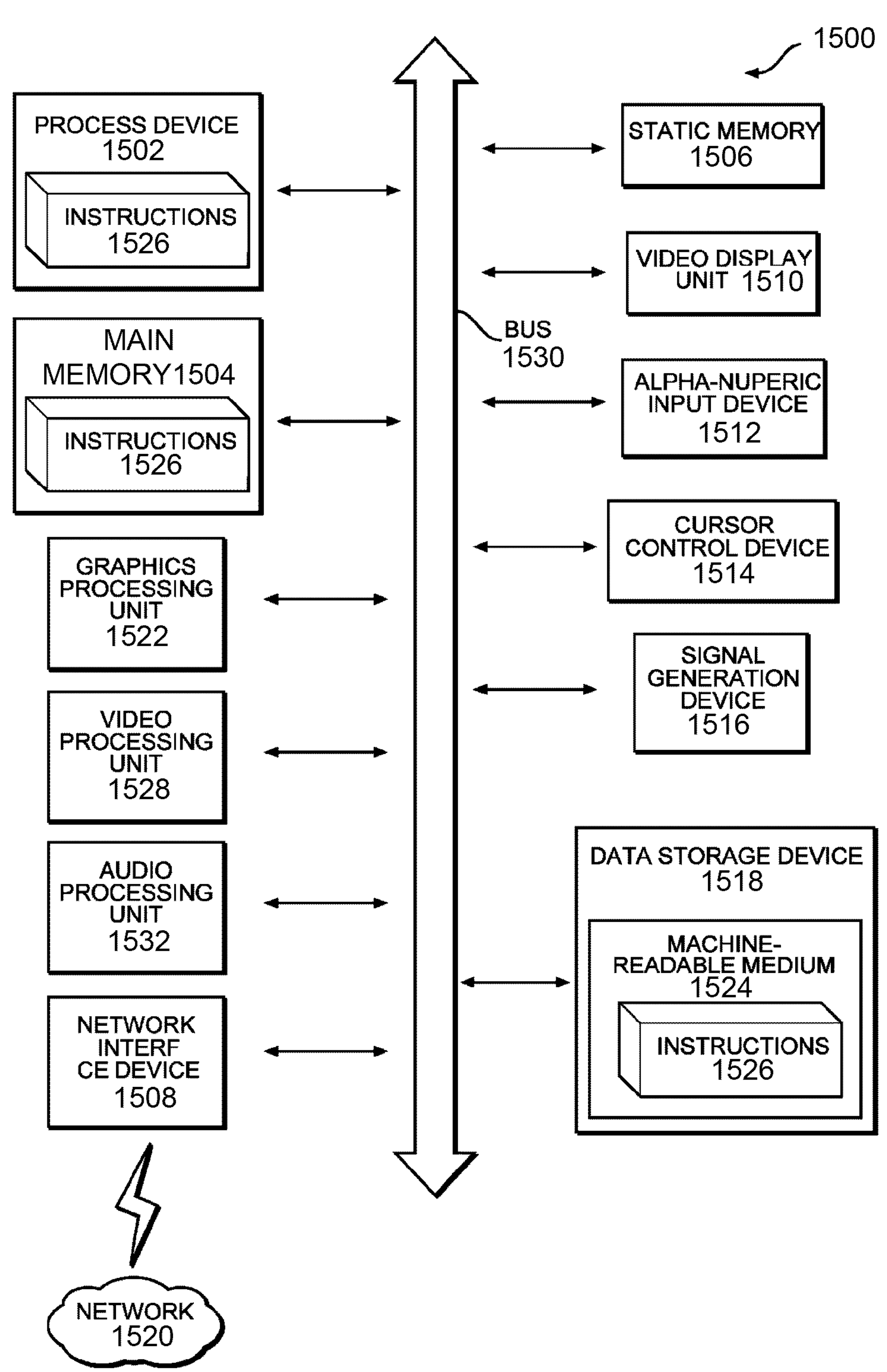
FIG. 15 illustrates an example machine of a computer system within which a set of instructions, for causing the machine to perform any one or more of the methodologies discussed herein, may be executed.

FIG. 15 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term “machine” shall also be taken to include any collection of machines that individually or jointly execute a set (or multiple sets) of instructions to perform any one or more of the methodologies discussed herein.

The example computer system 1500 includes a processing device 1502, a main memory 1504 (e.g., read-only memory (ROM), flash memory, dynamic random access memory (DRAM) such as synchronous DRAM (SDRAM) or Rambus DRAM (RDRAM), etc.), a static memory 1506 (e.g., flash memory, static random access memory (SRAM), etc.), and a data storage device 1518, which communicate with each other via a bus 1530.

Processing device 1502 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1502 may also be one or more special-purpose processing devices such as an application specific integrated circuit (ASIC), a field programmable gate array (FPGA), a digital signal processor (DSP), network processor, or the like. The processing device 1502 is configured to execute instructions 1526 for performing the operations and steps discussed herein.

The computer system 1500 may further include a network interface device 1508 to communicate over the network 1520. The computer system 1500 also may include a video display unit 1510 (e.g., a liquid crystal display (LCD) or a cathode ray tube (CRT)), an alphanumeric input device 1512 (e.g., a keyboard), a cursor control device 1515 (e.g., a mouse), a graphics processing unit 1522, a signal generation device 1516 (e.g., a speaker), graphics processing unit 1522, video processing unit 1528, and audio processing unit 1532.

The data storage device 1518 may include a machine-readable storage medium 1524 (also known as a computer-readable medium) on which is stored one or more sets of instructions or software 1526 embodying any one or more of the methodologies or functions described herein. The instructions 1526 may also reside, completely or at least partially, within the main memory 1504 and/or within the processing device 1502 during execution thereof by the computer system 1500, the main memory 1504 and the processing device 1502 also constituting machine-readable storage media.

In one implementation, the instructions 1526 include instructions to implement functionality corresponding to the components of a device to perform the disclosure herein. While the machine-readable storage medium 1524 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Figure 16A:
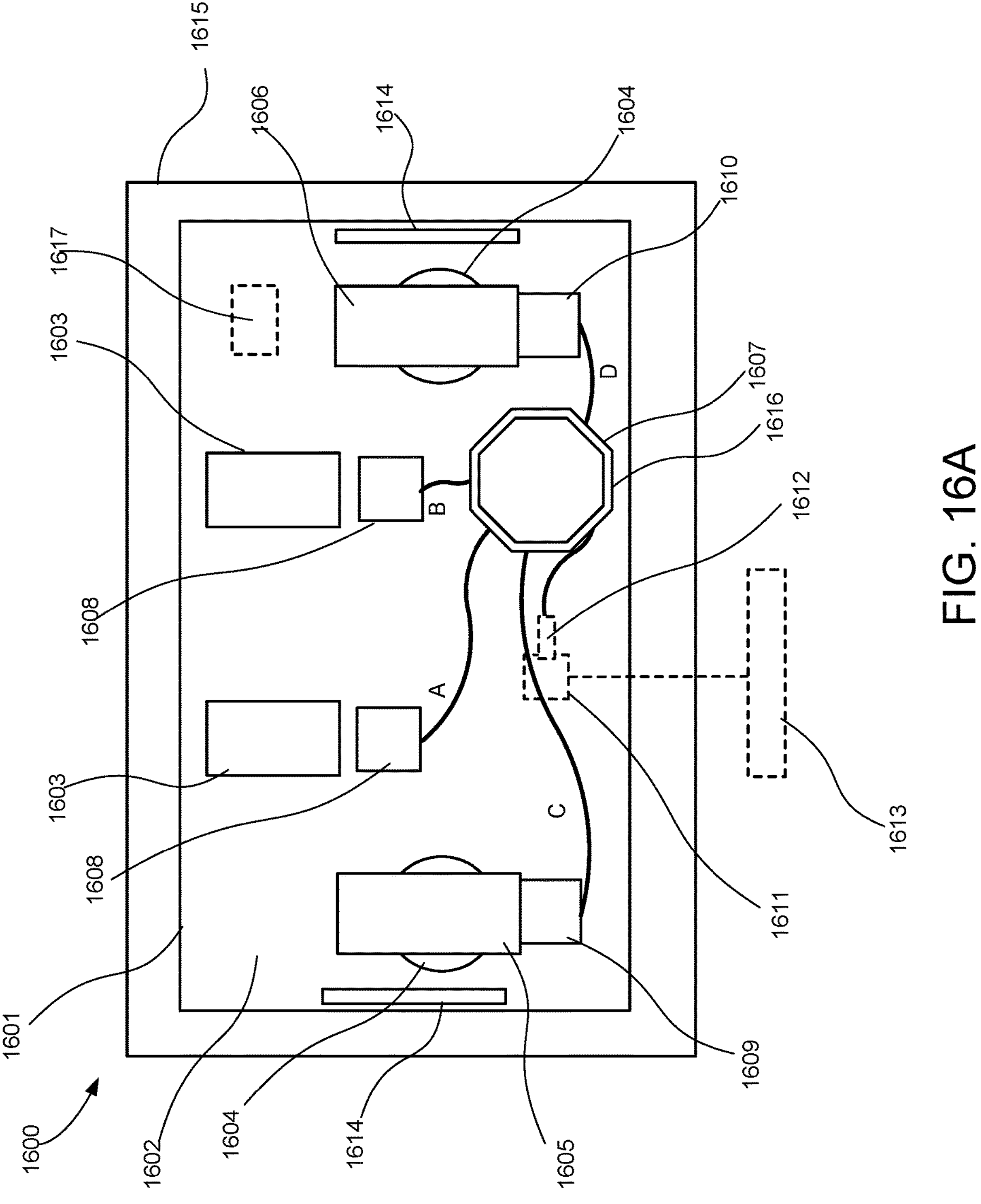
FIG. 16A is a schematic illustration of a tray assembly of a cell culturing system, according to an embodiment.
Figure 16B:
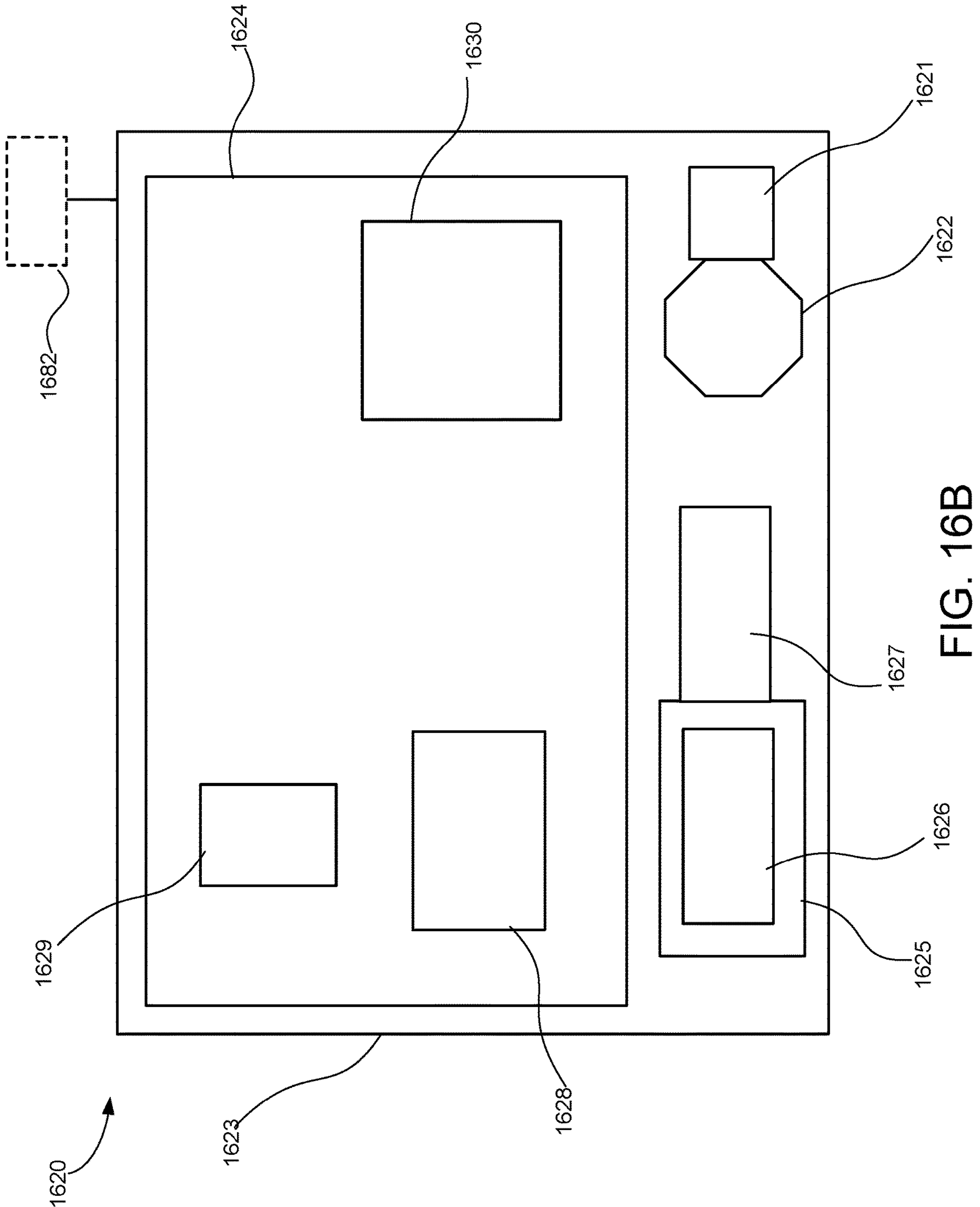
FIG. 16B is a schematic illustration of a base unit of a cell culturing system, according to an embodiment.
Figure 16C:
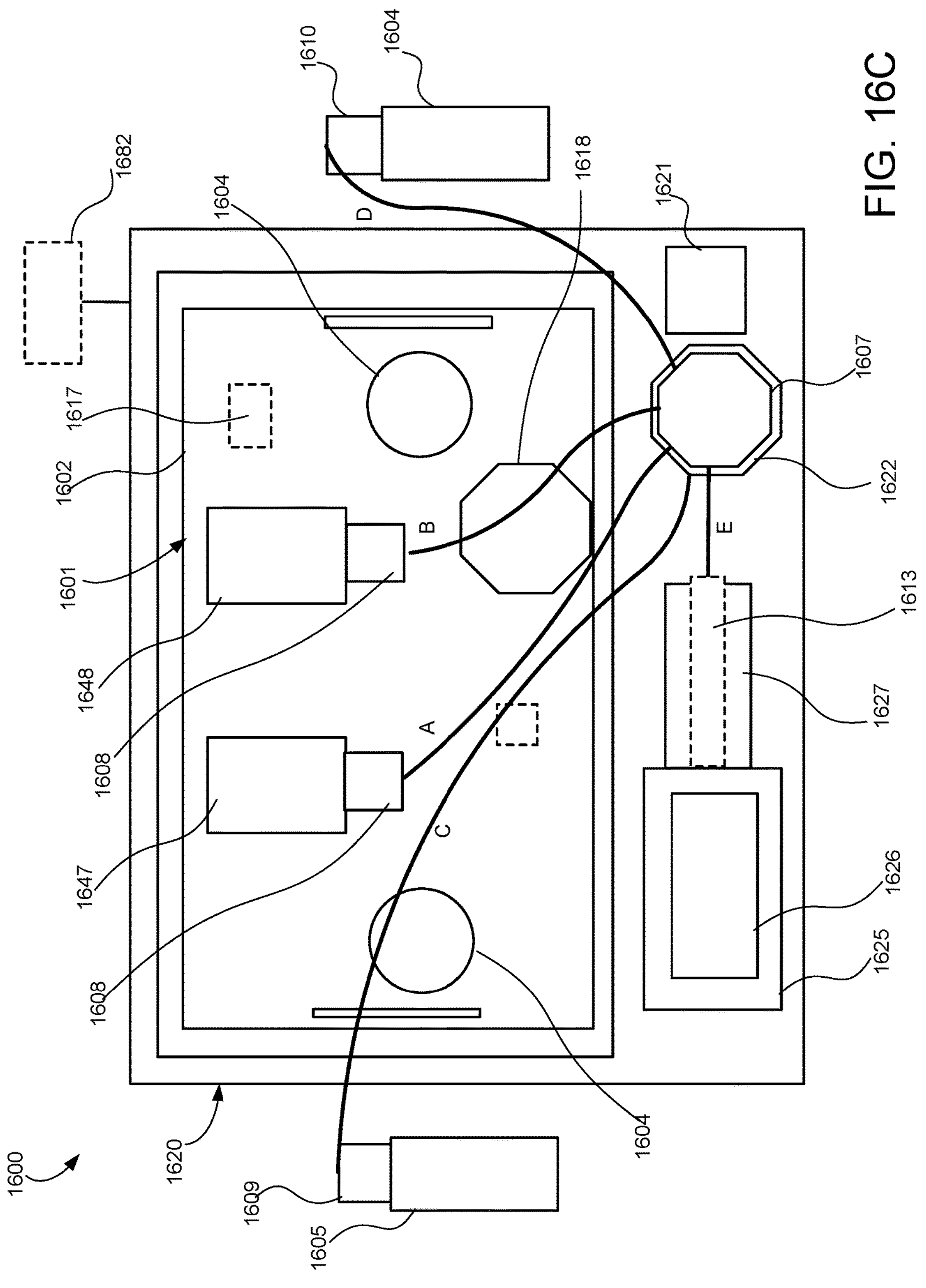
FIG. 16C is a schematic illustration of a cell culturing system, according to an embodiment, including the tray assembly shown in FIG. 16A and the base unit shown in FIG. 16B.

FIGS. 16A-16C illustrate a schematic view of an automated cell culture system according to another embodiment. This example automated cell culture system 1600 includes a consumable or disposable cell culture tray assembly 1601 (also referred to herein as "tray assembly," see FIG. 16A) and a reusable base unit 1620 (see FIG. 16B). The disposable tray assembly 1601 includes various components described below, some of which are preassembled on (or with) the tray assembly 1601 and enclosed within a protective overwrap to maintain the components in a sterile state. Some of the components of the tray assembly 1601 can be added to the tray assembly 1601 within an aseptic environment (e.g., a laminar flow hood) prior to using the tray assembly 1601 in a cell culturing procedure. When the tray assembly 1601 has been assembled and is ready for use, the tray assembly 1601 can be coupled to the base unit 1620 as described in more detail herein.

As shown in FIG. 16A, the tray assembly 1601, includes a tray 1602 that can be removably coupled to the base unit 1620 as described herein. In some embodiments, the tray 1602 can include one or more transparent or cut-out portions such that objects disposed on a top surface of the tray 1602 can be viewed from below the tray 1602. For example, as described in more detail below, the cell culture system 1600 can optionally include an imaging device and/or other sensors that are disposed in the base unit 1620 and below the tray 1602 when the tray assembly 1601 is coupled to the base unit 1620. The transparent portion(s) or cut-out(s) can allow for images and/or other data to be obtained through the transparent portion or cut-out, such as the contents of a cell culture container coupled to the tray 1602, as described in more detail below. In some embodiments, the tray assembly 1601 can include a cell counting chip 1617 shown in FIG. 16A. The cell counting chip 1617 can also include a bottom transparent portion and can be used to obtain information about the contents of a cell culture container as described below. In some embodiments, the cell counting chip 1617 may be coupled to or mounted within the base unit 1620 instead of being preassembled on the tray assembly 1601.

The tray assembly 1601 also includes one or more couplers 1603 that can be used to hold cell culture vessels or containers. The tray 1602 can optionally include holders 1604 that can be used to removably couple a reagent container 1605 and a waste container 1606 to the tray 1602 (e.g., to secure the containers during shipping, initial setup, or the like). Although two couplers 1603 are shown, in other embodiments, there could be only one or more than two couplers 1603. For example, in some embodiments a tray assembly can be configured to support only one cell culture container and thus includes only a single coupler 1603 that maintains the cell culture container in a fixed position on the tray. Similarly, although only one waste container 1606 and one reagent container 1605 are shown, in alternative embodiments, there can be multiple waste and reagent containers. Moreover, although FIG. 16A shows the waste container 1606 and the reagent container 1605 as being part of the tray assembly 1601, in other embodiments, the waste container 1606 and/or the reagent container 1605 can be separate components within the automated cell culture system 1600 that are not coupled to the tray 1602 during use. For example, in some embodiments, the reagent container 1605 can be used to contain cell culture media and can be placed in a refrigerated portion (not shown) of the automated cell culture system 1600 or another refrigeration location. The couplers 1603 and holders 1604 can be separate components attached to the tray 1602 or can be a component integrally or monolithically formed with the tray 1602. For example, in some embodiments, the couplers 1603 and/or the holders can include a deformable bracket, a movable pin, or any other suitable structure to couple the containers to the tray 1602. In some embodiments, the tray assembly 1602 can optionally include handles 1614 that can be used by a user to move and carry the tray assembly 1602. The handles 1614 can be separate components from the tray 1602 or formed integrally or monolithically with the tray 1602. In some embodiments, the tray assembly 1601 may not include holders 1604. In some embodiments, although not shown, the tray assembly 1601 can be preassembled with one or more cell culture containers.

The tray assembly 1601 also includes a multiport valve 1607 and one or more container lids 1608 (FIG. 16A shows two container lids 1608). The container lids 1608 can be coupled to the tray 1602 with disposable packaging mounts (not shown in FIGS. 16A-16C). The lids 1608 are each configured to be coupled to different cell culture container as described below. In this example embodiment, there are two lids 1608, but it should be understood that a different number of lids 1608 can be provided to accommodate a different number of cell culture containers. Each of the lids 1608 can include a liquid exchange port (also referred to herein as "fluid port") and a gas exchange port (each not shown in FIGS. 16A-16C). As shown, each of the fluid ports is coupled to a select port of the multiport valve 1607 with tubing (See tubing A, B, C and D in FIG. 16A). The gas exchange ports can allow gas transfer out of the cell culture container to which it is coupled. For example, in some embodiments, the lids 1608 can be similar to the cell culture vessel lid 803 or the lid 2408 shown and described herein. For example, the lids 1608 can include a gas filter that prevents microbes and/or contaminants from entering the cell culture container, thereby allow cell culturing and fluid transfer via lids 1608 while maintaining a closed (and/or sterile) system with other containers within the system (e.g., the reagent container 1605, the waste container 1606 or other containers). In some embodiments, the tray assembly can optionally include lids 1609 and 1610 that are coupled to the reagent container 1603 and the waste container 1606, respectively. The lid 1609 and/or the lid 1610 can be similar in structure and function as the lid 1608 and/or the cell culture vessel lid 803.

The multiport valve 1607 can include the same or similar components and functions in the same or similar manner as the multiport valves described above for previous embodiments (e.g., the multiport valve 600 or the multiport valve 2407 described herein). The multiport valve 1607 can include a master port configured to be coupled to a fluid pump 1613 of the base unit (described below and shown in FIGS. 16B and 16C), and multiple selectable ports that can be fluidically coupled to liquid exchange ports of the lids 1608, 1609, 1610 and/or other components of the cell culture assembly 1600 as described herein. For example, one port of the selectable ports can be aseptically and/or fluidically coupled to a first liquid exchange port of a first lid 1608, and a second selectable port can be aseptically and/or fluidically coupled to a second liquid exchange port of a second lid 1608. In some embodiments, a third port of the multiport valve 1607 can be coupled to the liquid exchange port of the reagent container 1605, a fourth port can be coupled to the liquid exchange port of the waste container 1606 and a fifth port can be coupled to a liquid exchange port of a cell harvest container (not shown in FIGS. 16A-16C). The multiport valve 1607 can be coupled to various other components, such as, for example, a cell counting chip, cell harvest container(s), various reagent and enzyme containers, etc. An example system schematic illustrating some example couplings of a multiport valve is provided in FIG. 59. In this manner, when actuated the multiport valve 1607 can facilitate fluid exchange between various containers within the automated cell culture system 1600. For example, as described herein, the multiport valve 1607 can be actuated to facilitate the addition of cell culturing media or reagents to the cell culture containers, the removal of cells from the cell culture containers (e.g., cell passaging or cell harvesting), or any other fluid movement associated with cell culturing.

The multiport valve 1607 can be preassembled and coupled to the lids 1608, 1609, 1610 on the tray assembly 1601 and enclosed within the protective overwrap 1615. This arrangement allows the end user to receive the prepackaged tray assembly 1601 within the protective overwrap. In some embodiments, tray assembly 1601 can be sterilized prior to being placed in the protective overwrap. As described herein, the user can then load the desired cells, reagents, cell culture media, or the like into the containers and can couple the pre-connected lids to the containers within an aseptic environment. The tray assembly 1601 can then be coupled to the base unit and moved into an incubation environment where fluid exchange can be performed to ensure the desired cell culturing, as described herein.

The multiport valve 1607 is configured to engage a valve actuator 1621 of the base unit 1620. The multiport valve 1607 can include a mounting portion 1616 configured to matingly couple to a valve connector 1622 of the base unit 1620 in some embodiments. For example, the mounting portion 1616 can have a shape such that it can be coupled to the valve connector 1622 in a puzzle-like manner. Examples of such a mounting portion and valve connector are described below with reference to particular embodiments. As shown in FIGS. 16B and 16C, when the multiport valve 1607 is engaged to the valve actuator 1621 of the base unit 1620, the valve actuator 1621 can actuate the multiport valve 1607 to move to a selected port to allow for selective fluid transfer to and from the various containers of the tray assembly 1601 and cell culture containers (described below). In some embodiments, the multiport valve 1607 can be coupled to the valve actuator 1621 while remaining coupled to the tray 1602. For example, a valve connector (not shown) coupled to the valve actuator 1621 can be disposed on the base unit 1620 below where the tray assembly 1602 is removably coupled to the base unit 1620 (e.g., similar to the base unit 301 or the base unit 2120 described herein). In some embodiments, the multiport valve 1607 can be removed from the tray 1602 (while remaining coupled to the lids, thereby preserving the closed system) and attached to the mating valve connector 1622 of the base unit 1620 as shown, for example, in FIGS. 16B and 16C. FIG. 16B shows the connector 1622 without the multiport valve 1607 coupled thereto, and FIG. 16C shows the multiport valve 1607 coupled thereto. In other words, the multiport valve 1607 can be detached from a mating mounting pocket 1618 (see FIG. 16C) of the tray 1602 and attached to the valve connector 1622 of the base unit 1620. As described above, the mounting portion 1616 of the valve 1607 is shaped to matingly engage the mounting pocket 1618 and to matingly engage the valve connector 1622 of the base unit 1620 to ensure proper positioning and alignment within both the tray assembly 1601 and the base unit 1620. This relocation of the multiport valve 1607 can be done with the lids 1608, 1609, 1610 remaining aseptically coupled to the multiport valve 1607. Removing the valve 1607 from the tray 1602 allows the interface between the valve 1607 and the valve actuator 1621 to be stationary, which is well-suited for those embodiments that include an agitator to move the tray 1602 relative to the base unit 1620. Similarly stated, by coupling the valve 1607 directly to the base unit 1620, the interface between the valve 1607 and the valve actuator 1621 is not disrupted by the relative movement between the tray 1601 and the base unit 1620.

Also shown in FIG. 16A is an optional pump holder 1611, that can be used to hold a port connector 1612 that is fluidically coupled to the master port of the multiport valve 1607. This port is used to connect the fluid pump 1613 to the tray fluidics 1602 during preparation of the tray assembly 1601 for a cell culturing procedure. The fluid pump 1613 can be used produce fluid movement in the cell culture system 1600 as described herein. The fluid pump 1613 can be any suitable pump that produces pressure and/or flow within the cell culture system 1600. For example, the fluid pump 1613 can be a syringe that includes a piston rod and a syringe body. The syringe is only one example of a type of fluid pump that can be used in the cell culture system 1600. Various other positive displacement fluid pumps can be used, such as, for example, a peristaltic pump. In some embodiments, the pump can be a single-port pump, whereas in other embodiments, the pump can be a two-port pump, as described herein. When a syringe is used as the pump 1613, it can be attached to the multiport valve 1607 and to the optional syringe holder 1611 in an aseptic environment prior to a cell culturing procedure.

The base unit 1620 (see FIGS. 16B and 16C) includes a housing 1623 that supports various components of the base unit 1620 and can define (or include) a receiving portion 1624 to receive and removably couple the tray assembly

1601 thereto. In some embodiments, the receiving portion 1624 can include an opening in which the tray assembly 1601 can be placed and supported by a tray support (not shown). In some embodiments, the tray assembly 1601 is supported by a support portion of the base unit 1620 such that the tray assembly 1601 is elevated above a top surface of the base unit 1620. In some embodiments, the tray assembly 1601 is supported at least in part by engagement with an agitator (described below) of the base unit 1620. In some embodiments, the tray assembly 1601 can be removably coupled to a separate support member that is couplable to the housing 1623 of the base unit 1620. The base unit 1620 can also include one or more transparent portions or open portions corresponding to transparent portions of the tray 1602 such that images and/or other sensor data associated with the contents of the cell culture containers can be obtained.

The base unit 1620 includes the valve connector 1622 and valve actuator 1621 described above and also includes a fluid pump portion 1627 and a pump actuator 1626. The pump actuator 1626 can be disposed, for example, at least partially within an opening 1625 defined by the housing 1623. As described above, in some embodiments, the fluid pump 1613 can be a syringe or other type of positive displacement fluid pump that is fluidically coupled to the multiport valve 1607 and then coupled to the fluid pump portion 1627 of the base unit 1620. In some embodiments, in which a syringe is the fluid pump 1613, the fluid pump portion 1627 can include a holder (not shown in FIGS. 16A-16C) that can be used to hold and support the syringe 1613 on the housing 1623. The holder can be a separate component or a component formed integrally or monolithically with the housing 1623. The fluid pump 1613 can be fluidically coupled to the master port of the multiport valve 1607. In this example embodiment, as shown in FIG. 16C (showing the tray assembly 1601 coupled to the base unit 1620), the multiport valve 1607 is shown detached from the tray assembly 1601 and coupled to the valve connector 1622 and the fluid pump 1613 is coupled to the master port with tubing E. The fluid pump 1613 can include a movable member within a pump body (not shown in FIGS. 16B and 16C). During operation of the system 1600, the movable member of the fluid pump 1613 (e.g., plunger, rotor) can be actuated to cause a suction force to bring fluid into the pump body and can actuate the movable member to push fluid out of the pump body as described above for previous embodiments.

In some embodiments, the base unit 1620 can also include an agitator 1628. The agitator 1628 can include, for example, an orbital shaker that moves the tray 1602 in a circular or half-circular motion. The agitator 1628 can be configured to agitate the removable tray assembly 1601 in relation to the housing 1623 as described above for previous embodiments. The agitator 1628 may agitate the tray 1602 in a rocking motion, vibrating motion, circular swirling motion, or other motions useful in cell culturing. In some embodiments, individual cell culture vessels/containers may be independently agitated by independent agitators displaced between the cell culture vessel and the removable tray assembly 1601 as previously described. In some embodiments, an agitator may not be included.

In some embodiments, the base unit 1620 can also optionally include one or sensors 1629 (only one shown in FIGS. 16B and 16C) and an electronic control system 1630 to control the operation of any of the components of the cell culture system 1600 (e.g., the valve actuator 1621, the pump actuator 1626). The electronic control system 1630 can optionally be incorporated within, coupled to, or provided by a remote computing system, such as, for example, within a cloud computing environment. In some embodiments, the sensor(s) 1629 can be mounted to a device to allow for the sensor(s) to be movable relative to the housing 1623 of the base unit 1620. An example of such an embodiment is described below with reference to FIGS. 32-34. The sensors 1629 can include, for example, one or more imaging devices, a microscope, a color monitor or any other type of sensor as described herein. The sensor(s) can be used to capture images or other types of output that can be used to determine obtain information about the contents within a cell culture container (e.g., 1647, 1648), such as, for example, the density of the contents to determine a quantity of cells within the container (for example, for suspension cells) during a cell culturing procedure, or a percentage confluence (i.e., percentage of coverage of the container area with cells) in the case of, for example, adherent cells. In some embodiments, the sensor(s) 1629 can be used to capture images and/or other types of output of a sample portion of the contents of a cell culture container via the cell counting chip 1617. For example, a sample of the fluid mixture within a cell culture container can be extracted into the cell counting chip 1617, and a sensor 1629 can be moved to a position in alignment with the cell counting chip 1617 and used to image or otherwise collect information associated with the sample fluid mixture on the cell counting chip 1617. In some embodiments, the sensor(s) 1629 can be operatively coupled to or incorporated within the electronic control system 1630.

As described above, in some embodiments, a light or light source 1682 (see FIGS. 16B and 16C) can also be provided that can be used in combination with, for example, an imaging device. In some embodiments the light can be movable with respect to the housing of the base unit 1620. For example, a light source can be mounted above the tray assembly 1601 of the system on a movable multi-axis gantry, which allows it to be controlled to move to the same position as the microscope within the base unit. In some embodiments, the light source can be operatively coupled to the same gantry as the imaging device such that the imaging device and light source can be moved together. In some embodiments, the system 1600 may include one or more cameras or pairs of LEDs and light sensors to image the contents of cell culture containers.

In some embodiments, the sensor(s) 1629 can include a valve position sensor configured to produce a valve position signal associated with a rotation position of the valve actuator. In this manner the valve position sensor can detect which of the selectable ports is fluidically coupled to the master port (e.g., the fluid pump 1613). In some embodiments, the sensor(s) 1629 can include a pump position sensor configured to produce a pump position signal associated with the movement of the pump. In this manner, the pump position sensor can indicate the travel of the pump and/or the volume of the fluid moved by the pump. As described herein, the electronic control system 1630 can determine, based on the pump position signal, an estimated amount of fluid within (or being added to) one of the cell culture containers.

Figure 17:
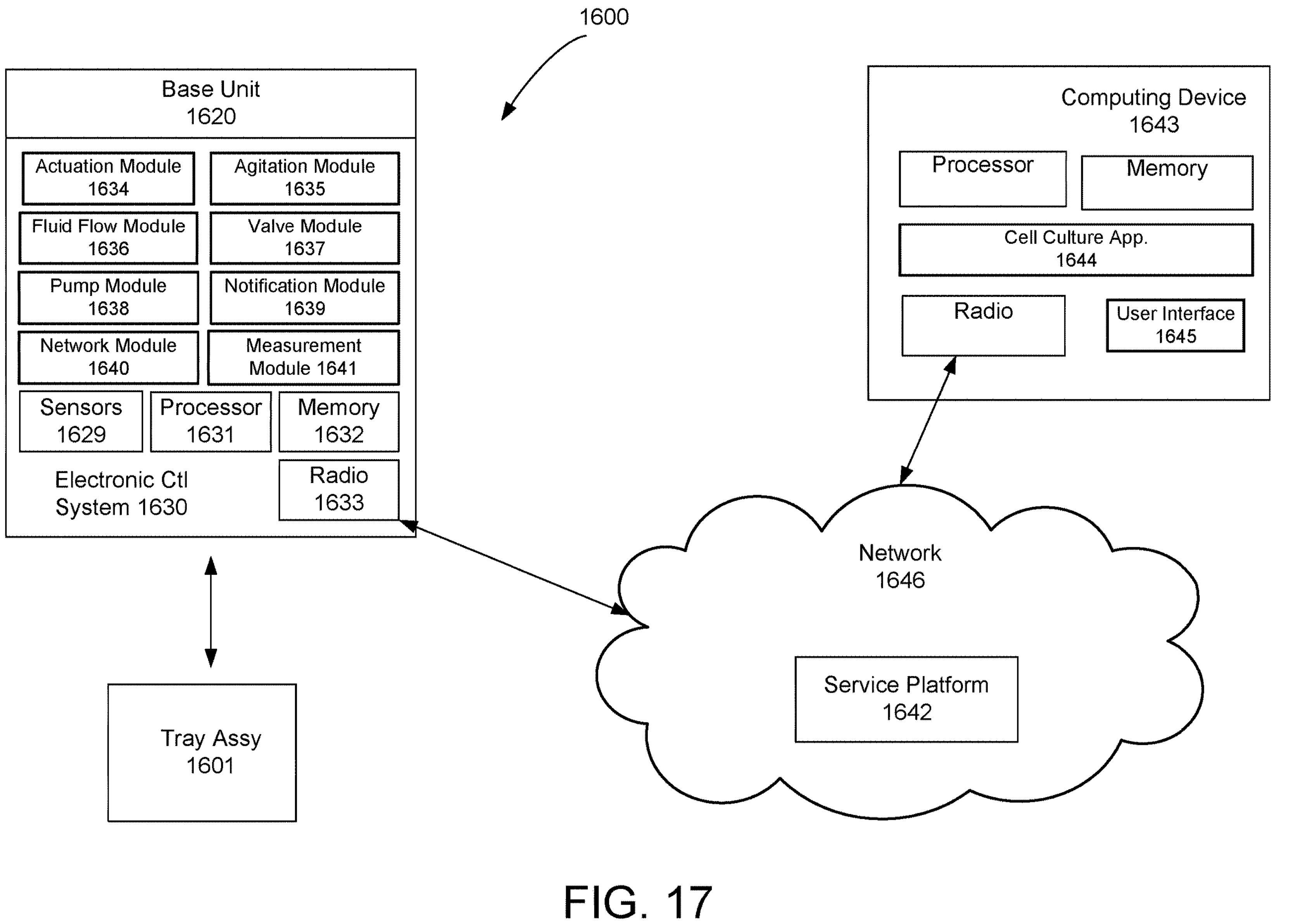
FIG. 17 is a schematic illustration of an electronic control system of a cell culturing system, according to an embodiment.

FIG. 17 is a schematic illustration of the electronic control system 1630 that can be used to control operation of the cell culture system. The components and architecture of the electronic control system 1630 are provided as an example, and in some embodiments, the electronic control system 1630 (or any of the electronic control systems described herein) can include different components than those shown in FIG. 17. Moreover, in some embodiments, a base unit and/or a cell culturing assembly need not include the electronic control system as described in FIG. 17. For example, in some embodiments, the base unit 1620 (or any of the base units described herein can include the computer system 1500 described herein). In other embodiments, the base unit 1620 need not include an electronic control system.

As shown in FIG. 17, the electronic control system 1630 includes one or more processor 1631, one or more memory component 1632, a radio 1633 and various modules, such as an actuation module 1634, an agitation module 1635, a fluid flow module 1636, a valve module 1637, a pump module 1638, a measurement module 1641 (also referred to as a cell sensor module) and/or a network module 1640. Although FIG. 17 illustrates the electronic control system 1630 being within the base unit 1620, as described above, the electronic control system 1630 or portions thereof can be provided outside of the base unit 1620 (e.g., within a cloud computing environment). The electronic control system 1630 can automatically control the fluid flow into and out of the various containers through actuation of, for example, the pump actuator 1626 and the valve actuator 1621. The electronic control system 1630 can also automatically control the actuation of the agitator 1628, the sensor(s) 1629, and the valve actuator 1621. Operation and actuation of the fluid pump 1613, valve actuator 1621, selection of ports on the multiport valve 1607, etc. can be the same as or similar to operation of these components as described above for previous embodiments. As described above for previous embodiments, in operation, the combination of fluid pumps, valves of the multiport valve, containers, and cell culture vessels may be used to transfer liquids to and from the cell culture vessels and the containers.

During preparation for a cell culturing procedure, the tray assembly 1601 can be placed in an aseptic environment (e.g., a laminar flow hood) and the overwrap 1615 can be removed. While in the aseptic environment (e.g., the flow hood), cell culture vessels or containers 1617, 1618 can be prepared (e.g., cells and reagent added to the containers), secured to the lids 1608 and placed within the couplers 1603 on the tray 1602. The cell culture containers 1617, 1618 can be any known type of cell culture vessel, such as, for example, a flask or dish as described above for previous embodiments. The waste container 1606 and the reagent container 1605 can be placed in an upright position within the holders 1604. In other embodiments, the waste container 1606 and/or the reagent container 1605 can be placed in any suitable location for transportation within other locations of the cell culturing system 1600.

The tray assembly 1601 can then be coupled to the base unit 1620 as shown in FIG. 16C. In this embodiment, the multiport valve 1607 is decoupled from the tray assembly 1601 and matingly coupled to the valve actuator 1621, while remaining fluidically coupled to the various lids 1608, 1609, 1610. The fluid pump 1613 can be fluidically coupled to the multiport valve 1607 via a length of tubing E. In the case of a syringe being used as the fluid pump 1613, as described above, the syringe can be coupled to the multiport valve 1607 within the aseptic environment and coupled to the tray 1602 prior to the tray assembly 1601 being coupled to the base unit 1620. The syringe 1613 can then be moved to the holder (not shown) of the base unit 1620 and coupled to the pump actuator 1626, while remaining fluidically coupled to the multiport valve 1607 via tubing. The waste container 1606 and the reagent container 1605 can be removed from the tray 1602 and placed, for example, at a location alongside or near the tray 1602, and/or within the incubator, or a refrigerator. A more detailed description of the method of preparing the cell culture system 1600 for use is described below with reference to FIGS. 21-30. The tray assembly 1601 can be coupled to the base unit 1620, within the aseptic environment or outside of the aseptic environment. The cell culture system (with tray assembly 1601 coupled to the base unit 1620) can be placed in an incubator ready for a cell culturing procedure. In some embodiments, the tray assembly 1601 can be coupled to the base unit 1620 within the incubator.

Any of the base units and/or tray assemblies described herein can be used to perform any of the computer-implemented methods described herein. Said another way, any of the base units and/or tray assemblies described herein can include (or interface with) an electronic control system to facilitate automated (or semi-automated) method of culturing cells. As shown in FIG. 17, the electronic control system 1630 can communicate with other remote computing devices (e.g., computing device 1643), via a network 1646 (e.g., the Internet), through, for example, a service platform 1642 and a cell culture Application (i.e., App) 1644. The electronic control system 1630 can in addition to, or alternatively, communicate with a remote computing device through a direct connection such as, a cable connected to a USB port of the base unit 1620. The components, modules, and/or functions described in connection with the cell culturing system 1600 can be included within any of the cell culturing systems described herein. For example, although not shown, the cell culturing systems 200, 300 and 400 can include an electronic control system similar to or the same as the electronic control system 1630. Moreover, although the cell culturing system 1600 is shown and described as including only one connected computing device 1643, in other embodiments, the cell culturing system 1600 (and any of the cell culturing systems described herein) can include any number of any of connected remote computing devices.

The service platform 1642 can be any suitable computer-implemented interface and/or computing entity, such as a server or personal computer, that is configured to communicate via the network 1646 with the remote computing device 1643 and/or any other portions of the cell culturing system 1600 (e.g., a call center interface, other remote computing devices, or the like, not shown). More specifically, the service platform 1642 can receive information from the devices within the cell culturing system 1600 (e.g., base units or remote computing devices) manipulate the information and produce information to any other devices within the cell culturing system 1600. For example, in some embodiments, cell density or cell confluence information associated with the tray assembly 1601 can be transmitted from the base unit 1620 to the remote computing device 1643. The remote computing device 1643 can produce notifications for the user via the cell culture application 1644 and can receive input from a user in response to such notifications. The remote computing device 1643 can then transmit the input (or instructions) to the service platform 1642. Based on the user input, the service platform 1642 can transmit instructions to the base unit 1620, which can then execute the instructions to perform the desired task (e.g., cell passaging). In this manner, the service platform 1642 can control and/or manage certain instructions, notifications and/or features. Similarly stated, in this manner the service platform 1642 can function as the "back end" for the cell culturing system 1600.

The network 1646 can be a piconet, the Internet, an intranet, a local area network (LAN), a wide area network (WAN), a virtual network, a telecommunications network, any other suitable communication system and/or combination of such networks. The network 1646 can be implemented as a wired and/or wireless network. The base unit 1620 and the remote computing device 1643 can be coupled to (or connected with) the network via any suitable mechanism and/or by any protocol. For example, in some embodiments, the base unit 1620 can be in direct communication with the network 1646, the remote computing devices 1643 and/or the service platform 1642 via the LTE Direct protocol or any other suitable protocol (e.g., the 5G mobile wireless standard based on the IEEE 802.11ac standard for broadband technology).

Although FIG. 17 identifies the base unit 1620, the electronic control system 1630 can be incorporated into (or used with) any of the base units described herein. As described above, the base unit 1620 includes or is attached to an electronic control system 1630. For example, in some embodiments, the electronic control system 1630 can be coupled to and/or within a housing 1623 and/or any other portion of the base unit 1620. Similarly stated, the electronic control system 1630 can be integrated within the base unit 1620. In other embodiments, however, the electronic control system 1630 can be separate from but operably coupled to the base unit 1620 (e.g., connected wirelessly or via a wired connection). Although the electronic control system 1630 is shown as including one or more processors 1631, one or more memory components 1632, a radio 1633 and various modules, such as an actuation module 1634, an agitation module 1635, a fluid flow module 1636, a valve module 1637, a pump module 1638, a measurement module and/or a network module 1640, in other embodiments, an electronic circuit system need not include all (or any) of these modules, and can include any other modules described herein. For example, in some embodiments, an electronic control system may only include a flow module and is configured to perform the cell passaging and flow methods associated therewith, and need not include, for example, the agitation module.

The processor 1631, and any of the processors described herein can be any suitable processor for performing the methods described herein. In some embodiments, processor 1631 can be configured to run and/or execute application modules, processes and/or functions associated with the cell culturing system 1600. For example, the processor 1631 can be configured to run and/or execute the actuation module 1634, the agitation module 1635 and/or the network module 1640 and/or any of the other modules described herein, and perform the methods associated therewith. The processor 1631 can be, for example, a Field Programmable Gate Array (FPGA), an Application Specific Integrated Circuit (ASIC), a Digital Signal Processor (DSP), and/or the like. The processor 1631 can be configured to retrieve data from and/or write data to memory, e.g., the memory 1632. As described herein, in some embodiments, the processor 1631 can cooperatively function with the radio 1633 and/or execute instructions from code to provide signals to communicatively couple the electronic control system 1630 to the computing device 1643 (e.g., via wireless communication) and/or any other computing entity via a network such as network 1646. In some embodiments, the processor 1631 is a Bluetooth® low energy (BLE) processor.

The memory 1632 can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 1632 stores instructions to cause the processor 1631 to execute modules, processes and/or functions associated with such cell culturing system 1600 and/or the base unit 1620. For example, the memory 1632 can store instructions to cause the processor 1631 to execute any of the application modules described herein, and perform the methods associated therewith.

As described above, one or more of the sensor(s) 1629 can be separate and/or included within the electronic control system 1630 can include, for example, imaging devices, optical sensors, accelerometers, temperature sensors, contact sensors, position sensors and/or any other suitable input device. In some embodiments, the sensor(s) 1629 can include a sensor operable to monitor and/or measure the position (or selection) of the ports of the multiport valve 1607, the fluid pump 1627 position, temperatures, agitation, etc. For example, in some embodiments, a sensor 1629 can include a position sensor operable to detect a position of a multiport valve of the system. As yet another example, the sensor 1629 can include an optical sensor operable to detect the density (or amount) of cells within a cell culture container coupled to the tray 1602. In such embodiments, the optical sensor could detect the attenuation of light (e.g., to detect the density of cells within a light path). The optical sensor could alternatively capture an image (e.g., via a photocell, microscope, charge coupled device or the like) to determine the amount of cells within the cell culture container. As yet another example, a sensor 1629 can include an accelerometer operable to detect a characteristic movement or vibration signature of the tray assembly 1601 when the device is being agitated.

The radio 1633 (also referred to as a receiver, transmitter and/or transceiver) can be operable to send signals to, and/or receive radio signals, such as Bluetooth®, ZigBee, Wi-Fi, 1631 is Bluetooth® processor, the radio 1633 can be integral with the processor 1631. In other embodiments, the radio 1633 can include a processor distinct from the processor 1631. The radio 1633 can be operable to communicatively couple the electronic control system 1630 to the computing device 1643 and/or any other computing entity via a network 1646. The radio 1633 can include or be coupled to a ceramic chip antenna, a stamped antenna, a sintered antenna, a PCB conductive trace antenna, and/or any other suitable antenna.

The measurement module 1641 (also referred to in some embodiments as the cell sensor module) can be a hardware and/or software module (stored in memory 1632 and/or executed in the processor 1631). As described in more detail herein, in some embodiments, the measurement module 1641 is configured to receive multiple different signals from the sensors 1629 of the electronic control system 1630 and produce information to various other modules within the electronic control system 1630.

The flow module 1636 can be a hardware and/or software module (stored in memory 1632 and/or executed in the processor 1631). As described in more detail herein, the flow module 1636 can be configured to receive an indication (e.g., from the sensor(s) 1629) and/or transition information associated with a change in status of a pump or a multiport valve of the base unit 1620 and determine, based on the indication or the transition information, what valves of the multiport valve 1607 to open and close to cause fluid to move into and/or out of a particular container of the system 1600.

The network module 1640 can be a hardware and/or software module (stored in memory 1632 and/or executed in the processor 1631). The network module 1640 is configured to exchange information associated with the base unit 1620 and the remote computing device 1643 to facilitate the communication process. For example, the network module 1640 of the base unit 1620 can cause the remote computing device 1643 and the base unit 1620 to exchange short term and/or long-term security keys to complete the pairing and bonding process.

A notification module 1639 can be a hardware and/or software module (stored in memory 1632 and/or executed in the processor 1631). The notification module 1639 is configured to produce notifications associated with any of the methods and/or application modules described herein. For example, in some embodiments, the notification module 1639 can produce a notification that is transmitted via the radio 1633 and is for receipt by a notification module of the remote computing device 1643. In this manner, the notification module 1639 executed in the cell culture application can produce outputs (e.g., wireless communication signals, GUI elements, audible outputs, visual outputs, or the like) to notify the user of events.

The agitation module 1635, the valve module 1637, and the pump module 1638 can each be a hardware and/or software module (stored in memory 1632 and/or executed in the processor 1631). These modules can be configured to receive an indication (e.g., from the sensor(s) 1629) and/or transition information associated with a change in status of, for example, a pump or a multiport valve of the base unit 1620, and determine, based on the indication or the transition information, what actions to perform at the particular device (e.g., pump, valve, agitator). In some embodiments, the valve module 1637 and/or the pump module 1638 can provide information associated with a position of the multiport valve 1607 and the pump 1627, respectively. In some embodiments, the modules 1637 and 1638 can include (or receive information from) an encoder. In some embodiments, an actuator module 1634 can perform some or all of the functions of the agitation module 1635, valve module 1637, and/or pump module 1638.

The computing device 1643 can be, for example, a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), or a computer (e.g., a laptop, desktop, smart TV, etc.), and/or any other suitable computing entity. The computing device 1643 can include a processor, a memory, a user interface 1645, and a radio.

The user interface 1645 of the remote computing device 1643 can be, for example, a monitor or screen that displays visual elements to a user. The user interface 1645 can be a touch screen (of a smart mobile phone) upon which a series of graphical user interface (GUI) elements (e.g., windows, icons, input prompts, graphical buttons, data displays, notification, or the like) can be displayed. In some embodiments, the graphical user interface elements (see e.g., the GUI elements 1645A, 1645B, and 1645C described with reference to FIGS. 18-20) are produced by the cell culture application 1644. Moreover, the user interface can also receive input from the user, such as, for example, input via a touch screen, input via a microphone, or the like.

Figure 19:
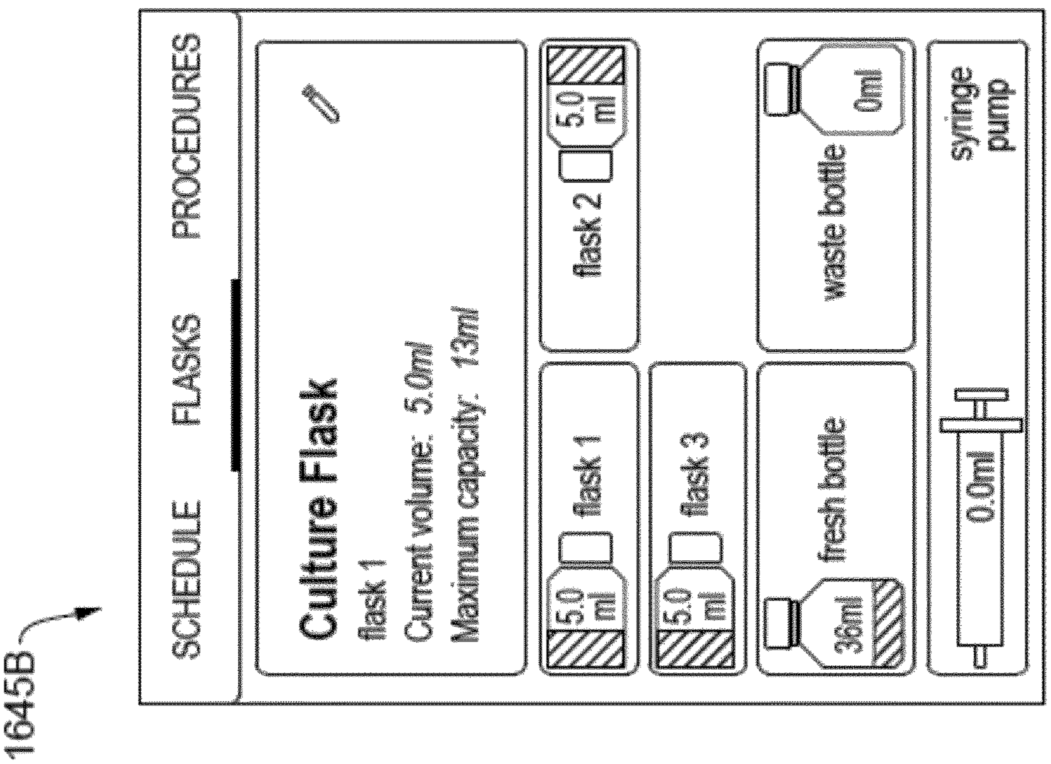
Figure 18:
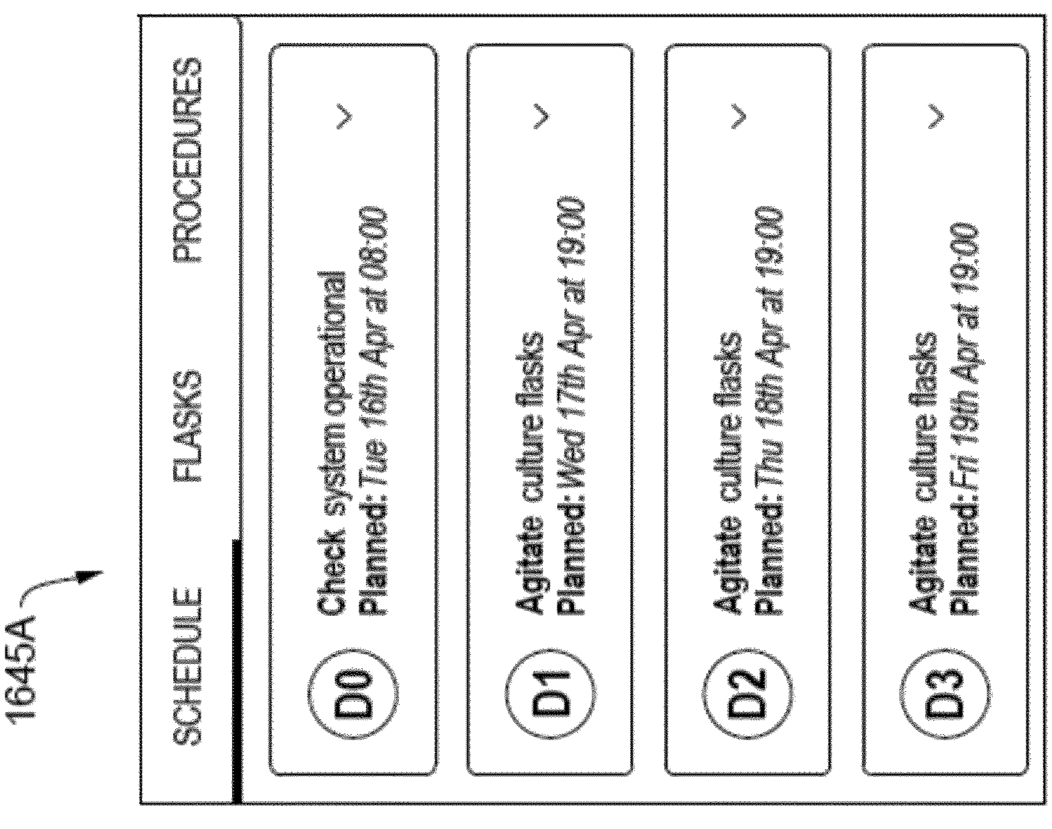
Figure 21:
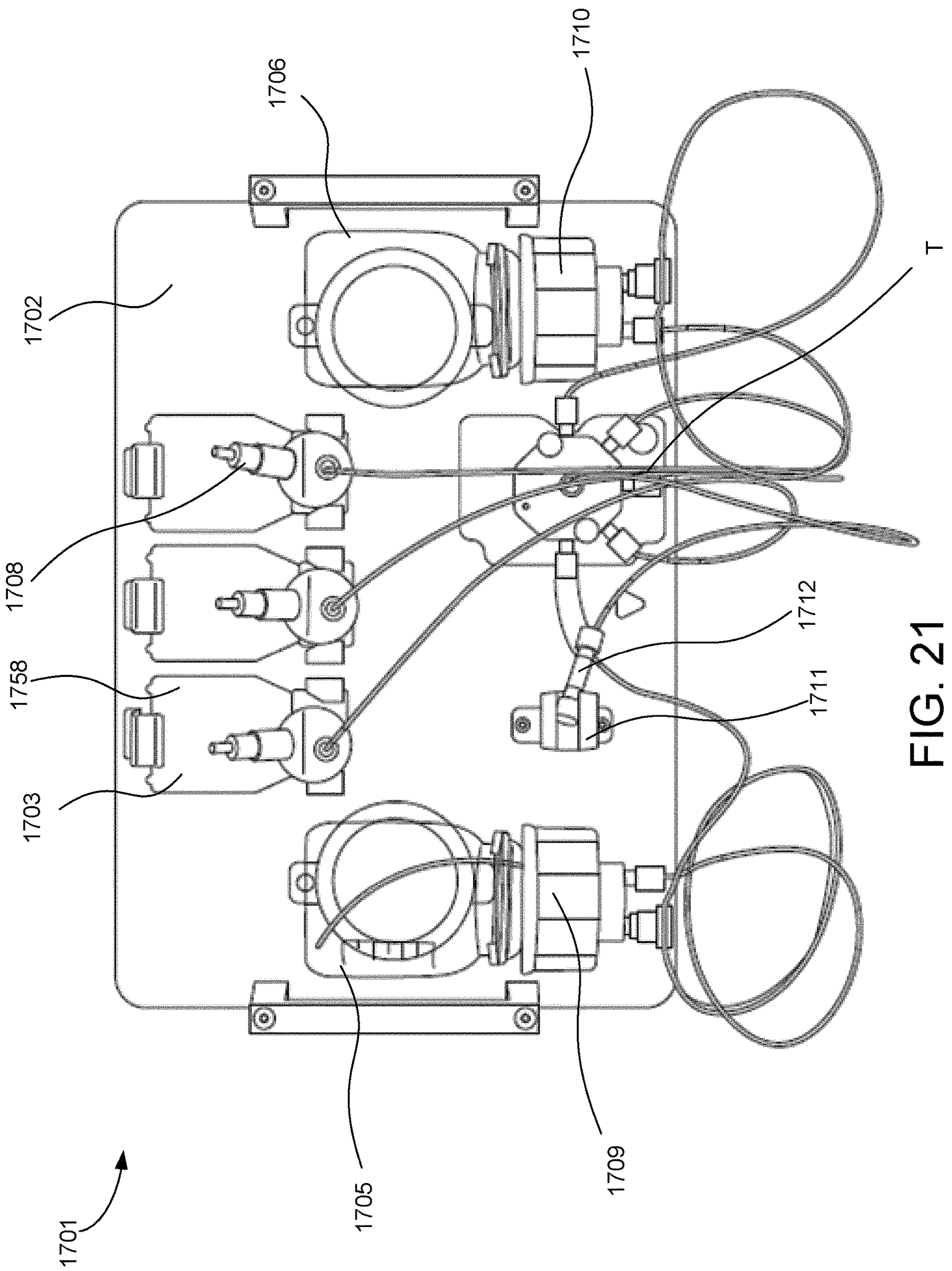
FIG. 21 is a top view of a tray assembly of a cell culturing system, according to an embodiment.

The cell culture application 1644 (also referred to as "application" or "cell culture app") is configured to communicate with the electronic control system. In some embodiments, the application 1644 can communicate directly with an electronic control system 1630 disposed on the base unit 1620. In some embodiments, the application 1644 can communicate with the electronic control system 1630 via a computing cloud environment. The application 1644 can be used to set-up, execute and monitor various steps of a cell culturing procedure using the cell culture system 1600. For example, the application 1644 can be used to cause the remote computing device 1643 to produce a series of prompts and information (e.g., via the user interface) to facilitate the cell culture methods described herein. Specifically, the cell culture application 1644 can cause the remote computing device 1643 to produce a graphical user interface (GUI) element that can include a prompt to enter various data for the cell culture procedure. FIGS. 18-20 are sample screenshots showing various GUI elements that can be produced by the remote computing device.

FIGS. 21-30 illustrate a method of preparing a cell culture system for use in a cell culturing procedure. The cell culture system 1700 illustrated in FIGS. 21-30 can include the same or similar components as other embodiments described herein (for example, the cell culturing system 1600 or the cell culturing system 2000), and therefore, some details of the cell culturing system 1700 are not described with respect to this embodiment.

Figure 22:
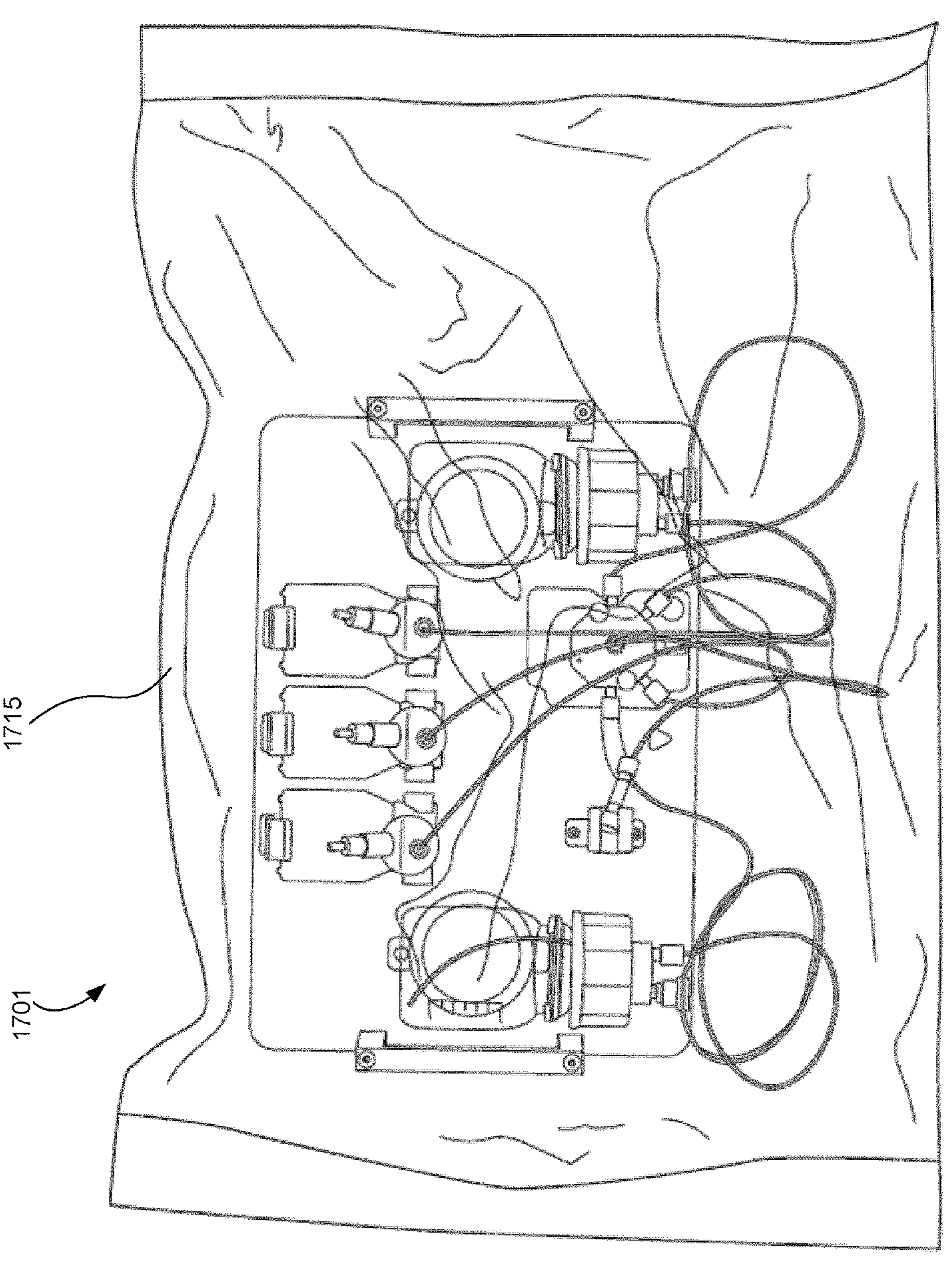
FIG. 22 is a top view of the tray assembly of FIG. 21 shown disposed within a protective overwrap.

The cell culturing system 1700 (also referred to herein as "system") includes a tray assembly 1701 and a base unit 1720 (see FIGS. 27-30). As shown, for example, in FIG. 21, the tray assembly 1701 includes a tray 1702 with the same or similar components disposed thereon as described above for other embodiments (e.g., the tray assembly 1601 or the tray assembly 2001). For example, the tray assembly 1701 includes a waste container 1706 coupled to a lid 1710, a reagent container 1705 coupled to a lid 1709 and three lids 1708 each configured to be coupled to a cell culture container (shown in FIGS. 25-27). The lids 1708, 1709 and 1710 can include a liquid exchange port (also referred to as "fluid port") and a gas exchange port as described above for previous embodiments. The tray assembly 1701 also includes a multiport valve 1707 with a master port and multiple selectable ports to which the lids 1708, 1709, 1710 can be selectively coupled via a length of tubing. The waste container 1706 and the reagent container are shown coupled in a horizontal orientation on holders 1704. The tray assembly 1701 also includes couplers 1703 to which the cell culture container can be coupled as described below. Below where the cell culture containers will be disposed are transparent portions (or openings/cutout portions) 1758 of tray 1702. In this embodiment, a syringe holder 1711 is provided and holds a syringe port 1712 thereto. The syringe port 1712 is also coupled to the multiport valve 1707 with tubing T. FIG. 22 illustrates the tray assembly 1701 encased within an overwrap 1715 to maintain the sterility of the tray assembly 1701 during transport and storage. This arrangement allows for the tray assembly 1701 to be assembled at a centralized facility, placed in the protective overwrap 1715 and sterilized. The sterilization can be performed by any suitable method, including radiation sterilization, sterilization via ethylene oxide (EtO), or electron beam sterilization. The prepackaged, sterilized tray assembly 1701 can then be stored until needed for a cell culturing procedure.

Figure 23:
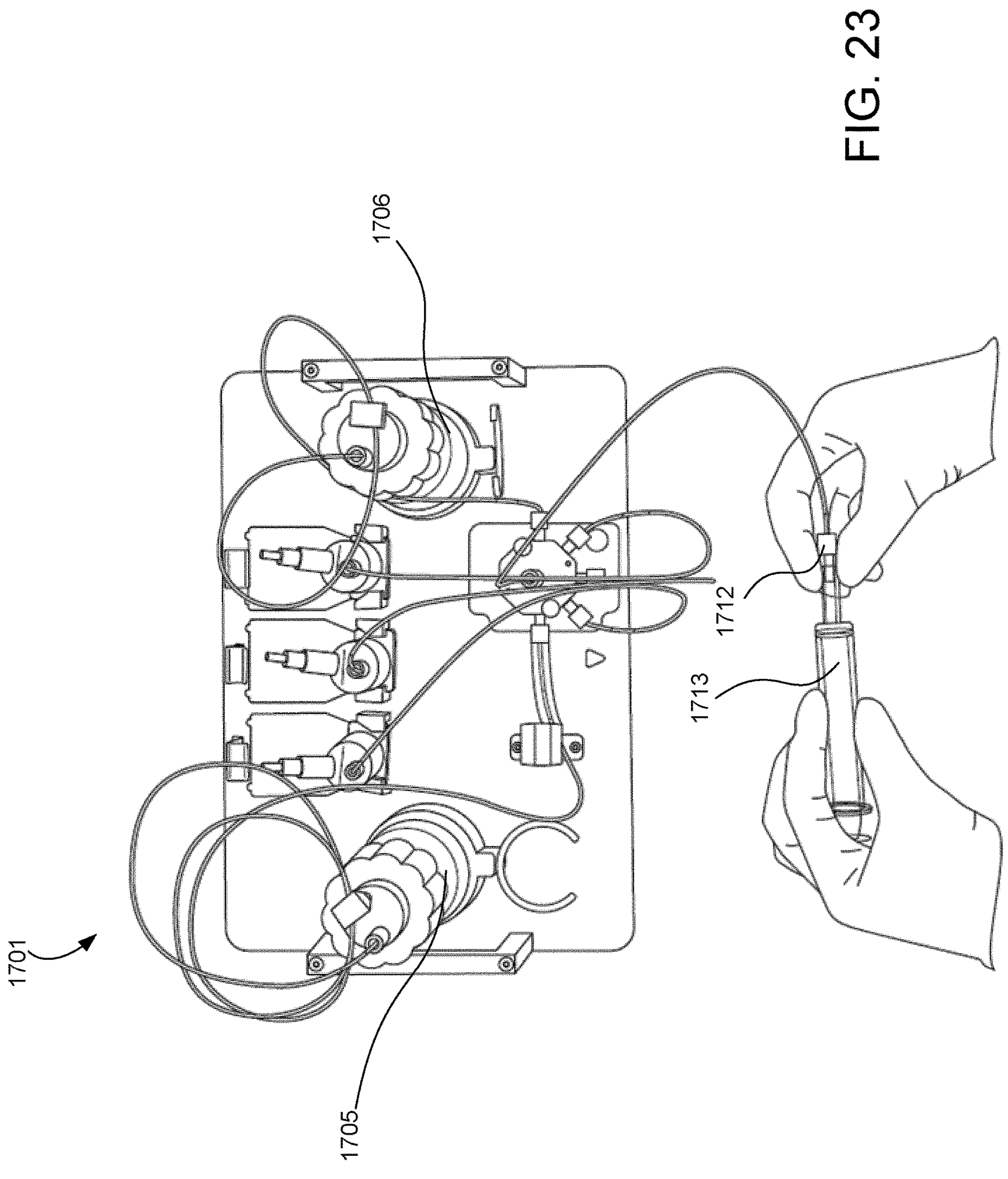
FIG. 23 is a top view of the tray assembly of FIG. 21 illustrating a fluid pump being coupled to the tray assembly.
Figure 24:
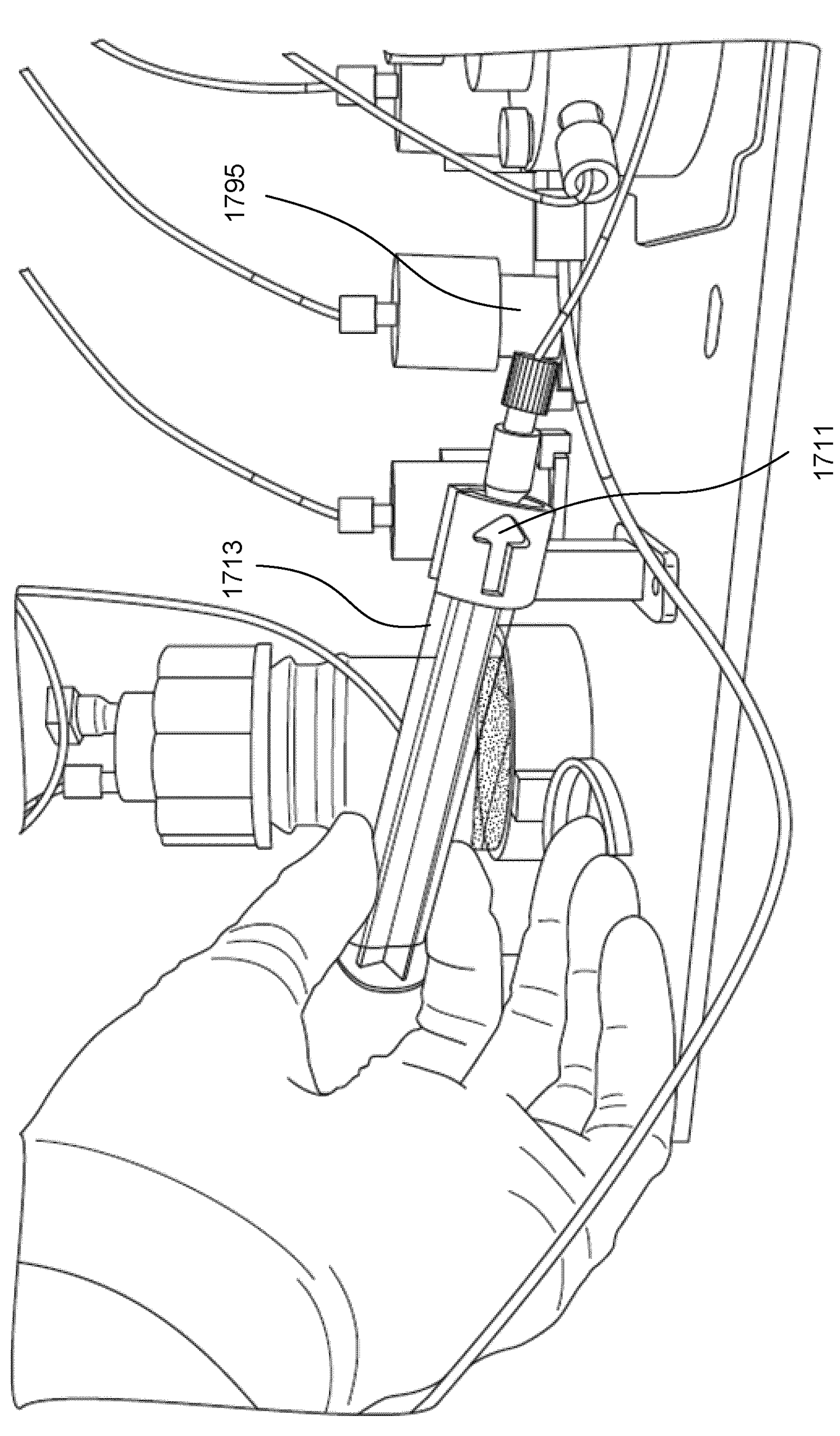
FIG. 24 is a perspective view of a portion of the tray assembly of FIG. 21 illustrating the fluid pump of FIG. 23 being coupled to the tray assembly.

The first steps in preparation for a cell culturing procedure is to prepare the cells and media (e.g., reagent) and to prepare the tray assembly 1701, which are done within an aseptic environment (e.g., laminar flow hood). The cells and media are placed within cell culture containers or vessels, which in this example, there are positions for three cell culture containers (1747, 1748, 1749 shown, for example, in FIGS. 26-27). The tray assembly 1701 is placed in the aseptic environment (e.g., a hood) and the overwrap 1715 is removed. The waste container 1706 and the reagent container 1705 can be moved to a vertical orientation within the holders 1704 as shown in FIG. 23, with the lids 1709 and 1710 in an upright position. In this example, the fluid pump 1713 is a syringe, which can be removed from an outer sterile wrap, and the port 1712 can then be coupled to the fluid pump 1713 as shown in FIG. 23. The fluid pump 1713 is then placed within the holder 1711 as shown in FIG. 24. In some embodiments, the fluid pump 1713 (e.g., syringe) is not included within the prepackaged tray assembly 1701, but rather is a separate component. In other embodiments, the fluid pump 1713 (e.g., syringe) is included within the prepackaged tray assembly 1701.

Figure 25:
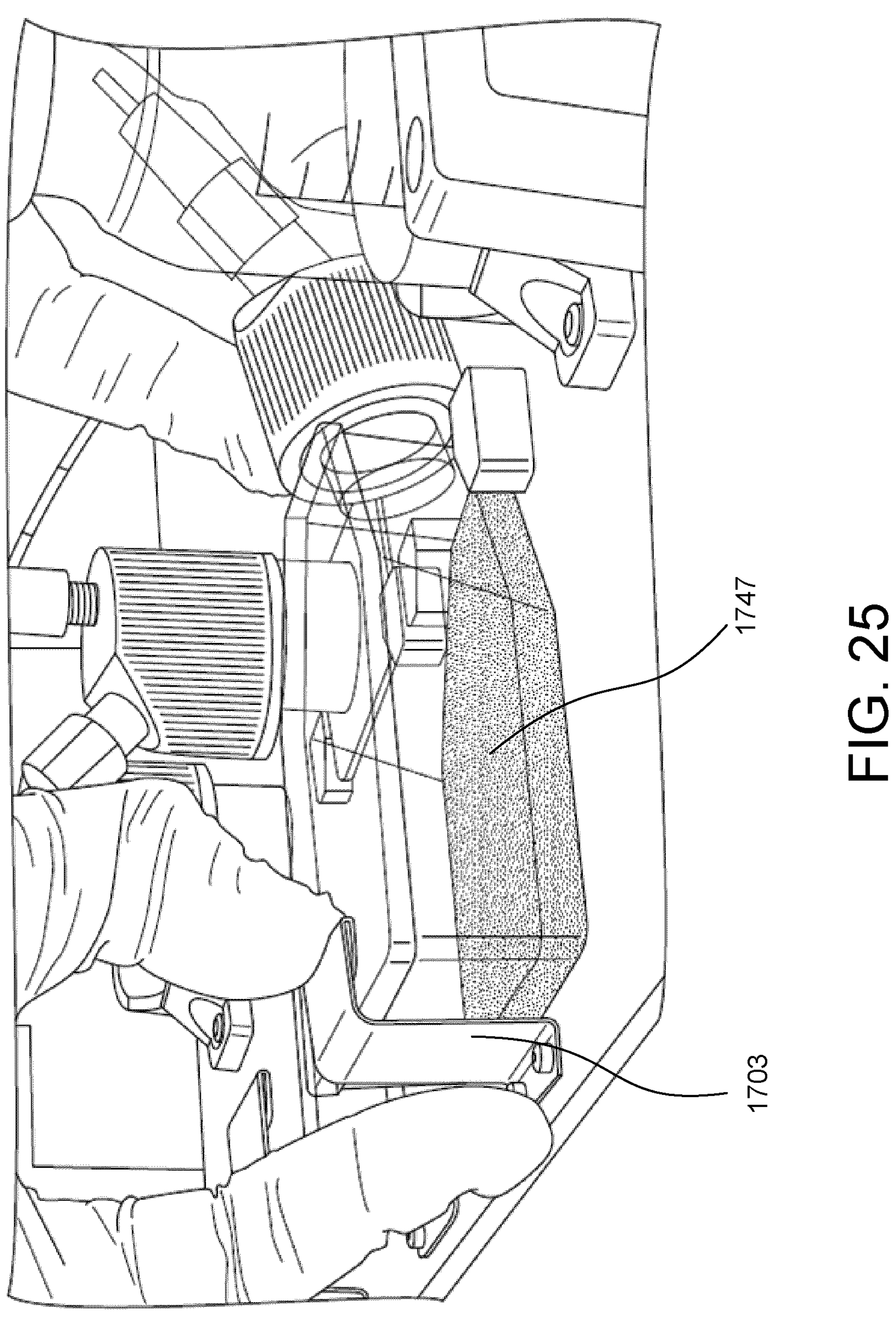
FIG. 25 is a perspective view of a portion of the tray assembly of FIG. 21 illustrating a cell culture container being coupled to the tray assembly.

After the cell culture container are loaded with the cells and initial amount of cell culture media, the lids 1708 are secured to the cell culture containers 1747, 1748, 1749 with the cells and medium therein. The lids 1708 are first removed from the shipping supports 1795 (see FIG. 24) to which they are coupled. The shipping supports 1795 are sized and configured to be received within the interior of the lids 1708 to secure the lids 1708 during shipment, storage and initial setup. This arrangement reduces the likelihood of undesired movement during the initial setup and possible contamination of the interior portion of the lids. The lids 1708 are then coupled to their respective containers while remaining fluidically coupled to the multiport valve 1707). The containers 1747, 1748, 1749 are coupled to the couplers 1703 such that the container vessels are disposed in a horizontal position as shown in FIG. 25. In this position, the bottom surface of the cell culture containers 1747, 1748, 1749 is aligned with the transparent portion 1758 of the tray.

Figure 26:
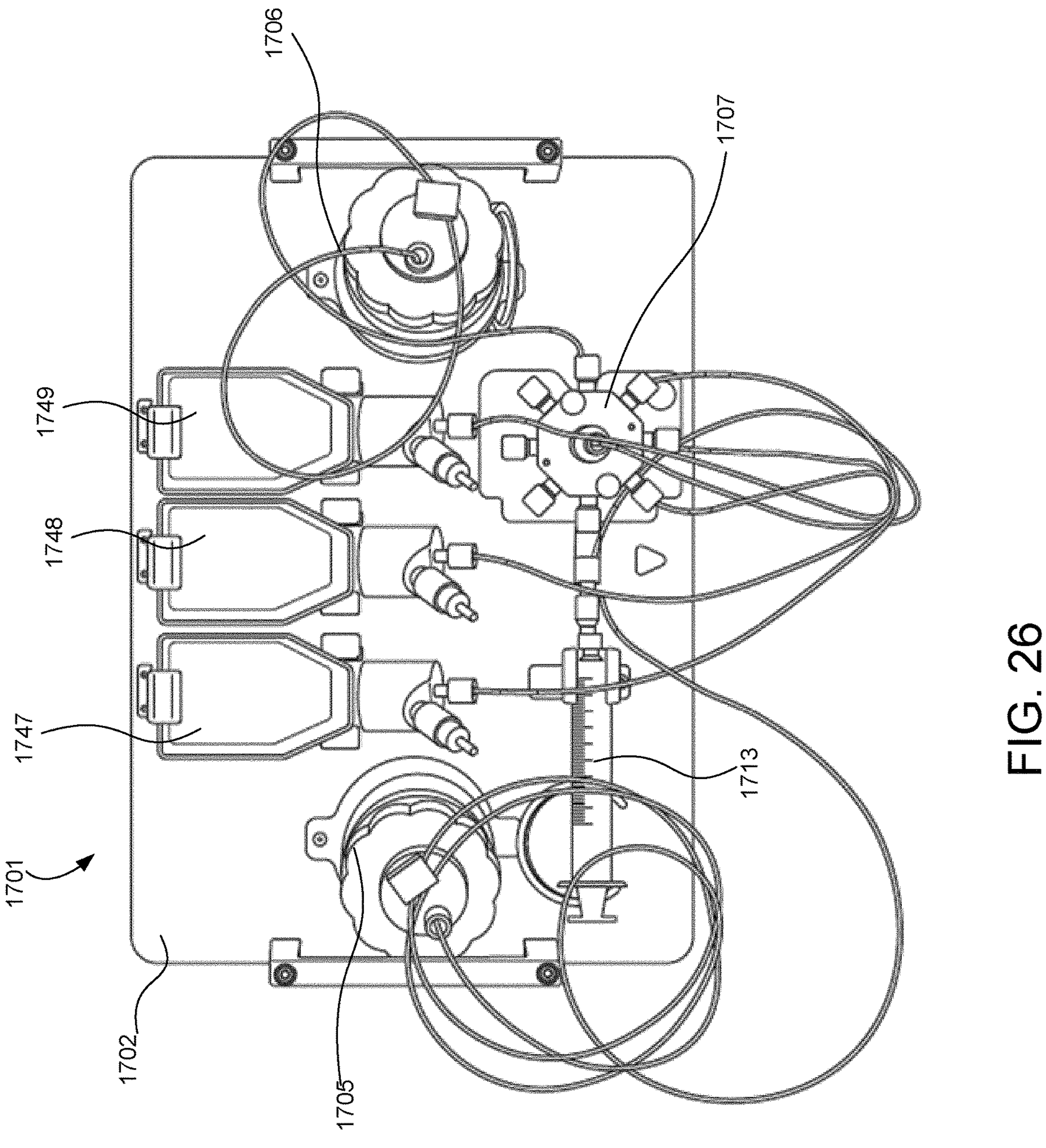
FIG. 26 is a top view of the tray assembly of FIG. 21 showing the fluid pump of FIG. 23 and three cell culture containers coupled to the tray assembly.
Figure 27:
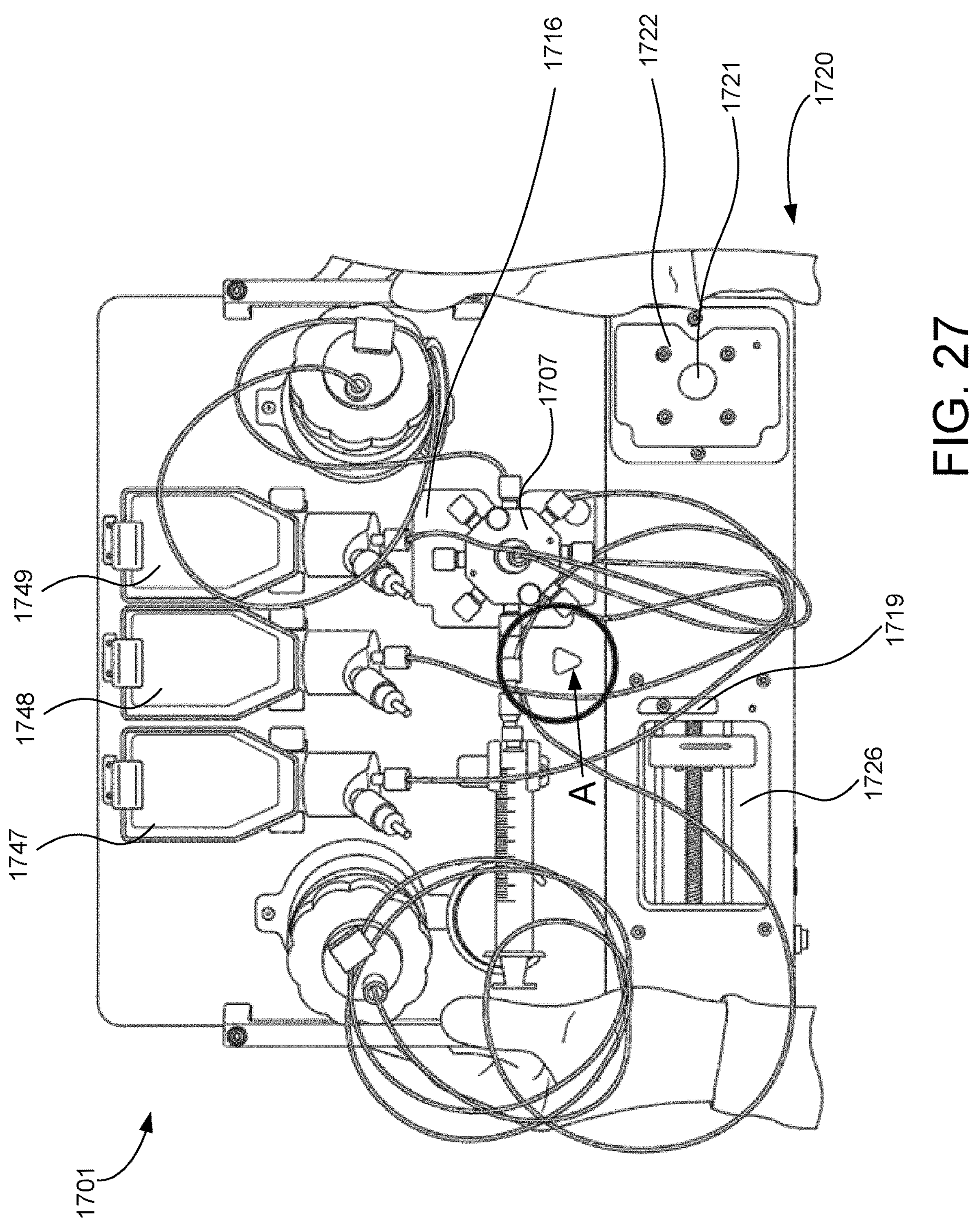
FIG. 27 is a top view of the tray assembly of FIG. 21 shown couple to a base unit, according to an embodiment.
Figure 28:
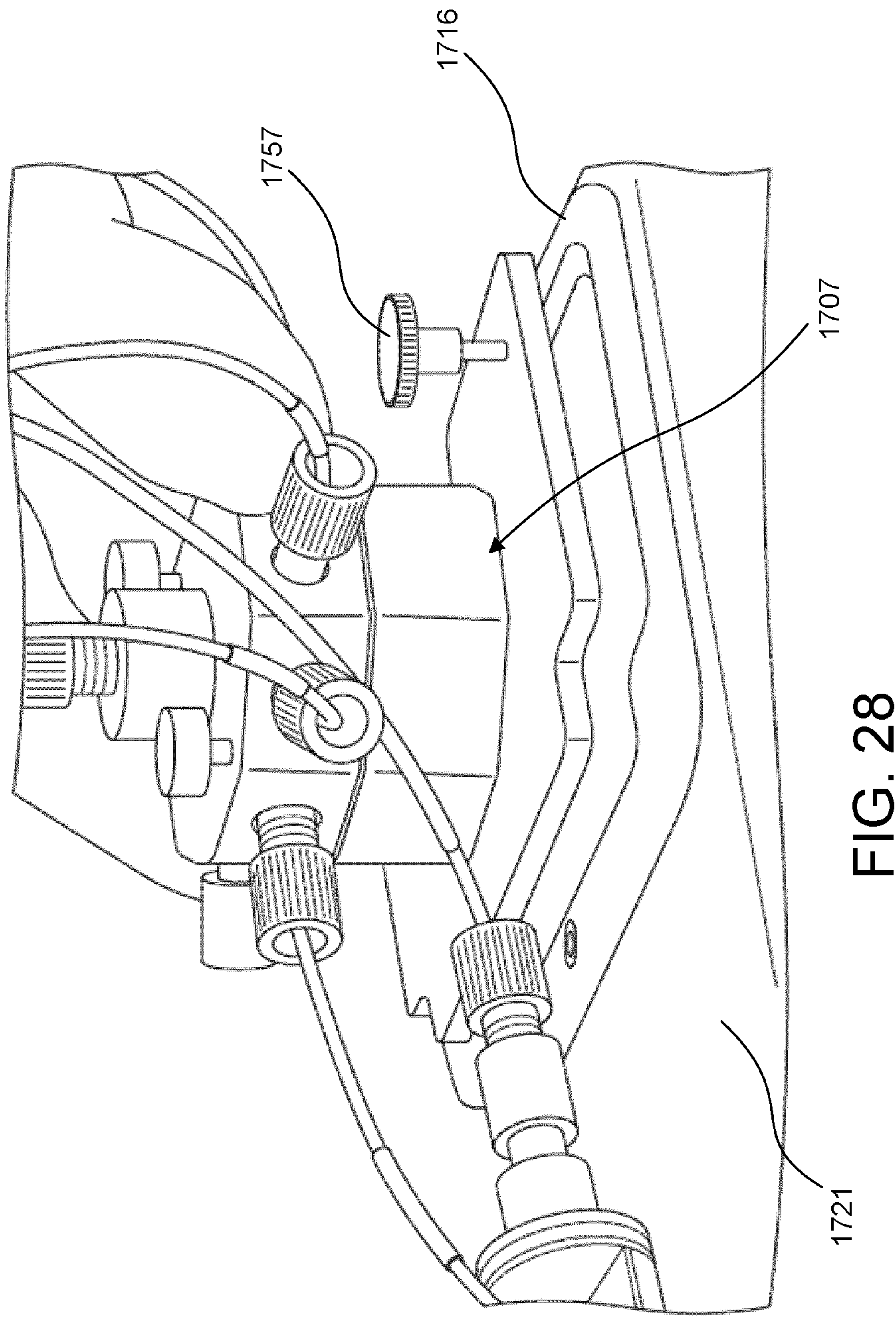
FIG. 28 is a perspective view of a multiport valve being couple to the base unit of FIG. 27.
Figure 29:
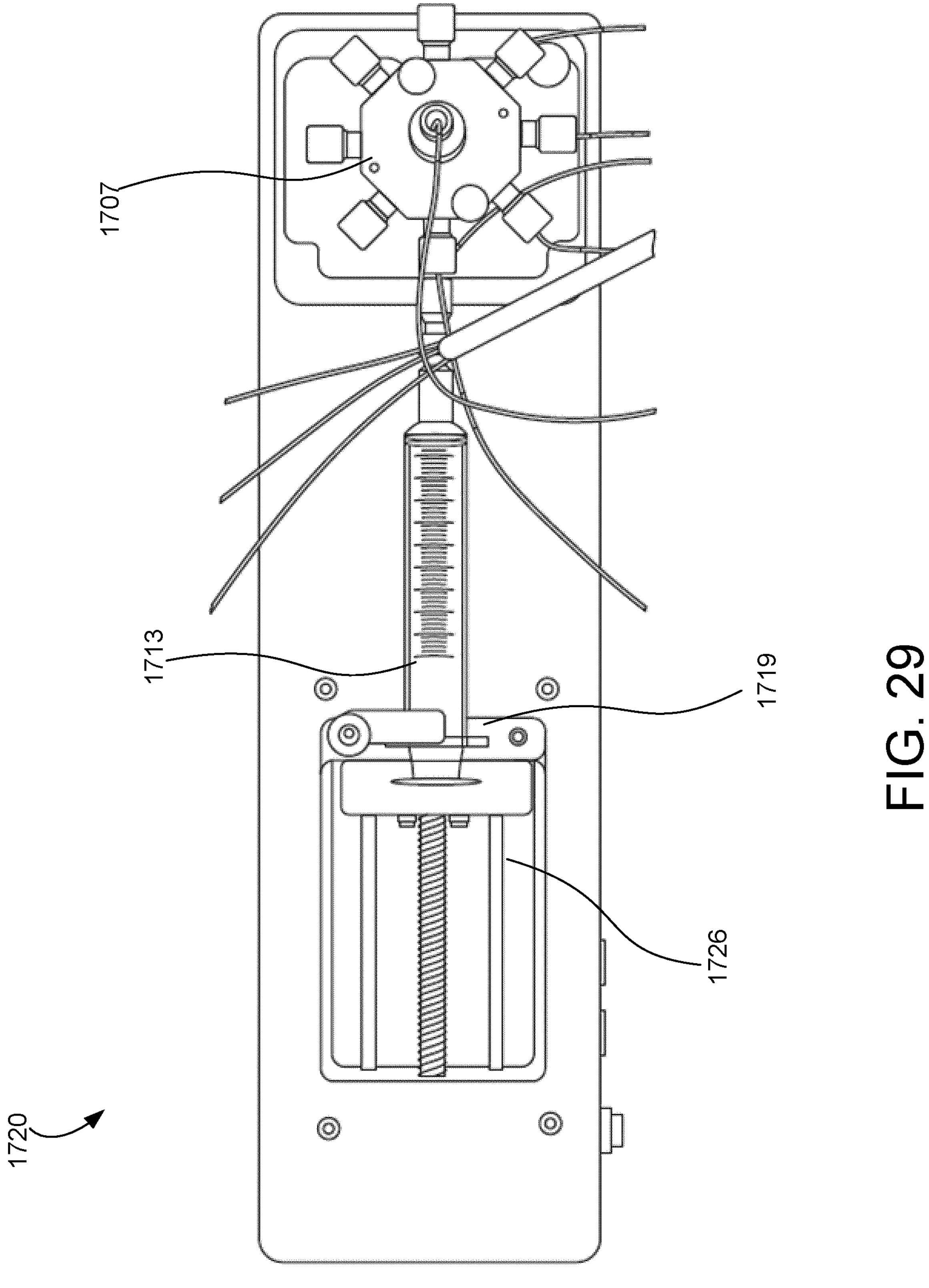
FIG. 29 is a top view of a portion of the base unit of FIG. 27.
Figure 30:
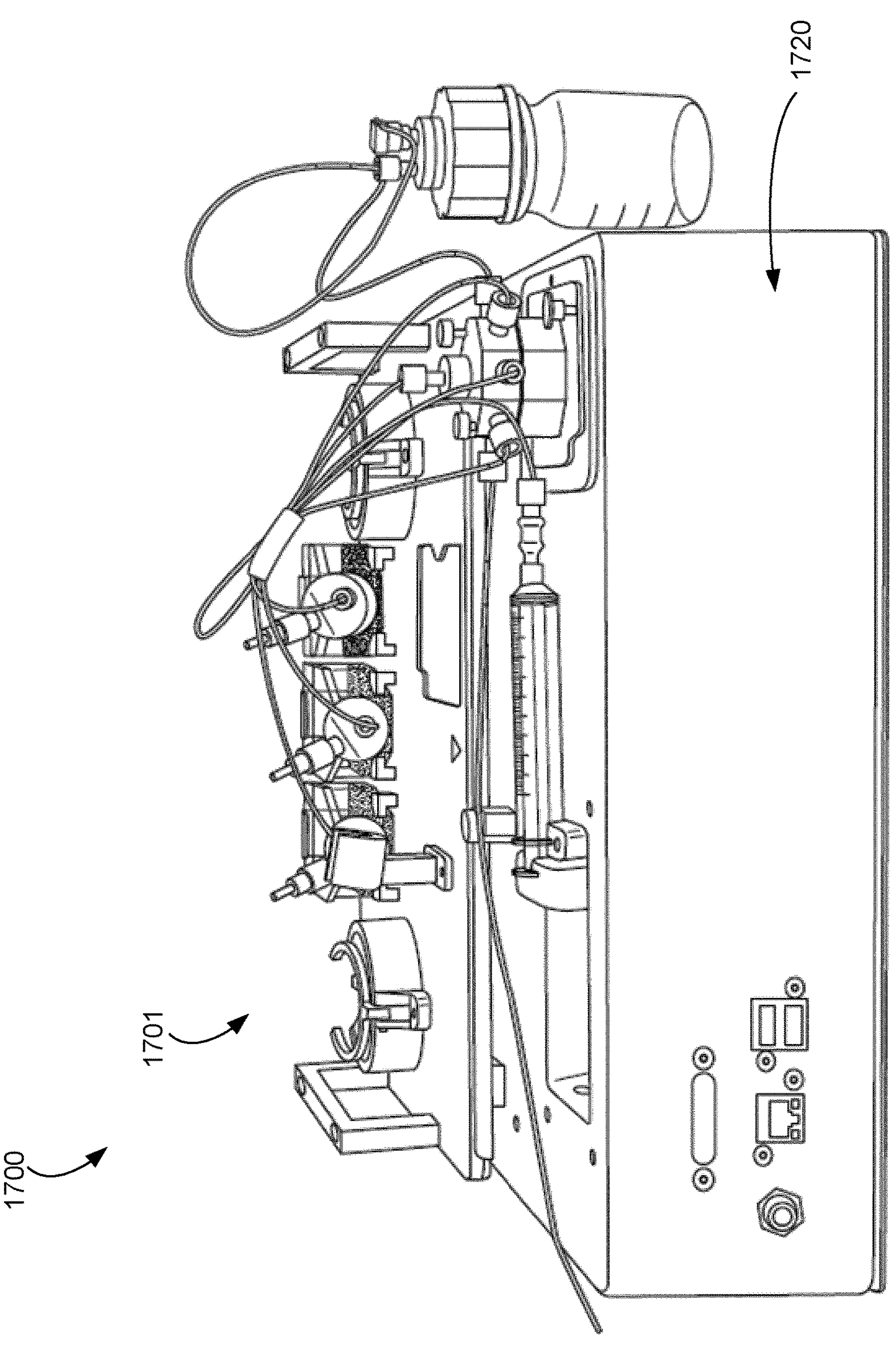
FIG. 30 is a perspective view of the tray assembly of FIG. 21 couple to the base unit of FIG. 27.

With the tray assembly 1701 fully assembled, as shown in FIG. 26, the tray assembly 1701 can be placed on the base unit 1720 as shown in FIG. 27. This can be done outside of the aseptic environment as components (e.g., containers, lids, valve, syringe) are fluidically coupled in a closed system. The tray assembly 1701 should be oriented with the arrow (labeled A and encircled) on the tray 1702 pointing towards the base unit 1720 as shown in FIG. 27. As also shown in FIG. 27, the base unit 1720 includes a pump actuator 1726, a valve connector 1721 and a valve actuator 1722. In this embodiment, the multiport valve 1707 is removable from the tray 1702 and can be coupled to the base unit 1720. More specifically, a mounting portion 1716 of the multiport valve 1707 can be detached from the tray 1702 by removing the fastener 1757 and attaching the mounting portion 1716 to a mating valve connector 1722 of the base unit 1720 with the same or a different fastener 1757, as shown in FIGS. 28 and 29. The fluid pump 1713 (e.g., syringe) is decoupled from the tray assembly 1701 and coupled to a holder 1719 of the base unit 1720 as shown in FIG. 29. This operation is performed while the fluid pump 1713 remains fluidically coupled to the multiport valve 1707, thereby maintain the closed system. The holder 1719 can be part of a fluid pump portion (e.g., 1627) of the base unit 1720 as described above for system 1600. The waste container 1706 and the reagent container 1705 can be removed from the tray 1702 and placed near the base unit 1720, as shown in FIG. 30 (or in any other suitable location).

Figure 58:
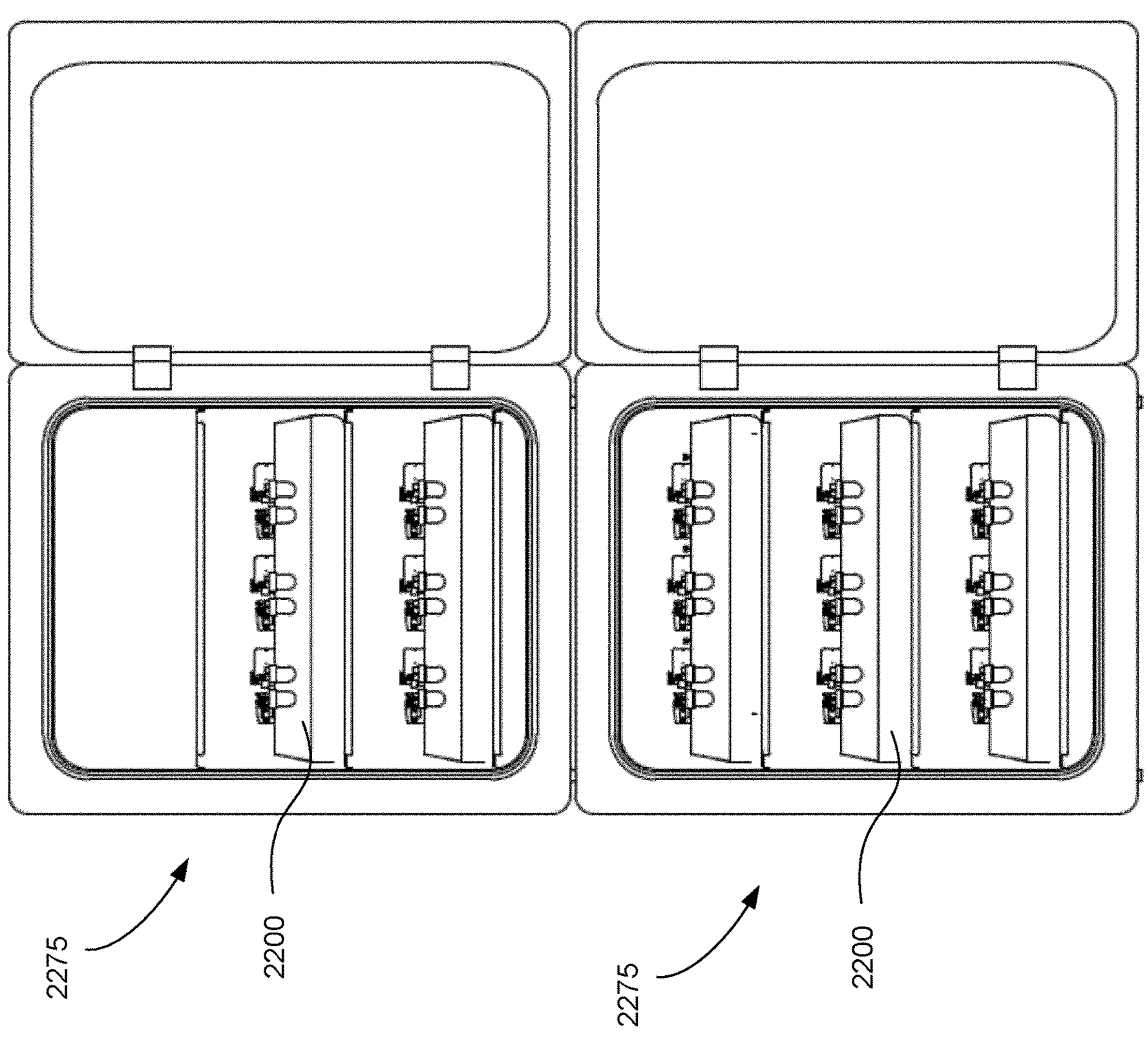
FIG. 58 is a front view of a pair of incubators with multiple cell culturing systems disposed on shelves therein.

The base unit 1720 and the tray assembly 1701 can then be moved into an incubation environment (e.g., an incubator 2275 as shown in FIG. 58) to facilitate the cell growth in a temperature-controlled environment if the tray assembly 1701 is coupled to the base unit 1720 outside of the incubator. In some embodiments, the base unit 1720 is disposed within the incubator when the tray assembly 1701 is coupled thereto.

Figure 31:
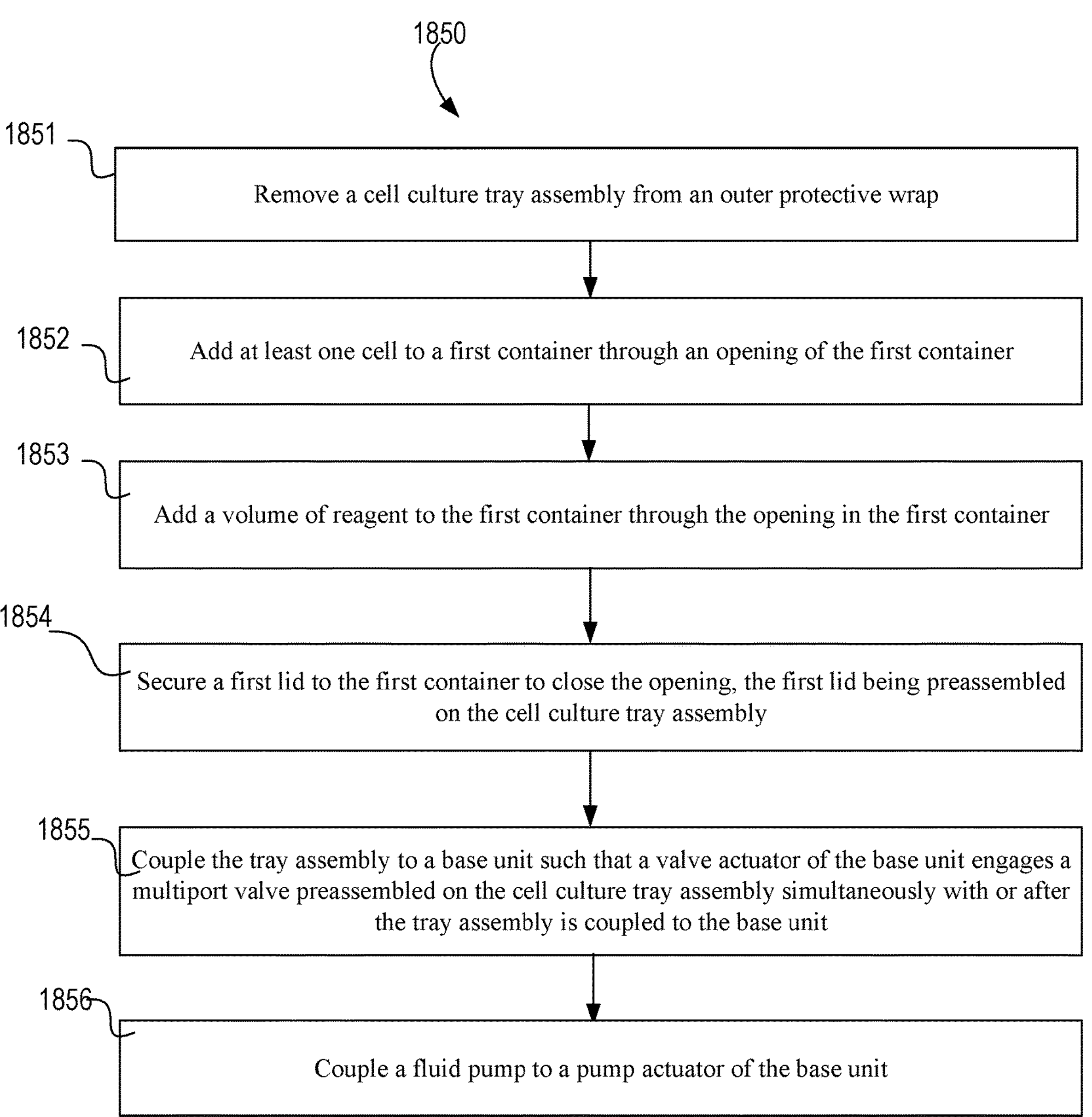
FIG. 31 is a flowchart illustrating a method of preparing a cell culturing system for use in a cell culturing procedure, according to an embodiment.

FIG. 31 is a flowchart illustrating a method 1850 of preparing a cell culture system for use in a cell culturing procedure. The method 1850 can be performed with any of the cell culture systems described herein, such as, for example, the cell culture system 1700 described above with reference to FIGS. 23-30. At 1851, a cell culture tray assembly is removed from an outer protective wrap. The tray assembly can be any of the tray assemblies described herein and includes a tray, a first lid, a second lid, and a multiport valve. The first lid is coupled to the tray and configured to be removably coupled to a first container, and the second lid is coupled to the tray and configured to be removably coupled to a second container. The multiport valve is coupled to the tray and includes a master port and multiple selectable ports. A first selectable port is aseptically coupled to the first liquid exchange port of the first lid, and a second selectable port is aseptically coupled to the second liquid exchange port of the second lid. As described herein, by having the lids precoupled to the appropriate ports, fewer operations are performed during the initial setup, thereby reducing the likelihood of contamination and error. At 1852, at least one cell sample is added to a first container through an opening of the first container and at 1853, a volume of reagent (e.g., a cell culture media) is added to the first container through the opening of the first container. At 1854, the first lid is coupled to the first container to close the opening. In some embodiments, the second lid can optionally be coupled to the second container. At 1855, the tray assembly is coupled to a base unit. In some embodiments, when the tray assembly is coupled to the base unit, a valve actuator of the base unit simultaneously engages the multiport valve of the tray assembly. In some embodiments, the valve actuator engages the multiport valve after the tray assembly is coupled to the base unit. At 1856, a fluid pump is coupled to a pump actuator of the base unit. For example, the fluid pump can be a syringe or a peristaltic pump that can be coupled the base unit. After preparation of the cell culturing assembly, any of the methods of cell culturing described herein can be performed.

Figure 32:
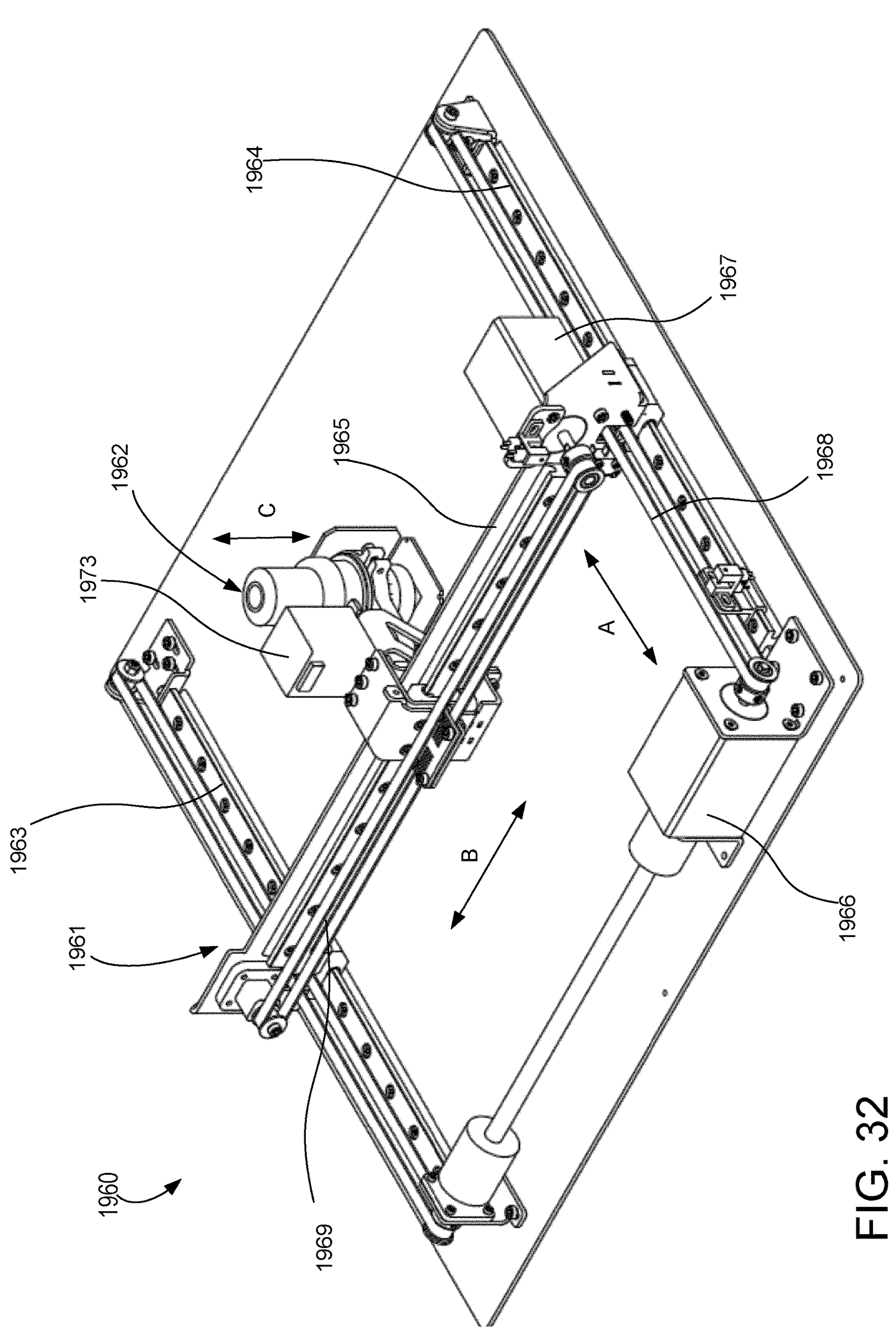
FIG. 32 is a perspective view of an imaging device of a base unit of a cell culturing system, according to an embodiment.
Figure 33:
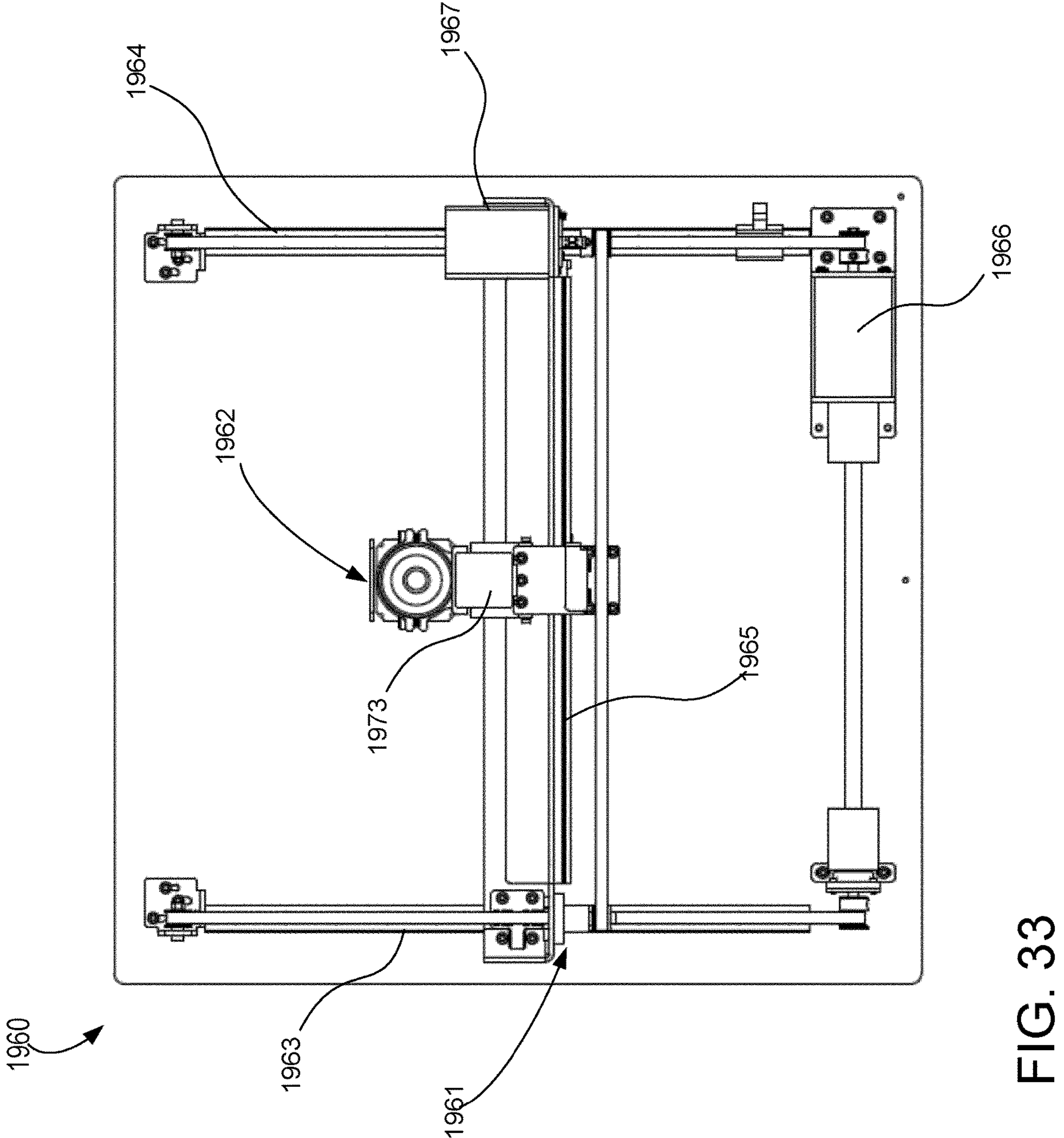
FIG. 33 is a top view of the imaging device of FIG. 32.
Figure 34:
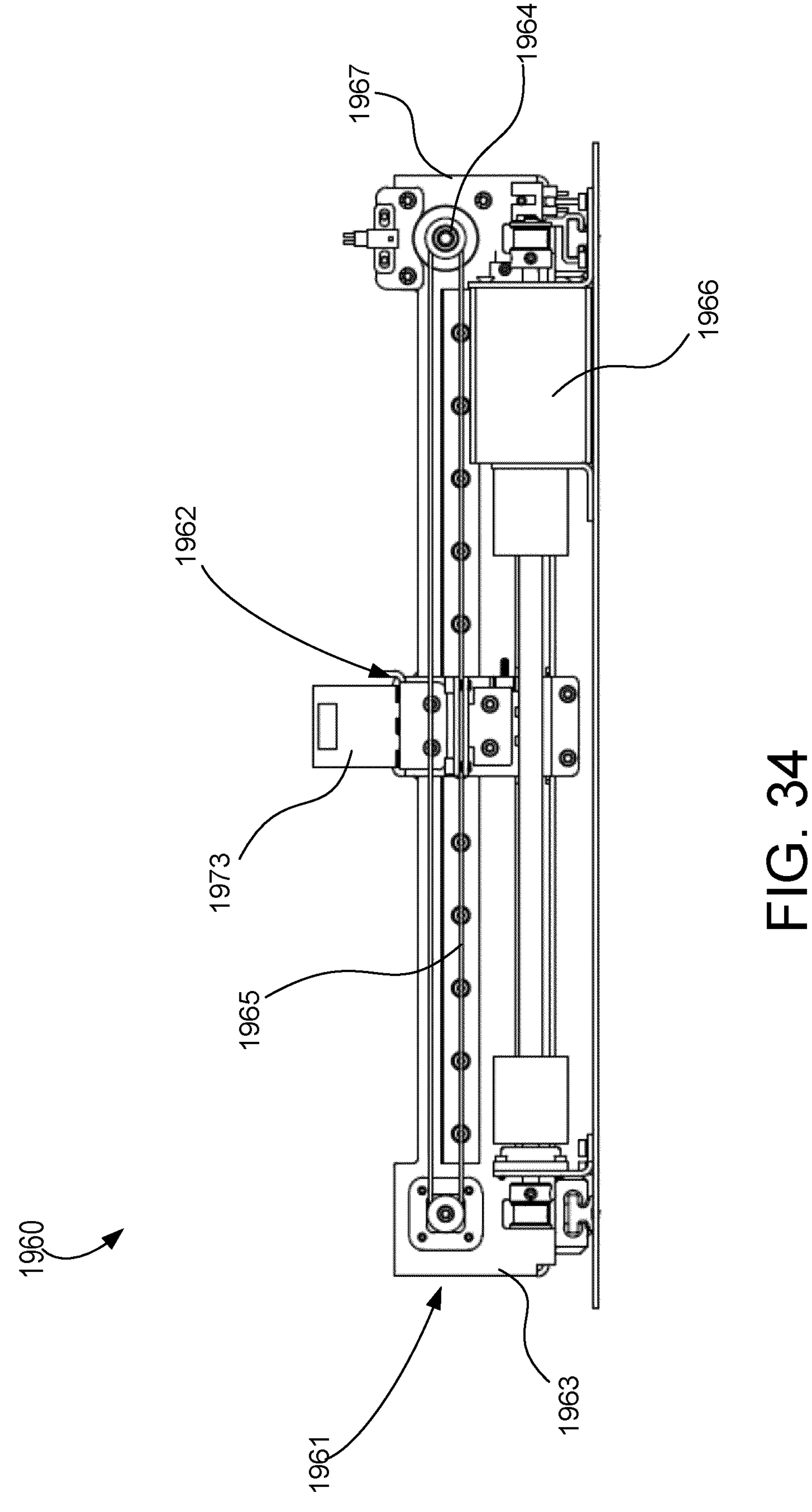
FIG. 34 is a side view of the imaging device of FIG. 32.
Figure 35:
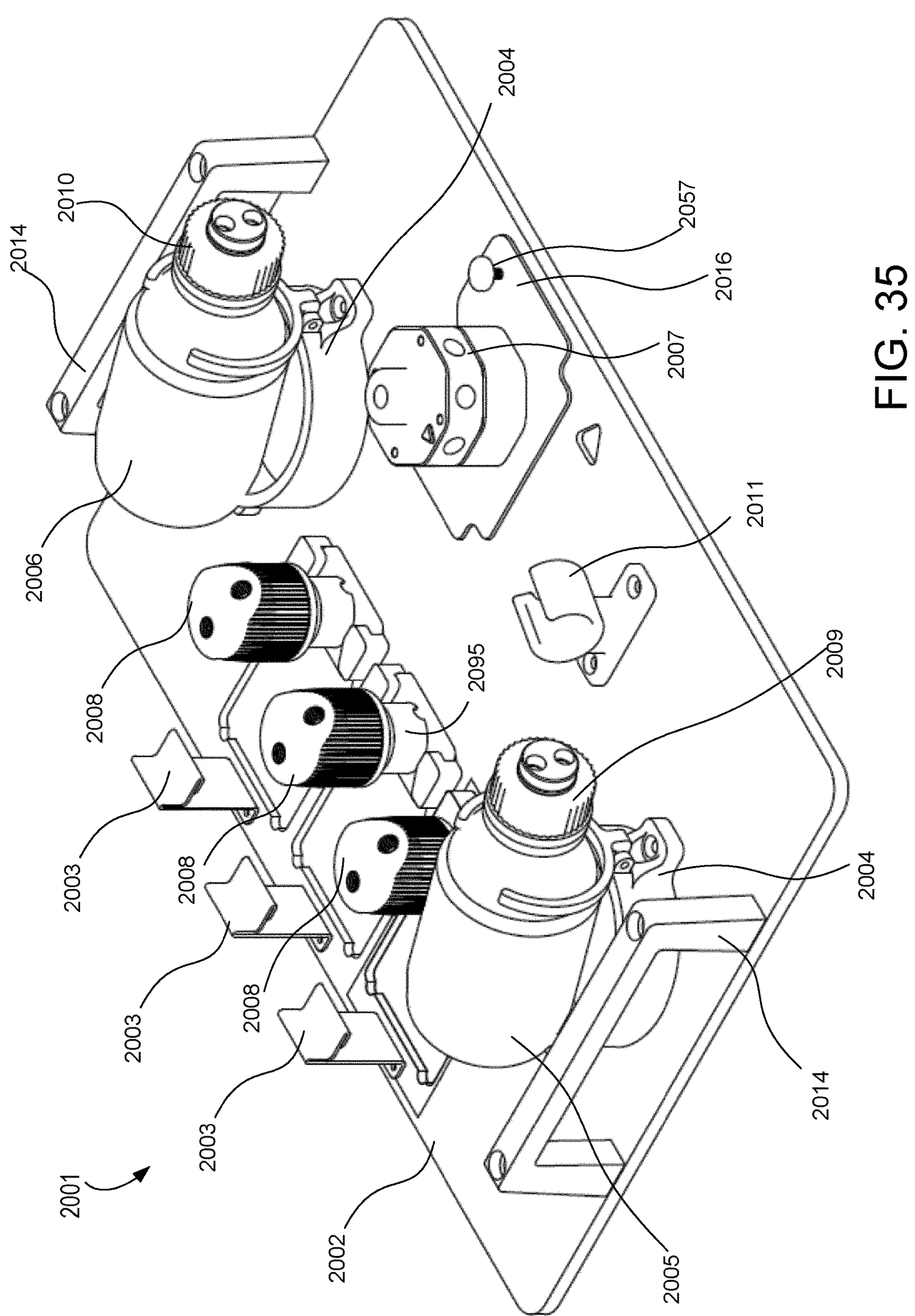
FIG. 35 is a perspective view of a tray assembly of a cell culturing system, according to another embodiment.
Figure 36:
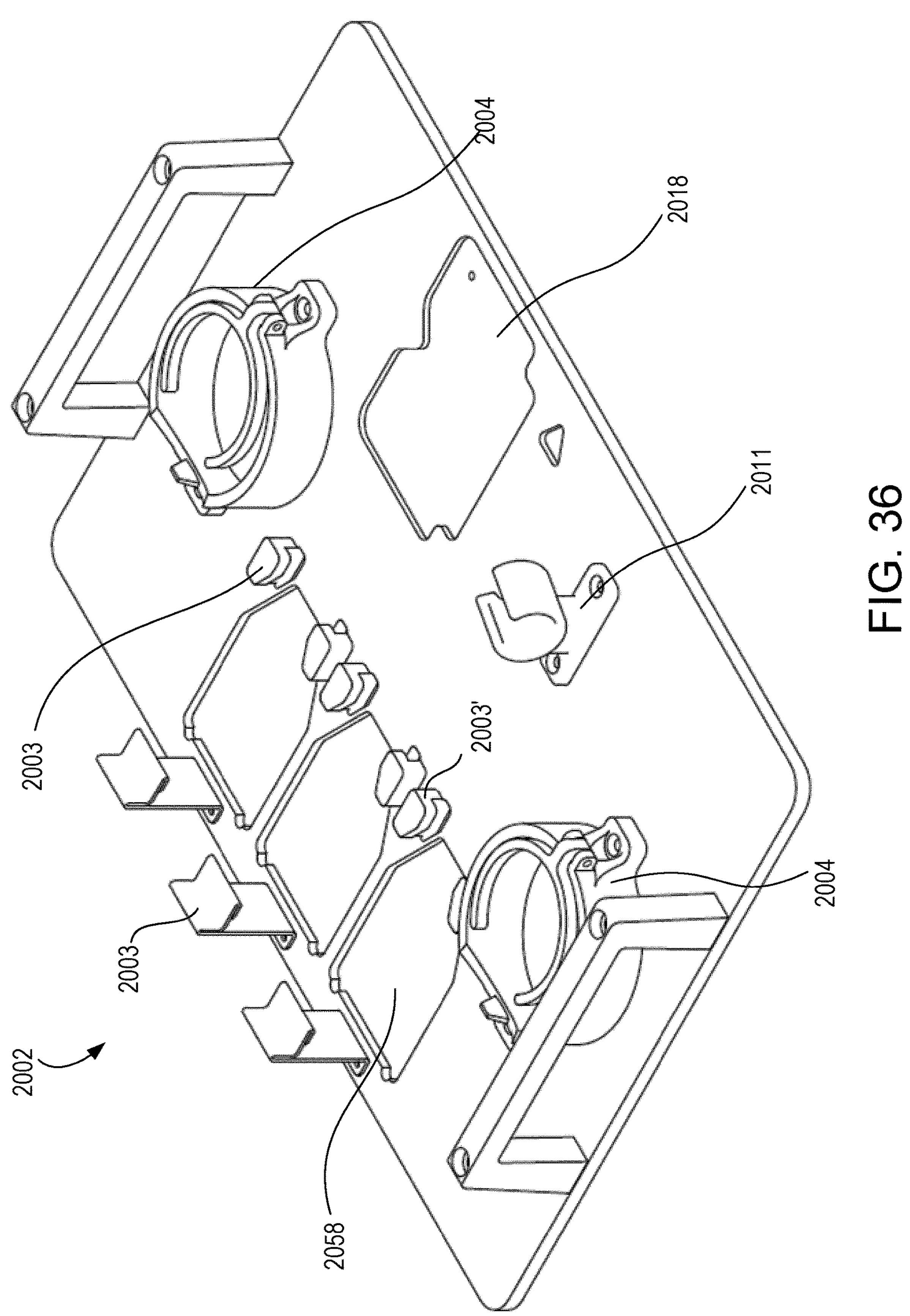
FIG. 36 is a perspective view of a portion of the tray assembly of FIG. 35 with removable components removed.

As described above, in some embodiments, an automated cell culture system can include an imaging device that includes a microscope that may be moved relative to the housing of a base unit to image the contents of any cell culture vessel of the automated cell culture system. In some embodiments, the microscope may be mounted on a mechanical system that is capable of moving the microscope into alignment with the cell culture vessels or a cell counting chip. The mechanical system can be any suitable assembly for moving the imaging device, such as a 2-dimensional or 3-dimensional gantry mechanism or a hinged robotic arm mechanism. FIGS. 32-34 illustrate an example embodiment of such an optical imaging system (also referred to as a microscope imaging device). The microscope imaging device 1960 can be mounted within the housing of any of the base units of the cell culture systems described herein. For example, the microscope imaging device 1960 can be included within the base unit 1720, the base unit 2020, or any other base units described herein. The microscope imaging device 1960 includes an imaging device 1962 that can view through a window or transparent portion in the top of the base unit and through cut outs (or transparent portions) in both the tray (see, e.g., the transparent portion 1758 described herein) and any shaking platform (e.g., support for a tray in contact with an agitator). Thus, the microscope imaging device 1960 can be used to collect information related to the contents of a cell culture container and/or within a cell counting chip as described herein. For example, in some embodiments, the microscope imaging device 1960 can obtain images of a cell culture container and/or a cell counting chip during a cell culturing procedure, and the images can be used to determine, for example, the density of the contents to determine a quantity of cells within the container (for example, for suspension cells), or a percentage confluence (i.e., percentage of coverage of the container area with cells) in the case of, for example, adherent cells.

The microscope imaging device 1960 includes a gantry system 1961 that provides for movement of the imaging device 1962 in multiple directions relative to the housing of the base unit (not shown in FIGS. 32-34). The gantry 1961 includes a set of rails 1963, 1964 and a cross-rail 1965. The cross-rail 1965 is mounted to and can move back and forth relative to the rails 1963 and 1964 in the direction of arrow B. More specifically, a first motor 1966 can drive a belt 1968 to which the cross-rail 1965 is operatively coupled. The image device 1962 is movably mounted to the cross-rail 1965 and is operatively coupled to a belt 1969 that is driven by a second motor 1967 to move the imaging device 1962 in a direction of arrow B. The imaging device 1962 is further moveable in a direction of arrow C via a motor 1973 for focusing the imaging device 1960. Thus, during operation, the imaging device 1962 can be moved in the direction of arrow A via the movement of the rail 1965 relative to the rails 1963 and 1964, in the direction of arrow B via its movement relative to the rail 1966, and in the direction of arrow C relative to the base of the imaging device 1960 to be positioned at a desired location relative to a cell culture container and/or a cell counting chip.

A light(s) or light source (not shown) can be mounted above the tray assembly of the system on another multi-axis gantry which allows it to be controlled to move to the same position as the microscope within the base unit. In some embodiments, the light source can be operatively coupled to the same gantry (e.g., gantry 1961) as the microscope such that the microscope 1962 and light source can be moved together. In some embodiments, the microscope imaging device 1960 can be controlled by any of the electronic control systems and according to any of the methods described herein. For example, in some embodiments, the microscope imaging device 1960 (and any associated light source) can be controlled to automatically image a cell culture container (e.g., to produce a sensor output associated with the cells within the container). A cell sensor module of an electronic control system (e.g., the electronic control system 1630) or any other electronic control system described herein can receive the sensor output and produce a signal associated with a quantity of cells within the container (e.g., cell density or a percentage confluence). Based on this information the electronic control system can then produce one or more signals (e.g., valve control signals, pump control signals, agitator signals, or the like) to cause the transfer of the cells from within the cell culture container to another container within the system. Similarly stated, in some embodiments, the microscope imaging device 1960 can provide input for automated cell passaging or cell harvesting operations.

FIGS. 35-44 illustrate another embodiment of a cell culturing system 2000, for use in a cell culturing procedure. The cell culture system 2000 can include the same or similar components as other embodiments described herein (including the cell culture system 1700) and can have the same or similar functions as the previous embodiments described herein, and therefore, some details of the cell culturing system 2000 are not described with respect to this embodiment.

The cell culturing system 2000 (also referred to herein as "system") includes a tray assembly 2001 (see, e.g., FIGS. 35-37) and a base unit 2020 (see, e.g., FIGS. 38-44). As shown, for example, in FIG. 35, the tray assembly 2001 includes a tray 2002 with handles 2014 and with the same or similar components disposed thereon as described above for previous embodiments (e.g., tray assemblies 1601 and 1701). For example, the tray assembly 2001 includes a waste container 2006 coupled to a lid 2010, a reagent container 2005 coupled to a lid 2009 and three lids 2008 configured to be coupled to a cell culture container (not shown in FIGS. 35-44). The lids 2008, 2009 and 2010 can include a liquid exchange port (also referred to as "fluid port") and a gas exchange port as described above for previous embodiments. The tray assembly 2001 also includes a multiport valve 2007 with a master port and multiple selectable ports to which the lids 2008, 2009, 2010 can be selectively coupled via a length of tubing (not shown). For example, as described herein, the lids 2008, 2009, 2010 can be coupled to the multiport valve 2007 preassembled and within the overwrap. FIGS. 35-44 do not show the tubing and connections between the various components and the multiport valve 2007 for illustration purposes. The multiport valve 2007 is coupled to the tray 2002 via a mounting portion 2016 that matingly couples to and fits within a mounting pocket 2018 of the tray 2002 in a puzzle-like manner. For example, the multiport valve 2007 can be coupled to the mounting pocket 2018 with a fastener 2057.

Figure 37:
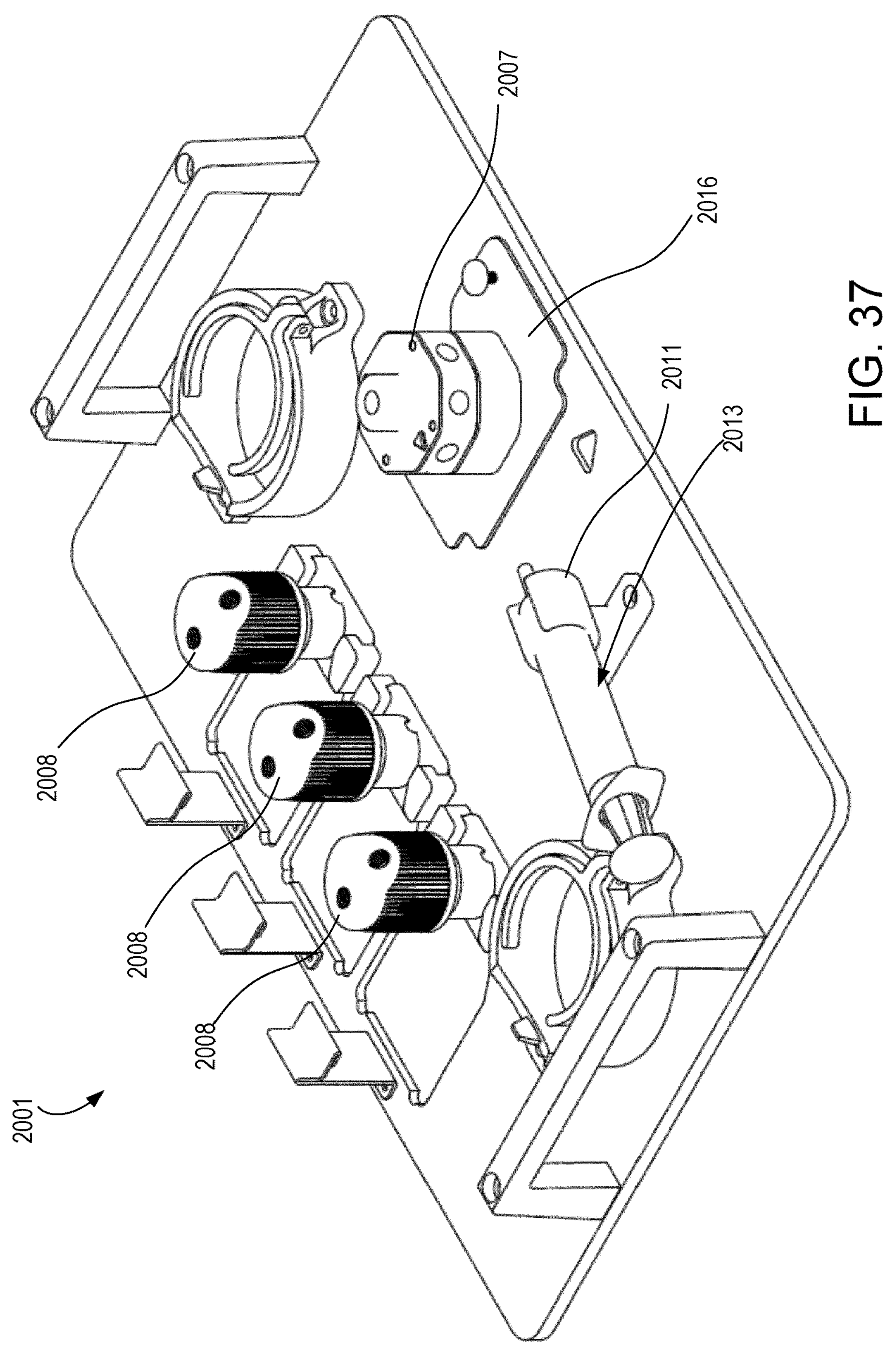
FIG. 37 is a perspective view of a portion of the tray assembly of FIG. 35. Showing a multiport valve, lids and a fluid pump coupled to the tray.
Figure 38:
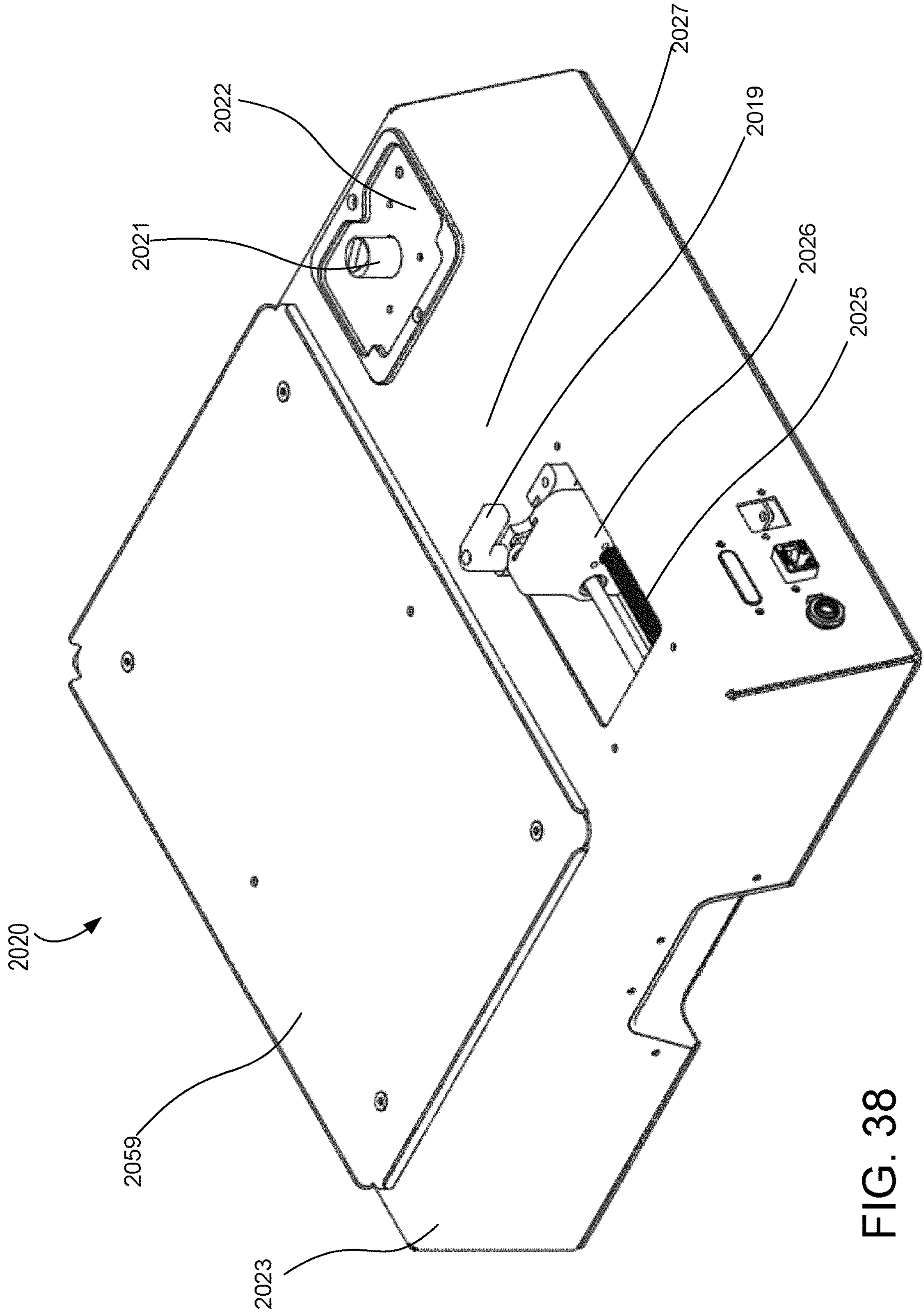
FIG. 38 is a perspective view of a base unit of the cell culturing system that can be used with the tray assembly of FIG. 35.
Figure 39:
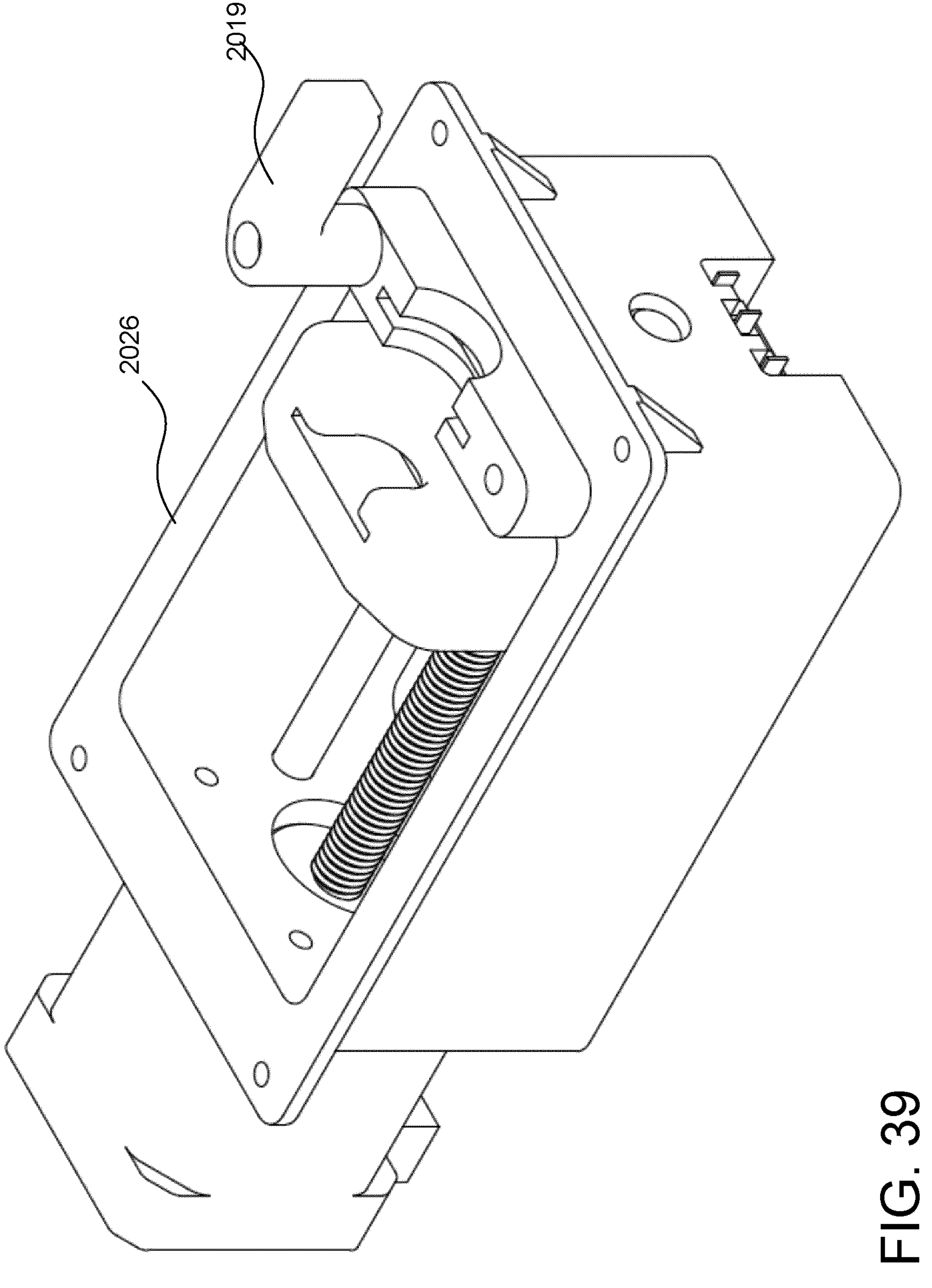
FIG. 39 is a perspective view of a pump actuator of the base unit of FIG. 38.

The waste container 2006 and the reagent container 2005 are shown coupled in a horizontal orientation on holders 2004. The tray assembly 2001 also includes couplers 2003, 2003' to which the cell culture containers can be coupled as described herein. Specifically, the coupler 2003 is a bracket that extends around a first end portion of the cell culture container (not shown) and the coupler 2003' is a pair of tabs that receive a flange portion of a second end portion of the cell culture container. The couplers 2003' also function to retain the temporary shipping supports 2095 to which the lids 2008 are coupled during storage, shipment, and initial setup. The couplers 2003, 2003' retain the cell culture containers in a predetermined, fixed location on the tray 2002. Below where the cell culture containers will be disposed are transparent portions 2058 (see, e.g., FIG. 36) of tray 2002. In this embodiment, a pump holder 2011 is provided that can hold a pump port (not shown) as described above for previous embodiments. As described above, the tray assembly 2001 is preassembled and placed within an overwrap (not shown) to maintain the sterility of the tray assembly 2001 during transport and storage. FIG. 37 illustrates the tray assembly 2001 when the overwrap is removed (i.e., within an aseptic environment), with the waste container 2006 and the reagent container 2005 removed and a fluid pump 2013 coupled to the holder 2011. As shown in FIG. 37, in this embodiment, the fluid pump 2013 is a syringe.

Figure 40:
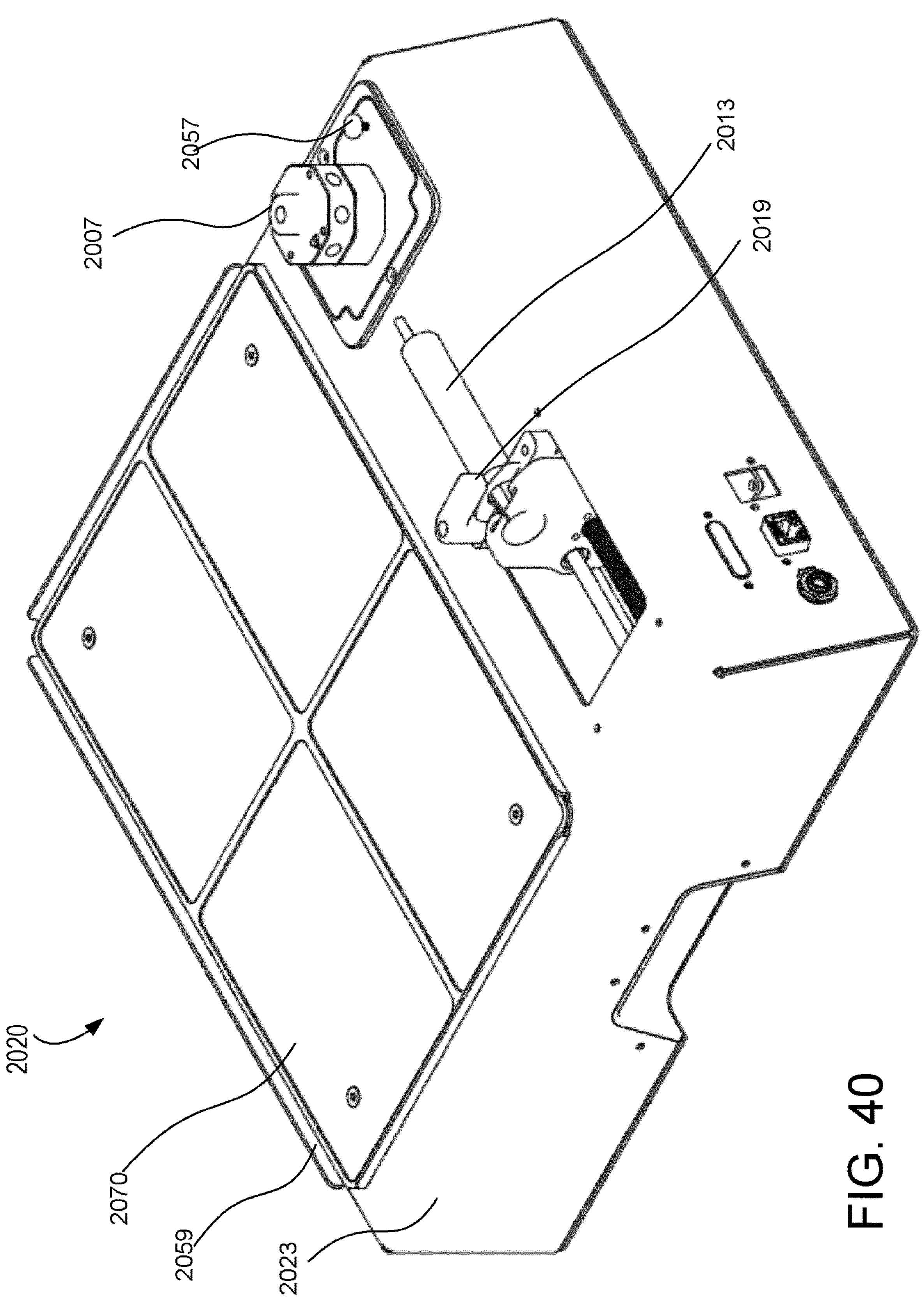
FIG. 40 is a perspective view of the base unit of FIG. 38 with a fluid pump and multiport valve coupled thereto.
Figure 41:
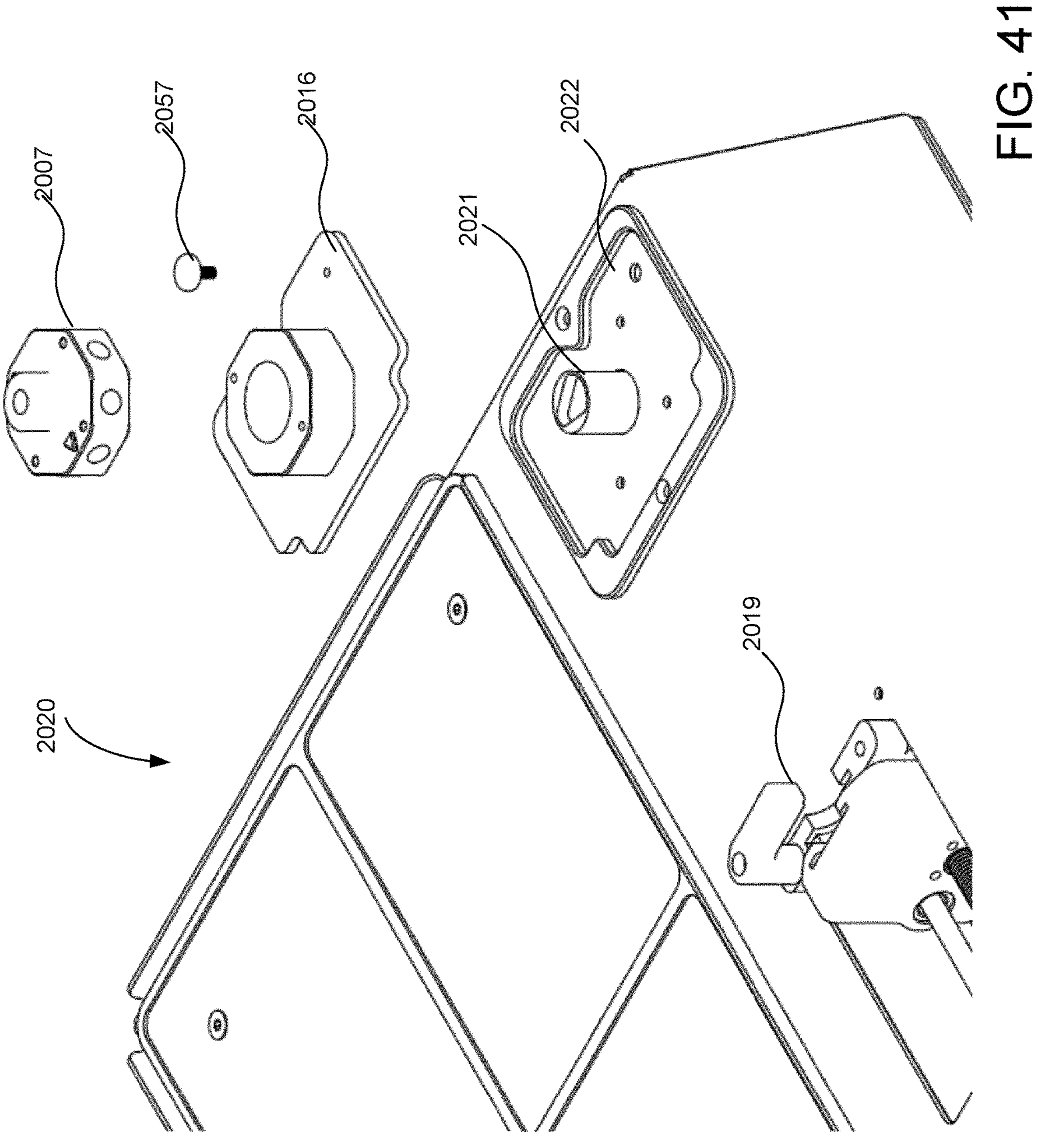
FIG. 41 is a partial exploded view of a portion of the base unit of FIG. 38, illustrating the multiport valve prior to being assembled to the base unit.

As described above for previous embodiments, the preassembled tray assembly 2001 can be removably coupled to the base unit 2020. FIGS. 38-44 illustrate the base unit 2020. The base unit 2020 includes a housing 2023, a pump actuator 2026 disposed partially within a recess or pocket 2025 of the housing 2023. The pump actuator 2026 (see, e.g., FIGS. 38-40) includes a pump holder 2019 to which the fluid pump 2013 can be locked in place and operatively connected to the pump actuator 2026. Although the pump holder 2019 is shown as slotted member that receives a syringe flange and a movable member to secure the syringe flange in place, in other embodiments, the pump holder 2019 can be any suitable structure or mechanism for securing the pump (which can be any suitable pump) to the pump actuator. The base unit 2020 also includes a valve connector 2022 configured to matingly couple to the multiport valve 2007 and a valve actuator 2021 configured to engage the multiport valve 2007 when coupled thereto. For example, as described above, when the tray assembly 2001 is coupled to the base unit 2020, the multiport valve 2007 can be uncoupled from the tray 2002 and coupled to the valve connector 2022 of the base unit 2020 such that the multiport valve 2007 operatively engages the valve actuator 2021 as shown in FIGS. 40 and 41. More specifically, the mounting portion 2016 of the multiport valve 2007 can be detached from the tray 2002 by removing the fastener 2057 and attaching the mounting portion 2016 to the mating valve connector 2022 of the base unit 2020 with the same or a different fastener 2057. FIG. 41 is a partial exploded view illustrating the components of the multiport valve 2007 prior to being coupled to the valve connector 2022.

Figure 42:
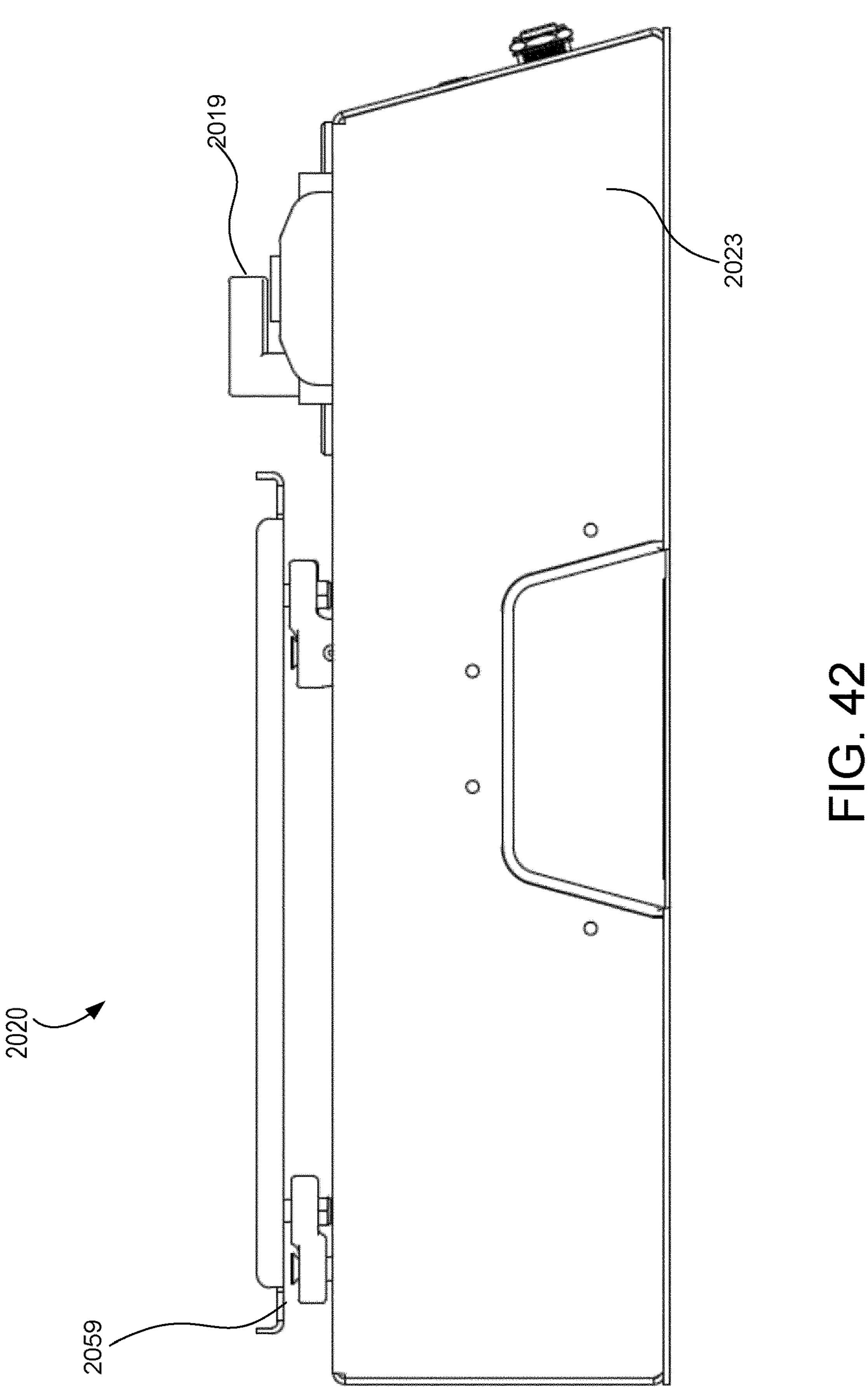
FIG. 42 is a side view of the base unit of FIG. 38.

In this embodiment, a support plate 2059 is coupled to the housing 2023 and provides a receiving portion 2024 on which the tray assembly 2001 can be placed. In this embodiment, the support plate 2059 is elevated above a top surface of the housing 2023. FIG. 42 is a side view illustrating the elevation of the support plate 2059. The support plate 2059 is coupled to an agitator 2028 (see FIG. 44) disposed within an interior of the housing 2023. As described above, the agitator 2028 can be used during a cell culturing procedure to agitate the tray assembly 2001 and the contents of the cell culture containers coupled thereto.

FIG. 40 illustrates the base unit 2020 with the syringe 2019 coupled to the syringe holder 2019 and the multiport valve 2007 coupled to the valve connector 2022. FIG. 40 also shows an optional mat 2070 disposed on the top surface of the support plate 2059. The mat 2070 can be, for example, a rubber mat configured to protect the surface of the support plate 2059 and/or provide dampening when the tray assembly 2001 is agitated by the agitator 2028. Similarly stated, in some embodiments, the support plate (or receiving portion) of a base unit can include a damping member that dampens any relative motion or contact between the support plate on the containers mounted thereto.

Figures 43, 44:
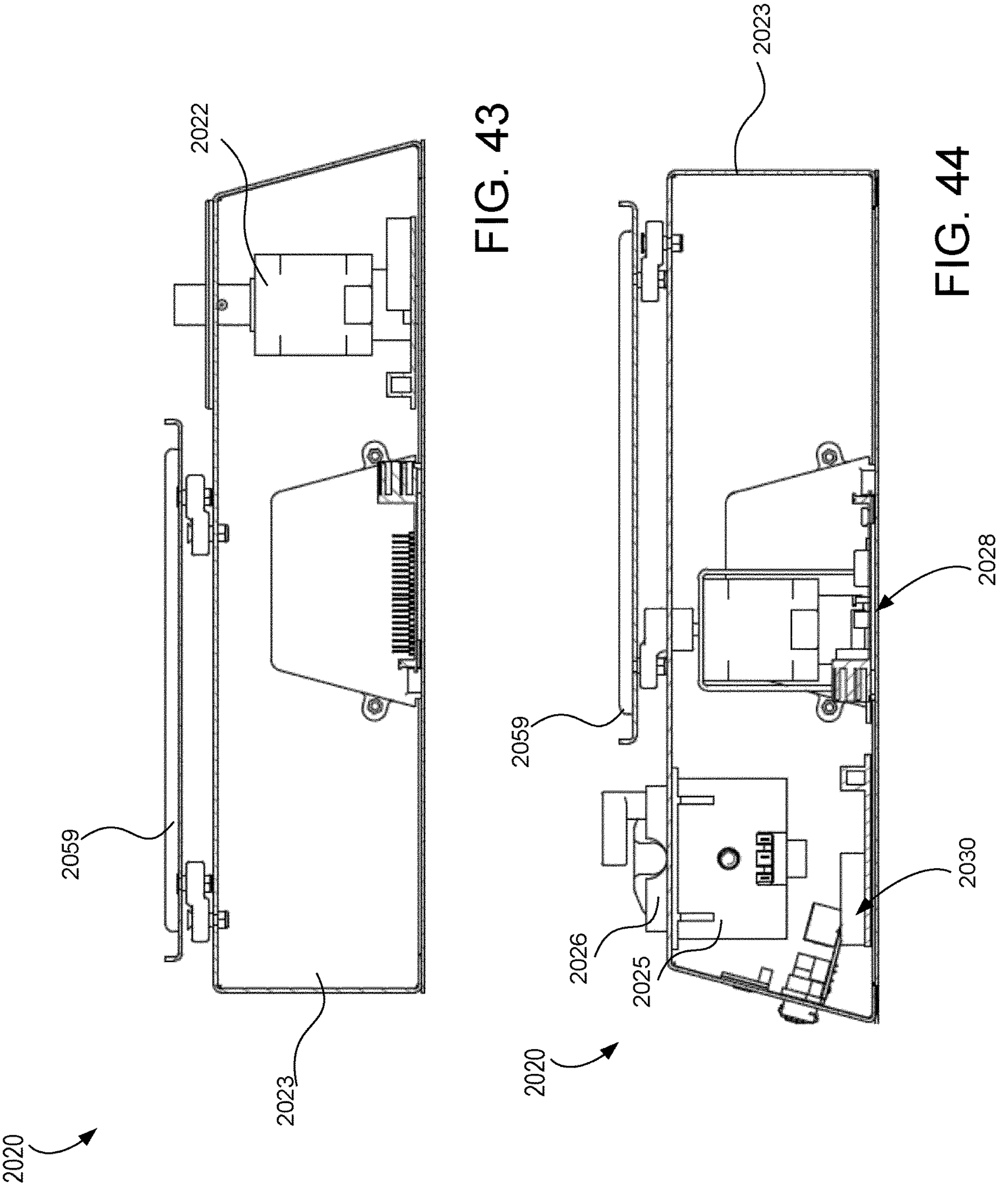
FIG. 43 is a side view and FIG. 44 is an opposite side view of the base unit of FIG. 38 illustrating the interior of the base unit.
Figure 45:
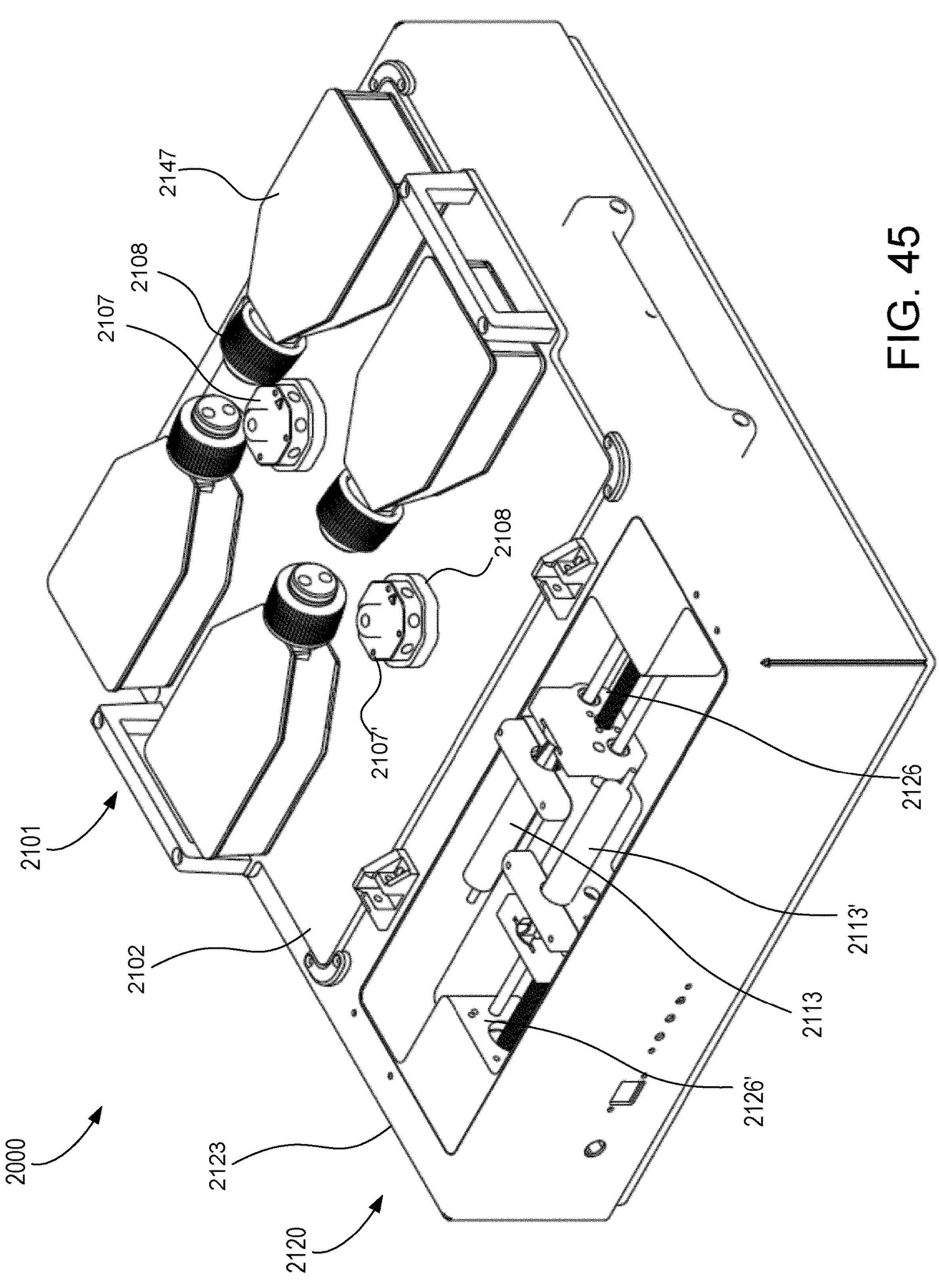
FIG. 45 is a perspective view of a cell culturing system, according to another embodiment.
Figure 46:
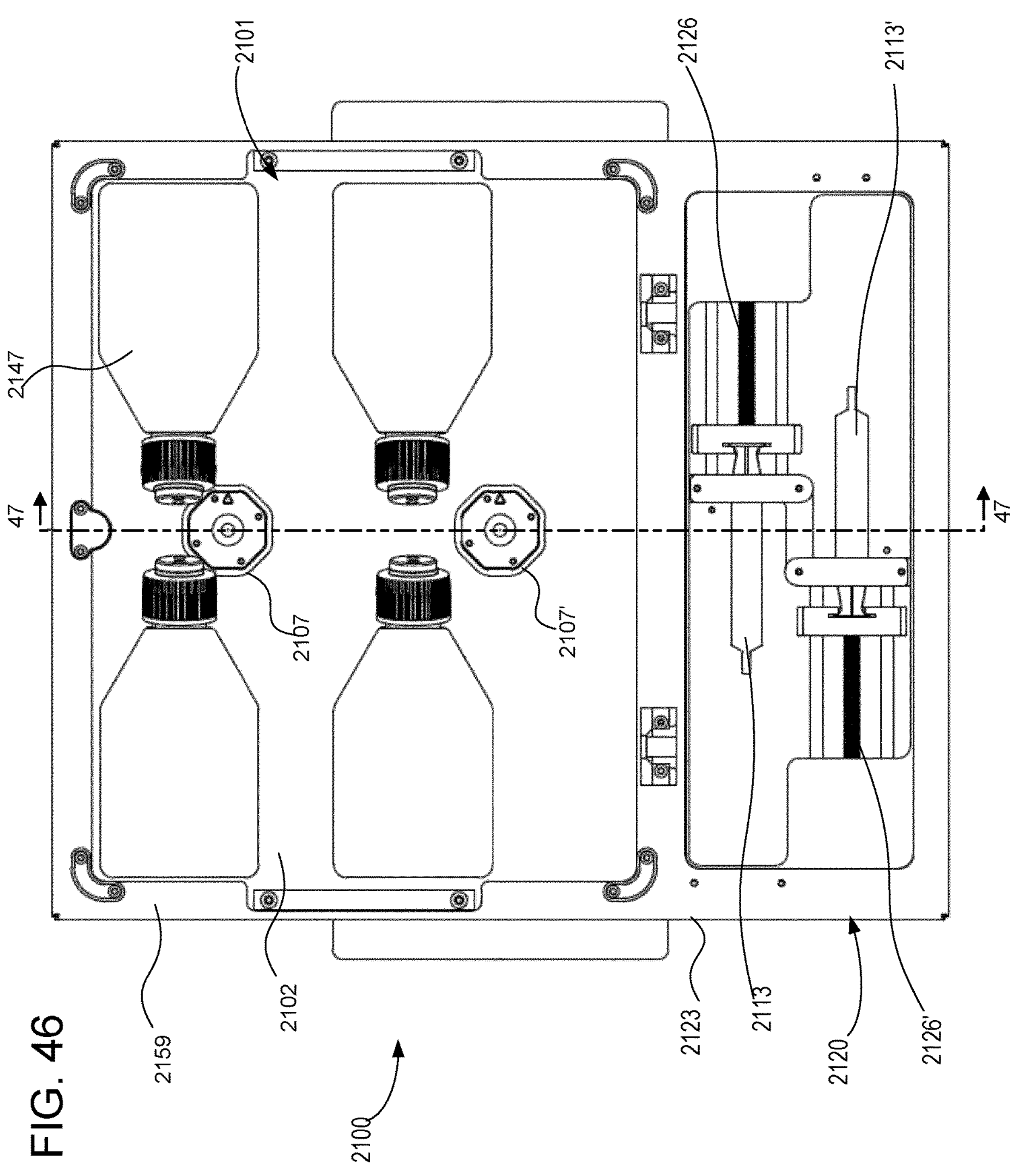
FIG. 46 is a top view of the cell culturing system of FIG. 45.

FIGS. 43 and 44 are opposite side views of the base unit 2020 showing the interior of the housing 2023. FIG. 43 shows the valve actuator 2022 and FIG. 44 shows the agitator 2028 and the pump actuator 2026 within the pocket 2025. Also shown in FIG. 44 is the electronic control system 2030. The electronic control system 2030 can be configured the same as or similar to and function the same as or similar to, the electronic control system 1630 described above. The electronic control system 2030 can optionally be capable of communicating with other computing devices and/or within a cloud computing environment and can include some or all of the components and features describe above with respect to FIG. 17. Although not shown, the system 2000 can also include one or more sensors and/or lights (e.g., microscope, imaging device, etc.), such as the microscope imaging device 1960 described herein.

FIGS. 45-51 illustrate another embodiment of a cell culture system that can be used in a cell culturing procedure. The cell culture system 2100 can include some of the same or similar components as other embodiments described herein and can have the same or similar functions as the previous embodiments described herein, and therefore, some details of the cell culturing system 2100 are not described with respect to this embodiment. In this embodiment, the cell culturing system 2100 does not include an agitator and includes two multiport valves/valve actuators, and two fluid pumps/fluid actuators.

The cell culturing system 2100 (also referred to herein as "system") includes a tray assembly 2101 and a base unit 2120. As shown, for example, in FIG. 45, the tray assembly 2101 includes a tray 2102 with two multiport valves 2107 and 2107', and four cell culture containers 2147 are shown disposed thereon. The containers 2147 can be preassembled on the tray assembly 2101 or added to the tray 2102 just prior to a cell culture procedure. For example, in some embodiments, the containers 2147 are preassembled on the tray 2102 as the tray assembly 2101 is provided within an overwrap. The preassembled containers can be coupled to or uncoupled from lids 2108 (described below) when disposed within the overwrap. During preparation for a cell culturing procedure, cells and reagent can be added to the containers, and the lids 2108 attached to the containers, prior to the tray assembly 2101 being coupled to the base unit 2120. In some embodiments, the containers 2147 are not preassembled on the tray 2102 (are not provided within the overwrap), but rather are added to the tray during preparation for the cell culture procedure, as described above. The containers are filled with cells and reagent (e.g., cell culture media), coupled to the lids 2108 and added to the tray assembly 2101.

The lids 2108 can be configured the same as the lids described above for previous embodiments, including the cell culture vessel lid 803 or the lid 2408. For example, the lids 2108 can include a liquid exchange port (also referred to as "fluid port") and a gas exchange port, and the fluid ports can be aseptically coupled to one of the multiport valves 2107, 2107' with tubing (not shown) as described above for previous embodiments. For example, two of the container 2147/lids 2008 can be fluidically coupled to the valve 2107 and two of the containers 2147/lids 2108 can be fluidically coupled to the valve 2107'. In this embodiment, the multiport valves 2107, 2107' are fixed to the tray 2102 and remain on the tray 2102 when the tray assembly 2101 is coupled to the base unit 2120. The multiport valves 2107, 2107' can each include a master port and multiple selectable ports to which the lids 2008 (and/or other lids/containers) can be selectively coupled via a length of tubing (not shown). The multiport valves 2107, 2107' can be coupled to the tray 2102 via a mounting portion (not shown) that matingly couples to and fits within a mounting pocket 2118 of the tray 2102.

Figure 47:
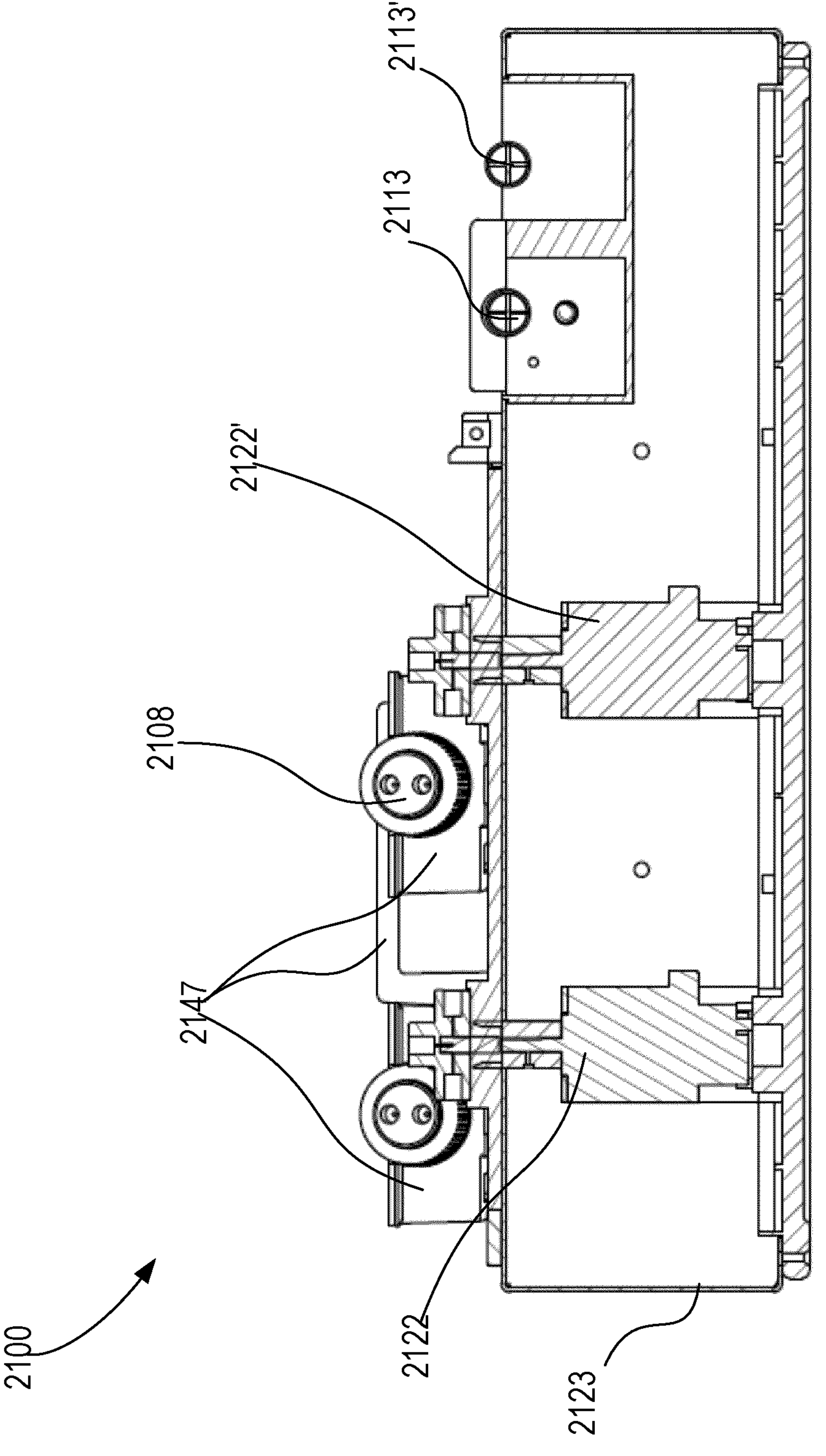
FIG. 47 is a cross-sectional view taken along line 47-47 in FIG. 46.
Figure 48:
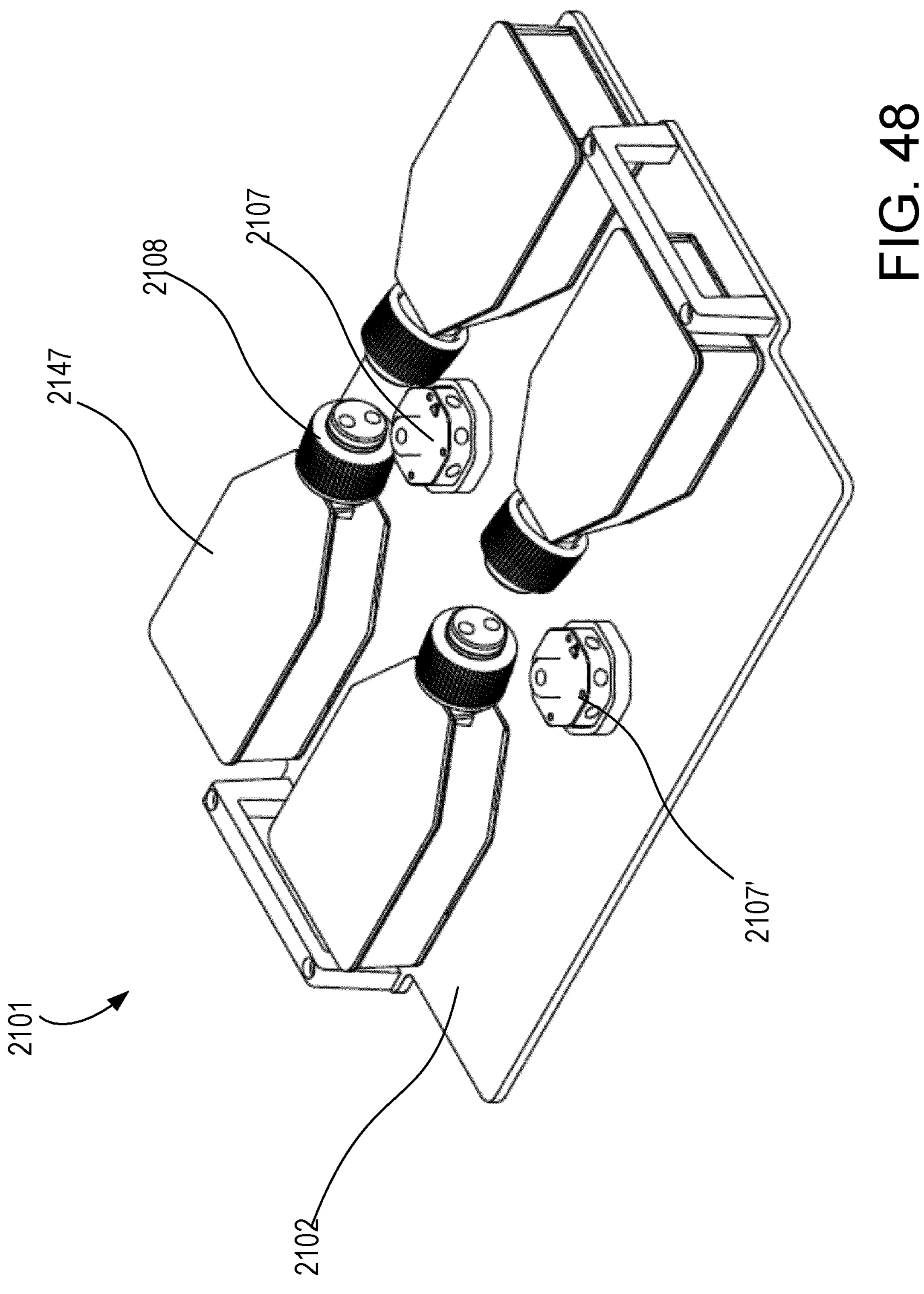
FIG. 48 is a perspective view of a tray assembly, according to an embodiment.
Figures 49, 50:
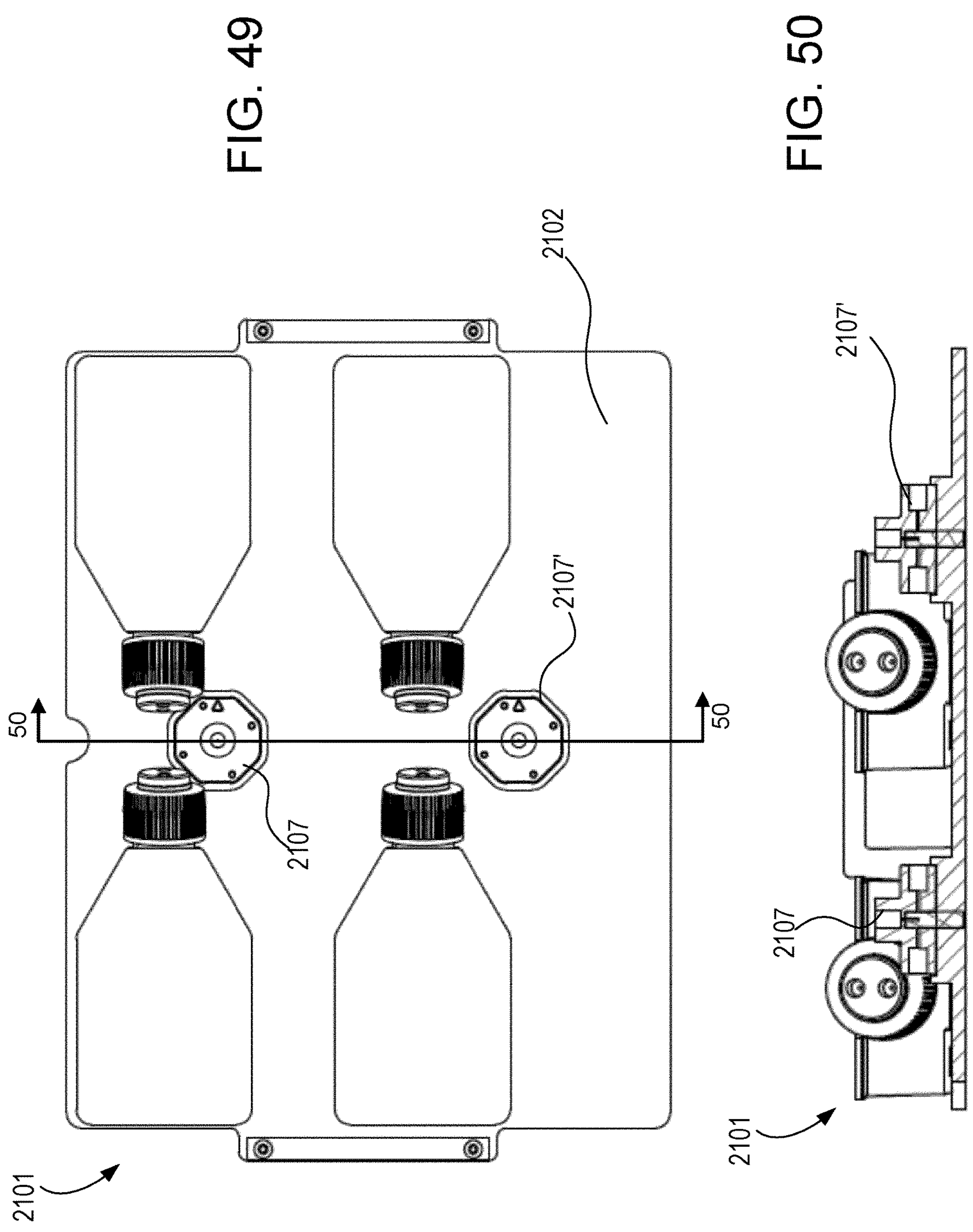
FIG. 49 is a top view of the tray assembly of FIG. 48.
FIG. 50 is a cross-sectional view taken along line 50-50 in FIG. 49.
Figure 51:
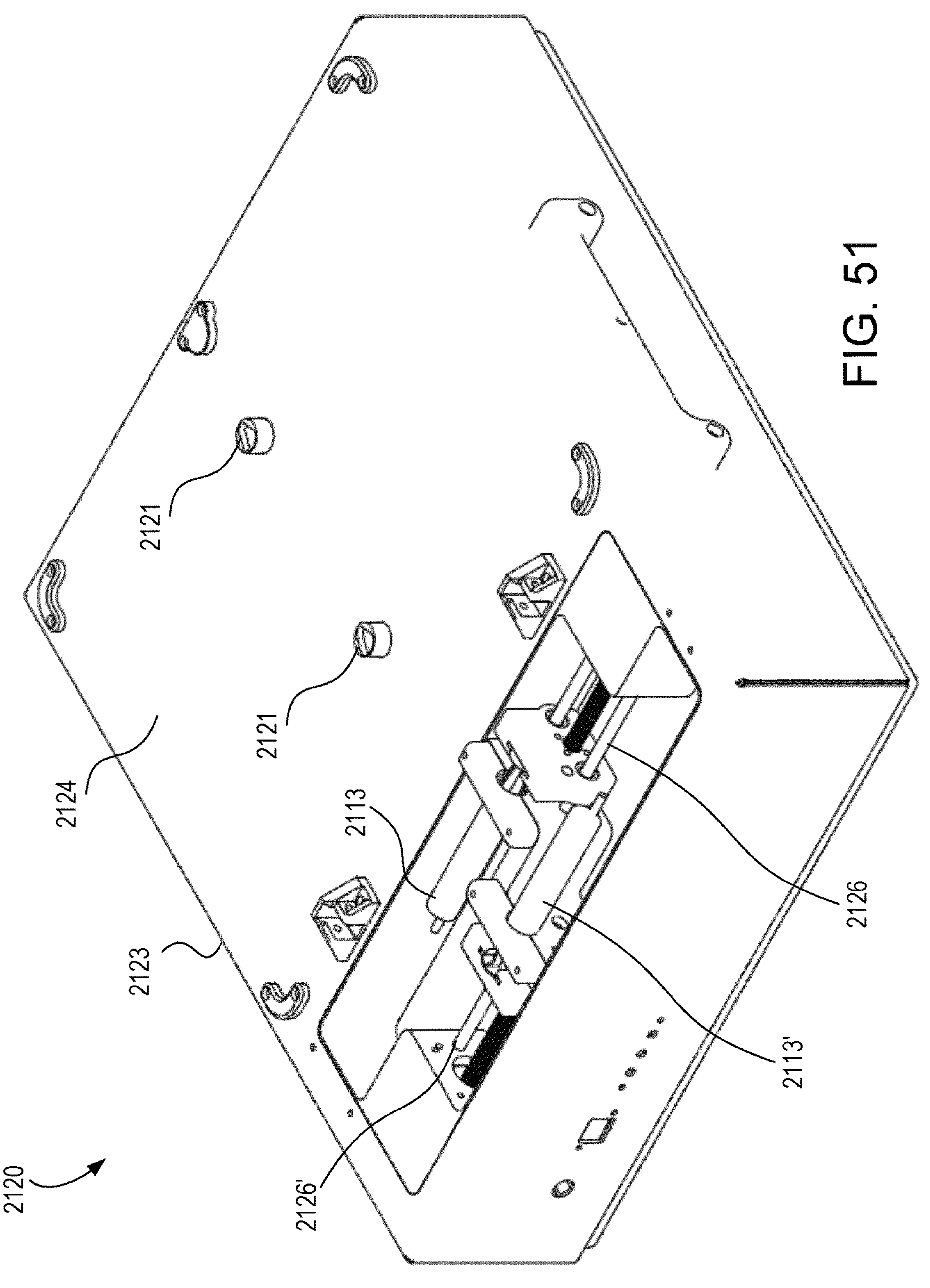
FIG. 51 is a perspective view of a base unit, according to an embodiment.

In this embodiment, the base unit 2120 includes a housing 2123 that defines a tray receiving portion 2124 and includes the two valve actuators 2122, 2122'. The valve actuators 2122, 2122' each include a valve connector portion 2171, 2171' that extends from a top surface of the base unit 2120 within the receiving portion 2124 as shown in FIG. 51. When the tray assembly 2101 is coupled to the base unit 2120, the multiport vales 2107, 2107' can operatively engage the valve actuators 2122 and 2122' of the base unit 2120 via the valve connector portions 2171 as shown in FIG. 47.

In this embodiment, the base unit 2120 also includes two fluid actuators 2126 and 2126' that are couplable to fluid pumps 2113 and 2113', respectively. The fluid pumps 2113, 2113' can be, for example, syringes, peristaltic pumps or another type of positive displacement fluid pump. The use of two pumps 2113, 2113' and two valves 2107 can provide for separate fluidic connections between the valves 2107, 2107' and the various containers of the system to allow, for example, separate fluid inputs and outputs to and from a particular container (e.g., containers 2147). For example, waste removal from one container can be separate from and not pass through the same fluidic channels as other fresh media. Two pumps can also allow for more inputs and outputs to the containers by replicating fluidics.

In this embodiment, the system 2100 does not include an agitator. Although not shown, the system 2100 can also include an electronic control system, one or more sensor (e.g., microscope, imaging device, etc.). The system 2100 can also include various other containers such as a waste container, reagent containers, cell harvest containers, etc., that can each be couplable to one of the multiport valves 2107, 2107'.

FIGS. 52-58 illustrate another embodiment of a cell culture system that can be used in a cell culturing procedure. The cell culture system 2200 can include some of the same or similar components as other embodiments described herein and can have the same or similar functions as the previous embodiments described herein, and therefore, some details of the cell culturing system 2200 may not be illustrated and are not described in detail with respect to this embodiment. This embodiment illustrates an example cell culturing system that includes multiple separate tray assemblies that can each include lids and/or containers that can be fluidically coupled to a separate multiport valve and a separate fluid pump system. Said another way, each tray assembly is fluidically coupled to its own multiport valve and fluid pump but is fluidically isolated from the multiport valves and fluid pumps of the other trays. The separate tray assemblies can then be coupled to a single base unit. In some embodiments, each of the separate tray assemblies can be preassembled and disposed within a protective overwrap and shipped separately. In some embodiments, the separate tray assemblies can be preassembled and shipped together within a protective overwrap. By maintaining each of the tray assemblies in fluidic isolation from the other tray assemblies, the cell culture system is capable of culturing multiple different types of cells without the risk of cross-contamination. For example, each tray assembly can be configured for a different cell type. This embodiment also allows for more different types of cells to be cultured and incubated within a dimensionally smaller device. For example, with a multiple tray system as described below, the system can be used to grow three types of cells on a single shelf and/or within a single base unit of an incubator, without sharing fluidics between the three cell types. In some embodiments, a single, larger tray (the width of two or three of the smaller trays) can be used when desired to grow more of a single type of cell.

In this embodiment, the cell culturing system 2200 (also referred to herein as "system") includes a base unit 2220 and three tray assemblies 2201, 2201', 2201" that can be coupled to the base unit 2220 as described above for previous embodiments. The three tray assemblies (collectively referred to as tray assemblies 2201) and the base unit 2220 can include the same or similar features and components as described above for previous embodiments. This embodiment also includes three multiport valves 2207, 2207', 2207" (collectively referred to as multiport valves 2207) and three fluid pumps 2213, 2213', 2213" (collectively referred to as fluid pumps 2213).

In this embodiment, the tray assemblies 2201 can each include a tray 2202, 2202', 2202" (collectively referred to as trays 2202) (see e.g., FIG. 55), having a multiport valve 2207, 2207', 2207", a cell counting chip 2217, 2217', 2217" (collectively referred to as counting chips 2217), a first cell culture container 2247, 2247', 2247" (collectively referred to as cell culture containers 2247), and a second cell culture container 2248, 2248', 2248" (collectively referred to as cell culture containers 2248) disposed thereon. In this example embodiment, the containers 2247 are smaller than the containers 2248. It should be understood, however, that the tray assemblies 2201 can accommodate other sized containers not shown. In some embodiments, one or all of the tray assemblies 2201 can include the same two containers. The use of a larger container (e.g., 2247) and a smaller container (e.g., 2248) within the same tray assembly 2201 may be desirable, for example, to use for a cell expansion process. For example, the cells can be placed in the smaller container 2248 to promote better growth when there are fewer cells, and then the cells can be moved to the larger container as the growth surface of the smaller flask gets crowded during the expansion process. The use of the same sized containers within the same tray assembly 2201 may be desirable, for example, for a cell maintenance process, where a cell line is to be kept in culture for when it is next needed.

Figure 57:
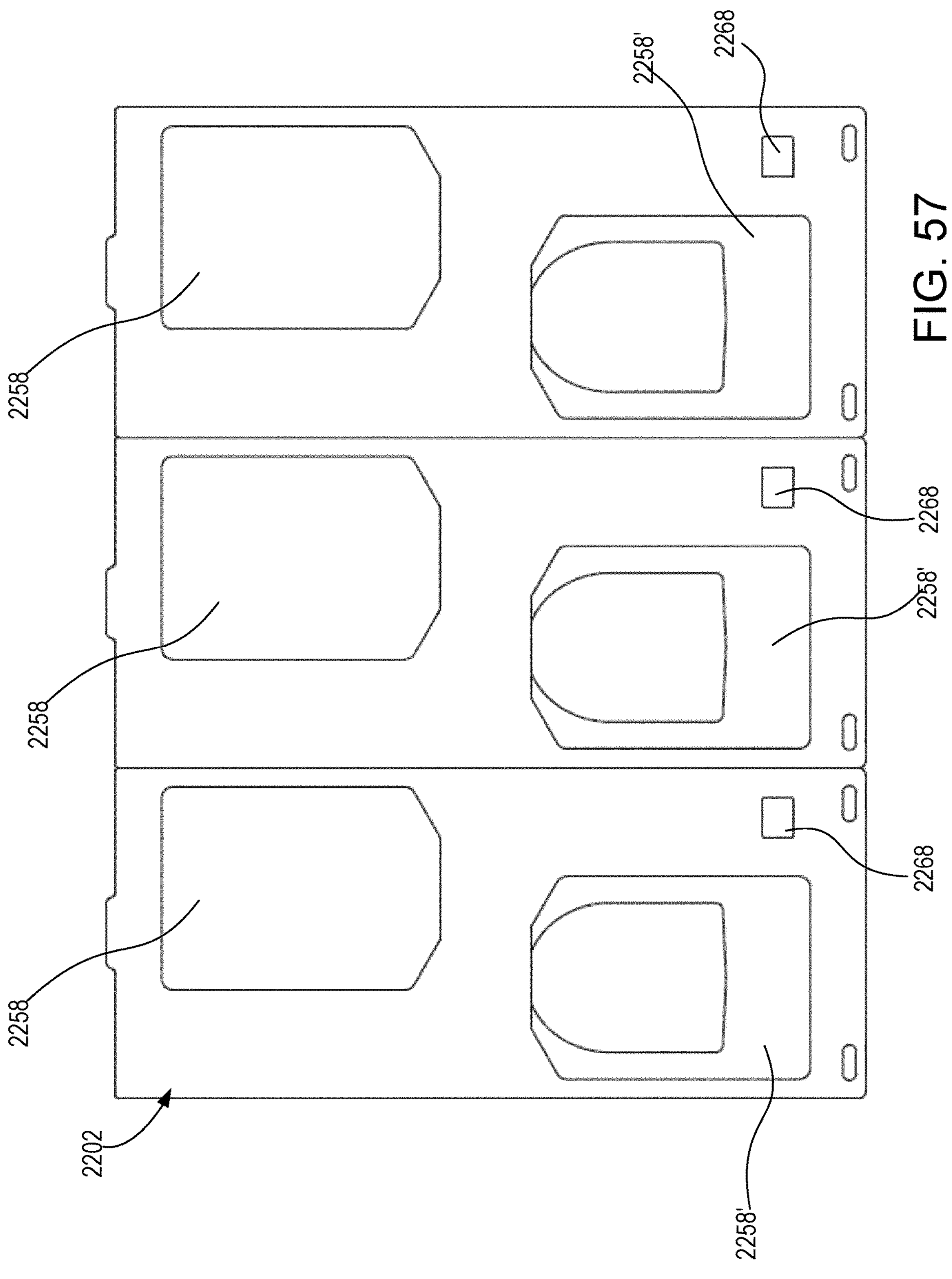
FIG. 57 is a top view of the tray of the tray assembly of FIG. 55.

The trays 2202 can include transparent portions or partial cut-outs 2258 and 2258', as shown in FIG. 57, on which the containers 2247 and 2248, respectively, can be disposed. As described above for previous embodiments, the transparent portions or partial cut-outs 2258, 2258' can provide for sensor data to be obtained associated with the cell culture containers 2247 and 2248. For example, an imaging device or other sensor can be movably disposed within the housing of the base unit 2220 (described below) and moved to a location below the transparent portions or cut-outs 2258, 2258'. As shown in FIG. 57, the transparent portions or cut-outs 2258' illustrate an optional container cradle that can accommodate two different sized containers. Similarly, the trays 2202 also include transparent portions or cut-outs 2268 at a location where the cell counting chips 2217 are disposed to provide for sensor data to be obtained associated with a sample fluid disposed on the cell counting chips 2217 as described above for previous embodiments.

The containers 2247 (and 2247', 2247") and 2248 (and 2248', 2248") can be preassembled on the trays 2202 or added to the trays 2202 prior to a cell culture procedure (e.g., in accordance with the methods described herein). For example, in some embodiments, the containers 2247 are preassembled on the tray 2202 and the tray assembly 2201 is provided within an overwrap (not shown, but similar to the overwraps described herein). The preassembled containers can be either coupled to or uncoupled from a lid 2208 (described below) within the preassembled tray 2202. During preparation for a cell culturing procedure, cells and reagent can be added to the containers 2247, 2248, and the lids 2208 attached to the containers 2247, 2248, prior to the tray assemblies 2201 being coupled to the base unit 2220. In some embodiments, the containers 2247 are not preassembled on the tray 2202 (are not provided within the overwrap), but rather are added to the trays 2202 during preparation for the cell culture procedure. The containers 2247, 2248 can be filled with cells and reagent, coupled to the lids and added to the tray assembly 2201.

The lids 2208 can be configured the same as the lids described above for previous embodiments. For example, the lids 2208 can include a liquid exchange port (also referred to as "fluid port") and a gas exchange port. The fluid ports can be aseptically coupled to one of the multiport valves 2207, 2207', 2207" with tubing (not shown) as described above for previous embodiments. For example, for each tray assembly 2201, the two containers 2247 and 2248 with lids 2208 coupled thereto can be fluidically coupled to a select port of the valve 2207 of that tray assembly 2201. The multiport valves 2207 can each include a master port and multiple selectable ports to which the lids 2208 (and/or other lids/containers) can be selectively coupled. The multiport valves 2207 can be coupled to the tray 2202 via a mounting portion (not shown) that matingly couples to and fits within a mounting pocket (not shown) of the trays 2202 in a puzzle-like manner, as described above for previous embodiments.

Figure 52:
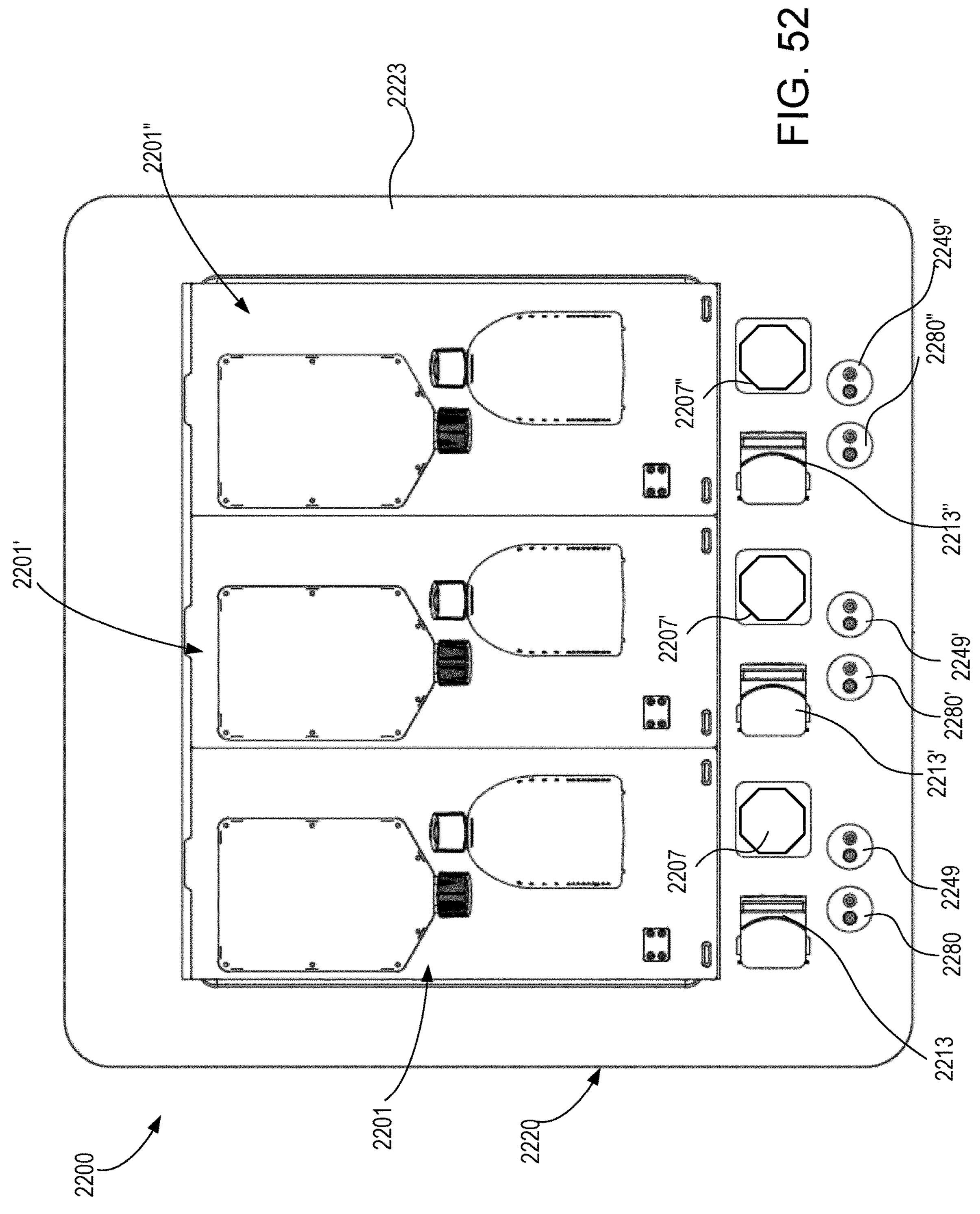
FIG. 52 is to view of a cell culturing system, according to another embodiment.
Figure 53:
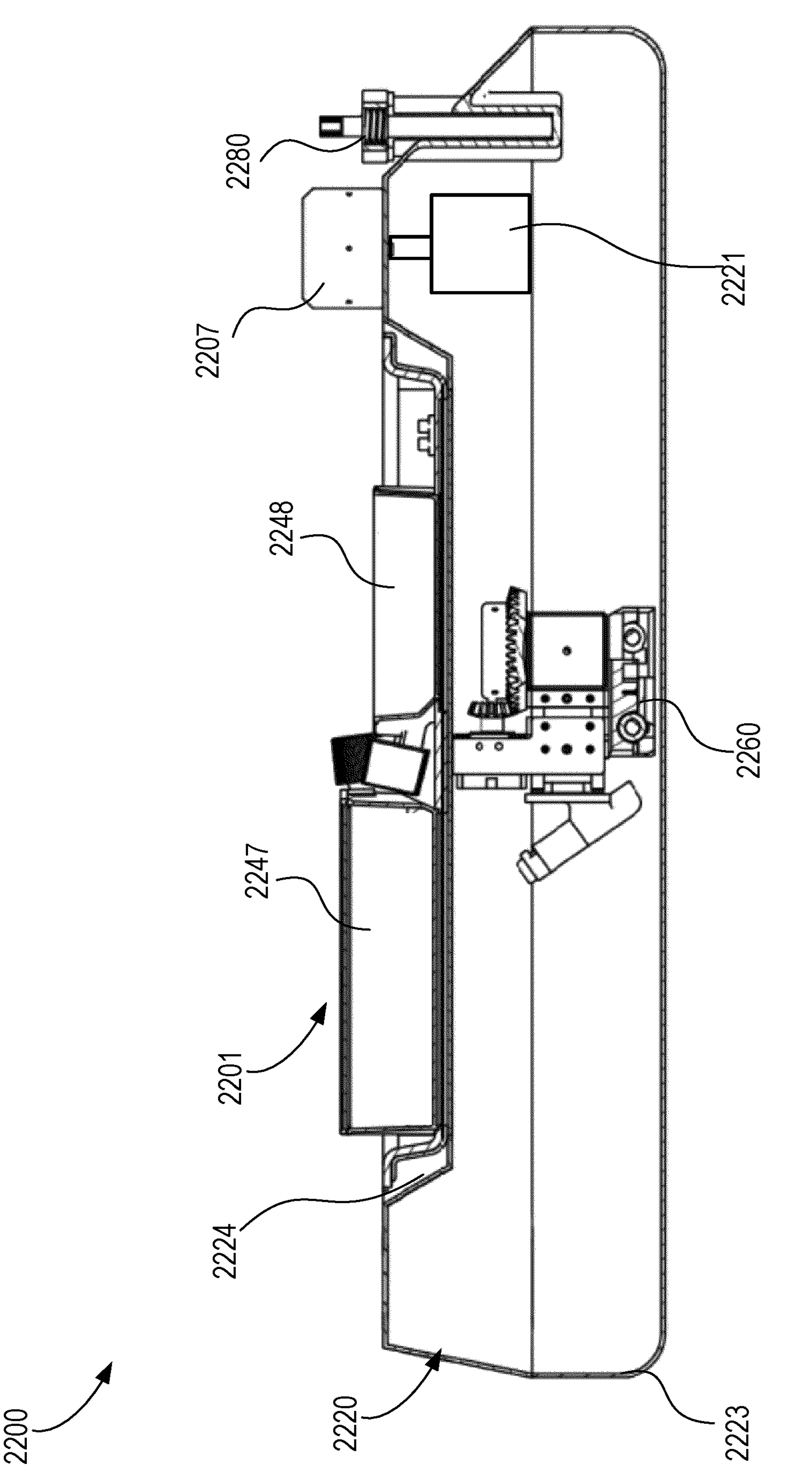
FIG. 53 is a side view of the cell culturing system of FIG. 52 illustrating an imaging system disposed within an interior of the base unit.
Figure 54:
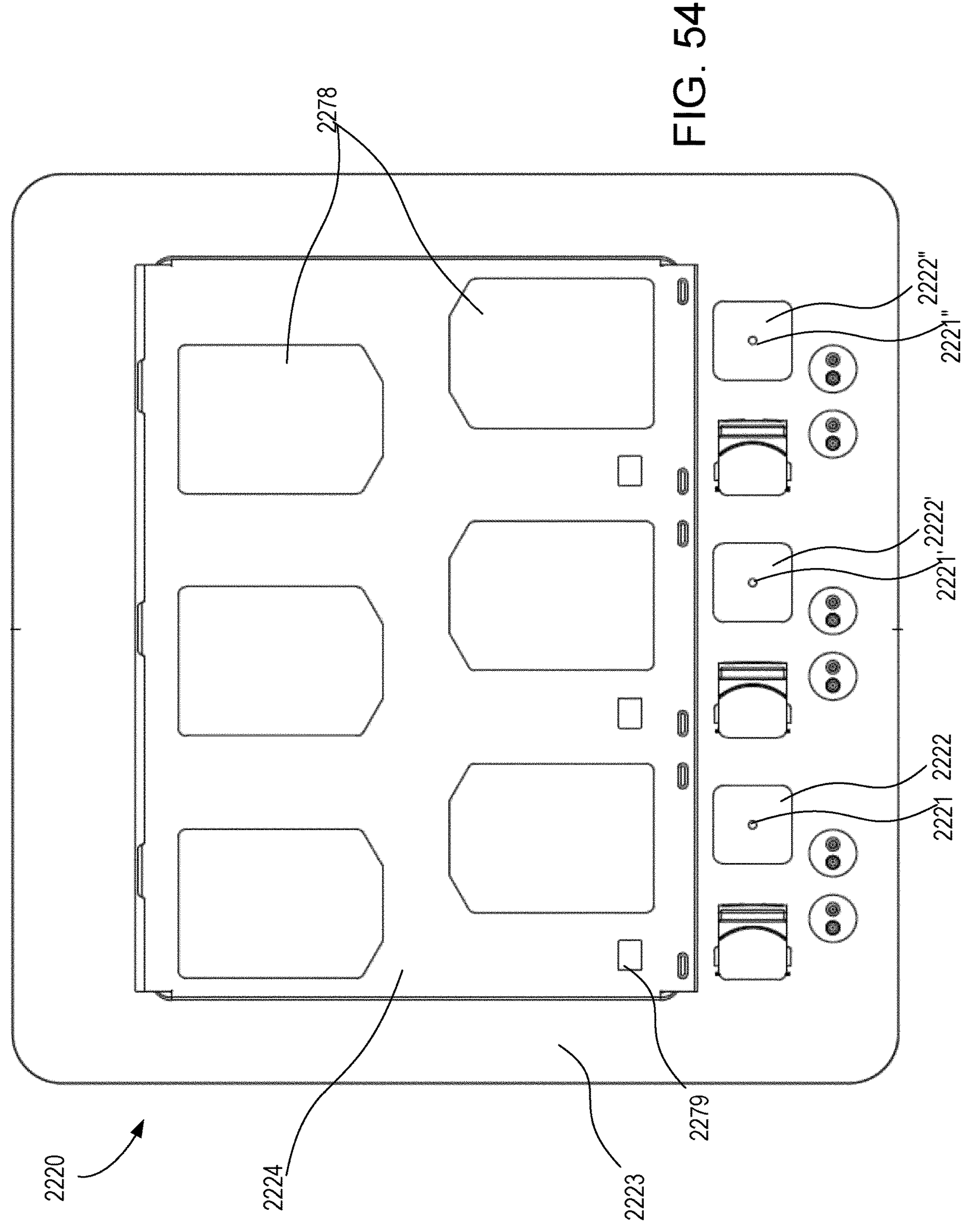
FIG. 54 is a top view of a base unit of the cell culturing system of FIG. 52.
Figure 55:
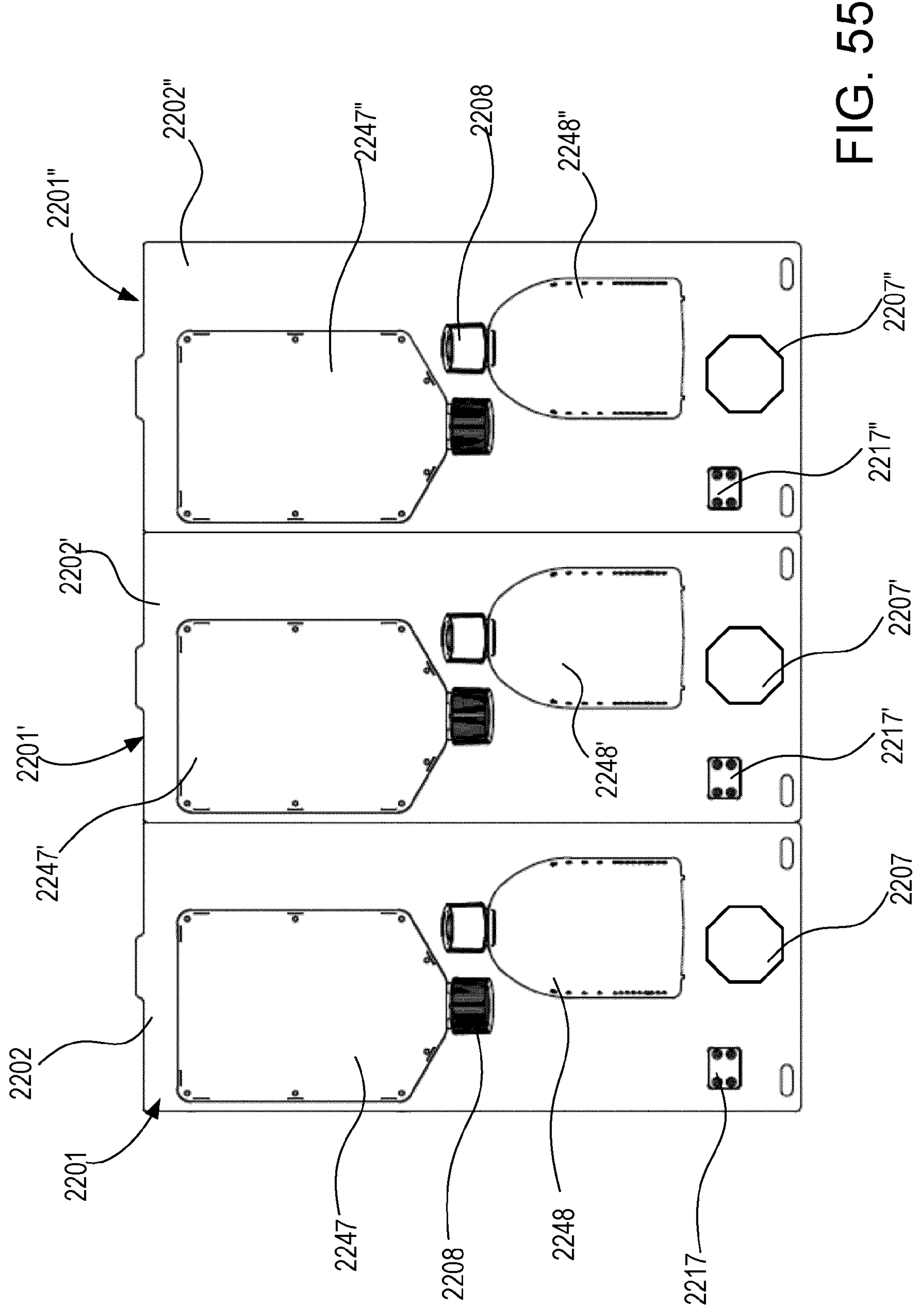
FIG. 55 is a top view of a tray assembly of the cell culturing system of FIG. 52.
Figure 56:
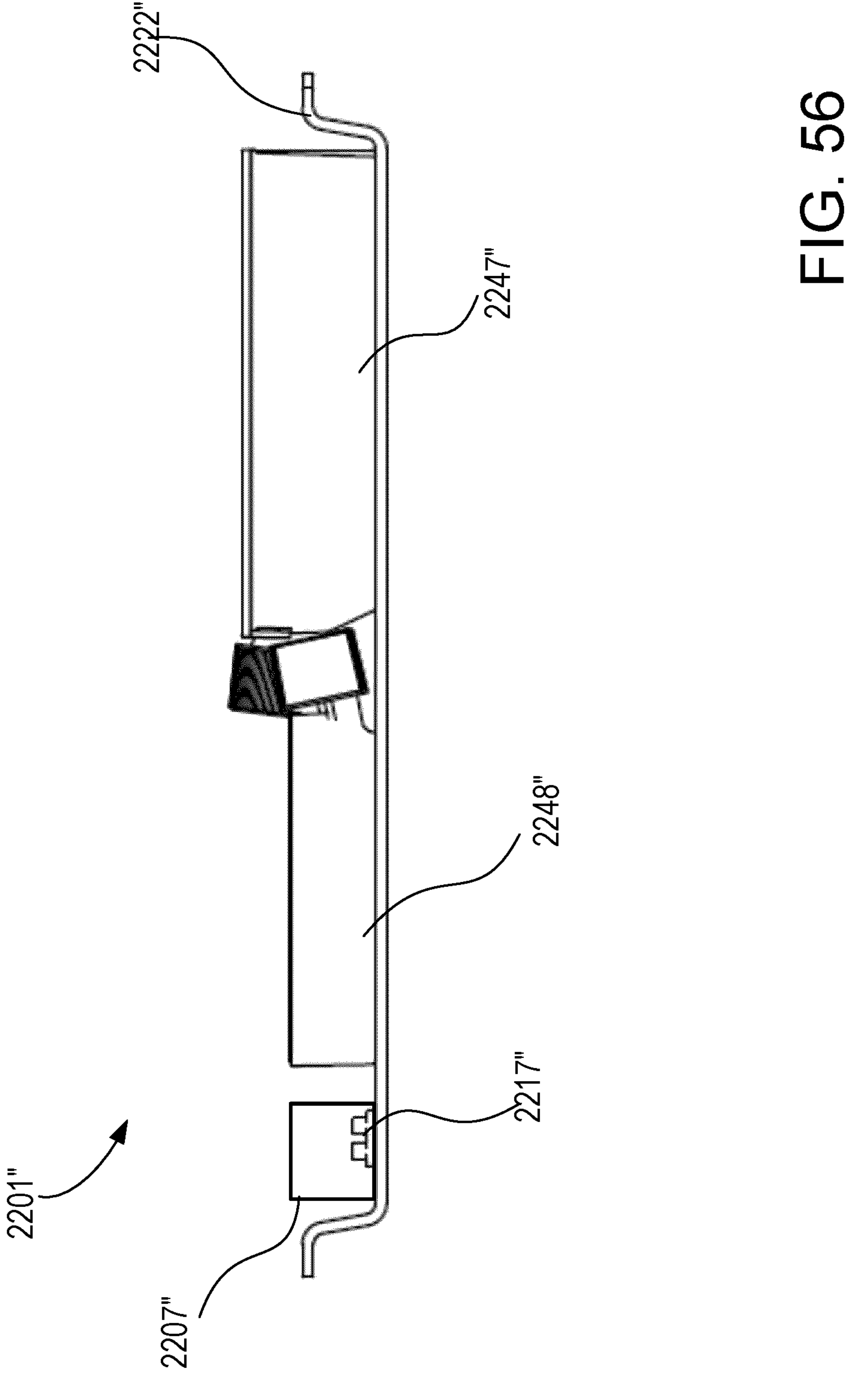
FIG. 56 is a side view of the tray assembly of FIG. 55.

In this embodiment, the base unit 2220 includes a housing 2223 that defines a tray receiving portion 2224 that can receive each of the three tray assemblies 2201. The housing 2223 also defines sections 2278 that can be transparent portions or cutouts that correspond to the transparent portions 2258 of the tray assemblies 2201. The housing 2223 also defines sections 2279 that can be transparent portions or cutouts that correspond to the transparent portions 2268 of the tray assemblies 2201 where the cell counting chips 2217 are located. As shown in FIGS. 52-54, the base unit 2220 can also optionally include multiple vials or vessels 2280 and multiple vials or vessels 2249. The vessels 2280 (2280', 2280") can be, for example, a holding vessel for an associated fluid pump 2213. For example, the fluid pumps 2213 can be, for example, peristaltic pumps, and the vessels 2280 can each serve as a holding vessel for one of the pumps such that the pump can function similar to a syringe type pump. More specifically, the vessel 2280' can be a holding vessel for the fluid pump 2213', and the vessel 2280" can be a holding vessel for the fluid pump 2213". The holding vessels 2280 can receive a volume of fluid from a first location within the system where it is held until the pump is actuated to move the volume of fluid to a second location within the system. The vessels 2249 (2249', 2249") can be used to hold various other fluids that can be fluidically coupled to one of the separate fluid systems via one of the multiport valves 2207 (2207', 2207"). For example, the vessels 2249 can be used for waste, or to hold a fluid (e.g., a reagent) to warm the fluid after it has been refrigerated. For example, it may be desirable to refrigerate a container (or vessel) to keep the media therein at a desired temperature (e.g., 4 degrees Celsius). The media can be pumped from the refrigeration to a vessel, such as vessels 2249, such that the media can passively heat up to, for example, 37 degrees Celsius due to the temperature of the incubator in which the system 2200 is disposed.

Each tray assembly 2201 (2201', 2201"), when coupled to the base unit 2220, can be fluidically coupled to one of the fluid pumps 2213 (2213', 2213") to provide a separate closed fluid flow system. As described above, when the tray assemblies 2201 (2201', 2201") are coupled to the base unit 2220, the multiport valves 2207 (2207', 2207") can operatively engage valve actuators 2221, 2221', 2221"(collectively referred to as valve actuators 2221) of the base unit 2220 via the valve connector portions 2222, 2222' and 2222" (collectively referred to as valve connectors 2222), respectively. More specifically, in this embodiment, the multiport valves 2207 are removably coupled to the trays 2202 and can be coupled to a separate valve connector 2222 (2222', 2222") (see, e.g., FIG. 54) and valve actuator 2221 (2221', 2221") of the base unit 2220 as described above, for example, for multiport valve 2007. The fluid pumps 2213 can each be fluidically coupled to the master port of the corresponding multiport valve 2207. The fluid pumps 2213 (2213', 2213") can each be coupled to a pump actuator (not shown) within or coupled to the housing 2223 of the base unit 2220. Although the fluid pumps 2213 are described as peristaltic pumps, the fluid pumps 2213, can be other types of fluid pumps, such as syringes or another type of positive displacement fluid pump.

As shown in FIG. 53, the cell culturing system 2200 also includes an imaging device 2260 movably disposed within the housing 2223 such that it can be moved to locations aligned with the sections 2278 and 2279. The imaging device 2260 can be, for example, a microscope mounted to a gantry system to provide movement of the imaging device in multiple directions (similar to the microscope imaging device 1960 described above). Although not shown for this embodiment, the cell culturing system 2200 can also include an agitator, an electronic control system, and one or more additional sensor(s) (e.g., in addition to the imaging device 2260), as described herein.

In some embodiments, a single imaging device (e.g., 2260) and/or single agitator can be used to image cells on all three tray assemblies 2201. In some embodiments, separate imaging devices and/or separate agitators can be used for each tray assembly. The system 2200 can also include various other containers such as a waste container, reagent containers, cell harvest containers, etc., that can each be couplable to one of the fluidic systems via the multiport valves 2207, 2207', 2207". The cell culturing system 2200 can also include various couplers or coupling portions for holding cell culture containers (e.g., 2003, 2103) and holders for holding other containers, such as waste and reagent containers (e.g., 2005, 2006).

FIG. 58 illustrates an example of two incubators 2275 stacked on top of each other, and in which multiple cell culturing systems 2200 (i.e., tray and base unit) can be placed for a cell culturing procedure. As shown in FIG. 58, in this embodiment, three cell culturing systems 2200 can be placed on shelves within each incubator 2275.

Figure 59:
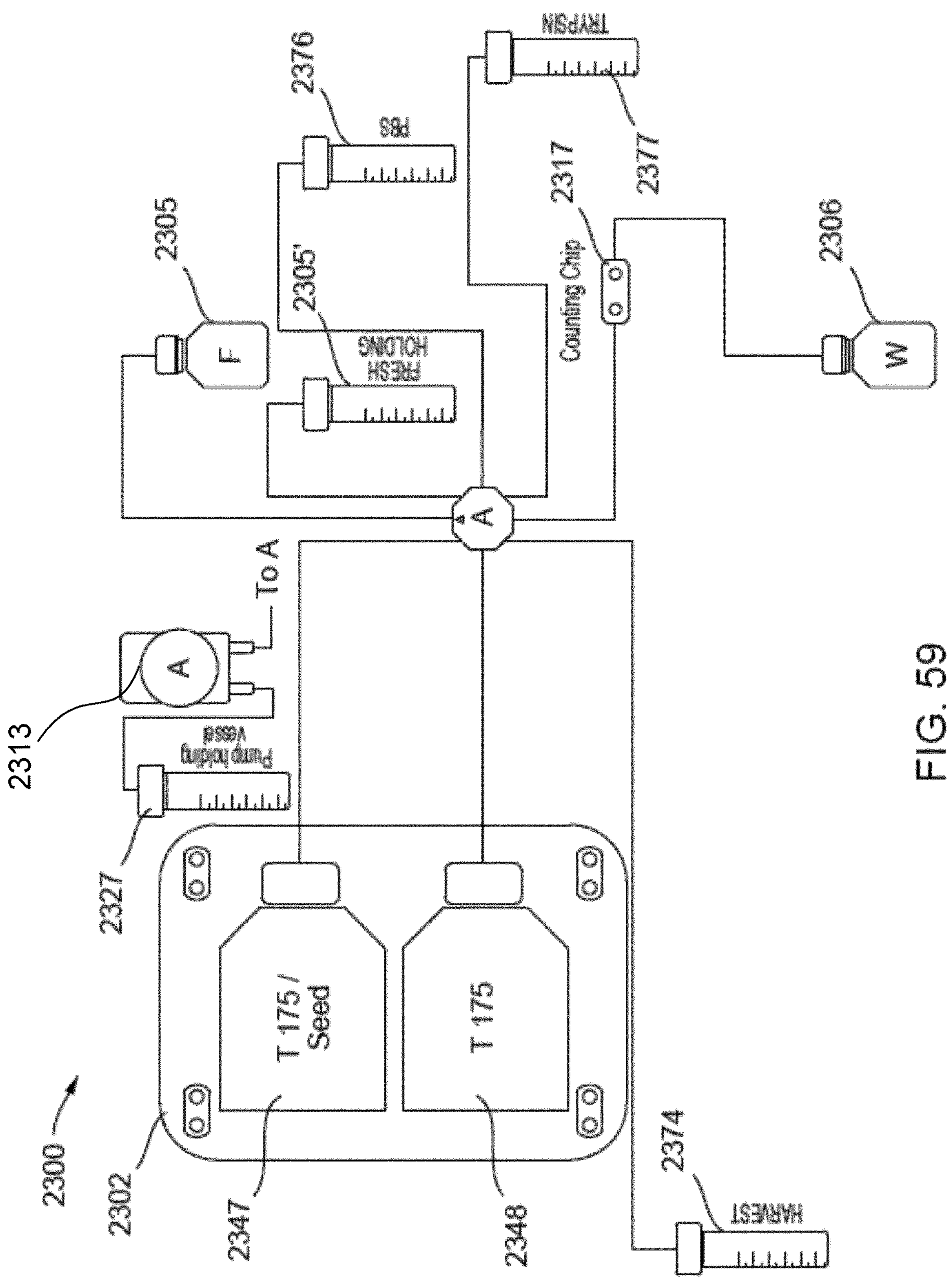
FIG. 59 is system diagram illustrating an example fluidic setup within a system during a cell culturing procedure.

FIG. 59 is a system diagram illustrating an example fluid flow within a system during cell culturing procedures and the various containers and other components that can be coupled within a cell culturing system as described herein. Thus, the system diagram is described with respect to various components of a cell culturing system 2300, but it should be understood that this example diagram can apply to any of the embodiments described herein.

FIG. 59 illustrates a tray 2302 with two cell culture containers 2347 and 2348 coupled thereto. The cell culture containers 2347 and 2348, and a cell counting chip 2317 are each fluidically coupled to a select port of a multiport valve 2307. A fluid pump with fluid holding vessel 2327 is fluidically coupled to a master port of the multiport valve 2307. Multiple other containers are also fluidically coupled to the multiport valve 2307 including reagent containers 2305 and 2305', a cell harvest container 2374, a waste container 2306, a container 2376 containing a cell buffer (e.g., PBS) and a container 2377 containing an enzyme (e.g., Trypsin).

During a cell culturing procedure, the pump holding vessel holds fluid solutions that are pumped in from a starting location (e.g., a reagent container 2305, 2305') within the system, the valve 2307 selects a destination channel (e.g., one of the containers 2347, 2348), and then the solution is pumped to that location. An isotonic and non-toxic buffer solution (e.g., PBS) is used for washing out components that get reused, such as, for example, the pump holding vessel. As shown in the supporting Table 1 in FIG. 60, in this example, the container 2305 can first be placed in a refrigerator to maintain the media within the container 2305 at a desired temperature (e.g., 4 degrees Celsius). Media from the container 2305 can then be pumped prior to a procedure (e.g., an hour before) into 2305' so that it can passively heat up to about 37 degrees Celsius due to the temperature in the incubator. For detaching cells, e.g., during passaging or harvesting, media can first be pumped out of the cell culture containers (2347, 2348) from which the cells are to be detached and pushed to waste. A buffer (e.g., in 2376) can be added to the cultures combined with optional agitation to wash the cells, and then the buffer removed from the culture and pushed to waste. The enzyme (e.g., in container 2377) can be pumped into the relevant cell culture containers, left for a while with optional agitation to aid the detachment, and then the solution diluted with fresh media (e.g., from 2305') to quench the enzyme, and then the cell suspension is passaged/harvested/with the enzyme diluted in the mixture. FIGS. 61A and 61B include a Table 2, which includes an example of a cell passaging procedure for maintaining an adherent cell line, listing for each step, the source for the fluid, the destination, the type of fluid and the volume within each of the cell culturing containers during the procedure. Although specific procedures are outlined in FIG. 61, the system 2300 can be used to perform any of the methods for cell culturing described herein (including the methods described above with reference to FIGS. 12-14).

Figures 62A, 62B, 62C:
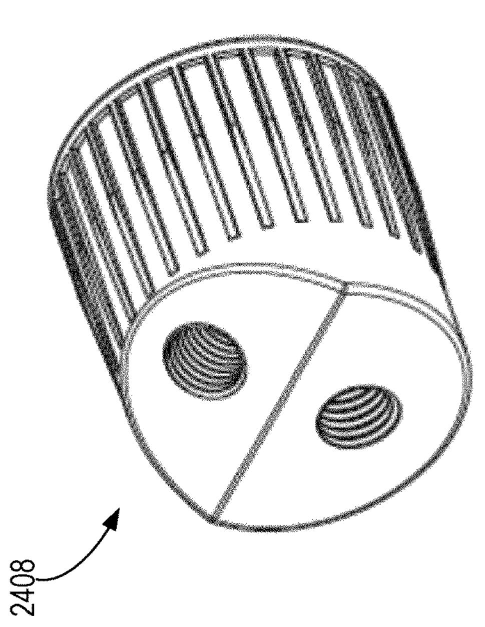
FIGS. 62A-62C illustrate a container lid according to an embodiment.
Figures 63A, 63B, 63C, 63D:
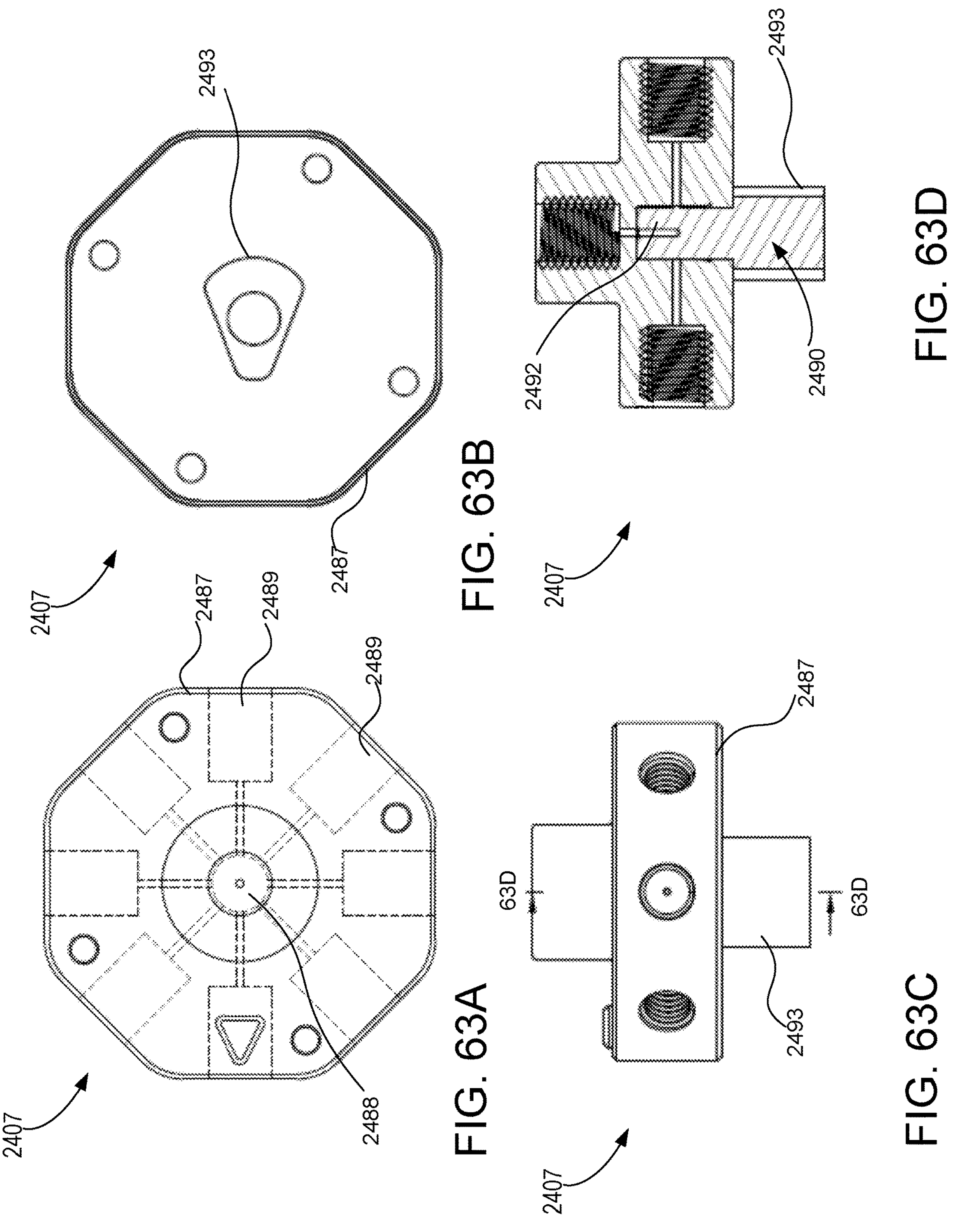
FIG. 63A is a top view of a multiport valve, according to an embodiment.
FIG. 63B is a bottom view of the multiport valve of FIG. 63A.
FIG. 63C is a side view of the multiport valve of FIG. 63A
FIG. 63D is a cross-sectional view taken along line 63D-63D in FIG. 63C.

FIGS. 62A-62C illustrate container/vessel lid 2408 according to an embodiment. The lid 2408 can be used in any of the embodiments of a cell culture system described herein. The lid 2408 can be screwed on to the mouth of a cell culture container or other container as described herein such that the lid 2408 engages with the threads of the mouth of cell culture container. In this example embodiment, the lid 2408 has a liquid port 2483 and a gas port 2484. A liquid channel 2485 is threadedly engaged with the liquid port 2483. A gas filter 2486 (see FIG. 62C) is threadedly engaged with gas port 2483. Gas filter 2486 may allow gas exchange in and out of the cell culture container while blocking any microbes or pathogens from entering the cell container. In an embodiment, the gas filter 2486 is a 0.22 micron filter.

Figures 64A, 64B, 64C:
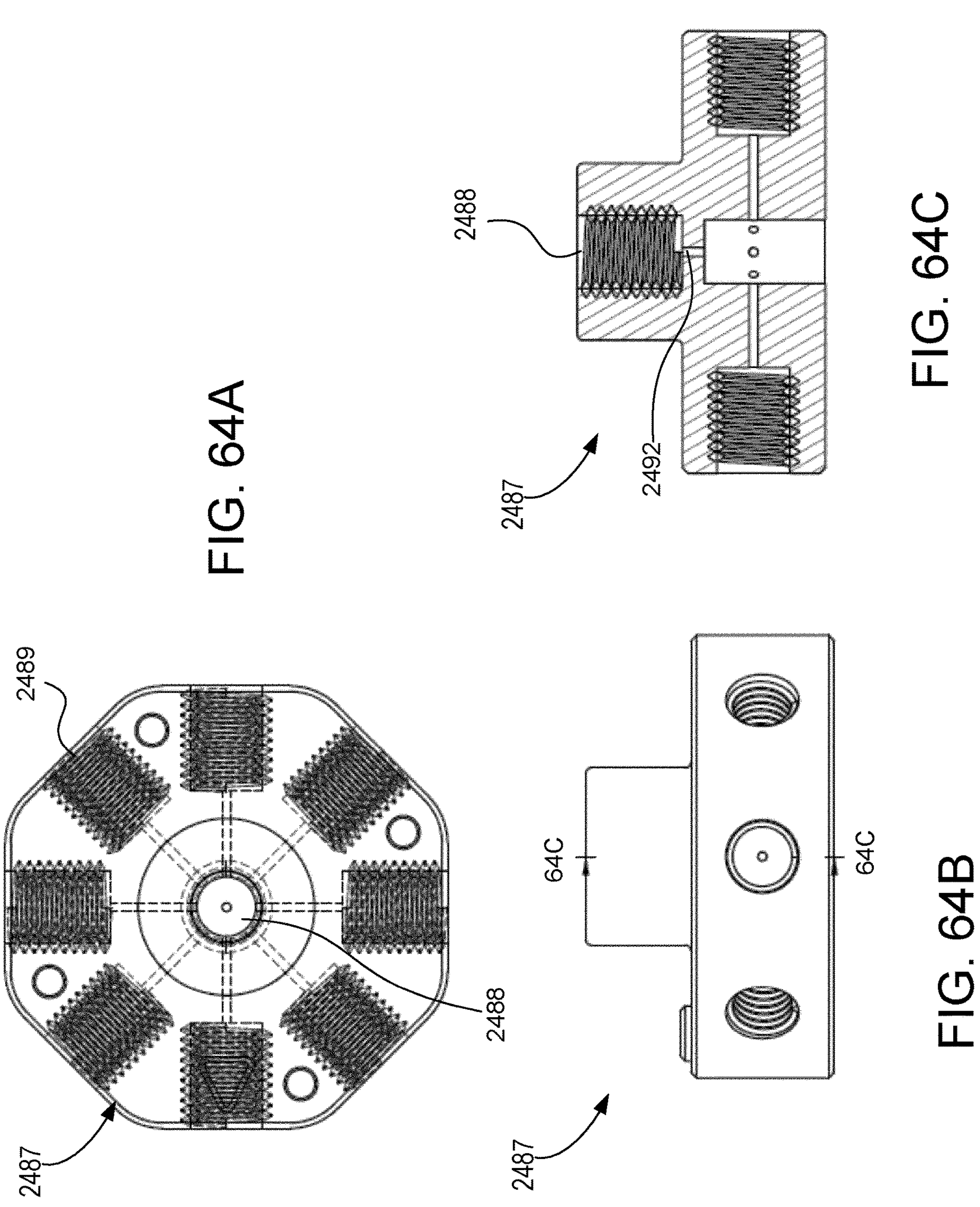
FIG. 64A is a cross-sectional view of the valve body of the multiport valve of FIGS. 63A-63D.
FIG. 64B is a side view and FIG. 64C is a cross-sectional side view of the valve body of FIG. 64A.

FIGS. 63A-63D illustrate an example embodiment of a multiport valve 2407 according to an embodiment. The multiport valve 2407 can be used in any of the embodiments of a cell culturing system described herein. In this embodiment, the multiport valve 2407 includes a valve body 2487 having a master port 2488 on a top side and multiple selectable ports 2489 dispersed around its circumference of the valve body 2487 (see, e.g., FIGS. 64A-64C).

Figures 65A, 65B, 65C:
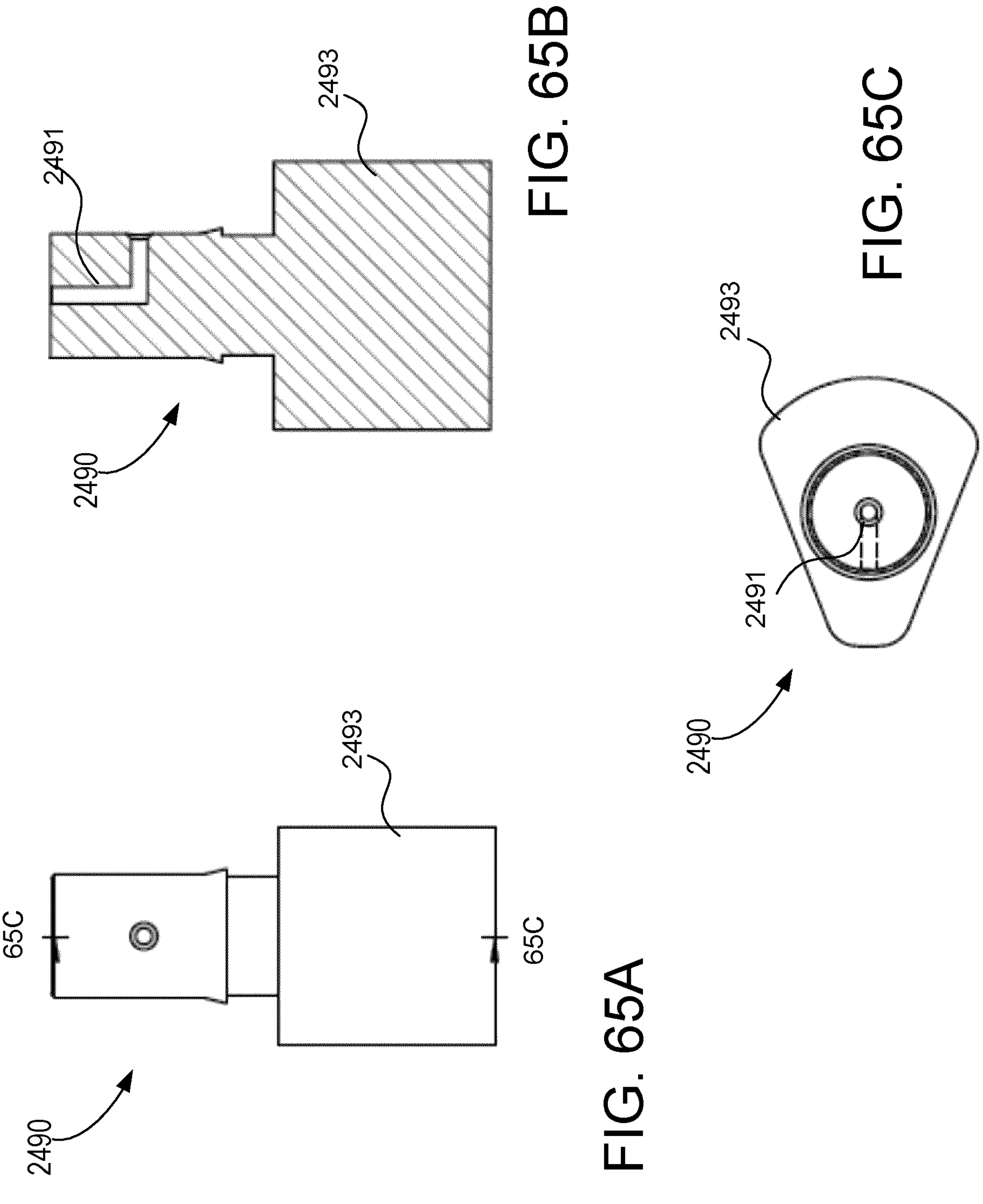
FIG. 65A is a side view of a valve rotor of the multiport valve of FIG. 63A.
FIG. 65B is a cross-sectional view taken along line 65B-65B in FIG. 65A.
FIG. 65C is a top view of the valve rotor.

The valve body 2487 has a cylindrical cavity on its underside to which a rotatable cylindrical valve rotor 2490 is inserted. Within rotatable cylindrical valve rotor 2490 is a fluid channel 2491 (see FIGS. 65A-65C). Within the valve body 2487 is a fluid channel 2492, which fluidly connects the master port 2488 to the fluid channel 2491 of the valve rotor 2490. The connection between fluid channel 2492 and fluid channel 2491 allows for the master port 2488 to be selectively fluidly connected to one of the side ports 2489 via rotation of the valve rotor 2490 (and therefore the fluid channel 2491). The valve rotor 2490 includes a mechanical coupler 2493 (see FIG. 65C), which is configured to mechanically couple to a valve actuator of the system, which can have a cavity shaped to accept the mechanical coupler 2493 and transfer rotational mechanical energy to the multiport valve 2407.

The multiport valve 2407 can be made of any appropriate material, and the valve body 2487 and valve rotor 2490 may be made of the same or different materials. Examples of materials that may be used include plastics, TFE-based materials such as polytetrafluoroethylene PTFE, metals, rubbers, or similar materials. In some embodiments, the valve body 2487 and valve rotor 2490 may be machined to fit with very close tolerances so that a fluid-tight seal is created between the two components. In some embodiments, additional gaskets, bearings, seals, and/or flanges may be incorporated into multiport valve 2407 to provide for a fluid-tight connection between valve body 2487 and valve rotor 2490.

Figure 66A:
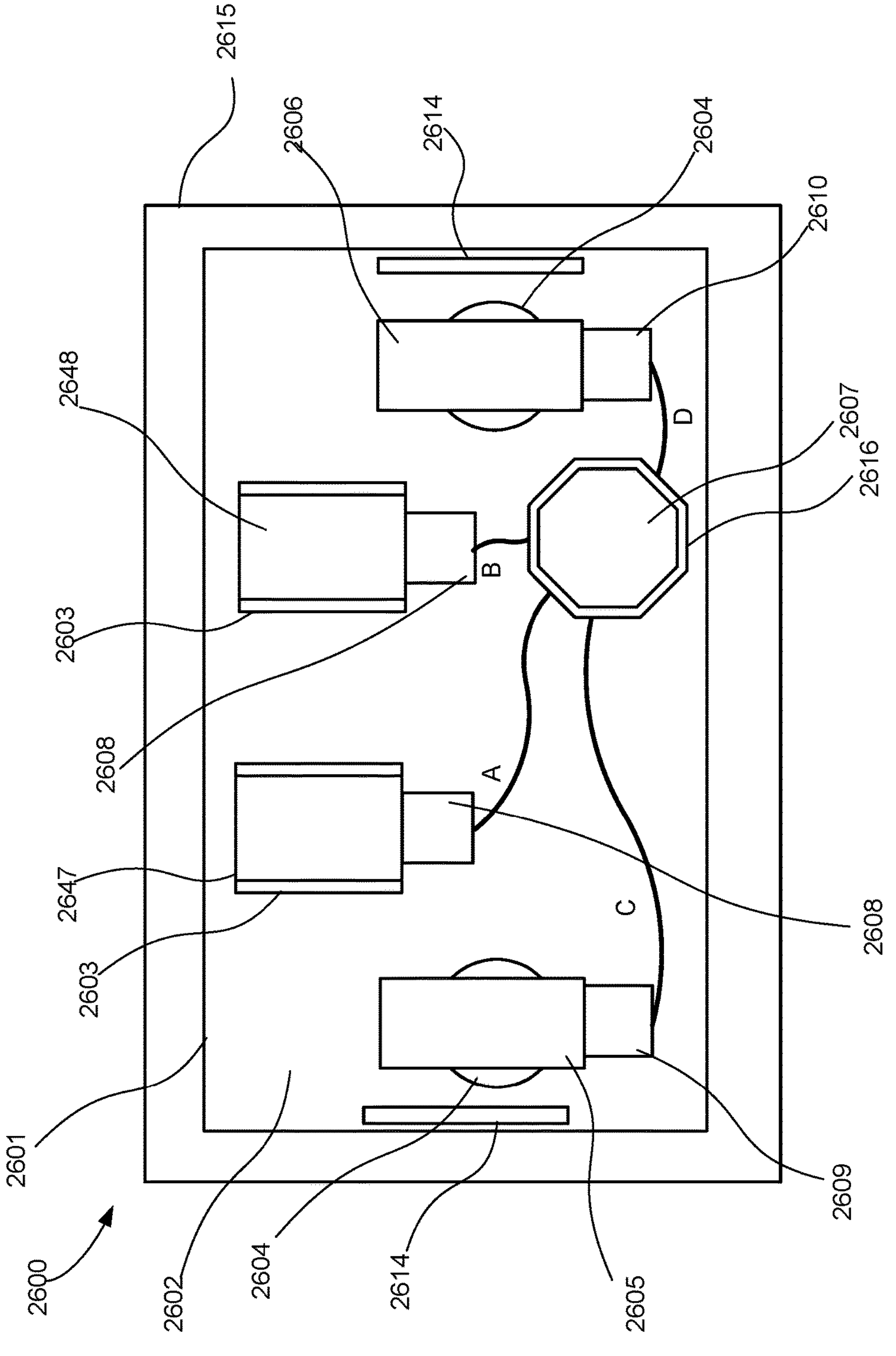
FIG. 66A is a schematic illustration of a tray assembly of a cell culturing system, according to an embodiment.

FIGS. 66A-66D illustrate a schematic view of an automated cell culture system according to another embodiment. This example automated cell culture system 2600 includes a consumable or disposable cell culture tray assembly 2501 (also referred to herein as "tray assembly," (see FIG. 66A) and a reusable base unit 2620 (see FIG. 66B). The disposable tray assembly 2601 includes various components described below, some of which are preassembled on (or with) the tray assembly 2601 and enclosed within a protective overwrap 2615 to maintain the components in a sterile state. Some of the components of the tray assembly 2601 can be added to the tray assembly 2601 within an aseptic environment (e.g., a laminar flow hood) prior to using the tray assembly 2601 in a cell culturing procedure. When the tray assembly 2601 has been assembled and is ready for use, the tray assembly 2601 can be coupled to the base unit 2620 as described in more detail herein. As shown in FIG. 66A, the tray assembly 2601, includes a tray 2602 that can be removably coupled to the base unit 2620 as described herein. In some embodiments, the tray 2602 can include one or more transparent or cut-out portions such that objects disposed on a top surface of the tray 2602 can be viewed from below the tray 2602. For example, as described in more detail below, the cell culture system 2600 can optionally include an imaging device and/or other sensors (not shown) that are disposed in the base unit 2620 and below the tray 2602 when the tray assembly 2601 is coupled to the base unit 2620. The transparent portion(s) or cut-out(s) can allow for images and/or other data to be obtained through the transparent portion or cut-out, such as the contents of a cell culture container coupled to the tray 2602, as described in more detail below.

A cell counting chip 2617 (see FIG. 66D) is also included in the cell culture system 2600 as described in more detail below. The tray assembly 2601 also includes one or more couplers 2603 that can be used to hold cell culture vessels or containers as described above for previous embodiments. The tray 2602 can also optionally include holders 2604 that can be used to removably couple a reagent container 2605 and a waste container 2606 to the tray 2602 (e.g., to secure the containers during shipping, initial setup, or the like). Although two couplers 2603 are shown, in other embodiments, there could be only one or more than two couplers 2603. For example, in some embodiments a tray assembly 2601 can be configured to support only one cell culture container and thus includes only a single coupler 2603 that maintains the cell culture container in a fixed position on the tray 2602. Similarly, although only one waste container 2606 and one reagent container 2605 are shown, in alternative embodiments, there can be multiple waste and reagent containers. Moreover, although FIG. 66A shows the waste container 2606 and the reagent container 2605 as being part of the tray assembly 2601, in other embodiments, the waste container 2606 and/or the reagent container 2605 can be separate components within the automated cell culture system 2600 that are not coupled to the tray 2602 during use. For example, in some embodiments, the reagent container 2605 can be used to contain cell culture media and can be placed in a refrigerated portion (not shown) of the automated cell culture system 2600 or another refrigeration location. The couplers 2603 and holders 2604 can be separate components attached to the tray 2602 or can be a component integrally or monolithically formed with the tray 2602. For example, in some embodiments, the couplers 2603 and/or the holders 2604 can include a deformable bracket, a movable pin, or any other suitable structure to couple the containers to the tray 2602. In some embodiments, the tray assembly 2602 can optionally include handles 2614 that can be used by a user to move and carry the tray assembly 2602. The handles 2614 can be separate components from the tray 2602 or formed integrally or monolithically with the tray 2602. In some embodiments, the tray assembly 2601 may not include holders 2604. In this embodiment, the tray assembly 2601 can be preassembled with one or more cell culture containers. For example, in some embodiments, the cell culture containers can be provided as part of the consumable tray assembly, but removable from the tray if desired. In some embodiments the cell culture containers can be provided a part of the consumable tray assembly but fixed or permanently coupled to the tray assembly. For example, the cell culture containers can be fused to the container lids, the fluidic tubing and/or the multiport valve, etc.

Figure 66B:
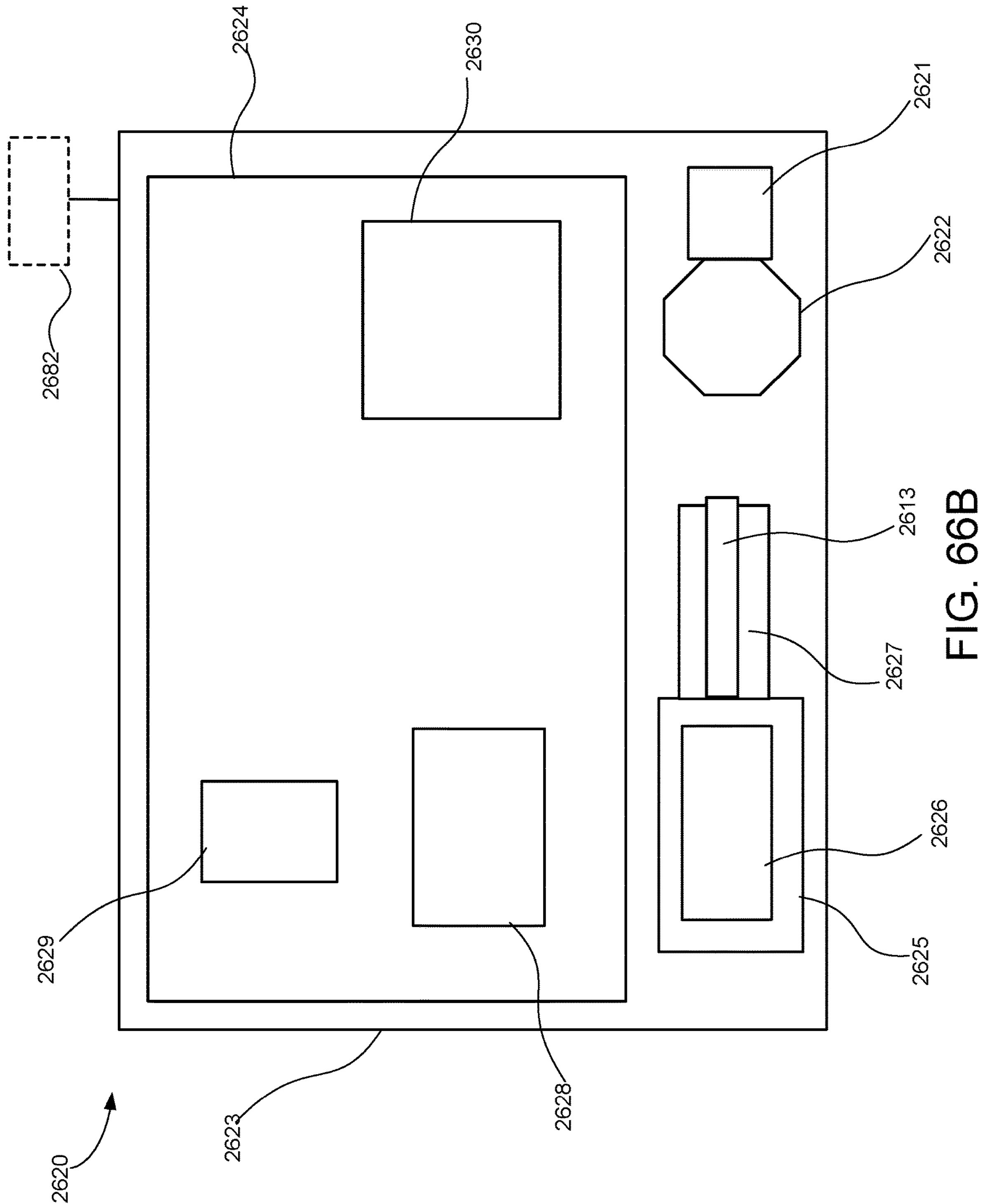
FIG. 66B is a schematic illustration of a base unit of a cell culturing system, according to an embodiment.
Figure 66C:
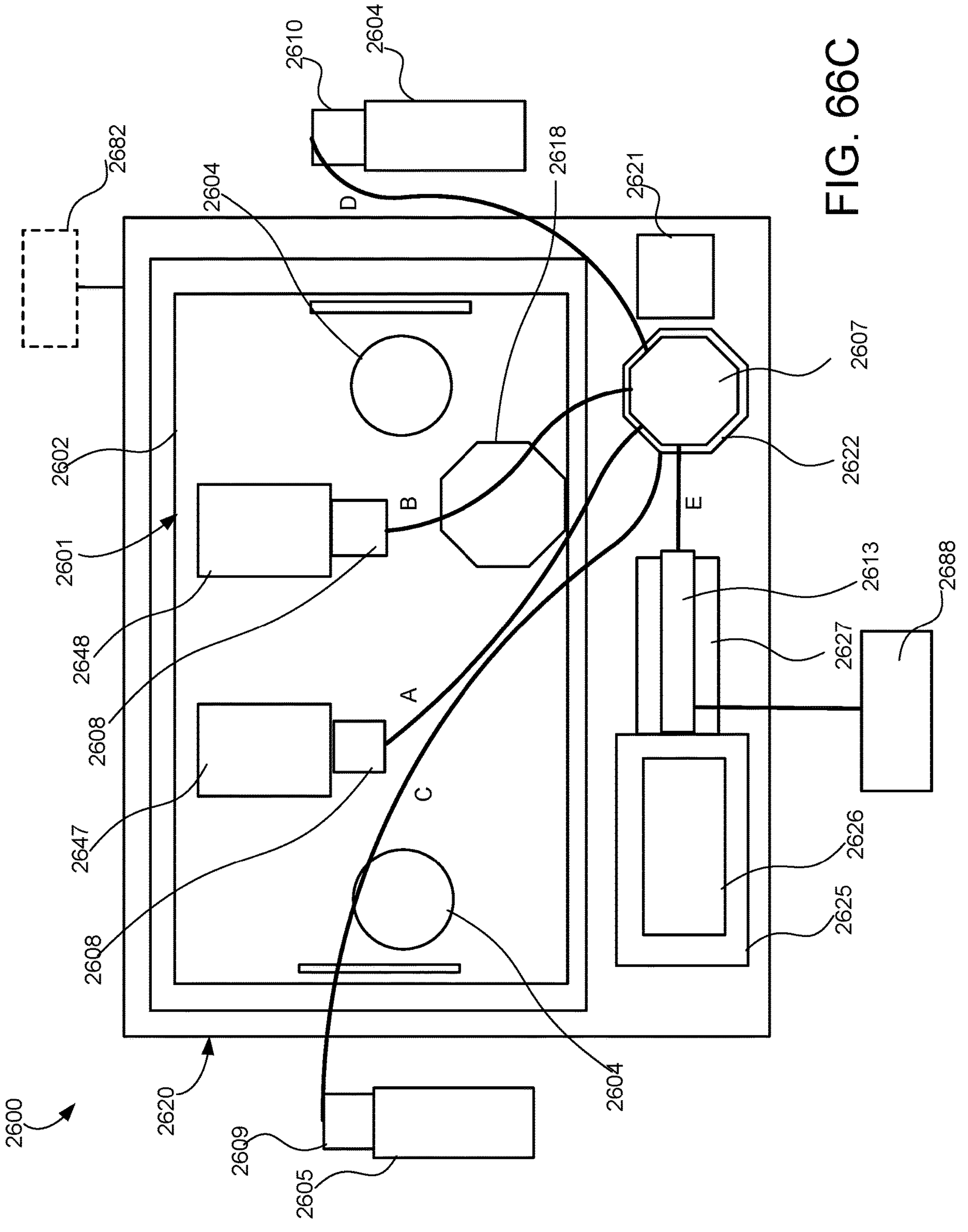
FIG. 66C is a schematic illustration of a cell culturing system, according to an embodiment, including the tray assembly shown in FIG. 66A and the base unit shown in FIG. 66B.

As shown in FIGS. 66A and 66C, two cell culture containers, 2647 and 2648 are included in the tray assembly 2601. The cell culture containers 2647 and 2648 are each coupled to a container lid 2608. In this embodiment, the container lids 2608 are coupled to the cell culture containers 2647, 2648. Thus, the container lids 2608 and the containers 2647, 2648 can be pre-connected, coupled to the tray 2602, and sterilized within the protective overwrap 2615. Thus, a pre-sterilized tray assembly with preconnected and sterilized cell culture containers can be used, eliminating the need to connect cell culture containers to the tray in the flow hood. In this example embodiment, there are two containers 2647 and 2648 and two lids 2608, but it should be understood that a different number of containers and lids 2608 can be provided. Each of the lids 2608 can include a liquid exchange port (also referred to herein as "fluid port") and a gas exchange port (each not shown in FIGS. 66A-66C) as described above, for example, with reference to FIGS. 62A-62C.

As shown, each of the fluid ports is coupled to a select port of the multiport valve 2607 with tubing (See tubing A, B, C and D in FIG. 66A). The gas exchange ports can allow gas transfer out of the cell culture container to which it is coupled. For example, in some embodiments, the lids 2608 can be similar to the cell culture vessel lid 803 or the lid 2408 shown and described herein. For example, the lids 2608 can include a gas filter that prevents microbes and/or contaminants from entering the cell culture container, thereby allow cell culturing and fluid transfer via lids 2608 while maintaining a closed (and/or sterile) system with other containers within the system (e.g., the reagent container 2605, the waste container 2606 or other containers). In some embodiments, the tray assembly 2601 can optionally include lids 2609 and 2610 that are coupled to the reagent container 2603 and the waste container 2606, respectively. The lid 2609 and/or the lid 2610 can be similar in structure and function as the lids 2608 and/or the cell culture vessel lid 803.

The tray assembly 2601 also includes a multiport valve 2607 preassembled on the tray 2602, as described above for previous embodiments and as described in more detail below. As shown, each of the fluid ports is coupled to a select port of the multiport valve 2607 with tubing (see tubing A, B, C and D in FIG. 66A). Thus, with the cell culture containers 2647 and 2648 preassembled on the tray 2602 and coupled to the lids 2608, the containers are permanently in fluidic communication with the multiport valve 2607. The multiport valve 2607 can include the same or similar components and functions in the same or similar manner as the multiport valves described above for previous embodiments (e.g., the multiport valve 600 or the multiport valve 2407 described herein).

Figure 66D:
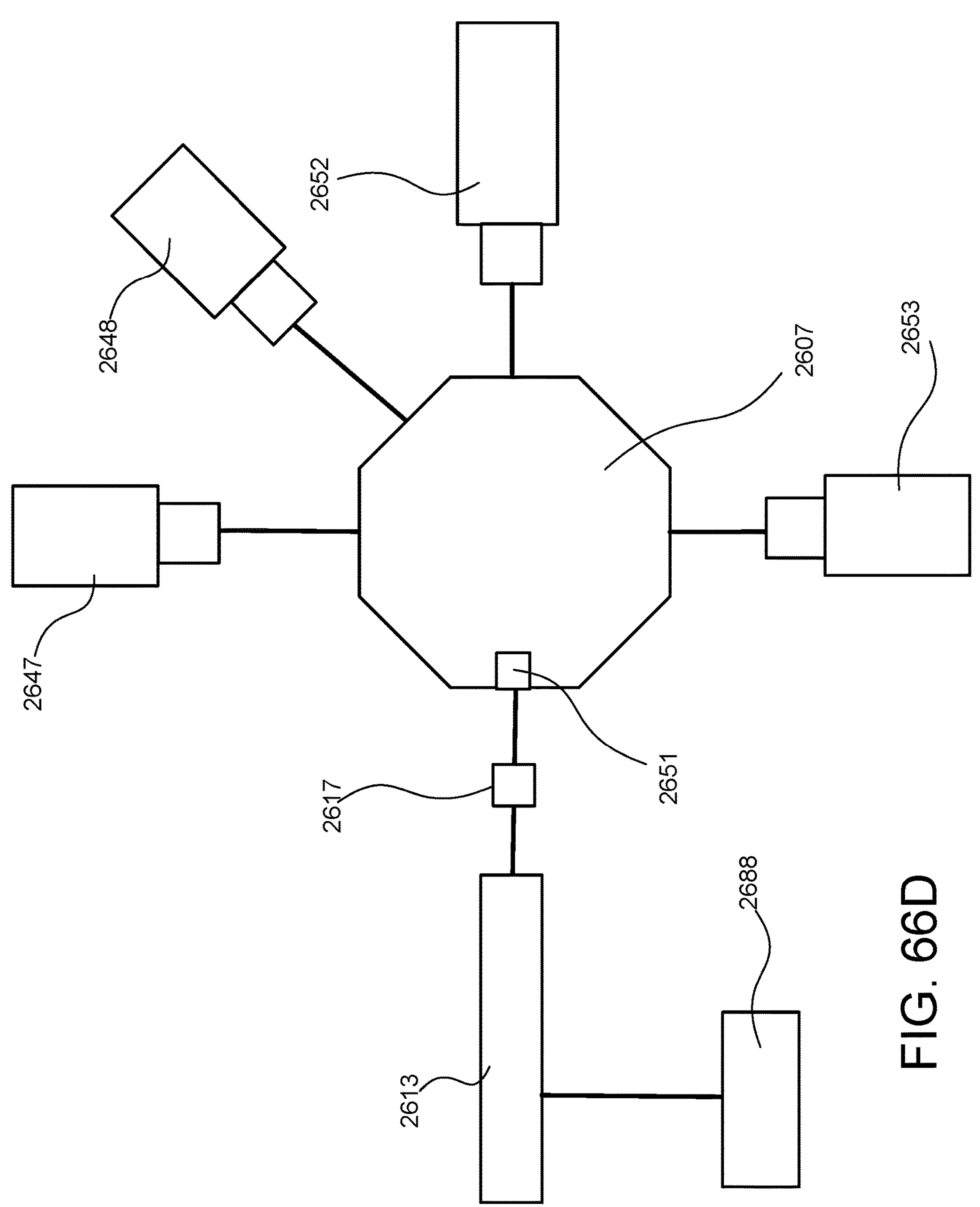
FIG. 66D is a is a schematic illustration of a portion of the cell culturing system of FIG. 66C showing the multiport valve coupled to various components, according to an embodiment.

More specifically, the multiport valve 2607 can include a master port 2651 (see FIG. 66D) configured to be coupled to a fluid pump 2613 of the base unit (described below and shown in FIGS. 66B and 66C), and multiple selectable ports that can be fluidically coupled to liquid exchange ports of the lids 2608, 2609, 2610 and/or other components of the cell culture assembly 2600 as described herein. For example, one port of the selectable ports can be aseptically and/or fluidically coupled to a first liquid exchange port of a first lid 2608 coupled to the container 2647, and a second selectable port can be aseptically and/or fluidically coupled to a second liquid exchange port of a second lid 2608 coupled to the container 2648, as shown in FIG. 66D. In some embodiments, a third port of the multiport valve 2607 can be coupled to the liquid exchange port of the reagent container 2605 (see FIGS. 66A and 66C), a fourth port can be coupled to the liquid exchange port of the waste container 2606 (see FIGS. 66A and 66C) and a fifth port can be coupled to a liquid exchange port of a cell harvest container 2652 (see FIG. 66D). An example system schematic illustrating some other example couplings of a multiport valve is provided in FIG. 59. In this manner, when actuated the multiport valve 2607 can facilitate fluid exchange between various containers within the automated cell culture system 2600. For example, as described herein, the multiport valve 2607 can be actuated to facilitate the addition of cell culturing media or reagents to the cell culture containers, the removal of cells from the cell culture containers (e.g., cell passaging or cell harvesting), or any other fluid movement associated with cell culturing.

In this embodiment, the cell counting chip 2617 is coupled to the master port 2651 of the multiport valve 2607 between the multiport valve 2607 and the fluid pump 2613 as shown in FIGS. 66C and 66D. The cell counting chip 2617 can include a bottom transparent portion and can be used to obtain information about the contents of a cell culture container as described herein. In some embodiments, the cell counting chip 2617 may be coupled to or mounted within the base unit 2620 instead of being preassembled on the tray assembly 2601. The cell counting chip 2617 can be disposed upstream of the pump 2613 such that cells can be counted without losing (or wasting) any cells. For example, the cells are pumped from one of the containers 2647, 2648 to the holding vessel 2688 and the cells are counted as they go through the cell counting chip 2617. The cells are then pumped back to the container 2647, 2648 from the holding vessel 2688. By having the cell counting chip 2617 within the flow path to the master port 2651 (rather than in a flow path that is connected to the waste chamber 2606), the cells can be counted and/or characterized within the cell counting chip 2617 in a non-destructive manner. Said another way, depending on the desired method, the counted cells are not destroyed (or sent to the waste container 2606).

In alternative embodiments, however, the cell counting chip is coupled to one of the other selectable ports of the multiport valve 2607. In such an embodiment, the cell counting chip can be disposed on one of the output lines that communicate with the waste container 2606, such that as cells pass through and are counted, the cell sample gets flushed to waste.

As described above for previous embodiments, the tray assembly 2601 can be enclosed within the protective overwrap 2615. In some embodiments, the tray assembly 2601 can be sterilized prior to being placed in the protective overwrap. To prepare the cell culture system for use in cell culturing, with the containers 2647 and 2648 included within the tray assembly, the cells to be cultured can be added to the cell culture containers 2647 and 2648 directly from the seeding vessel 2653. The seeding vessel 2653 can be provided separately or in some embodiments, included within the tray assembly 2601. The seeding vessel 2653 need not be in permanent fluidic communication with the multiport valve 2607, but rather, can be detached, filled with cells, and then reattached into fluid communication with the multiport valve 2607. The seeding vessel 2653 can have a detachable lid or the fluid line can be aseptically disconnected and reconnected. As described herein, the user can load the desired cells, reagents, cell culture media, or the like into the containers (e.g., containers 2647, 2648, 2605) within an aseptic environment. The tray assembly 2601 can then be coupled to the base unit 2620 and moved into an incubation environment where fluid exchange can be performed to ensure the desired cell culturing, as described herein. By using a single seeding vessel 2653 to load cells into the containers 2647 and 2648, the preparation process is simplified (as opposed to loading cells into each container and then coupling each container to its respective lid).

When the tray assembly 2601 is attached to the base unit 2620, the multiport valve 2607 is configured to be moved off the tray 2602 and engage a valve actuator 2621 of the base unit 2620 (see FIGS. 66B and 66C). The multiport valve 2607 can include a mounting portion 2616 configured to matingly couple to a valve connector 2622 of the base unit 2620 in some embodiments. For example, the mounting portion 2616 can have a shape such that it can be coupled to the valve connector 2622 in a puzzle-like manner. As shown in FIGS. 66B and 66C, when the multiport valve 2607 is engaged with the valve actuator 2621 of the base unit 2620, the valve actuator 2621 can actuate the multiport valve 2607 to move to a selected port to allow for selective fluid transfer to and from the various containers of the tray assembly 2601 and cell culture containers (described below). In some embodiments, the multiport valve 2607 can be coupled to the valve actuator 2621 while remaining coupled to the tray 2602. For example, a valve connector (not shown) coupled to the valve actuator 2621 can be disposed on the base unit 2620 below where the tray assembly 2602 is removably coupled to the base unit 2620 (e.g., similar to the base unit 301 or the base unit 2120 described herein). In some embodiments, the multiport valve 2607 can be removed from the tray 2602 (while remaining coupled to the lids and containers, thereby preserving the closed system) and attached to the mating valve connector 2622 of the base unit 2620 as shown, for example, in FIGS. 66B and 66C. FIG. 66B shows the connector 2622 without the multiport valve 2607 coupled thereto, and FIG. 26C shows the multiport valve 2607 coupled thereto. In other words, the multiport valve 2607 can be detached from a mating mounting pocket 2618 (see FIG. 66C) of the tray 2602 and attached to the valve connector 2622 of the base unit 2620. As described above, the mounting portion 2616 of the valve 2607 is shaped to matingly engage the mounting pocket 2618 and to matingly engage the valve connector 2622 of the base unit 2620 to ensure proper positioning and alignment within both the tray assembly 2601 and the base unit 2620. This relocation of the multiport valve 2607 can be done with the lids 2608, 2609, 2610 remaining aseptically coupled to the multiport valve 2607. Removing the valve 2607 from the tray 2602 allows the interface between the valve 2607 and the valve actuator 2621 to be stationary, which is well-suited for those embodiments that include an agitator, such as agitator 2628 described below, to move the tray 2602 relative to the base unit 2620. Similarly stated, by coupling the valve 2607 directly to the base unit 2620, the interface between the valve 2607 and the valve actuator 2621 is not disrupted by the relative movement between the tray 2601 and the base unit 2620.

The base unit 2620 (see FIGS. 66B and 66C) includes a housing 2623 that supports various components of the base unit 2620 and can define (or include) a receiving portion 2624 to receive and removably couple the tray assembly 2601 thereto. In some embodiments, the receiving portion 6624 can include an opening in which the tray assembly 2601 can be placed and supported by a tray support (not shown). In some embodiments, the tray assembly 2601 is supported by a support portion of the base unit 2620 such that the tray assembly 2601 is elevated above a top surface of the base unit 2620. In some embodiments, the tray assembly 2601 is supported at least in part by engagement with an agitator (described herein) of the base unit 2620. In some embodiments, the tray assembly 2601 can be removably coupled to a separate support member that is couplable to the housing 2623 of the base unit 2620. The base unit 2620 can also include one or more transparent portions or open portions corresponding to transparent portions of the tray 2602 such that images and/or other sensor data associated with the contents of the cell culture containers can be obtained.

The base unit 2620 includes the valve connector 2622 and valve actuator 2621 described above and also includes a fluid pump portion 2627 and a pump actuator 2626. The pump actuator 2626 can be disposed, for example, at least partially within an opening 2625 defined by the housing 2623. In this embodiment, the fluid pump 2613 is provided with the base unit 2620 and can be coupled to the fluid pump portion 2627. For example, the fluid pump can be a peristaltic pump coupled to the base unit 2620. In such an embodiment, when the tray assembly 2601 is coupled to the base unit 2620, the user can load a section of the tubing that is within the closed system (that includes the containers and the valve) from the tray assembly 2601 within the head of the peristaltic pump to complete the fluid pump. In use, the head of the peristaltic pump includes a roller (or set of rollers) that deform the section of tubing to move fluids (e.g., the cell sample) within the closed system. Thus, the section of tubing (which deforms) can also be referred to as the fluid pump, and the peristaltic pump head can be referred to as the pump actuator (or a portion of the pump actuator). In other embodiments, the head of the peristaltic pump can be detachable from (and separate from) the pump actuator of the base unit 2620. In such embodiments, the peristaltic pump head can be pre-attached to the tubing and included within the tray assembly 2601. Thus, when installing the tray assembly, the preconnected pump head (i.e., the pump head including the section of tubing) can be coupled to the pump actuator of the base unit 2620. The fluid pump 2613 can be used to produce fluid movement in the cell culture system 2600 as described herein. The fluid pump 2613 can be any suitable pump that produces pressure and/or flow within the cell culture system 2600. For example, in some embodiments, the fluid pump 2613 can be a syringe that includes a piston rod and a syringe body. Various other positive displacement fluid pumps can be used. For example, in some embodiments, the pump can be a single-port pump, whereas in other embodiments, the pump can be a two-port pump, as described herein. The fluid pump 2613 can be fluidically coupled to the master port 2651 of the multiport valve 2607 with closed tubing provided with the tray assembly 2601. In this example embodiment, as shown in FIG. 66C (showing the tray assembly 2601 coupled to the base unit 2620), the multiport valve 2607 is shown detached from the tray assembly 2601 and coupled to the valve connector 2622 and the fluid pump 2613 is coupled to the master port 2651 with tubing E. The fluid pump 2613 can include a movable member within a pump body (not shown in FIGS. 66B and 66C). During operation of the system 2600, the movable member of the fluid pump 2613 (e.g., plunger, rotor, or deformable portion of tube) can be actuated to cause a suction force to bring fluid into the pump body and can actuate the movable member to push fluid out of the pump body as described above for previous embodiments.

In some embodiments, the base unit 2620 can also include an agitator 2628. The agitator 2628 can include, for example, an orbital shaker that moves the tray 2602 in a circular or half-circular motion. The agitator 2628 can be configured to agitate the removable tray assembly 2601 in relation to the housing 2623 as described above for previous embodiments. The agitator 2628 may agitate the tray 2602 in a rocking motion, vibrating motion, circular swirling motion, or other motions useful in cell culturing. In some embodiments, individual cell culture vessels/containers may be independently agitated by independent agitators displaced between the cell culture vessel and the removable tray assembly 2601 as previously described. In some embodiments, an agitator may not be included.

In some embodiments, the agitator 2628 can include a plate to which the tray assembly 2601 is coupled when the tray assembly 2601 is coupled to the base unit 2620 (similar to the support plate 2059 described herein). The agitator plate can be coupled to an agitator actuator (not shown) with a threaded coupling or the like. In some embodiments, the agitator 2628 can be removably coupled to the agitator actuator with, for example, a magnetic coupling to provide for easy removal and attachment by a user. This arrangement allows the agitator plate to be removed for cleaning, sterilization, or the like. In other embodiments, the agitator plate can be removably coupled to the base unit and/or the agitator actuator by any suitable mechanism to facilitate easy removal (e.g., clips, pins, or the like).

In some embodiments, the agitator 2628 can agitate in an orbital pattern. In some embodiments, the agitator 2628 can be user-programmed to agitate in different patterns such as, for example, a FIG. 8 pattern. Sometimes some agitation patterns may be preferential for some applications. For example, a FIG. 8 pattern may be desirable for providing even distribution of cells (for example when seeding a new cell culture vessel) or mixing of fluids within a container. In some embodiments, the agitator 2628 can be user-programmed to agitate in a windshield wiper (or reciprocating) motion. Such an embodiment may be better for detachment of cells from within the container, e.g., during passaging or harvesting of adherent cells.

In some embodiments, the base unit 2620 can also optionally include one or sensors 2629 (only one shown in FIG. 66B) and an electronic control system 2630 to control the operation of any of the components of the cell culture system 2600 (e.g., the valve actuator 2621, the pump actuator 2626). The electronic control system 2630 and sensors 1629 can be the same as or similar to, and function the same as or similar to, electronic control systems and sensors described herein for other embodiments. As described above, in some embodiments, a light or light source 2682 (see FIGS. 66B and 66C) can also be provided that can be used in combination with, for example, an imaging device.

Figures 67A, 67B:
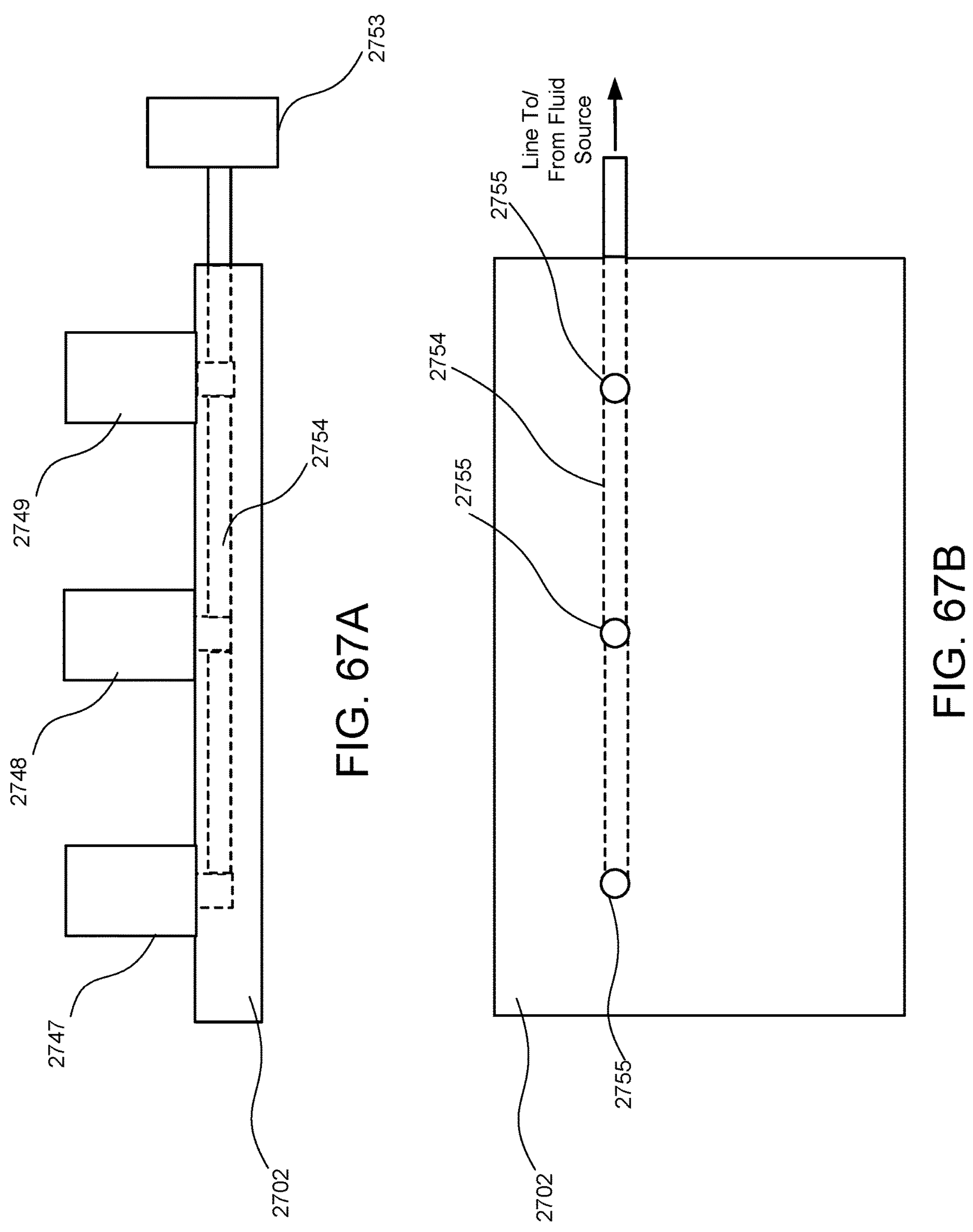
FIG. 67A is a side view of a portion of a tray assembly of a cell culturing system, according to an embodiment.
FIG. 67B is a top view of the tray of the tray assembly of FIG. 67A.

Although the tray assembly 2601 is shown and described as including tubing to interconnect the various containers to the multiport valve 2607, in other embodiments, a tray assembly can include fluid passages defined therein to minimize (or eliminate) the use of tubing. FIGS. 67A and 67B are a schematic side view and top view, respectively of an embodiment of a tray that can be included in a consumable tray assembly of a cell culture system as described herein. In this embodiment, the tray 2702 incudes fluidic channels that are integrally formed within the tray body. Thus, instead of fluidic tubing, fluidic paths are defined into the material (e.g., plastic) of the tray body itself. The fluid paths 2754 can be used to fill and empty cell culture vessels (e.g., cell culture containers, reagent container, waste container, etc.), which can also be part of a tray assembly as described above. More specifically, as shown in FIGS. 67A and 67B, the tray 2702 can include fluidic channels 2754 defined below the top surface of the tray 2702 that can be in fluid communication with openings 2755 defined in the top surface of the tray 2702 that can be placed in fluid communication with, for example, cell culture containers 2747, 2748, 2749. Thus, for example, the containers can be filled with cells from a seeding vessel 2753 from underneath via the fluidic channels 2754 and openings 2750. The openings 2755 can be actuated to be opened and closed (such as with a septum). Such a tray can provide for ease of manufacture and assembly of the tray assembly.

In some embodiments of a cell culture system described herein, to pump a fluid from a location within a first container (e.g., the container 2605) to a second container (e.g., the container 2747), the multiport valve is actuated such that the master port is connected to a port A of the multiport valve which is connected to the first container 2605. The pump pulls the solution (e.g., fluid) from container 2605 into the master port which transfers the fluid to a holding vessel just after the fluid pump, so that a solution from the container 2605 (e.g., nutrient media) fills the holding vessel. The multiport valve is actuated again such that the master port is connected to the second container 2647 via a port B of the multiport valve. The pump pumps the solution from the holding vessel and into the container 2647 via port B.

Figure 68:
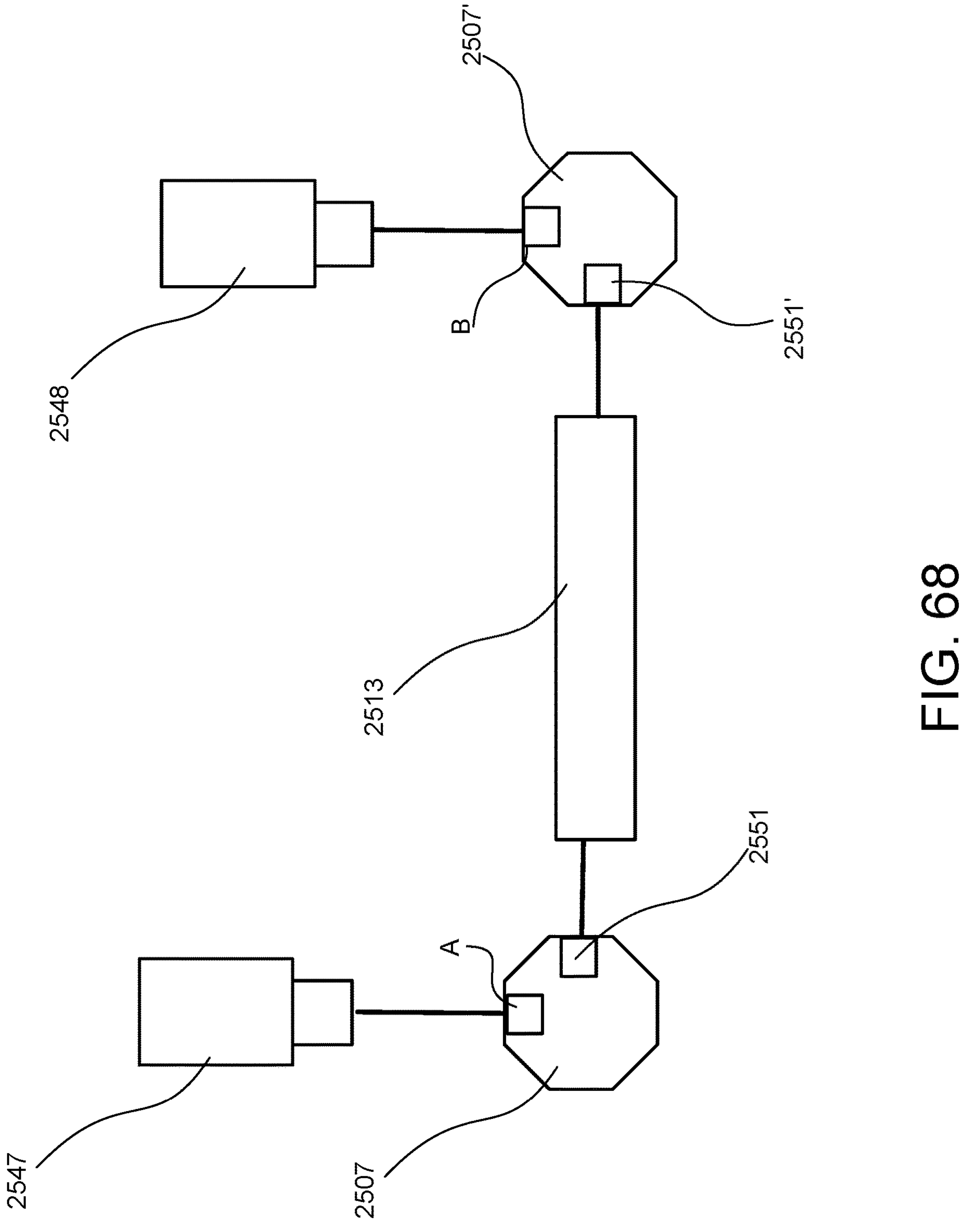
FIG. 68 is a schematic illustration illustrating an example fluidic setup within a portion of a system during a cell culturing procedure.

In an alternative embodiment, a cell culture system can be configured to pump fluid from a first container to a second container without using a holding vessel as described in the example above. For example, as shown FIG. 68, a cell culture system can include two multiport valves 2507 and 2507' each coupled to a fluid pump 2513. More specifically, a master port 2551 of multiport valve 2507 is fluidically coupled to a master port 2551' of the multiport valve 2507' with the fluid pump 2513 therebetween. Thus, the fluid pump can operate to selectively pump fluid in and out of each of the multiport valves 2507, 2507'. In such an embodiment, fluid can be moved, for example, from a container 2547 coupled to the multiport valve 2507 via a port A, to a container 2548 coupled to the multiport valve 2507' via a port B of the multiport valve 2507' without using a holding vessel. For example, the multiport valve 2507 is actuated to connect the master port 2551 to port A of the multiport valve 2507. Multiport valve 2507' is actuated to connect the master pot 2551' to the port B of the multiport valve 2507'. The pump 2513 is then actuated to pump fluid from container 2547 directly to container 2548. In some embodiments, a check valve can be used to optionally direct fluid from either container 2547 or 2548 to a holding vessel if desired. In this embodiment, by using an additional multiport valve, the number of fluid tubes can be reduced. In addition, having two multiport valves can provide for the fluidics to be distributed in a manner that is easier to manage. For example, in some embodiments, one valve can be connected directly to all the containers that are disposed outside of the system such as the reagent and waste containers, and a second valve can be connected to the cell culture containers and cell counting chip that are disposed within the system body (e.g., on the tray). In some embodiments, one of the multiport valves can be disposed outside of the incubator and connected to all the external solutions (such as, for example, refrigerated solutions), and the other multiport valve can be disposed inside the incubator and connected to all of the containers (e.g., flasks). Thus, only a single tube is needed to enter the incubator from outside of the incubator. Specifically, by having all of the external solutions coupled via one multiport valve, the input to the tray assembly is made via a single tube from the master port of the "external" multiport valve into the multiport valve of the tray assembly. This arrangement therefore eliminates the use of multiple tubes (one from each container of external solution) being routed from an external location (e.g., a refrigerator) into the tray assembly.

As described above with reference to FIGS. 32-34, the cell culture systems described herein can include an optical imaging system that can be mounted within the housing of any of the base units of the cell culture systems described herein. The microscope imaging device 1960 described above includes an imaging device 1962 that can view through a window or transparent portion in the top of the base unit and through cut outs (or transparent portions) in both the tray and any shaking platform (e.g., support for a tray in contact with an agitator). Thus, the microscope imaging device 1960 can be used to collect information related to the contents of a cell culture container and/or within a cell counting chip as described herein. For example, in some embodiments, the microscope imaging device 1960 can obtain images of a cell culture container and/or a cell counting chip during a cell culturing procedure, and the images can be used to determine, for example, the density of the contents to determine a quantity of cells within the container (for example, for suspension cells), or a percentage confluence (i.e., percentage of coverage of the container area with cells) in the case of, for example, adherent cells.

Figure 69:
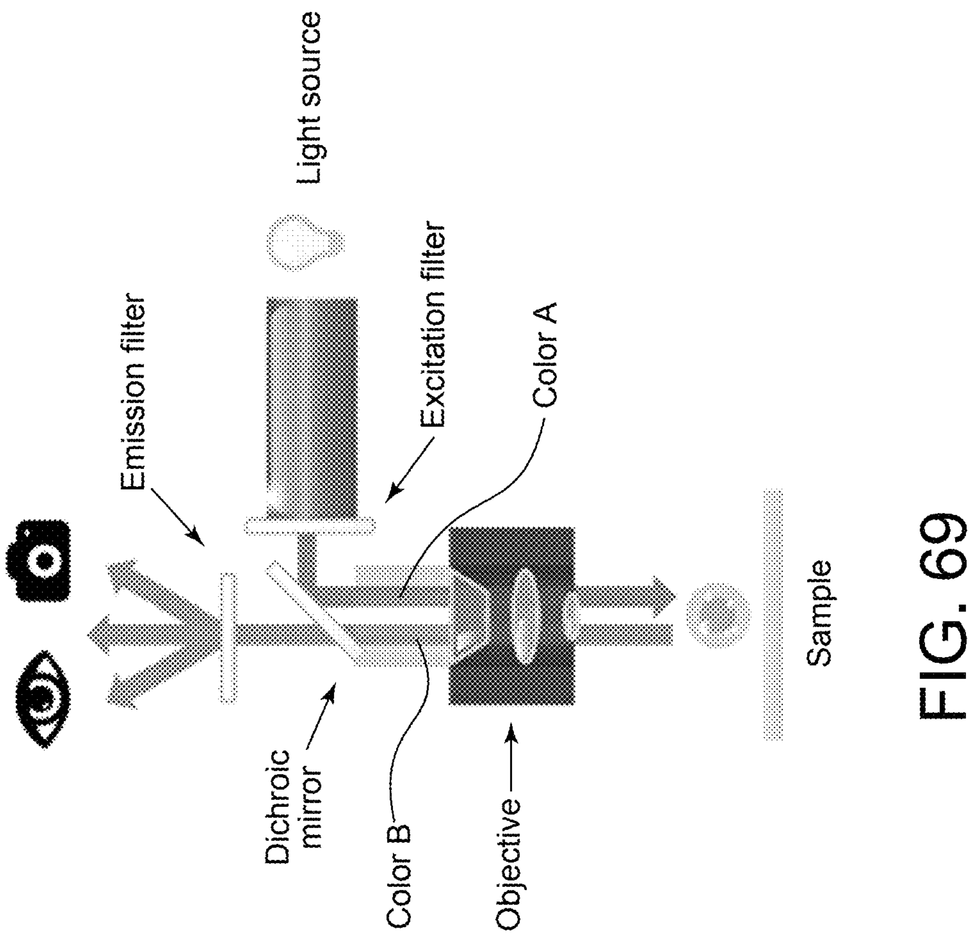
FIG. 69 illustrates an example of an epi-illumination for fluorescence system.

As also described above, in some embodiments, a light(s) or light source (not shown) can be mounted above the tray assembly of the system on another multi-axis gantry which allows it to be controlled to move to the same position as the microscope within the base unit. Alternatively, in some embodiments, a light source can be mounted on the same side of a sample to be imaged. This type of imaging and lighting is referred to as epi-illumination. FIG. 69 illustrates an example of epi-illumination for a fluorescence system, although epi-illumination may also be used for a brightfield application. In this fluorescence example, the sample to be imaged is illuminated with the light source from below the sample with a light of color A. The sample then emits its own light (e.g., "fluorescence") of color B, which is observed by the sensor. A dichroic mirror is included to stop reflected light of color A reaching the sensor but allows light of color B to pass through. Such an epi-illumination system can be incorporated within a cell culture system described herein.

In such an embodiment, the light source can be operatively coupled to the same gantry (e.g., gantry 1961 described above) as the imaging device (e.g., microscope) such that the imaging device and light source can be moved together. Alternatively, the light source and imaging device can each be mounted to a separate gantry or otherwise mounted separately from the imaging device and operated independently. As described above for previous embodiments, the microscope imaging device (e.g., imaging device 1960) and light source can be controlled by any of the electronic control systems and according to any of the methods described herein. For example, in some embodiments, the microscope imaging device 1960 (and any associated light source) can be controlled to automatically image a cell culture container (e.g., to produce a sensor output associated with the cells within the container). A cell sensor module of an electronic control system (e.g., the electronic control system 1630) or any other electronic control system described herein can receive the sensor output and produce a signal associated with a quantity of cells within the container (e.g., cell density or a percentage confluence). Based on this information the electronic control system can then produce one or more signals (e.g., valve control signals, pump control signals, agitator signals, or the like) to cause the transfer of the cells from within the cell culture container to another container within the system. Similarly stated, in some embodiments, the microscope imaging device (e.g., imaging device 1960) can provide input for automated cell passaging or cell harvesting operations.

In some embodiments of a cell culture system, a machine-readable optical label or bar code, such as a Quick Response code ("QR code") is included on the consumable tray assembly. In some embodiments, the imaging device (e.g., 1960 described above) can be used to observe and confirm that the consumable tray assembly is an approved consumable tray assembly. For example, when a tray assembly is coupled to a base unit, the imaging device can view/scan the QR code to confirm the tray assembly is an approved tray assembly to use with the base unit.

As described above with reference to FIG. 17, any of the cell culture systems described herein can include an electronic control system (e.g., electronic control system 1630) that can be used to control operation of the cell culture system. With reference to FIG. 17, the electronic control system 1630 can communicate with other remote computing devices (e.g., computing device 1643), via a network 1646 (e.g., the Internet), through, for example, a service platform 1642 and a cell culture Application (i.e., App) 1644. The electronic control system 1630 can in addition to, or alternatively, communicate with a remote computing device through a direct connection such as, a cable connected to a USB port of the base unit 1620. As shown in FIG. 17, the electronic control system 1630 includes a network module 1640 that can be a hardware and/or software module (stored in memory 1632 and/or executed in the processor 1631). The network module 1640 is configured to exchange information associated with the base unit 1620 and a remote computing device 1643 to facilitate the communication process. For example, the network module 1640 of the base unit 1620 can cause the remote computing device 1643 and the base unit 1620 to exchange short term and/or long-term security keys to complete the pairing and bonding process.

The electronic control system 1630 also includes a notification module 1639 that can be a hardware and/or software module (stored in memory 1632 and/or executed in the processor 1631). The notification module 1639 is configured to produce notifications associated with any of the methods and/or application modules described herein. For example, in some embodiments, the notification module 1639 can produce a notification that is transmitted via the radio 1633 and is for receipt by a notification module of the remote computing device 1643. In this manner, the notification module 1639 executed in the cell culture application can produce outputs (e.g., wireless communication signals, GUI elements, audible outputs, visual outputs, or the like) to notify the user of events.

The remote computing device 1643 can produce notifications for the user via the cell culture application 1644 and can receive input from a user in response to such notifications. The remote computing device 1643 can then transmit the input (or instructions) to the service platform 1642. Based on the user input, the service platform 1642 can transmit instructions to the base unit 1620, which can then execute the instructions to perform the desired task (e.g., cell passaging).

Figure 70:
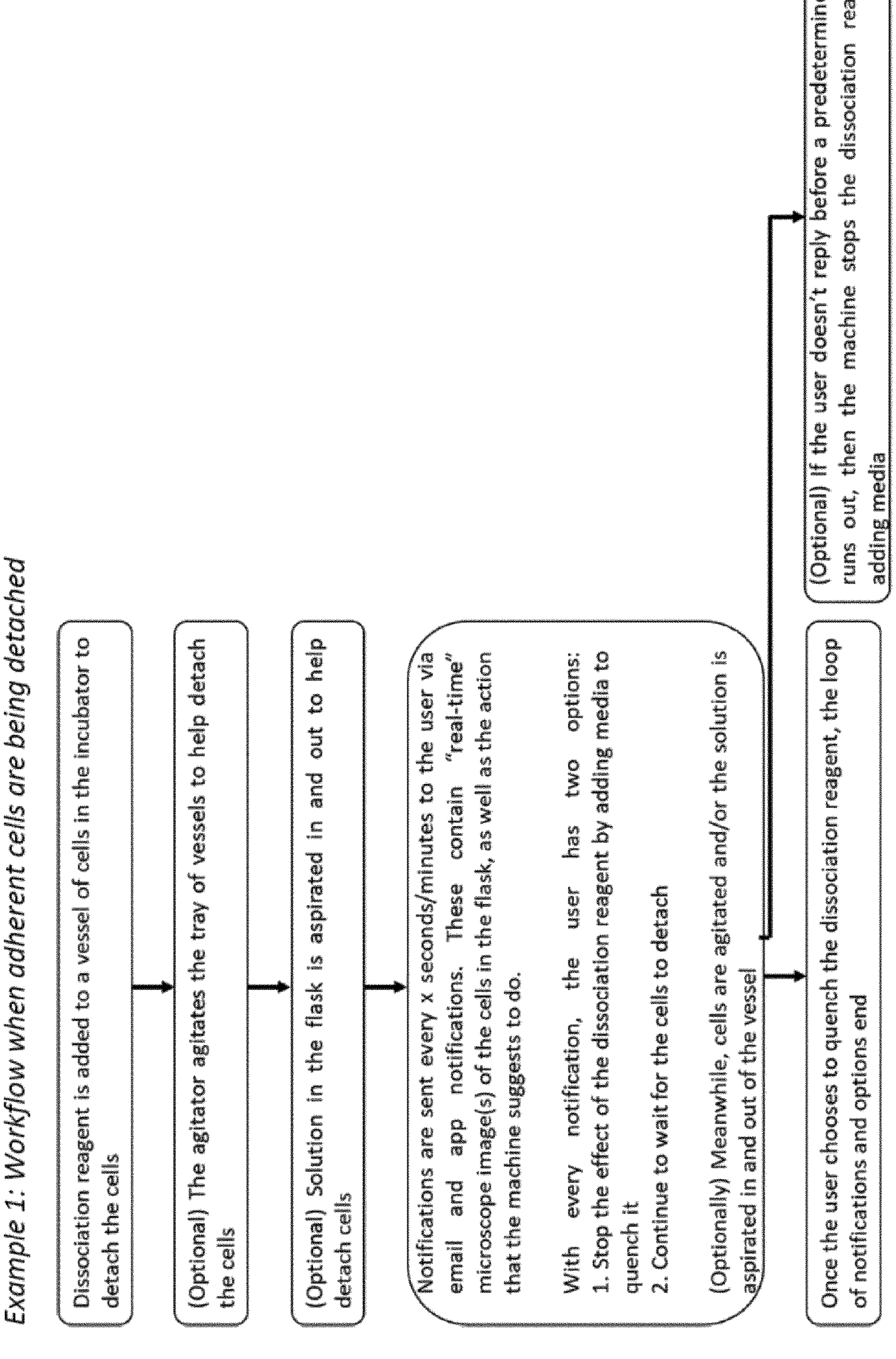
Figure 71:
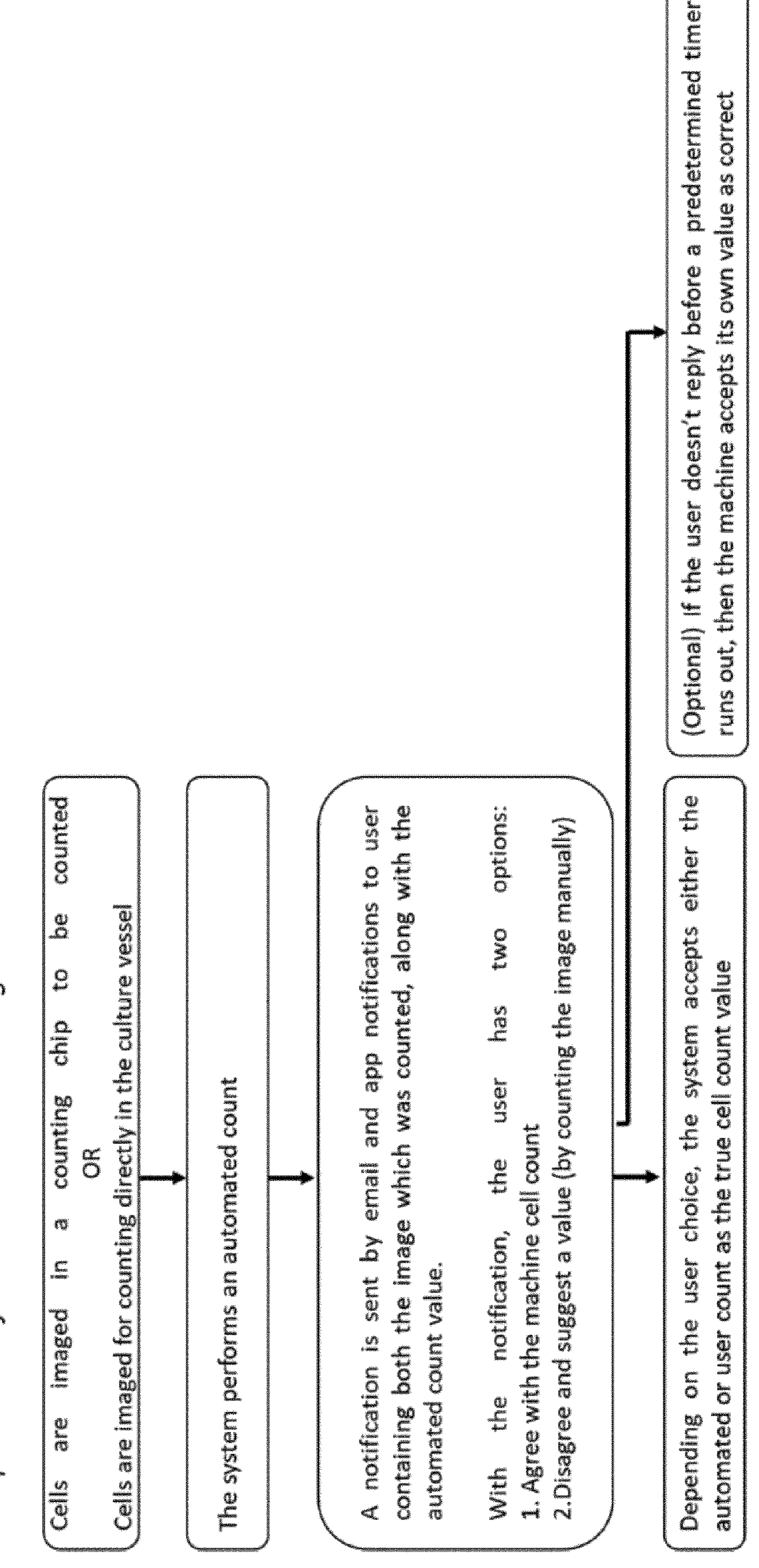
Figure 72:
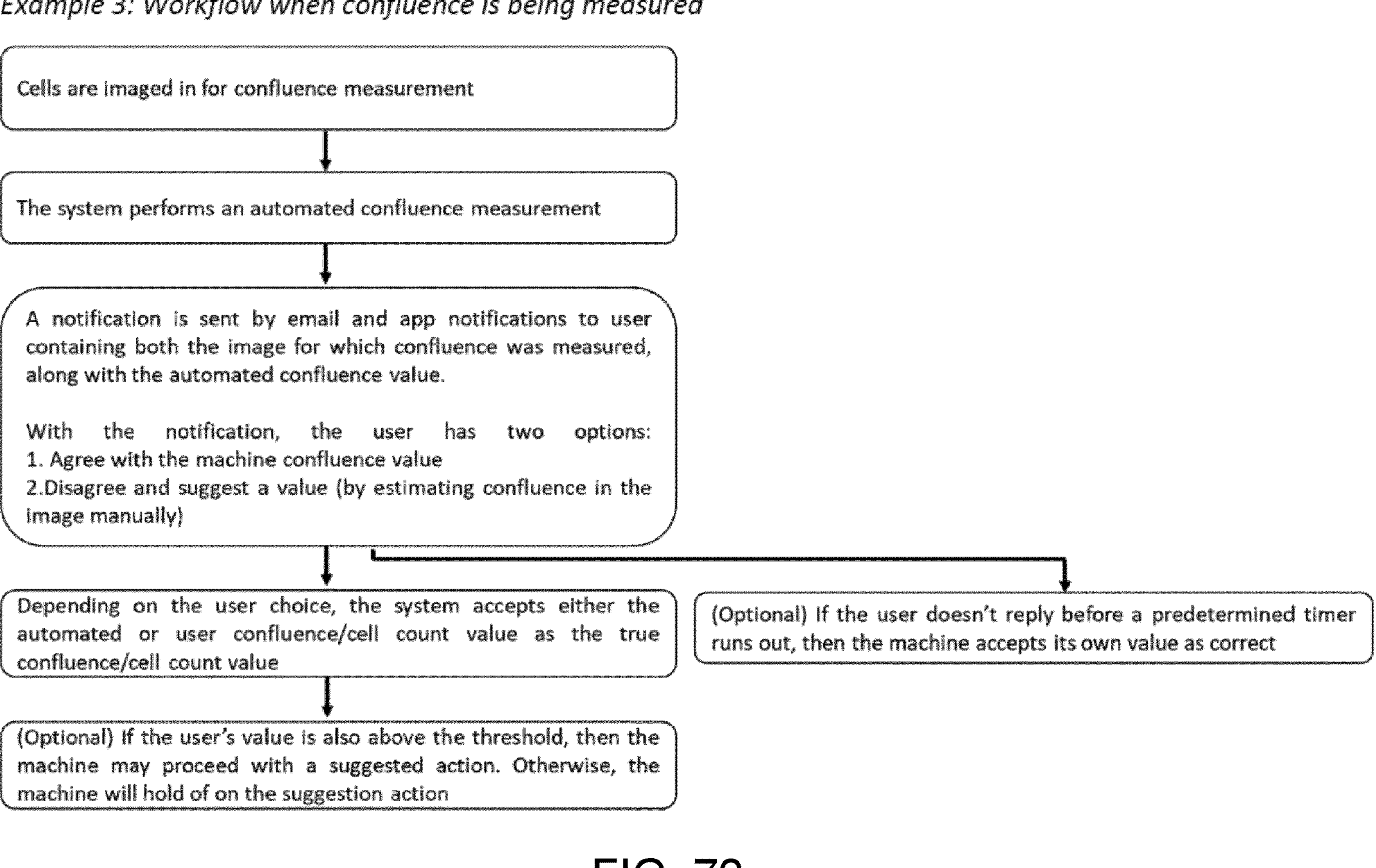

FIGS. 70-73 illustrate computer-implemented methods, where a user receives a notification from the notification module described above, and the notification can include, for example, an image and a suggested action. The user can review the data in the notification or otherwise access information received (e.g., a link can take the user to a notification page) and use the data to make decisions about the operation of the cell culturing system such as, for example, whether the system should proceed with its suggested course of action. In some embodiments, the computer-implemented methods can include receiving a user input to stop (or not proceed) with a specific action. In this manner, the user can override any activities, whether or not the user agrees (or disagrees) with the automated readings or other information provided by the system. FIG. 70 is a flowchart illustrating an example workflow when adherent cells are being detached; FIG. 71 is a flowchart illustrating a workflow when cells are being counted; FIG. 72 is a flowchart illustrating a workflow when confluence is being measured; and FIG. 73 is a flowchart illustrating a workflow when there is an automated confluence/cell count which exceeds a threshold and triggers a suggested action. As shown, in some embodiments, the computer-implemented methods include one or more modules that can produce signals and/or cause the system to perform certain tasks without further human intervention. For example, as shown in FIG. 71, a method can include performing an automated cell count using an imaging system as described herein. The method can further produce one or more notifications to allow a user to override the automatically generated count. The method can further proceed with the automated count if the user does not provide an override value.

In some embodiments of a cell culture system described herein, the system includes a tangential flow filtration ("TFF") system, (also sometimes referred to as cross-flow filtration or hollow-fiber filtration). TFF can be used for the in-line removal of cell dissociation reagent during, for example, passaging. As described herein, when a culture vessel or container of adherent cells (e.g., cells that stick to a surface) multiplies to a point where the percentage of the container floor that is covered in cells (% confluence) exceeds a certain threshold, some cells need to be detached and moved to a new vessel. As described herein (see e.g., FIGS. 12A and 12B), dissociation reagents are enzymes used to detach adherent cells (i.e., cells that stick to a surface) from a surface. Excessive exposure to cell dissociation reagents, however, can be detrimental to cell health. Typically, cell dissociation reagents are removed via a centrifugation process, which requires that the cells be removed from the system (for centrifugation) and then returned to the system. Because repeated handling of the cells, and especially removal and reintroduction to the system can lead to cell damage, loss of pluripotency, or the like, it is desirable to remove cell dissociation reagents while limiting handling of the cells. For example, centrifugation can cause cells to clump or be damaged due to forces applied to the cells during the centrifugation process. Further, using TFF can eliminate the need to remove cells by centrifugation, which requires user intervention. In addition, centrifuges can be bulky machines that are difficult to integrate in-line with a cell culturing system. Described below are methods that use tangential flow filtration to selectively remove dissociation reagents and/or other media components continuously, while maintaining the cells within the containers and/or the overall system. Moreover, with such a system, in some embodiments, the dissociation reagent can be fully removed from the cultured cells. The ability to fully remove the dissociation reagent can be highly important for dispensing usable cells. For example, in some cases, "fully removed" can mean that all but a trace amount of the dissociation agent exist in the cultured cells. For example, in some embodiments, fully removing the dissociation reagent can include removing at least 99 percent of the dissociation reagent.

More specifically, adherent cells behave differently or start to die when the surface they are growing on gets too crowded. In order to remedy this, cells are periodically detached via exposure to cell dissociation reagents that can be enzymatic or chemical, and then a portion of the cells are either moved to waste or to a new empty flask (e.g., cell culture container). For example, by including multiple cell culture containers on a single tray assembly, the systems described herein are well suited for passaging of cells to new (empty) cell culture containers when the initial container reaches capacity of the cells. The most commonly used cell dissociation reagents are a class of enzymes known as proteases—enzymes that break down proteins—which tend to be relatively indiscriminate about which proteins in a cell they digest. Thus, exposure of cells to cell dissociation reagents should be minimized to avoid compromising cell heath, and the cells should be exposed only for as long as required to detach the cells.

Typically, cell dissociation reagents are removed in a manual cell culture process by placing the cell suspension (mixture of cells, cell dissociation reagent and media) in a centrifuge tube, and spinning in a centrifuge, forcing the cells to sediment to the form of a pellet at the bottom of the tube. The supernatant (liquid above the cells) is then removed, and the cells are washed with a buffer. The centrifuging process is repeated and optionally the washing of cells with a buffer is repeated to ensure removal of the dissociation reagent. The cells are then resuspended in new media and reintroduced into one or more cell culture containers for continued culturing. This type of centrifuging process can be undesirable for a number of reasons. First, it can be very difficult to perform the centrifuging in-line, and so may require movement of the samples to a separate centrifuge and then back to the cell culture vessel. Second, centrifuges typically take up a lot of space in an integrated design. Centrifugal force is dependent on rotor diameter and speed of rotation, so either a large rotor is required or a motor is required that can move elements at high speed. Third, centrifuges can be dangerous if they mechanically fail during operation. For example, centrifuges can aerosolize dangerous biologics such as viruses. Centrifuges also apply force to cells which can affect the cell health.

Some known systems use standard (i.e., "flow through") filtration methods, which typically do not work well for separating the cells from the dissociation reagent, as the filter quickly becomes clogged, causing high pressure (or long process time) to be required for pushing liquid through.

Cells can also become caught in the filter, and as a result they do not detach even after backwashing.

An alternative to centrifuging and standard filtration methods above-mentioned problems, is to use tangential flow filtration for dissociation reagent removal. With tangential flow filtration, the solution is flowed parallel to the surface of the filter rather than through the filter, such that with each cycle components smaller than the pore size of the filter membrane will be able to permeate the filter (i.e., liquid and small solutes), and components larger than the pore size of the membrane will be retained, along with some unpermeated solution. For example, a pressure differential across the filter drives the smaller components through the filter and the larger components are retained by the filter and pass along the membrane surface. After a number of cycles, the liquid can be completely replaced without losing the solid. This approach reduces filter clogging, as the flow across the filter is constantly removing solid from clogging the filter.

Figure 74:
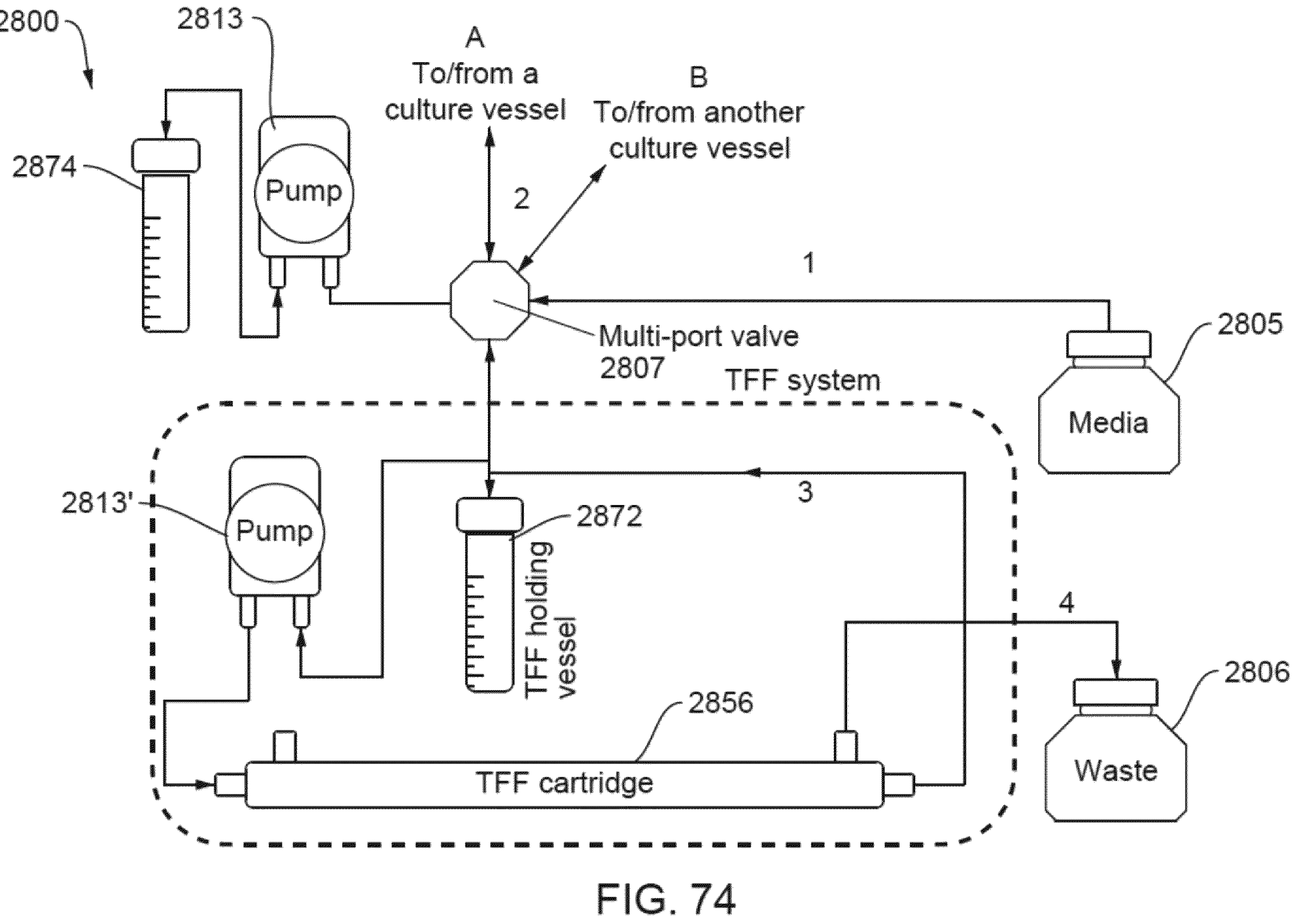
FIG. 74 is system diagram illustrating an example fluidic setup within a system during a cell culturing procedure, including a tangential flow filtration system.

As incorporated within a cell culturing system described herein, TFF can be used to remove cell dissociation reagent when performing cell passaging methods. FIG. 74 is a system diagram illustrating an example fluid flow within a system during cell culturing procedures, various containers and other components that can be coupled within a cell culturing system, and a TFF system coupled to and included within the fluid flow system. The system diagram is described with respect to various components of a cell culturing system 2800, but it should be understood that this example diagram can apply to any of the embodiments described herein. Said another way, the tangential flow filtering components and methods described with respect to the cell culturing system 2800 can be included in any of the cell culturing systems described herein, including, for example, the cell culturing systems 100, 200, 400, 1600, 1700, 2000, 2100, 2200, 2300, 2600, 2800, 3600, 4000.

FIG. 74 illustrates a portion of the cell culturing system 2800 including a multiport valve 2807 that is coupled to two cell culture containers A and B (not shown), and a media container 2805 that contains a dissociation reagent. A first fluid pump 2813 with fluid (or pump) holding vessel 2874 is fluidically coupled to a master port of the multiport valve 2807. The multiport valve 2807 is also fluidically coupled to a TFF holding vessel 2872, which is fluidically coupled to a second pump 2813' and a TFF cartridge 2856, which is coupled to a waste container 2806.

As shown in FIG. 74, the flow arrow 1 shows how the fresh media is fluidically coupled to the multiport valve, which is in turn coupled to cell culture containers A and B, the pump holding vessel 2874 and the TFF holding vessel 2872. The flow arrow 2 shows the fluid flow paths back and forth from the multiport valve 2807 to the cell culture containers A and B. The flow arrow 3 shows the cycling of cell solution through the TFF cartridge for dissociation reagent removal. The flow arrow 4 shows the flow of the permeate, which refers to the old media (dissociation reagent and new media that can be unintentionally lost) which flows through the pores of the TFF cartridge 2856 and into the waste container 2806.

In one example method of using TFF in a cell culturing system, after a dissociation reagent is added to the cells being cultured, and after the user confirms through images that the cells have attached or a set time taken for that type of cell to detach has elapsed, the system can optionally add a dissociation reagent neutralizer to slow down the effect of the dissociation reagent. TFF is then used to fully remove this solution of dissociation reagent and neutralizer from the cells, while new media is added. The cells are moved to a new vessel, or harvested as required. More specifically referring to FIG. 74, initially, after the cells have detached, the solution of detached cells (which includes dissociation reagent) is moved from, for example, containers A and/or B and into the TFF holding vessel 2872. The cell solution is circulated by the pump 2813', through the TFF cartridge 2856 and back into the TFF holding vessel 2872. Periodically (or continually), the TFF holding vessel 2872 is topped up with fresh media to replace the permeated old media that has been removed during the flow through the TFF filter cartridge 2856. The old media that passes through the filter cartridge 2856 is moved to the waste container 2806. Eventually, in one example, after about 5 cycles, up to 99% of the old media in the cell solution will be replaced with fresh media. The cells are pumped from the TFF holding vessel 2872 to the new cell culture vessel completing the passage. For example, the cell can be initially cultured into container A (not shown) and container B (not shown) can be empty of cells. Similarly stated, container B can be an "expansion container" to which a portion of the cells can be passaged for continued culturing after the dissociation reagent has been removed.

Figure 75:
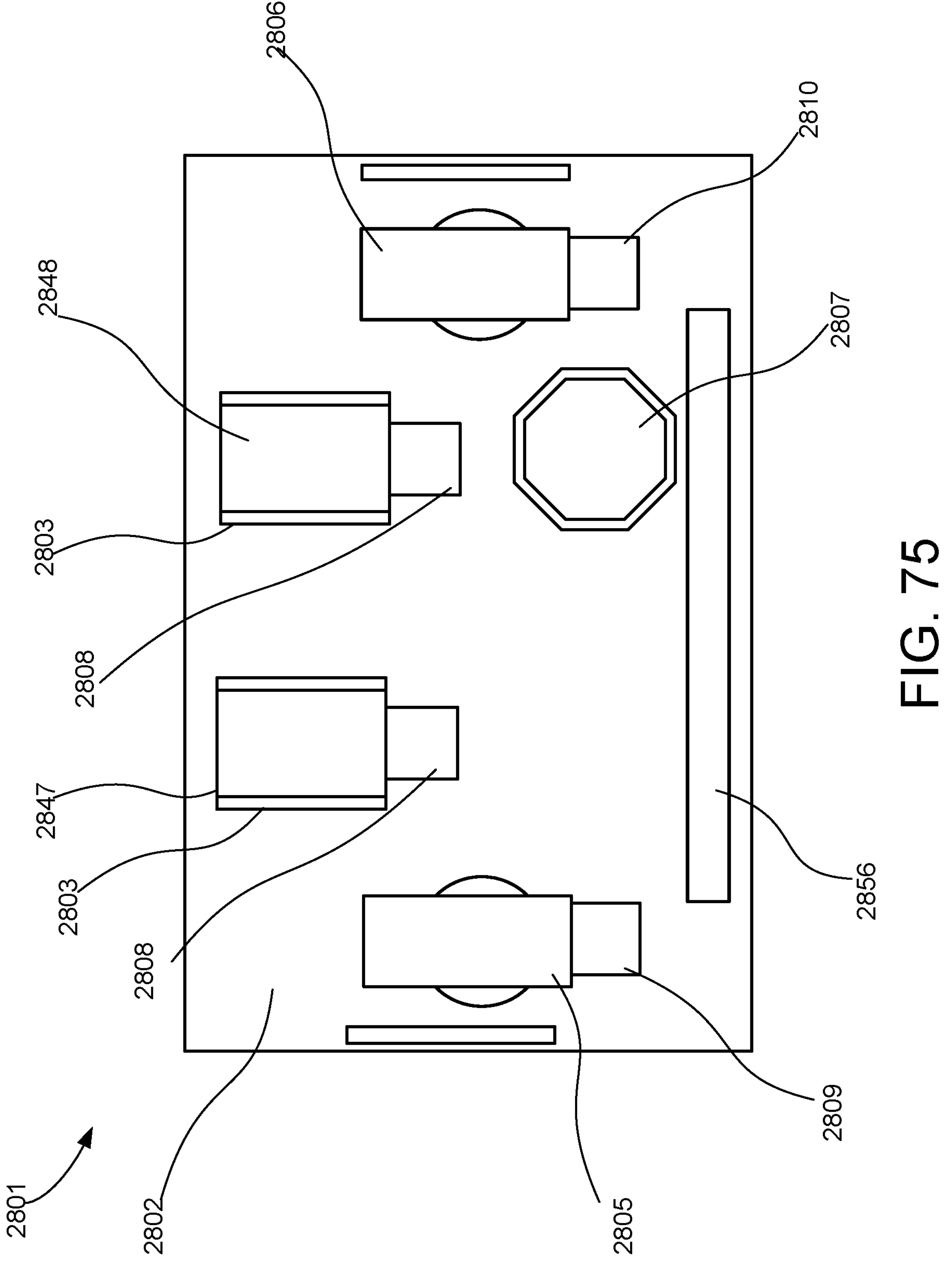
FIG. 75 is a schematic illustration of a tray assembly of a cell culturing system including a tangential flow filtration cartridge, according to an embodiment.

In some embodiments, a TFF cartridge can be included on the tray assembly for the cell culture system. For example, as shown in FIG. 75, a tray assembly 2801 is illustrated that includes a tray 2802, two cell culture containers 2847 and 2848, a waste container 2806, a media container 2805, a valve 2807 and the TFF filter cartridge 2856. The TFF filter cartridge 2856 can be fluidically coupled to one or more of the containers on the tray 2802 and to the valve 2807. The TFF filter cartridge 2856 can also be coupled to a fluid pump as included and described for other embodiments herein.

FIGS. 76-80 each illustrate an example cell culturing system that includes a TFF system. FIGS. 76-80 illustrate various components of the cell culturing systems to illustrate the components and functions of a TFF system, and some components of the cell culturing systems are not shown and described. It should be understood, however, that any of the cell culturing systems shown in FIGS. 76-80 can include any of the components included in other embodiments described herein. For example, although not necessarily shown in FIGS. 76-80, each of the cell culturing systems can include a multiport valve or a valve system to which the TFF is fluidically coupled, various containers (cell culture containers, waste, reagent, and media containers, etc.), tubing for fluidically connecting the various components, etc., as described herein for other embodiments. Thus, the portions of a cell culturing system shown and described with respect to FIGS. 76-80 illustrate only the TFF system portion of the cell culturing systems. Additionally, any of the TFF systems described in FIGS. 76-80 can be incorporated into any of the cell culture systems and/or tray assemblies described herein. For example, in some embodiments, the tray assembly 4101 or any of the other tray assemblies described herein can be modified to include any of the TFF systems described in FIGS. 76-80.

Figure 76:
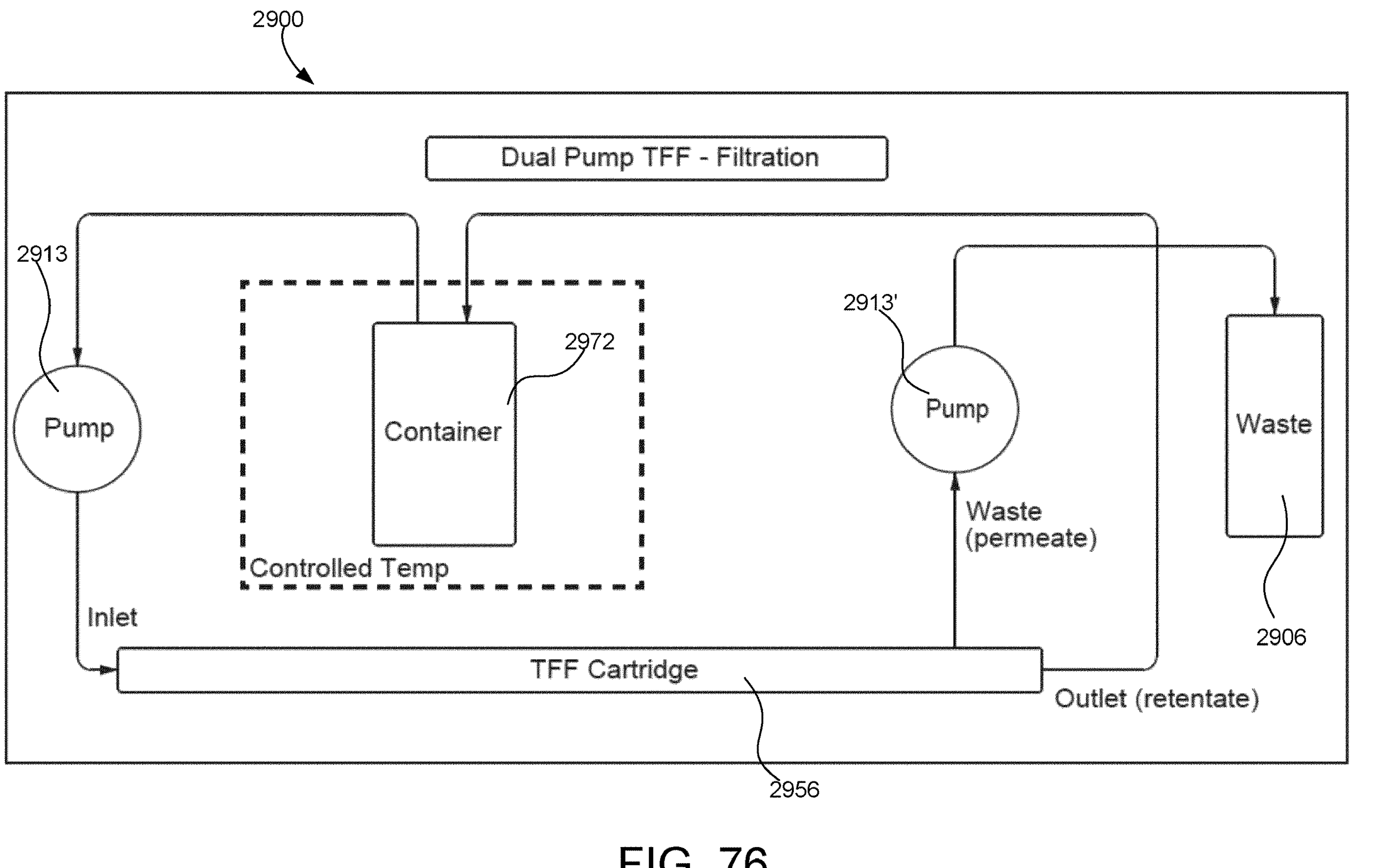
FIGS. 76-80 are each a schematic diagram illustrating an example fluidic setup within a cell culturing system according to an embodiment, including a tangential flow filtration system.

FIG. 76 illustrates a portion of a cell culturing system 2900 (also referred to herein as "system") including, a dual pump TFF system that includes a TFF cartridge 2956 for filtering cell solutions as described herein. The system 2900 includes a container 2972 that can function as a holding vessel that contains a cell sample solution that can include cells and other fluids such as media and/or reagents. In some embodiments, the container 2972 can be maintained at a controlled temperature to maintain the viability of the cells within the cell sample. For example, in some embodiments, the temperature is maintained (e.g., by a water bath) at about 37 degrees Celsius. A first fluid pump 2913 is fluidically coupled to the container 2972 and is also coupled to the TFF cartridge 2956. The TFF cartridge 2956 is also fluidically coupled to a second pump 2913' which is fluidically coupled to a waste container 2906.

As shown in FIG. 76, the flow arrows indicate the flow of cell sample solution through the TFF system. More specifically, the cell solution flows the from the container 2972 to the first pump 2913, and then to the inlet of the TFF cartridge 2956. The cell solution cycles through the TFF cartridge 2956 to for example, remove dissociation reagent. The retentate of the cell solution flows out the outlet of the TFF cartridge 2956 and back to the container 2972. The flow of the permeate, which refers to the old media (dissociation reagent and new media that can be unintentionally lost), flows through the pores of the TFF cartridge 2956, and out a second outlet of the TFF cartridge 2956 and into the waste container 2906. In this embodiment, the second pump 2913' helps pull the permeate out of the TFF cartridge 2956 and into the waste container 2906. Similarly stated, the second pump 2913' can maintain a desired flow rate of the permeate out of the TFF cartridge. Specifically, the operating conditions of the second pump 2913' can be adjusted to accommodate potential changes in the TFF filter (e.g., increased clogging or filter load), thereby maintain a desired outlet flow.

Figure 77:
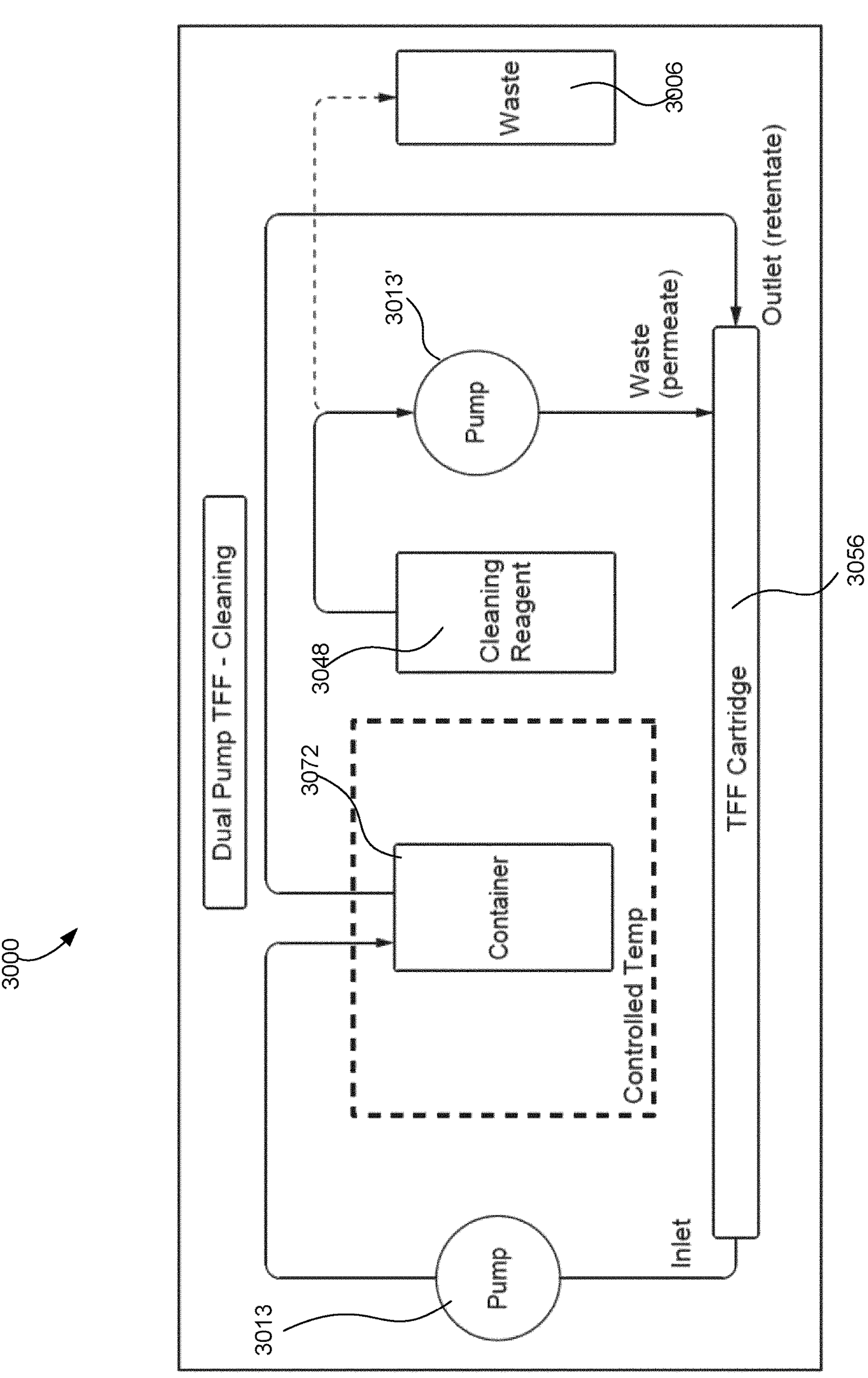

FIG. 77 illustrates a portion of a cell culturing system 3000 (also referred to herein as "system") including, a dual pump TFF system that includes a TFF cartridge 3056 for filtering cell solutions as described herein. In this embodiment, the TFF system illustrates an example use for also cleaning of a cell solution. The system 3000 includes a container 3072 that can function as a holding vessel that can contain a cell sample solution that can include cells and other fluids such as media and/or reagents. In some embodiments, the container 3072 can be maintained at a controlled temperature to maintain the viability of the cells within the cell sample. For example, in some embodiments, the temperature is maintained at about 37 degrees Celsius. A first fluid pump 3013 is fluidically coupled to the container 3072 and is also coupled to the TFF cartridge 3056. The TFF cartridge 3056 is also fluidically coupled to a second pump 3013' which is fluidically coupled to a waste container 3006 and a container 3048 with a cleaning reagent.

As noted above, this embodiment illustrates the TFF system used to perform a backflush to clean the TFF cartridge. For example, if the TFF filter is clogged, the filter will no longer be effective. In such a case, the TFF system can be actuated to run in a reverse flow configuration. In some embodiments, the filter clogging can be determined by a pressure drop or increase in power needed to run the pumps in the forward flow configuration (e.g., to clean the cells). When running in a reverse flow configuration, the cell sample from the container 3072 can first be conveyed into an appropriate container within the system. This will allow the container 3072 to contain water or other reagents used to facilitate the backflush operation. The second pump 3013' can pull cleaning reagent from the container 3048 and pump it into the TFF cartridge 3056. The cleaning reagent will go backwards through the porous filter media and into the main chamber of the TFF cartridge 3056, and out through the inlet port of the TFF cartridge 3056. The cleaning reagent is the conveyed into the container 3072 and is mixed with any other fluids (e.g., water, other reagents) therein. Liquid from the container 3072 flows backward into the retentate outlet of the TFF cartridge 3056. In this operation, the container 3072 can be filled with a media (rather than cells). This flow from the container 3072 can be controlled by the pump 3013, which can cause the flow in the main chamber of the TFF cartridge 3056 to go backwards. The two flow processes will flow into the main chamber of the TFF cartridge 3056 and out through the pump 3013'. The flow path to the waste container 3006 can be shut off, and the output flow of fluid from the TFF cartridge 3056 and pump 3013' can flow into the container 3072.

Figure 78:
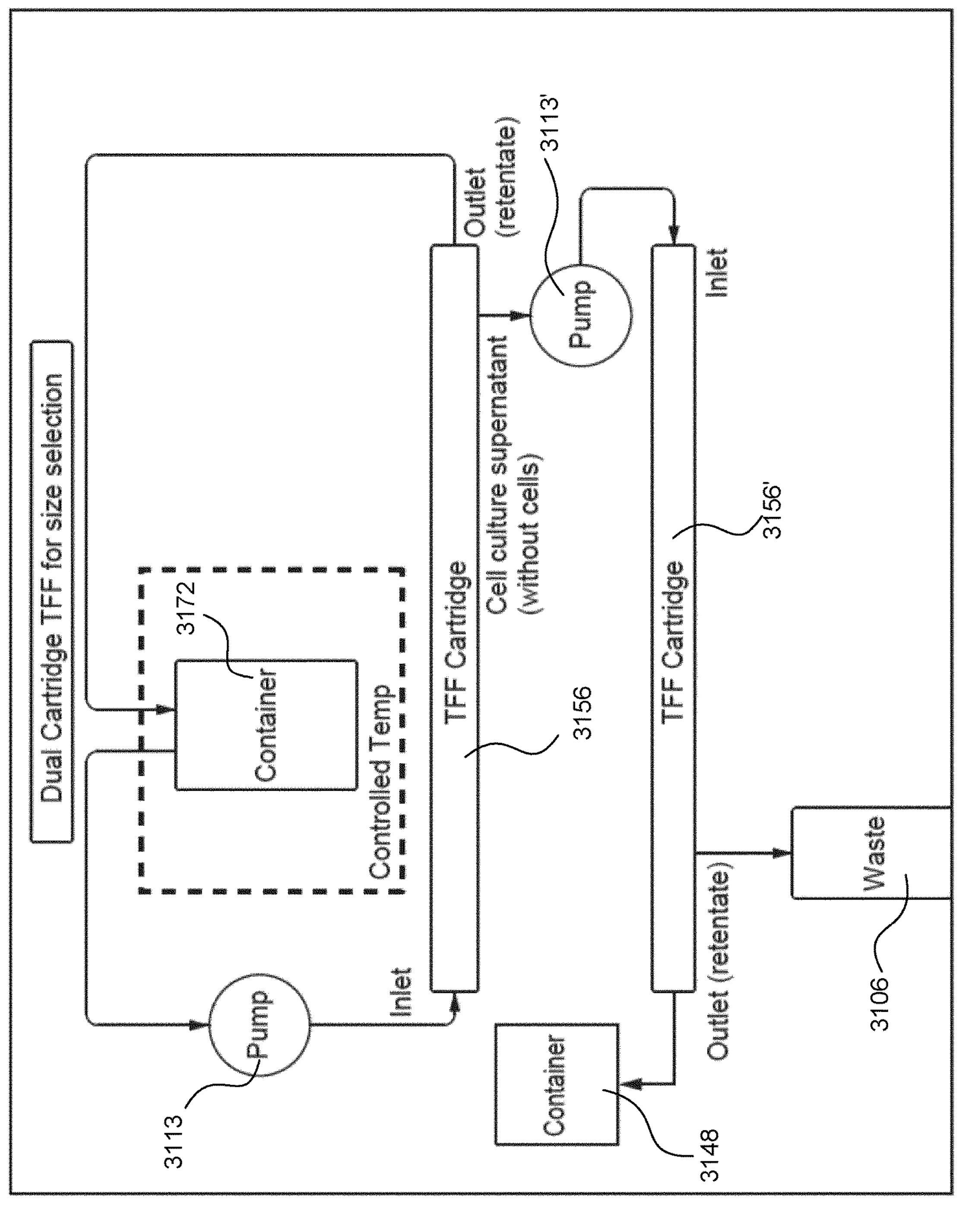

Another embodiment of a TFF system can include a dual cartridge filtration system which can allow cell passaging and extraction of biological material in a single filtration process. By having a system with two or more TFF filter devices with different pore size membranes connected in series, in place of a single TFF cartridge, different components can be separated based on size. In one example, the first TFF cartridge (or first filter portion of a cartridge) can remove cells, the second TFF cartridge (or second filter portion of a cartridge) could remove virus. In some embodiments, a third TFF cartridge (or third filter portion of a cartridge) could remove antibodies. Such a TFF system can provide for selective removal of media components. For example, changing cell culture media can sometimes be detrimental to cells, especially if they require self-secreted growth factors to function. The ability to change media without removing certain components can be beneficial for specific cell types. FIG. 78 illustrates a portion of a cell culturing system 3100 (also referred to herein as "system") including, a dual pump and dual cartridge TFF system. The TFF system includes a first TFF cartridge 3156 and a second TFF cartridge 3156' for filtering cell solutions as described herein. In this embodiment, the TFF system illustrates an example using the TFF system to clean or filter the cell solution as described above for systems 2900 and 3000, and also for filtering and collecting, for example, viruses from the permeate that is typically sent to waste. The system 3100 includes a container 3172 that can function as a holding vessel that contains a cell sample solution that can include cells and other fluids such as media and/or reagents. In some embodiments, the container 3172 can be maintained at a controlled temperature to maintain the viability of the cells within the cell sample. For example, in some embodiments, the temperature is maintained at about 37 degrees Celsius (e.g., via a water bath). A first fluid pump 3113 is fluidically coupled to the container 3072 and is also coupled to the first TFF cartridge 3156. The first TFF cartridge 3156 is also fluidically coupled to a second pump 3113' which is fluidically coupled to an inlet of the second TFF cartridge 3156'. The second TFF cartridge 3156' is fluidically coupled to a waste container 3106 and to a collection container 3148.

As shown in FIG. 78, the flow arrows indicate the flow of cell sample solution through the TFF system. More specifically, the cell solution flows the from the container 3172 to the first pump 3113, and then to the inlet of the first TFF cartridge 3156. The cell solution cycles through the first TFF cartridge 3156 to, for example, remove dissociation reagent. The retentate of the cell solution flows out of an outlet port of the first TFF cartridge 3156 and back to the container 3172. In this embodiment, the flow of the permeate, which refers to the old media (dissociation reagent and new media that can be unintentionally lost), flows through the pores of the TFF cartridge 3156, out a second outlet port of the first TFF cartridge 3156 and to an inlet port of the second TFF cartridge 3156'. In this embodiment, the second pump 3113' can be used to pump the permeate out of the first TFF cartridge 3156 and into the second TFF cartridge 3156'. The permeate from the first TFF cartridge 3156 can be filtered by the second TFF cartridge 3156' and the retentate from the second TFF cartridge 3156' can flow out a first port of the second TFF cartridge 3156' and into the collection container 3148. The retentate from the second TFF cartridge 3156' can include virus or other particles desired to be collected from the cell culture. The permeate from the second TFF cartridge flows out a second outlet port of the second TFF cartridge 3156' and into the waste container 3106.

Figure 79:
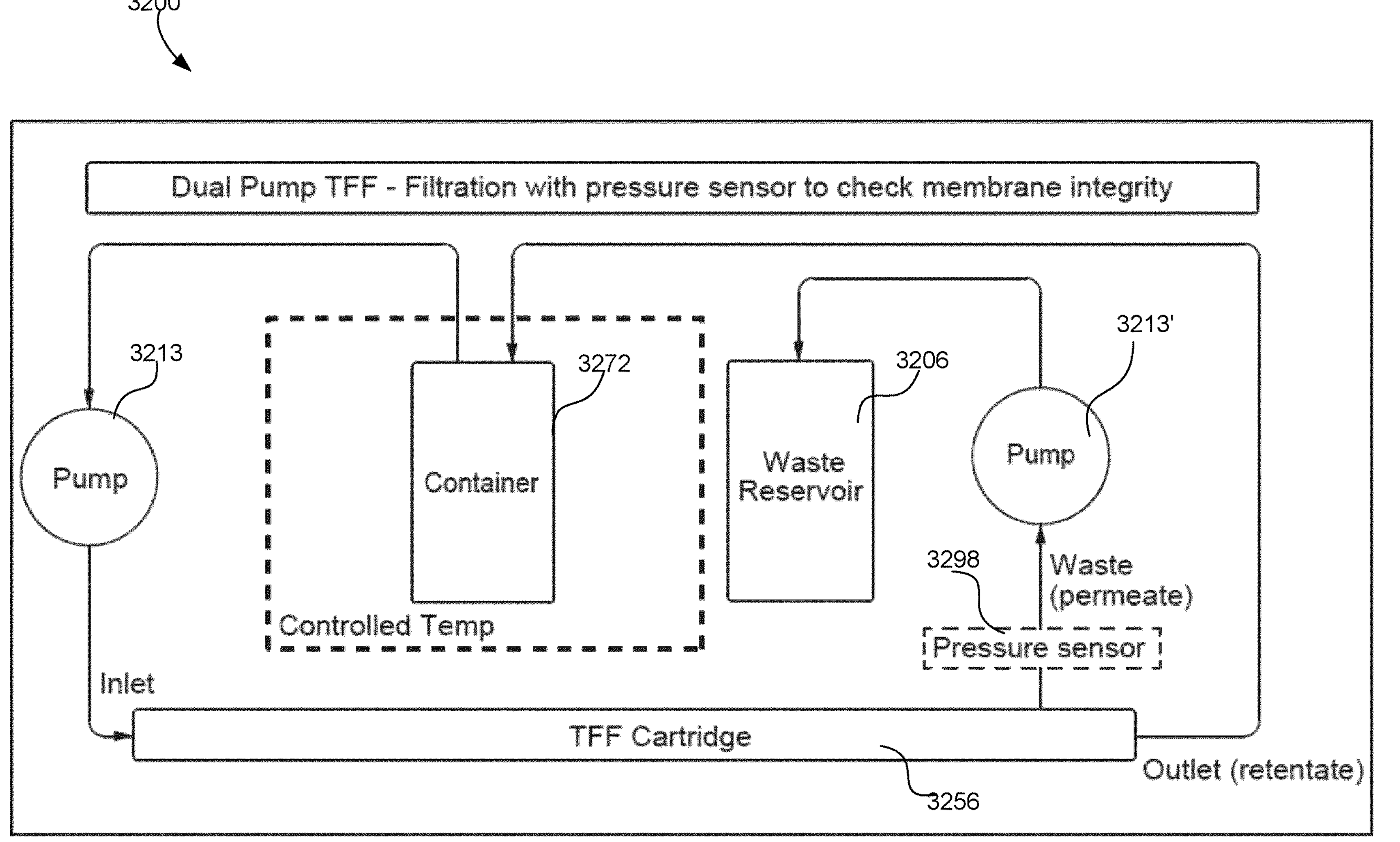

FIG. 79 illustrates a portion of a cell culturing system 3200 (also referred to herein as "system") including, a dual pump TFF system that includes a TFF cartridge 3256 for filtering cell solutions as described herein. The system 3200 includes a container 3272 that can function as a holding vessel that contains a cell sample solution that can include cells and other fluids such as media and/or reagents. In some embodiments, the container 3272 can be maintained at a controlled temperature to maintain the viability of the cells within the cell sample. For example, in some embodiments, the temperature is maintained at about 37 degrees Celsius. A first fluid pump 3213 is fluidically coupled to the container 3272 and is also coupled to the TFF cartridge 3256. The TFF cartridge 3256 is also fluidically coupled to a second pump 3213' which is fluidically coupled to a waste container 3206.

As shown in FIG. 79, the flow arrows indicate the flow of cell sample solution through the TFF system. More specifically, the cell solution flows the from the container 3272 to the first pump 3213, and then to the inlet of the TFF cartridge 3256. The cell solution cycles through the TFF cartridge 3256 to for example, remove dissociation reagent. The retentate of the cell solution flows out the outlet of the TFF cartridge 3256 and back to the container 3272. The flow of the permeate, which refers to the old media (dissociation reagent and new media that can be unintentionally lost), flows through the pores of the TFF cartridge 3256, and out a second outlet of the TFF cartridge 3256 and into the waste container 3206. In this embodiment, the second pump 3213' helps pull the permeate out of the TFF cartridge 3256 and into the waste container 3206. Similarly stated, the second pump 3213' can maintain a desired flow rate of the permeate out of the TFF cartridge. Specifically, the operating conditions of the second pump 3213' can be adjusted to accommodate potential changes in the TFF filter (e.g., increased clogging or filter load), thereby maintain a desired outlet flow. In addition, in this embodiment, a pressure sensor 3298 is disposed in the fluid line between the second pump 3213' and the TFF cartridge 3256. The pressure sensor 3298 can be used to measure pressures within the system to provide an indicator of the total flow through the system. For example, measuring the inlet pressure and the permeate pressure can provide some indication of a pressure drop (and therefore a drop in flow) through the porous membrane of the TFF cartridge 3256 (i.e., flow of the waste). The pressure drop can be correlated and used to evaluate, for example, flow of the waste, whether the filter media is getting clogged, etc. The use of positive displacement pumps (e.g., pumps 3213 and 3213'), rather than centrifugal pumps, provide for the speed of the pump to be directly correlated to flow rate. Thus, in some embodiments, a system may not include the pressure sensors shown. Instead, the flow rate can be determined based on the pump speed.

Figure 80:
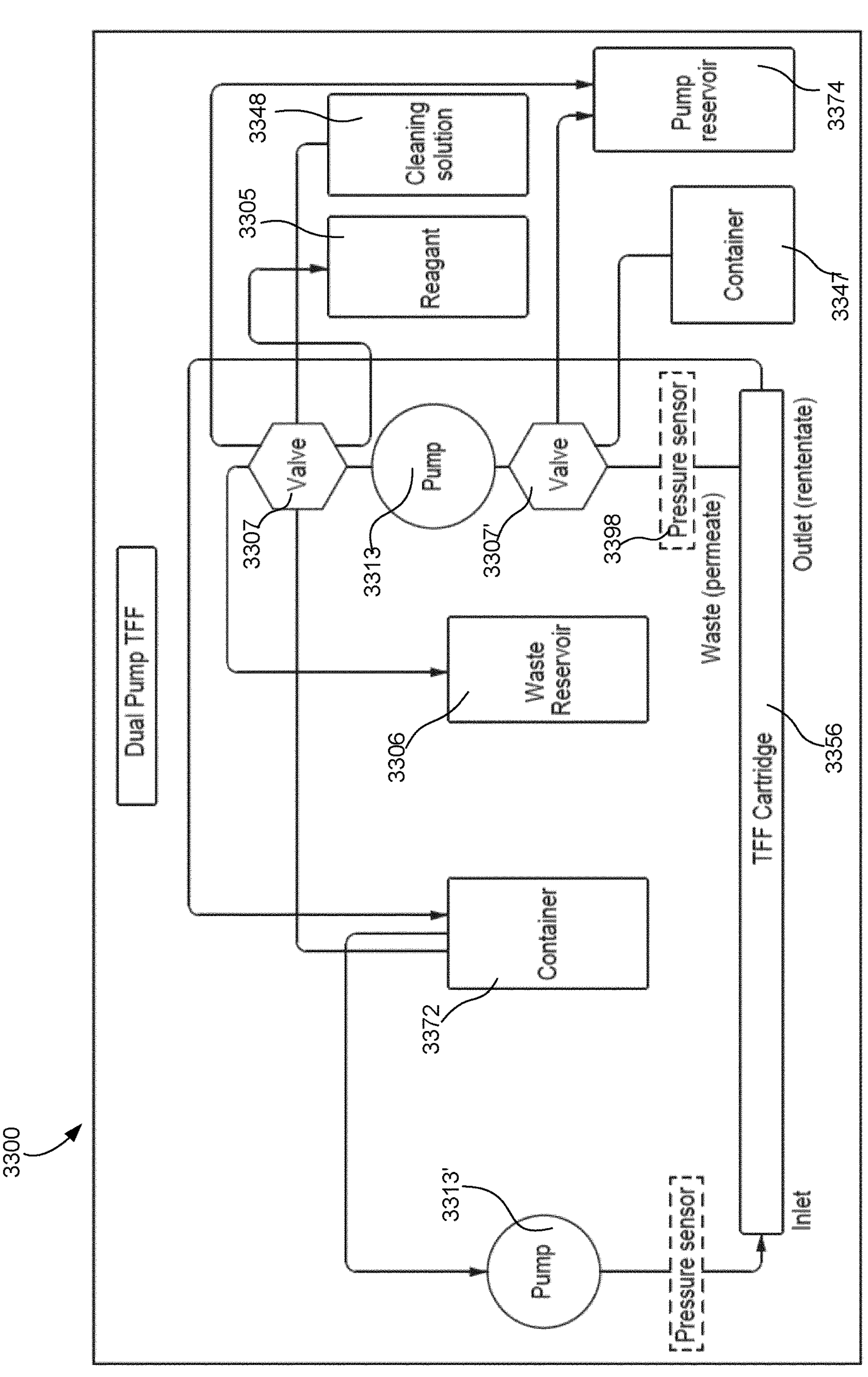

FIG. 80 illustrates a portion of a cell culturing system 3300 (also referred to herein as "system") including, a dual pump TFF system and dual multiport valves. The TFF system includes a TFF cartridge 3356 for filtering cell solutions as described herein. In this embodiment, a first multiport valve 3307 and a second multiport valve 3307' are coupled to a first pump 3313. The valves 3307 and 3307' and the first pump 3313 are configured to move fluid in and out of various containers of the system 3300 (e.g., cell culture containers, media containers, reagent containers, etc.) as well as between the containers and the TFF cartridge 3356 as described herein for other embodiments. As shown in FIG. 80, the second multiport valve 3307' is coupled to a cell culture container 3347 and to a pump reservoir 3374. The system 3300 also includes various other containers, such as a reagent container 3305 and a cleaning solution container 3348 shown in FIG. 80, which are coupled to the first multiport valve 3307'. The pump reservoir 3374 can be selectively coupled to the pump 3313 outlet via the second valve 3307'. The pump reservoir 3374 can be used to hold any fluid in the device. For the TFF process, the pump reservoir 3374 can, for example, hold "warmed fresh media." The pump reservoir 3374 can also be used to receive a solution from the permeate output if desired.

The system 3300 also includes a container 3372 that can function as a holding vessel that contains a cell sample solution that can include cells and other fluids such as media and/or reagents. In some embodiments, the container 3372 can be maintained at a controlled temperature to maintain the viability of the cells within the cell sample. For example, in some embodiments, the temperature is maintained at about 37 degrees Celsius. A second fluid pump 3313' is fluidically coupled to the container 3372 and is also coupled to the TFF cartridge 3356. The TFF cartridge 3356 is also fluidically coupled to the second multiport valve 3307, which is coupled to the first pump 3313, which is coupled to the first multiport valve 3307 and to a waste container 3306. In this embodiment, a first pressure sensor 3398 is disposed in the fluid line between the TFF cartridge 3356 and the second multiport valve 3307' and a second pressure sensor 3398' is disposed between the second pump 3313' and the TFF cartridge 3356. The first pressure sensor 3398 and the second pressure sensor 3398' can be used to provide the same or similar information as described above for pressure sensor 3298.

As shown in FIG. 80, the flow arrows indicate the flow of cell sample solution through the TFF system. More specifically, the cell solution flows the from the container 3372 to the second pump 3313, and then to the inlet of the TFF cartridge 3356. The cell solution cycles through the TFF cartridge 3356 to for example, remove dissociation reagent. The retentate of the cell solution flows out of an outlet of the TFF cartridge 3356 and back to the container 3372. The flow of the permeate, which refers to the old media (dissociation reagent and new media that can be unintentionally lost), flows through the pores of the TFF cartridge 3356, and out a second outlet of the TFF cartridge 3356. In this embodiment, the permeate flows through the first and second multiport valves 3307 and 3307' and the first pump 3313 and to the waste container 3306.

Using a TFF system to filter/remove the dissociation reagent allows for the in-line removal of undesirable components after a passage of adherent cells without losing cells in the process. As noted above, such cell loss or damage can occur with other filtration methods such as standard filtration or centrifugation as described above, or doing the removal off-line. With TFF, depleted media in a suspension cell culture can be replaced without losing the cells and without diluting the depleted media with fresh media. Further, concentrating a cell solution can be done without losing cells. A TFF system can also reduce or eliminate the need to change the media of a cell solution to discard debris formed within the solution.

TFF filtration can be performed, for example, following an adherent cell passage, to replace media that contains dissociation reagent in a cell solution with fresh media. TFF can also be performed following resuscitation of frozen cell solution, i.e., replacing frozen media in a cell solution with fresh media. As described herein, TFF can be used to replace depleted media in a suspension cell culture, without losing the cells or merely diluting the depleted media with fresh media. Another example use for TFF includes extracting purified biologics, such as viruses and proteins, directly from the culture without extracting cells at the same time (which would involve separating the biologics from the cells downstream).

TFF filtration can also be used when harvesting adherent cells. For example, to remove old media that contains dissociation reagent from a cell solution, without losing the cells, and replacing it with fresh media or another liquid that the harvested cells are required in for their intended use case. TFF can also be used when harvesting adherent cells for collection by the user by concentrating the cell solution to a desired cell density, or when harvesting cells to be frozen, for example, by removing media used to grow the cells, without losing the cells, and replacing with frozen medium.

In some embodiments, TFF can be used to remove contamination that is smaller than the cells being cultured, such as bacterial contamination, from a cell culture. The detached cell solution is cycled through the TFF, and the contaminations are slowly lost each cycle through the filter. The cell solution is periodically or continually topped up with fresh, uncontaminated media.

In some embodiments, TFF can be used to fully replace media in which stem cells are growing with a new media that is required for a specific step of a differentiation protocol (a protocol that turns stem cells into a specific kind of cell), ensuring that chemicals in the old media do not interfere with the differentiation process. This is done by cycling the detached cell solution through the TFF, such that old media is lost through the pores, while adding the new media periodically or continually to the cell solution.

In some embodiments, a TFF cartridge can eventually become too clogged to reuse. For example, in some cases, if the cell solution loses liquid too fast, the TFF filter can clog. In one example embodiment of a TFF system, the cell solution can be passed through the inside and then the outside of the cartridge to help prevent clogging. When passing cell solution through the inside, the old media seeps outwards into the permeate stream which goes to waste. The new media is added into the TFF holding vessel. Cells slowly get clogged against the inside of the cartridge over time. When passing cell solution through the outside of the cartridge (the permeate stream), the old media seeps inwards into the retentate stream (solution that passes along the surface of the membrane and back to a feed reservoir (e.g., the reservoir with the solution directed to the membrane) which goes to waste. The new media gets added into the TFF holding vessel, and as old media seeps in, it peels cells off the inner walls, which go to waste. Cells slowly get clogged against the outside of the cartridge.

In another example embodiment, a flow sensor can be included to prevent clogging of the filter cartridge. For example, in some embodiments, a flow sensor can be used to calibrate TFF for different types of cells at different densities in solution. In some embodiments, a flow sensor can be included as part of the consumable tray assembly. In some embodiments, a flow sensor can be placed within the permeate line and used to determine how much fluid is being removed so that the system can top up the holding vessel with fresh media at a similar rate. This can also be inferred by putting a flow sensor on the retentate line instead. If the system tops up too slowly, the cell solution can get too dense, and the filter can clog as there will not be enough liquid to move the cells through the fibers of the filter.

In some embodiments, the system can be provided with the flow sensor incorporated therewith, for example, either on the permeate or retentate line. In such an embodiment, the flow sensor can also be used to determine when enough total liquid has been removed, such that it can be discerned that the old media has been completely or almost completely removed. Thus, at that point, the system can stop filtering the solution. This arrangement therefore limits waste of new media, unnecessary cell handling, and time, but avoiding continued removal and waste of new media.

In an embodiment without a flow sensor, a listing or table of rate of fluid removal for different cell types at different concentrations can be provided with the system such that a user can select the correct settings for each cell type and density. This system would also be calibrated to know, for a given total volume of cell solution, how much total fluid needs to be removed to be able to remove the majority (similar amount to a centrifuge) of the old media—i.e., how long to circulate through the TFF system.

In yet another example embodiment, a TFF system can include pre-treated membranes or alternative membrane materials to enhance filtration capabilities. For example, pore sizes of membranes are generally defined based on an exclusion limit, therefore small pores always exist in larger pore membranes. Pre-coating and treatment could improve filtration process uniformity, i.e., by closing up the smallest pores. TFF can be used to break up large cell clumps due to constrained filter cross-section, and different cell types can be separated based on their propensity of being permeated from the filter.

In some embodiments, the TFF system can be used in any of the systems shown and described herein to facilitate methods of cell harvesting in which the cell density can be adjusted. Specifically, in certain situations when cells are used for testing purposes, it can be desirable to use a solution having a density (or amount) of cells within a predetermined range. Thus, if the harvested cell solution is below the desired density, current methods include additional steps of processing the cells (e.g., via a centrifuge operation) to remove some of the supernatant (e.g., solution) to increase the cell density. If, however, the harvested cell solution is above the desired density, current methods include additional steps of processing the cells to add additional solution. In some embodiments, a TFF system can produce cell solution for harvest that is within a desired cell density range. Specifically, after removal of the potentially damaging dissociation reagent, the cell solution can be measured (for example with the counting chip) to determine the current cell density. The cell solution can then be processed through the TFF to remove excess solution (if the cell density is too low) and then re-measured. Alternatively, additional cell media can be added if the cell density is too high. Thus, the cells can be harvested from the system at the desired density. In some embodiments, the user can select the desired harvest cell density (using an electronic control system, such as the electronic control system 1630). In this manner, the system can accommodate providing cells at a desired density for a variety of different cell types, use cases, etc.

Below are various methods and workflows for culturing and/or processing stem cells, according to various embodiments, that can include the use of a TFF system. It should be assumed that all workflows described below can use any embodiments of the system and methods described herein (e.g., the cell culture system 4000). For brevity, adding media, moving cells, measuring confluence, and removing and adding new liquids with TFF may not be described with respect to these workflows without going through explicit details. These details can be found herein, as described for other similar use cases such as feeding, passaging, removing dissociation reagent, and detecting confluence for adherent cells.

The workflows described including the use of TFF are particularly well-suited for culturing operations performed with pluripotent stem cells (PSCs), such as induced pluripotent stem cells (iPSCs) and embryonic stem cells (ESCs). In one example workflow, feeder-free PSC culture (grown as a single cell or clumps) can be maintained on the device. A wide range of dissociation reagents are used for detaching cells from cell culture containers during cell culture processes. However, these reagents should be eliminated from the media after cells are detached because they can be harmful to stem cells. Routinely, centrifugation is used for this purpose. A new approach includes the use of TFF to remove the dissociation regent from the cells. When the culture hits the desired/appropriate confluence (as detected by the microscope combined either with an algorithm or user input), dissociation reagent is added to detach the cells. The system then adds neutralizing solutions to neutralize dissociation reagent as soon as the cells are detected to have detached enough (as detected by the microscope combined either with algorithm or user input). TFF is then used to fully remove the dissociation reagent and the cells are moved to a new pre-coated flask.

Another example workflow maintains 3D aggregates of stem cells, such as, for example, embryoid bodies, organoids, and spheroids. As background, PSC-derived 3D structures are mostly generated for three main reasons: i) to test if PSCs have maintained their potency, i.e., ability to form many different types of cell, ii) to initiate the first step of differentiation protocols, and iii) to differentiate PSC toward a desired lineages as 3D culture can better recapitulate the physiological conditions. For these use cases, these 3D floating structures need to be fed by fresh media, for which removing the exhausted media in which they have been grown is necessary. Removing the media from such cultures is time-consuming and difficult as there is a risk that these structures can be damaged or removed from the culture during media change. Using TFF to change media ensures that this process can be done in an efficient way without losing the 3D structures. The system optionally continually agitates the flask, to stop the aggregates from sticking together. The system aspirates the aggregates, and then cycles the aggregate solution through the TFF. Some old media is typically lost through the pores of the filter each cycle, but the aggregates are retained. Periodically or continually, the aggregate solution is topped up with fresh media. Eventually all the old media is replaced with fresh media. The aggregates are either moved back to the old flask by the system, or seeded into a new flask.

Another example workflow involves feeder-free culture to maintain PSCs, where MEF cells are used to condition the media. In general, feeder-free culture is easier to handle, but requires more expensive conditioned media. This method combines the best of both approaches. One flask contains MEF cells. and these cells secrete chemicals that condition the media they are growing in. Periodically, the system pumps part or all of the supernatant from this first flask into a second flask of PSCs on the same machine, in order to feed the second flask. This avoids having to buy expensive media for the PSCs. Optionally, TFF can be performed on the media before feeding to the second flask in order to remove cellular debris (the filtered media is collected via the permeate).

Another example workflow involves co-culture ("feeder" culture) to maintain PSCs. Sometimes PSCs are grown on a bed of a different type of cells. These "feeder" cells secrete chemicals which help the PSCs to grow. In this workflow, one flask (which has been coated with gelatin or Matrigel) is seeded with mouse embryonic fibroblast (MEF) cells which have been mitotically inactivated (they cannot perform "mitosis", i.e., they cannot split). The MEF cells are maintained for 2-3 days. After this period, the PSCs are seeded in the same flask and grow on top of the MEF cells. The cells are passaged together into another coated flask for 1-2 passages. When it is desirable to recover only the PSCs, then one of the following steps are performed. A first option is to repeat the process a few times allowing both types of cell to attach in a coated flask, and then (detach) and passage them to a new flask. As the MEF cells do not divide but the PSCs do, after a few passages they will be diluted out. A second option is to passage into a flask, which is coated with gelatine. MEF cells attach first, so if the supernatant is extracted from the flask within 30 minutes (and as soon as the MEF cells are seen to have attached), then the supernatant will only contain PSCs. This supernatant can then be passaged to a new coated flask to be cultured. The third option is to use TFF to size-separate the larger MEF cells from the smaller pluripotent stem cells. The pluripotent stem cells will be collected in the permeate.

Another workflow includes co-culture to reprogram human fibroblasts to iPSCs. This workflow is the same as described above, except here MEFs are replaced with human fibroblast cells, and PSCs are replaced with a separate set of human fibroblast cells, which are to be reprogrammed. An additional reagent needs to cause the actual reprogramming.

In yet another workflow, feeder-free culture is used to reprogram human fibroblasts to iPSCs, where human fibroblasts are used to condition the media. In general, as described above, feeder-free culture is easier to handle, but requires more expensive conditioned media. One flask contains human fibroblast cells. These cells secrete chemicals that condition the media they are growing in. Periodically, part or all of the supernatant from this first flask is taken and used to feed a second flask of human fibroblast cells which are to be reprogrammed, on the same machine. This avoids having to buy expensive media for use during reprogramming. Optionally, TFF is performed on the media before feeding to the second flask, in order to remove cellular debris (the filtered media is collected via the permeate).

In another workflow, feeder-free culture is used to differentiate PSCs into a different type of cell B, where a type of cell A is used to condition the media. In this method, ne flask contains cell type A and these cells secrete chemicals that condition the media they are growing in. Periodically, part or all of the supernatant from this first flask is taken and used to feed a second flask of PSCs which are to be differentiated into a type of cell B, on the same machine. This avoids having to buy expensive media for use during differentiation. For media to differentiate PSCs into neuronal cells, cell type A could be stromal cells or astrocytes. Optionally, TFF is performed on the media before feeding to the second flask in order to remove cellular debris (the filtered media is collected via the permeate).

In another workflow, a monocyte culture is used to harvest macrophages. Monocytes are a type of cell that can differentiate into macrophages. When they split, one is a monocyte and one is a macrophage (so they basically "produce"

macrophages like a factory). A flask of adherent monocytes split and differentiate to produce macrophages into the culture (such that the monocyte population is roughly maintained). The macrophages are floating in the media. Periodically, the system extracts the media from the flask to collect the macrophages. The system uses TFF to concentrate down the harvested macrophages before they are collected so that the user does not need to take away a large amount of media. Optionally, the cells can also be counted before harvesting, so that the user knows the density of macrophages in the solution. Optionally, cell counting can be used over time to track macrophage production.

In another workflow, TFF is used to remove contaminating cells during maintenance of a PSC culture. During maintenance of PSCs, contaminating cells are those cells that the user does not want the PSCs to differentiate into (they are the result of unwanted differentiation). With a culture having some undifferentiated PSCs, as well as unwanted differentiated cells (i.e., contaminating cells), dissociation reagent can be used to detach all the cells. TFF can be used to separate the contaminating cells from the cells that are desired to be kept. If the PSCs are smaller than the contaminating cells, they will be collected in the permeate and the contaminating cells will go into the retentate. If the PSCs are bigger, then vice-versa. Optionally, the PSCs are passaged into a new flask, and the culture is now contaminant-free.

In yet another workflow, TFF is used to remove contaminating cells during differentiation of a PSC culture. This workflow is the same or similar to above. An example of use of such a method is when trying to form neural stem cells, neural crest stem cells may also be formed as contaminating cells. In both this method and the previous method, contaminating cell workflows could be triggered by the system detecting cells of an unwanted morphology.

Although the automated cell culture system 1600 and other systems are shown as including a multiport valve (e.g., the multiport valve 1607 or the multiport valve 2607), in other embodiments, an automated cell culture system 1600 can include any suitable valve assembly (or set of valves) configured to control the flow into and out of various containers in the system. For example, in some embodiments, an automated cell culture system can include a set of valves, each being individually actuatable, collectively configured to control the flow into and out of containers within the system. Each valve can be actuated by a single actuator, such as an electronic, pneumatic, or hydraulic actuator.

Figure 81:
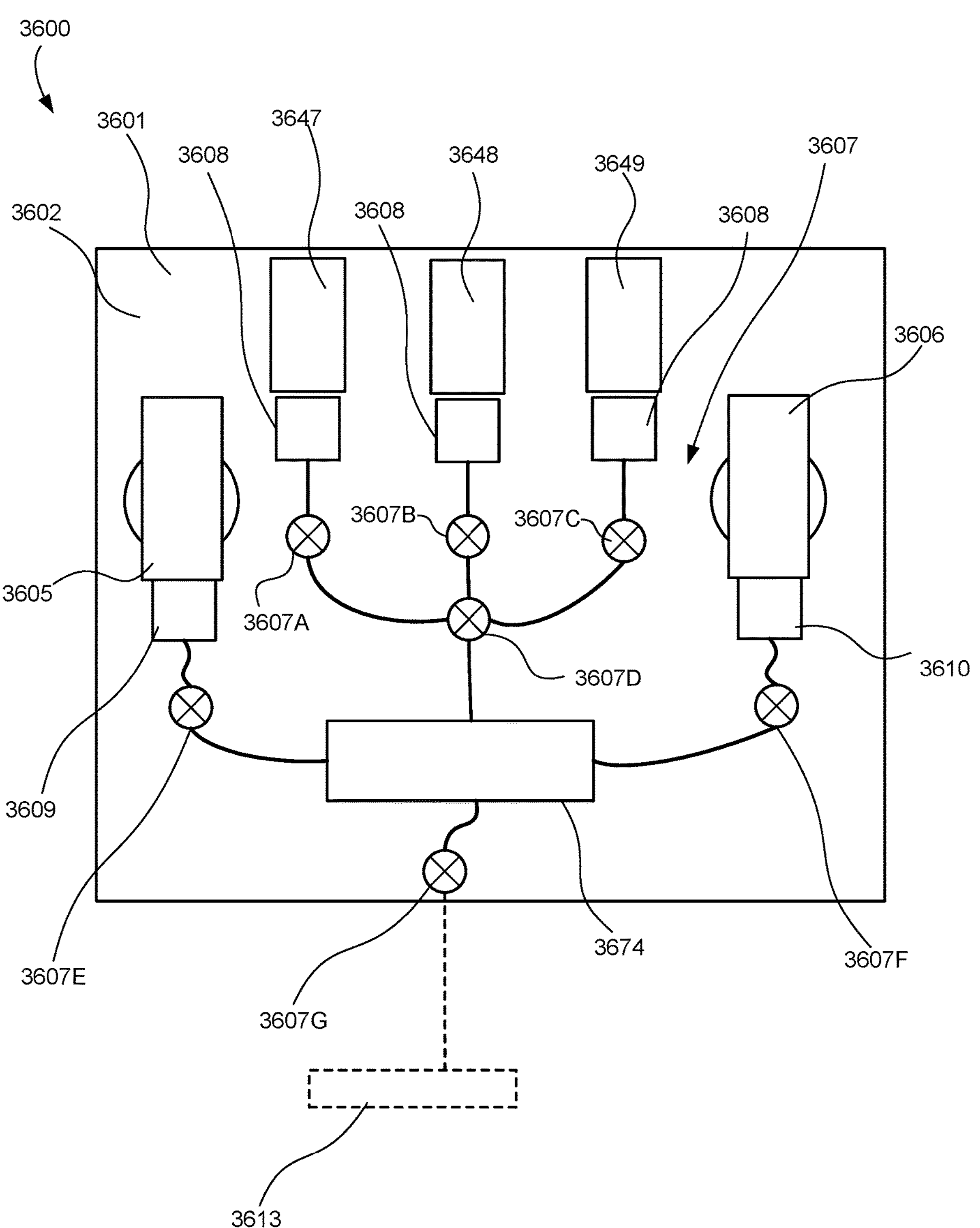
FIG. 81 is a schematic illustration of a tray assembly of a cell culturing system, according to an embodiment.

For example, FIG. 81 is a schematic view of a cell culture system 3600 according to an embodiment that is devoid of a multiport valve, but includes a valve assembly 3607 having a series of individual valves to control the fluid flow. Similar to the cell culture systems shown herein (e.g., the systems 1600, 1700, and 2000), the cell culture system 3600 includes a consumable or disposable cell culture tray assembly 3601 (also referred to herein as "tray assembly") and a reusable base unit (not shown, but which can be similar to any of the base units described herein). The disposable tray assembly 3601 includes various components described below, some of which are preassembled on (or with) the tray assembly 3601 and enclosed within a protective overwrap to maintain the components in a sterile state. In some embodiments, certain of the components of the tray assembly 3601 can be added to the tray assembly 3601 within an aseptic environment (e.g., a laminar flow hood) prior to using the tray assembly 3601 in a cell culturing procedure. When the tray assembly 3601 has been assembled and is ready for use, the tray assembly 3601 can be coupled to the base unit as described herein.

The base unit (not shown, but which can be, for example, the base unit 1620, 1720, or 2020) is a reusable component of the system that includes items that operate on or interact with the tray assembly 3601 to facilitate the cell culture methods described herein. For example, the base unit can include any or all of a fluid pumps 3613 or pump actuator (not shown) to produce the desired flow of fluid within the system 3600, an agitator (not shown), one or more sensors (not shown) to detect information associated with the contents of the cell culture containers, and an electronic control system.

The tray assembly 3601 is similar to and can include any of the components from any of the tray assemblies described herein, such as the tray assembly 1601, the tray assembly 1701, or the tray assembly 2001, and is therefore not described in detail below. As shown, the tray assembly 3601, includes a tray 3602 that can be removably coupled to a base unit. The tray 3602 includes a set of cell culture containers 3647, 3648, 3649, a waste container 3606, and a reagent container 3605. The containers are coupled together and to the pump 3613 by a valve assembly 3607 (which includes a set of independent valves 3607A-3607G), tubing, and a holding volume 3674. The holding volume 3674 can be a vessel or container, similar in structure to the other containers in the system. In other embodiments, the holding volume 3674 can be a manifold structure (e.g., constructed from tubing) that facilitates multiple inputs and outputs, as shown.

The containers can be coupled to the tray 3602 in any suitable manner. For example, in some embodiments, any or all the containers are not included in the sterile package as a part of the tray assembly 3601, but rather are provided separately, like the cell culture containers 1647, 1648 of the tray assembly 1601 described above. In such embodiments, the cell culture containers 3647, 3648, 3649, the reagent container 3605, and the waste container 3606 can be prepared (e.g., seeded with cells, filled with nutrients, or the like) and coupled to the tray 3602 in an aseptic environment (e.g., a flow hood). In other embodiments, any or all of the containers are included in the sterile package as a part of the tray assembly 3601, but can be removed from the tray during use (e.g., for placement in a refrigerator) and/or fluidically decoupled from the system to facilitate startup procedures. In yet other embodiments, any or all of the containers are included in the sterile package as a part of the tray assembly 3601 and are in permanently coupled to the tray 3602 and/or are not fluidically decoupled from the system during use, like the cell culture containers 2647, 2648 of the tray assembly 2601 described herein. Thus, the tray 3602 can include any suitable mounting clips or structure configured to couple the containers to the tray, as described herein.

Each of the containers is coupled to a container lid having a fluid exchange port and a gas exchange port, similar to the lid 803 or the lid 2408 shown and described herein. Specifically, the cell culture containers 3647, 3648, 3649 are each coupled to a lid 3608, the reagent container is coupled to a lid 3609, the waste container is coupled to a lid 3610. In some embodiments, the lids can be removably coupled to its respective container (e.g., to facilitate startup procedures, system maintenance, or the like). In other embodiments (e.g., as described for the cell culture system 2600), the lids are permanently coupled to their respective container. As shown, each lid is fluidically coupled within the system 3600 via tubing. In this manner, fluids can be transferred between various containers (e.g., for cell passaging, cell harvesting or the like), as described herein.

In contrast to the system 1600, which includes a multiport valve to selectively define fluid paths for the movement of fluid within the system, the cell culture system 3600 includes the valve assembly 3607, which has a set of valves 3607A-3607G that are each individually actuatable. The valves 3607A-3607G have a single input and a single output and can control the flow of fluid therethrough in either an "on/off" manner, or by throttling the flow (i.e., to control a flow rate through the valve). When used in an "on/off" manner the valves 3607A-3607G can provide a simple control system without the need for a valve position sensor or rotary actuator. Because each of the valves 3607A-3607G is independently actuatable, a series of different flow paths can be defined between the containers, the holding volume 3674, and the pump 3613. For example, the valve 3607A controls flow into and out of the cell culture container 3647, the valve 3607B controls flow into and out of the cell culture container 3648, and the valve 3607C controls flow into and out of the cell culture container 3649. The valve 3607D controls flow between each of the cell culture containers and the holding volume 3674. The valve 3607E controls flow into and out of the waste container 3606 and the valve 3607F controls flow into and out of the reagent (or cell nutrient) container 3605. The valve 3607G controls flow between the fluid pump 3613 and the holding volume 3674.

In some embodiment the above-described on/off valves 3607A-3607G are included on the tray 3602 and matingly engage a valve actuator in the base unit by the user. In other embodiments, the valves 3607A-3607G are closed tube sections that are placed into fixed pinch valves on the base unit. In some embodiments, there may be as few as three on/off valves/tube sections that get placed into valves—one to control flow to a first container, one to control flow to a second container, and one to control flow to a third location (e.g., a container or other location on the tray).

Although not shown, the system 3600 can include additional valves coupled to various other components, such as, for example, a cell counting chip, cell harvest container(s), various reagent and enzyme containers, etc. In this manner, when actuated the various valves in the valve assembly 3607 can facilitate fluid exchange between various containers within the automated cell culture system 3600. For example, as described herein, the valves can be actuated to facilitate the addition of cell culturing media or reagents to the cell culture containers, the removal of cells from the cell culture containers (e.g., cell passaging or cell harvesting), or any other fluid movement associated with cell culturing.

The valves 3607A-3607G can be any suitable valve having an input port and an exit port. In some embodiments, any (or all) of the valves 3607A-3607G can be pinch valves that receive a section of the tubing and that, when actuated, deform the tubing to close the section of tubing to prevent fluid flow therethrough. This arrangement can be advantageous in that it eliminates the fluid connections between the tubing and valves (i.e., because the section of tubing is maintained intact and is placed within a cradle or receiving portion of the pinch valve). In other embodiments, any (or all) of the valves 3607A-3607G can be needle valves, ball valves, or any other valve mechanism to control the flow therethrough.

In some embodiments, the valves 3607A-3607G can include an integrated valve actuator (e.g., solenoid) that is included on the consumable tray assembly 3601. Thus, in contrast to other tray assemblies described herein (e.g., the tray assembly 1601), the valves 3607A-3607G can be fixedly coupled to the tray 3602 and are not removed from the tray to be coupled to an actuator within the base unit (e.g., an external actuator, like the actuator 1621 described above). This arrangement can reduce the set-up time needed. In some embodiments, the integrated valve and actuator can be sterilizable via accepted methods to facilitate sterilization of the entire tray assembly, as described herein. For example, in some embodiments, the tray assembly with the actuator(s) fixedly coupled to the tray 3602 can be sterilized by any suitable low temperature methods (i.e., that do not adversely impact the function of the electronics). For example, in some embodiments, a tray assembly can be sterilized via ethylene oxide (EtO), which employs lower temperatures than some other sterilization methods.

Figure 82A:
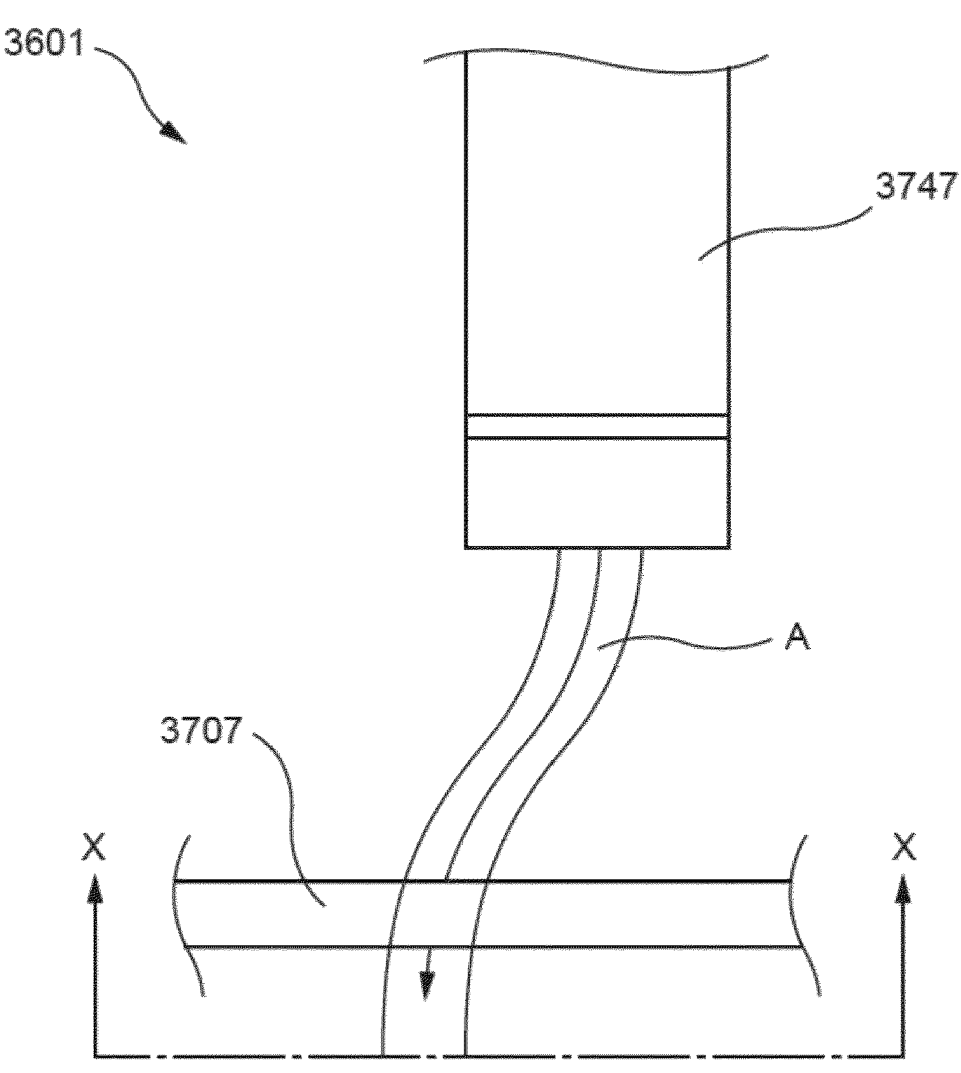
FIGS. 82A and 82B are schematic illustrations of a portion of a tray assembly according to an embodiment, in a first configuration.
Figure 82B:
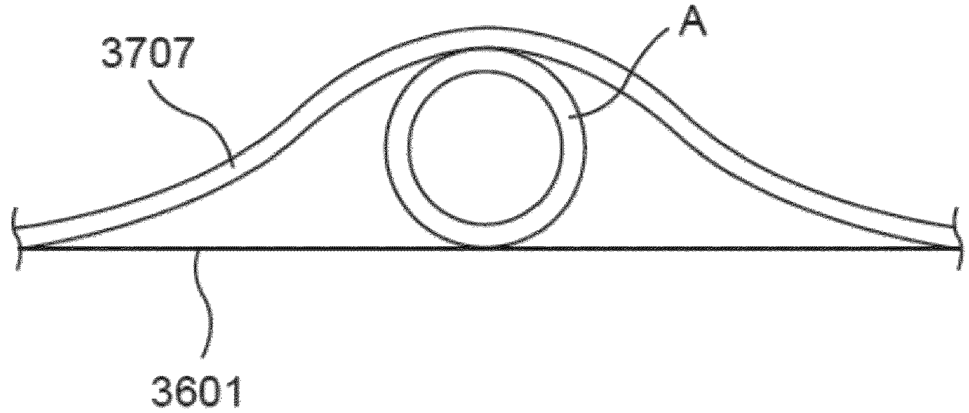
Figure 83A:
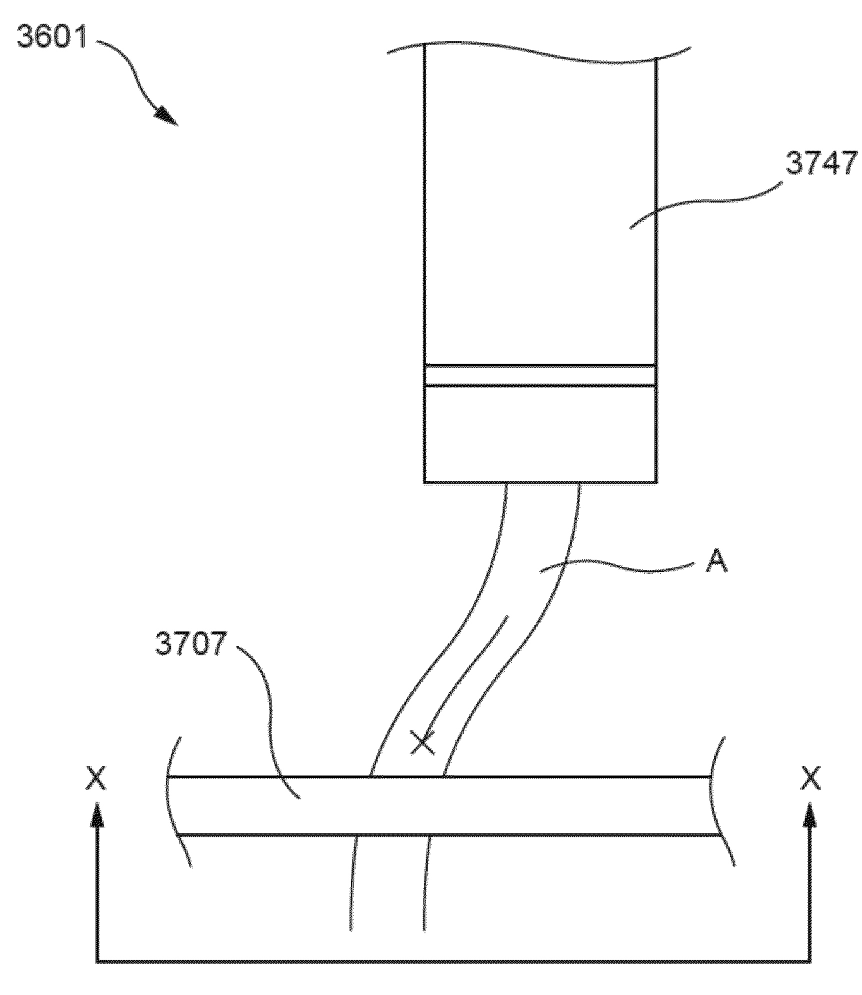
FIGS. 83A and 83B are schematic illustrations of a portion of a tray assembly shown in FIGS. 82A and 82B, in a second configuration.
Figure 83B:
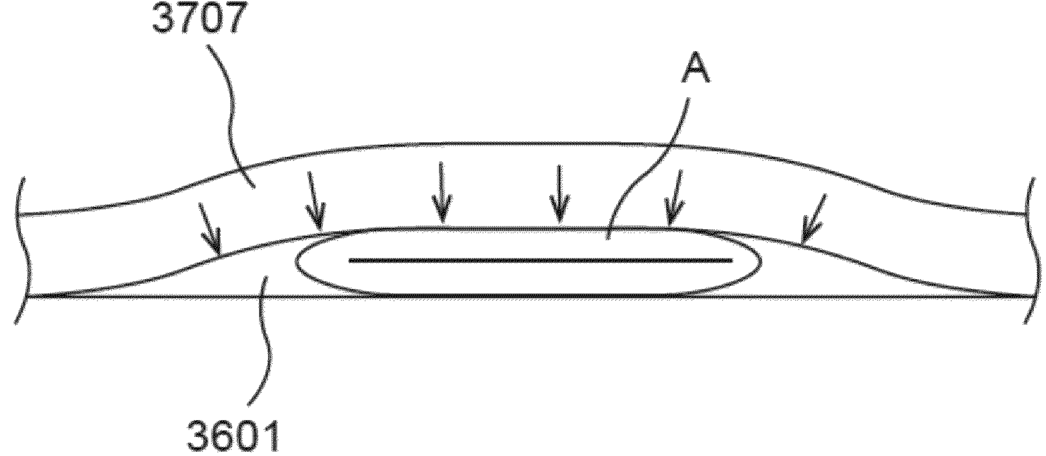

In other embodiments, a system can include one or more non-electronic valve actuators fixedly coupled to a tray. In this manner, a wider range of sterilization methods can be used. For example, by including non-electronic actuators fixedly coupled to the tray, sterilization methods that are not generally compatible with electronics, such as steam sterilization, can be used. In some embodiments, any of the tray assemblies or systems described herein can include one or more pressure-actuated valves, such as a pneumatic valve or a hydraulic valve. For example, FIGS. 82A, 82B, 83A, and 83B are a schematic illustrations of portion of a tray assembly 3701 including a pressure-actuated valve 3707, according to an embodiment. FIG. 82B is a cross-sectional view taken along line X-X in FIG. 82A and FIG. 83B is a cross-sectional view taken along line X-X in FIG. 83A. As shown, the tray assembly 3701 includes a container 3747, which can be any of the containers described herein (e.g., a cell culture container). The container 3747 can be coupled to other containers, a pump, or any other components of the tray assembly 3701 via the tubing A (which can be similar to the tubing shown and described in connection with FIGS. 16A-16C). The pressure actuated valve 3707 is a chamber, vessel or other structure that, when actuated, exerts a pressure to constrict the tubing A to prevent flow therethrough, as shown in FIGS. 83A and 83B. In some embodiments, the valve 3707 can be actuated by applying gas pressure within the valve 3707 to produce the pressure against the tubing A. In other embodiments, valve 3707 can be actuated by applying hydraulic pressure within the valve 3707 to produce the pressure against the tubing A. Although the valve 3707 is shown as including a single pressure member that intersects or crosses over the tubing A, in other embodiments, the valve 3707 can include a series of pressure members that intersect (or cross over) the tubing A.

FIGS. 84-101 illustrate another embodiment of a cell culturing system 4000, for use in a cell culturing procedure. The cell culture system 4000 can include the same or similar components as other embodiments described herein (including, for example, the cell culture systems 1700 and 2000) and can have the same or similar functions as the previous embodiments described herein, and therefore, some details of the cell culturing system 4000 are not described with respect to this embodiment.

The cell culturing system 4000 (also referred to herein as "system") includes a flask tray assembly 4101 (see, e.g., FIGS. 84-90), an input tray assembly 4281 (see, e.g., FIGS. 91-92), and an instrument 4300 (see, e.g., FIGS. 93-101). The flask tray assembly 4101 can be removably coupled to the instrument 4300 as described below. Similarly, the input tray assembly 4281 can also be removably coupled to the instrument 4300 as described below. The flask tray assembly 4101 can be packaged or stored in a sterile overwrap as described above for previous embodiments. In some embodiments, the input tray assembly 4281 is stored within the same overwrap as the flask tray assembly 4101. In some embodiments, the flask tray assembly 4101 and the input tray assembly 4281 are wrapped in separate sterile overwraps. In some embodiments, the flask tray assembly 4101 and/or the input tray assembly 4281 are placed in a double overwrap (e.g., double bagged), either together or separately.

Figure 84:
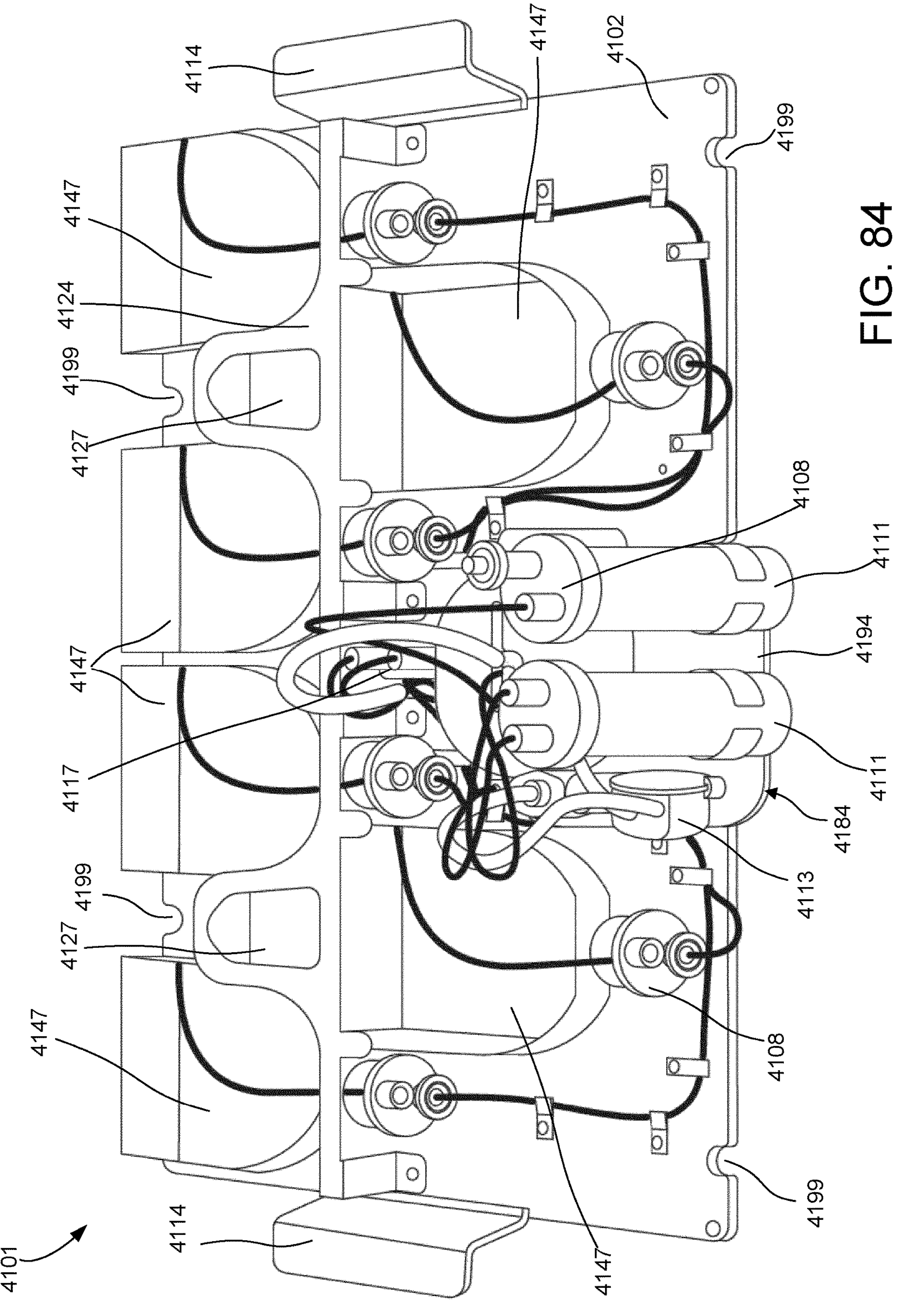
FIG. 84 is a top perspective view of a tray assembly of a cell culturing system, according to an embodiment.
Figure 85:
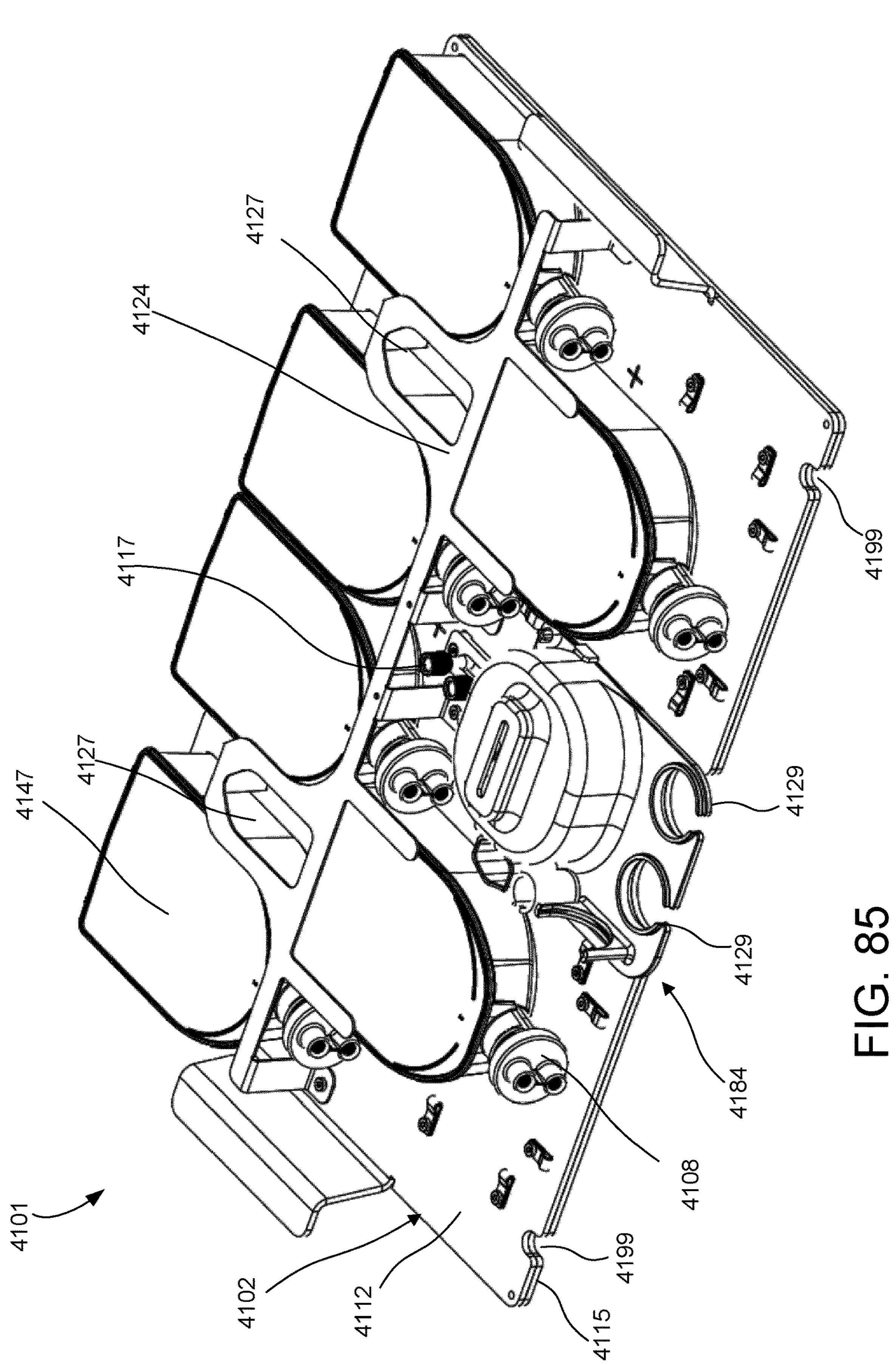
FIG. 85 is a perspective view of the tray assembly of FIG. 84.
Figure 86:
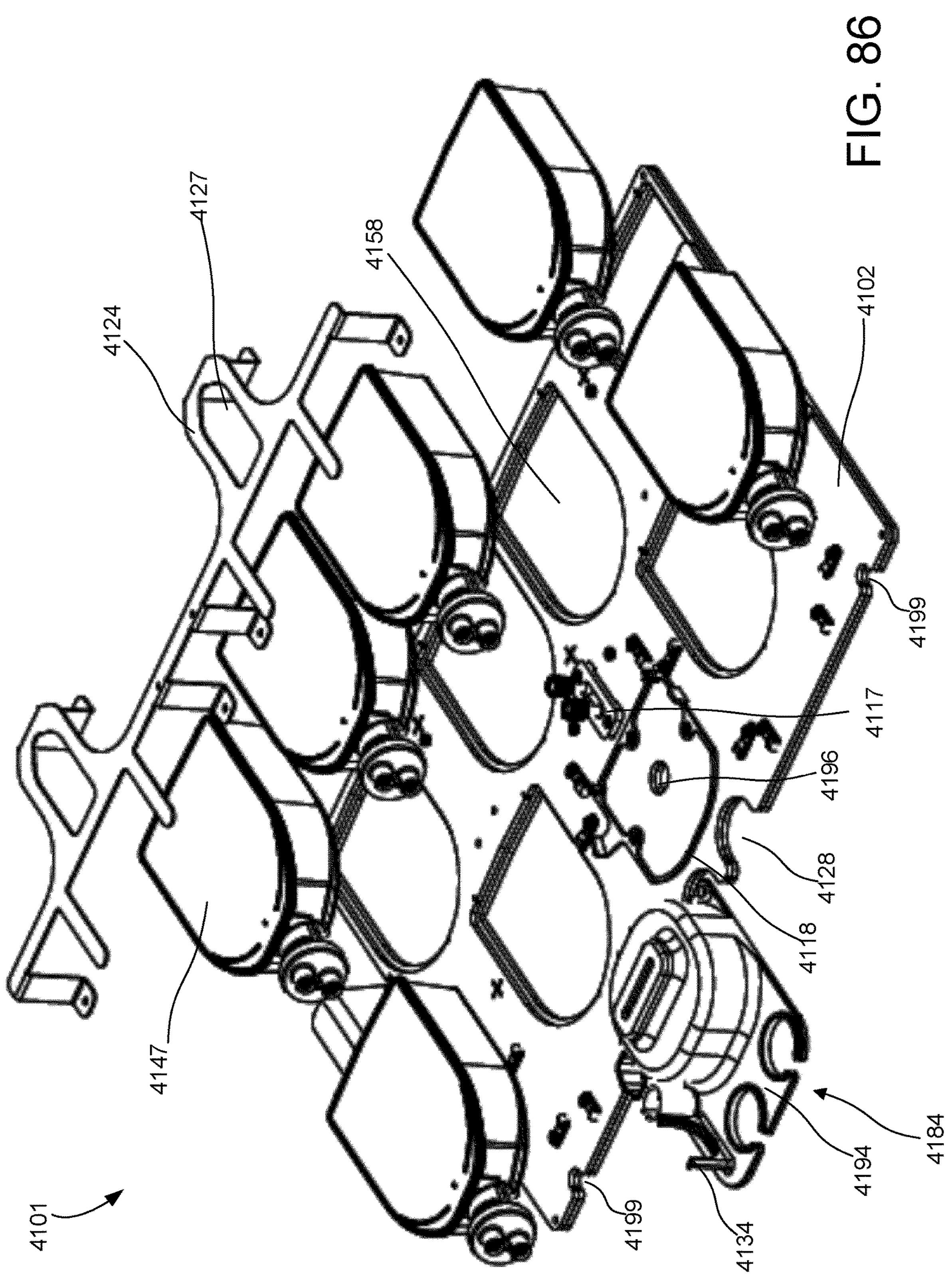
FIG. 86 is a partially exploded view of the tray assembly of FIG. 84.
Figure 87:
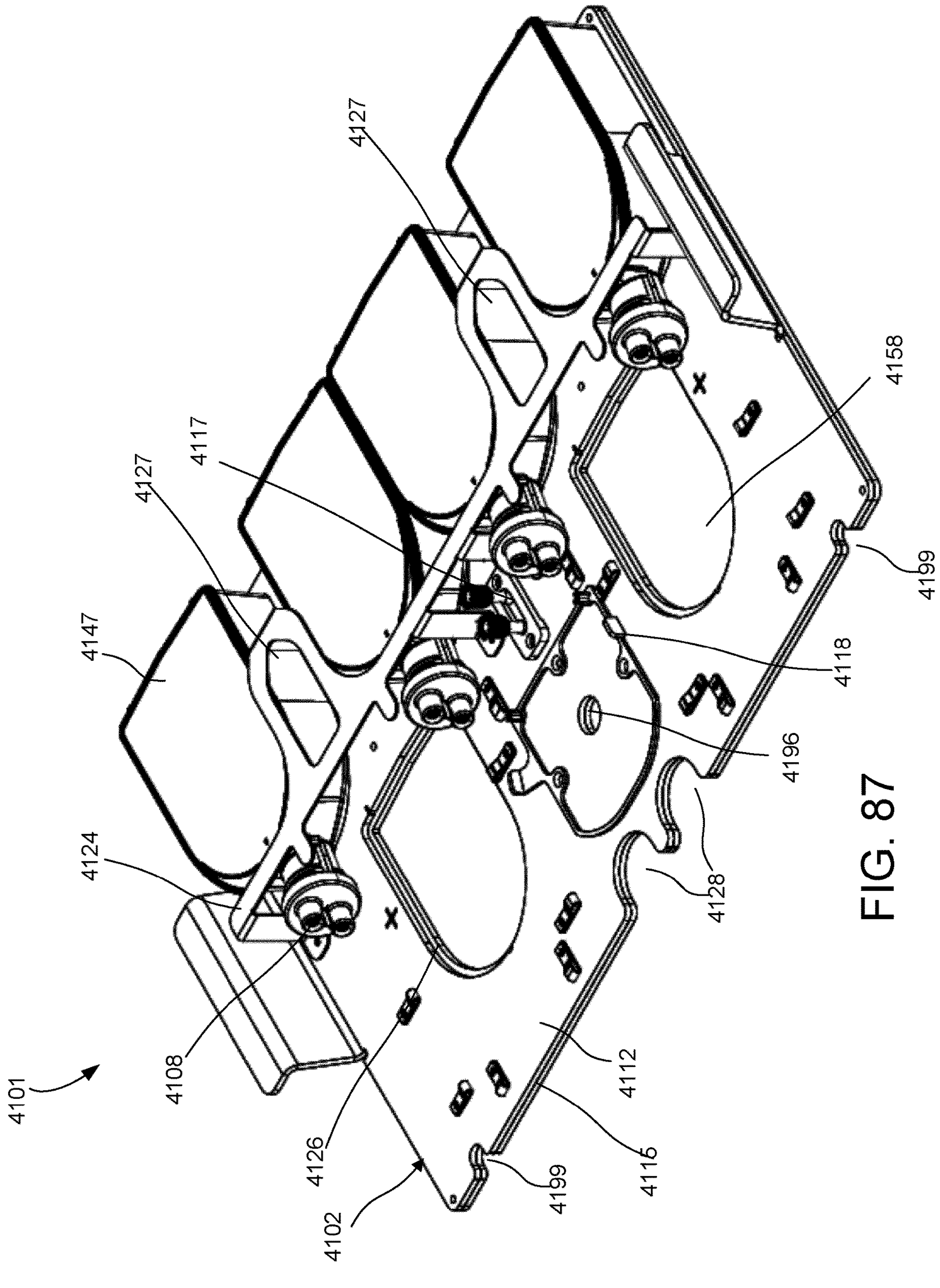
FIG. 87 is a perspective view of the tray assembly of FIG. 84 with the valve assembly and two containers removed for illustration purposes.

As shown, for example, in FIGS. 84-86, the flask tray assembly 4101 includes a tray 4102 with handles 4114, a valve assembly 4184, a cell counting chip 4117, six containers 4147 and corresponding six lids 4108, disposed on the tray 4102. The containers 4147 can be, for example, cell culture containers and be formed with a transparent material to allow for viewing within the interior of the containers 4147. In some embodiments, the containers may be laboratory flasks or dishes, for example. The containers can hold cell cultures, growth medium, and any other additives or reagents associated with cell culture. The cell cultures within the containers maybe any kind of adherent or suspension cell cultures. The containers 4147 can be preassembled on the tray 4102 of the tray assembly 4101 and provided within the overwrap surrounding the tray assembly 4101 as described above for previous embodiments. The preassembled containers 4147 can be coupled to or uncoupled from lids 4108 when disposed within the overwrap. During preparation for a cell culturing procedure and prior to the tray assembly 4101 being coupled to the instrument 4300, cells and reagent can be added to the containers 4147 via the lids 4108. For example if the lids 4108 are not already coupled to the containers 4147 prior to being overwrapped, the lids 4108 can be coupled to the containers 4147 and the cells and reagents can be introduced into the containers 4147 via the lids 4108. In other embodiments, the lids 4108 are pre-coupled to the containers 4147 to form a closed system (i.e., the containers 4147 are substantially isolated from an external environment in a manner that limits the ingress of microbes into the system). The cells and reagents can be introduced into the containers 4147 without opening the lids (i.e., while maintaining the closed system). In some embodiments, the containers 4147 are not preassembled on the tray 4102 (are not provided within the overwrap), but rather are added to the tray 4102 during preparation for the cell culture procedure, as described above for previous embodiments. In such a case, the containers 4147 are filled with cells and reagent (e.g., cell culture media), coupled to the lids 4108 and added to the tray assembly 4101.

The lids 4108 can be configured the same as the lids described above for previous embodiments, including the cell culture vessel lid 803 or the lid 2408. For example, the lids 4108 can include a liquid exchange port (also referred to as "fluid port") and a gas exchange port, and the fluid ports can be aseptically coupled to the valve (described below) of the valve assembly 4107 with tubing (shown in FIG. 84) as described above for previous embodiments and as described in more detail below. The lids 4108 can include an aseptic quick connect fitting (e.g., Equashield® fittings).

Figure 88:
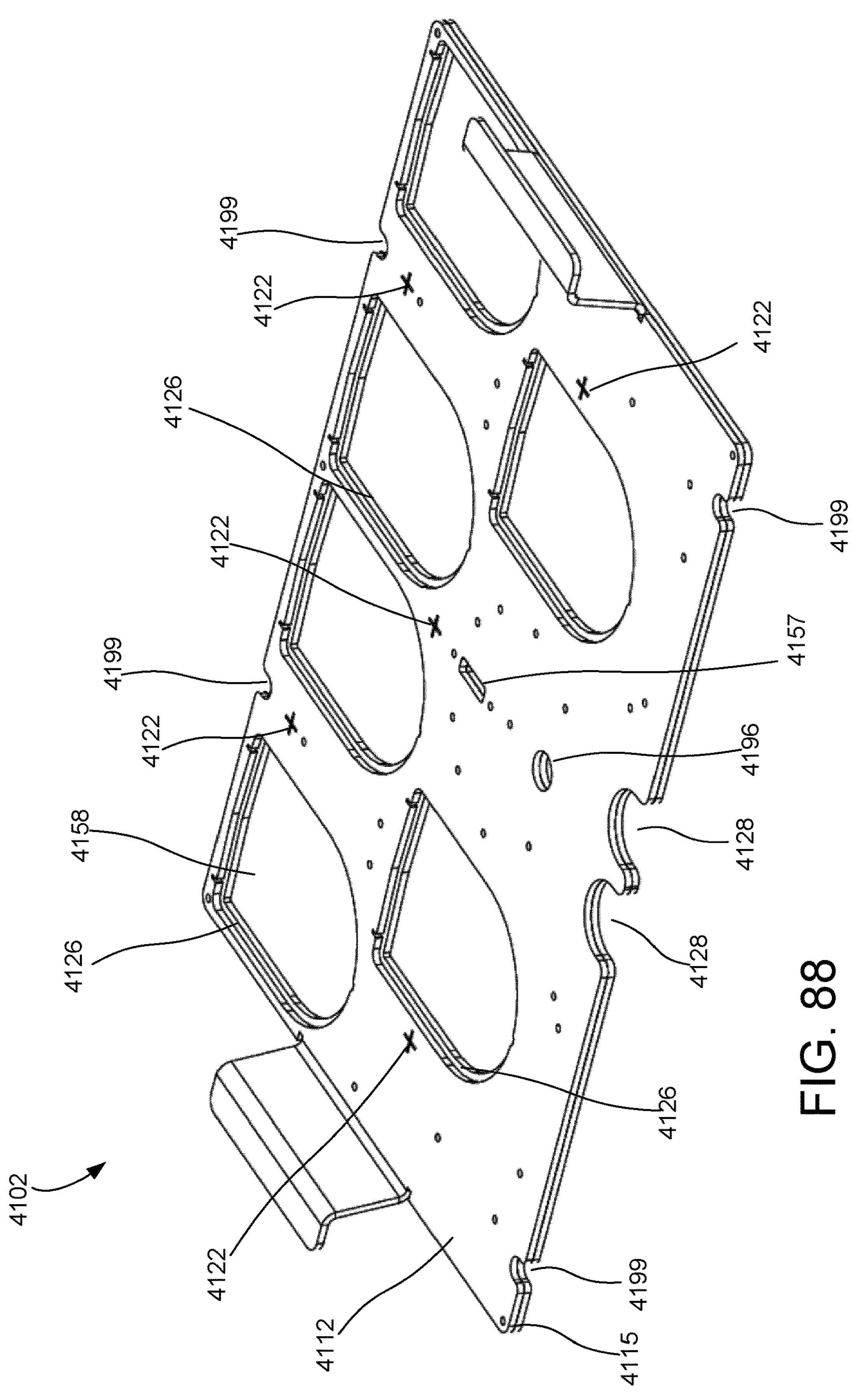
FIG. 88 is a perspective view of the tray of the tray assembly of FIG. 84.

In this embodiment, the tray 4102 includes a top portion 4112 and a bottom portion 4115 that are coupled together and each include multiple transparent or cut-out portions 4158 over which each of the containers 4147 are disposed, as best shown in FIG. 88. The cutout portions in the top portion 4112 are smaller than the cutout portions 1058 in the bottom portion 4115 such that when the top portion 4112 is coupled to the bottom portion 4115 a shoulder 4126 is formed about a perimeter of the cut-out portions 4158 on which the containers 4147 can rest. The transparent or cut-out portions 4158 allow for viewing of the contents of the containers 4147 when disposed within the instrument 4300. For example, as described for previous embodiments, the cell culture system 4000 can include an imaging device and/or other sensors (described in more detail below) that are disposed in the instrument 4300 below the tray 4102 when the tray assembly 4101 is coupled to the instrument 4300. The transparent portion(s) or cut-out(s) 4158 can allow for images and/or other data to be obtained through the transparent portion or cut-out, such as the contents within the containers 4147 coupled to the tray 4102. A bracket 4124 is provided that holds the containers 4147 on the tray 4102. As shown, for example, in FIGS. 84-87, the bracket 4124 is attached to the tray 4102 and disposed over a top surface of the containers such that a portion of the bracket 4124 contacts a top surface of each of the containers 4147 to assist in holding the containers on the tray 4102. The bracket 4124 defines two openings 4127 that can be used, for example to hold a tube (e.g., a Falcon™ tube), if desired during storage or use of the cell culturing system 4000. The tray 4102 also includes a transparent or cut-out portion 4157 (see, e.g., FIG. 88) over which the cell counting chip 4117 is disposed. As with the containers 4147, the cell counting chip 4117 can include a bottom transparent portion such that an imaging device and/or other sensors disposed in the base unit 4320 and can be used to obtain information about the contents within the cell counting chip 4117. In some embodiments, the cell counting chip 4117 may be coupled to or mounted within the instrument 4300 instead of being preassembled on the tray assembly 4101.

The tray 4102 also defines multiple alignment portions in the form of cut-out portions 4199 disposed around a perimeter edge of the tray 4102. The cut-out portions 4199 are used to align the tray 4102 on the instrument 4200 as described in more detail below. For example, the instrument 4300 includes alignment portions (see, e.g., protrusion 4342 in FIGS. 93 and 97) that matingly engage with the alignment portions 4199 of the tray 4102. The tray 4102 also defines multiple alignment markers 4122 and an opening 4197 that receives a mechanical coupler 4193 of a valve 4107 (described below) of the valve assembly 4184 when the valve assembly 4184 is coupled to the tray 4102. In some embodiments, the alignment markers 4122 are openings through the tray 4102 as shown, for example, in FIG. 88. The alignment markers 4122 can be used to align the tray with a sensor (e.g., an imaging device, a microscope) disposed within instrument 4300 described in more detail below.

Figure 90A:
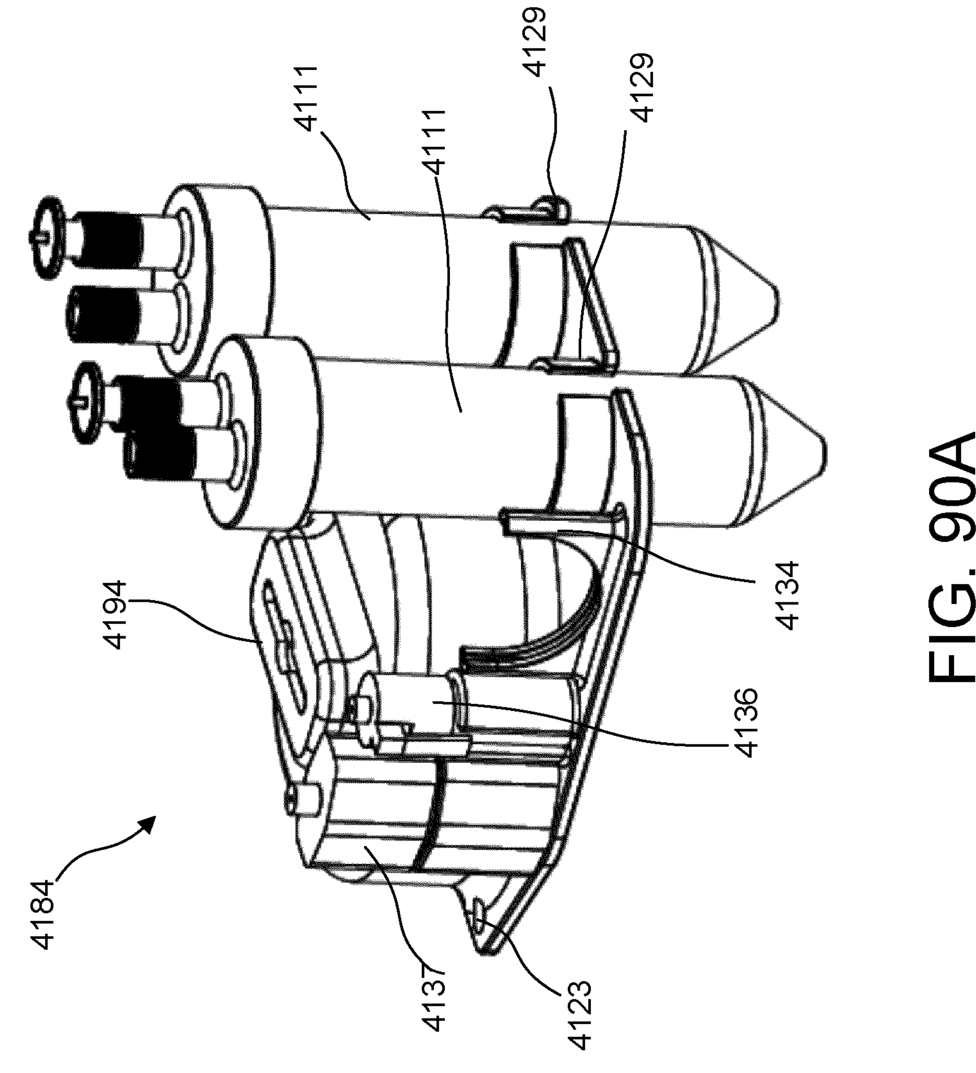
FIG. 90A is a perspective view of the valve assembly of tray assembly of FIG. 84, shown with two tubes disposed thereon.
Figure 89:
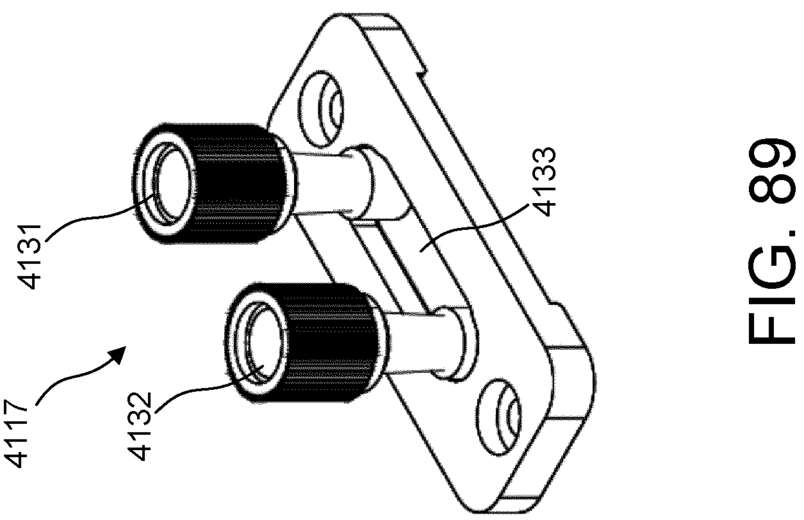
FIG. 89 is a perspective view of the cell counting chip of the tray assembly of FIG. 84.
Figure 90B:
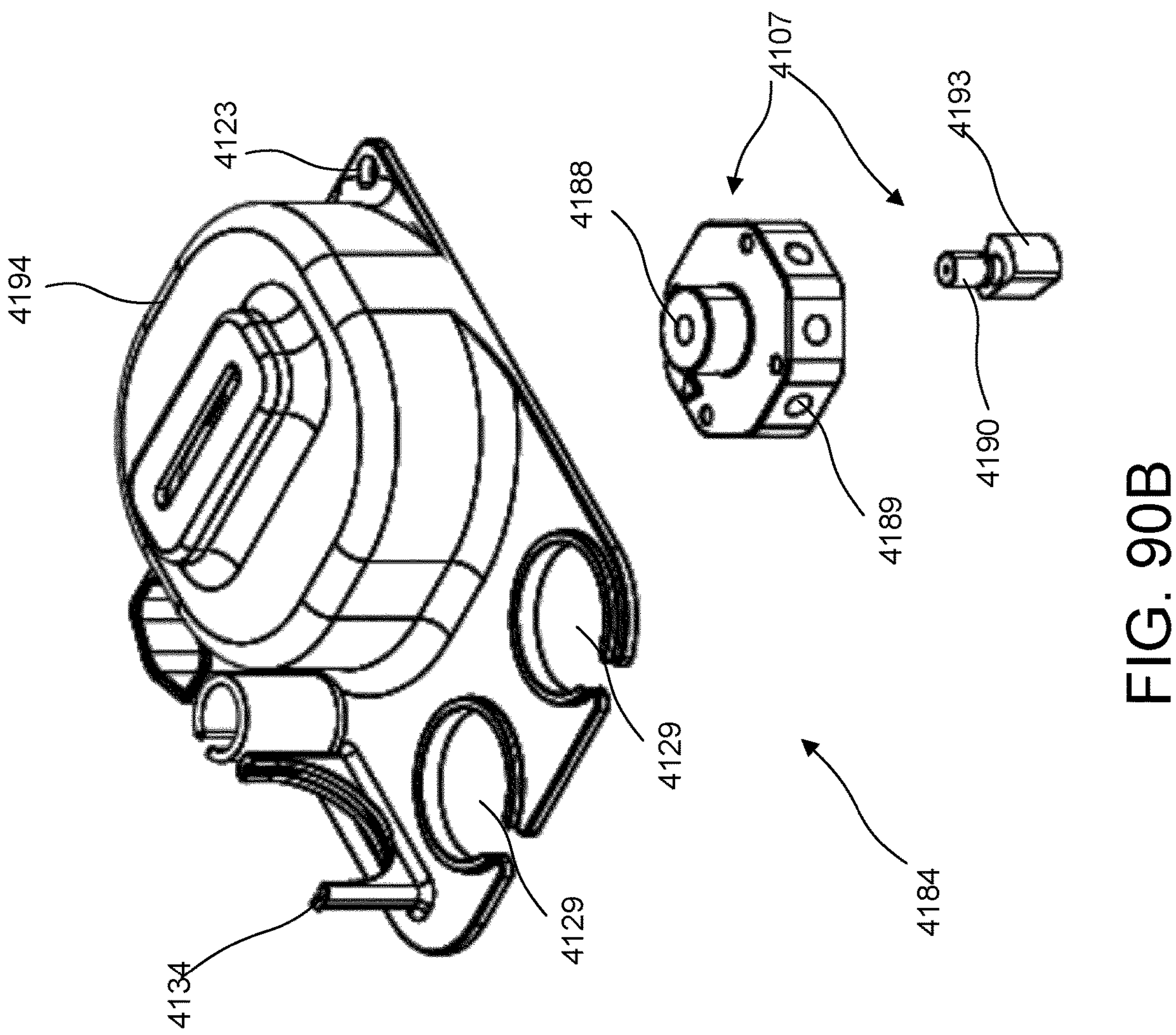
FIG. 90B is an exploded view of a portion of the valve assembly of the tray assembly of FIG. 84.
Figures 90C, 90D:
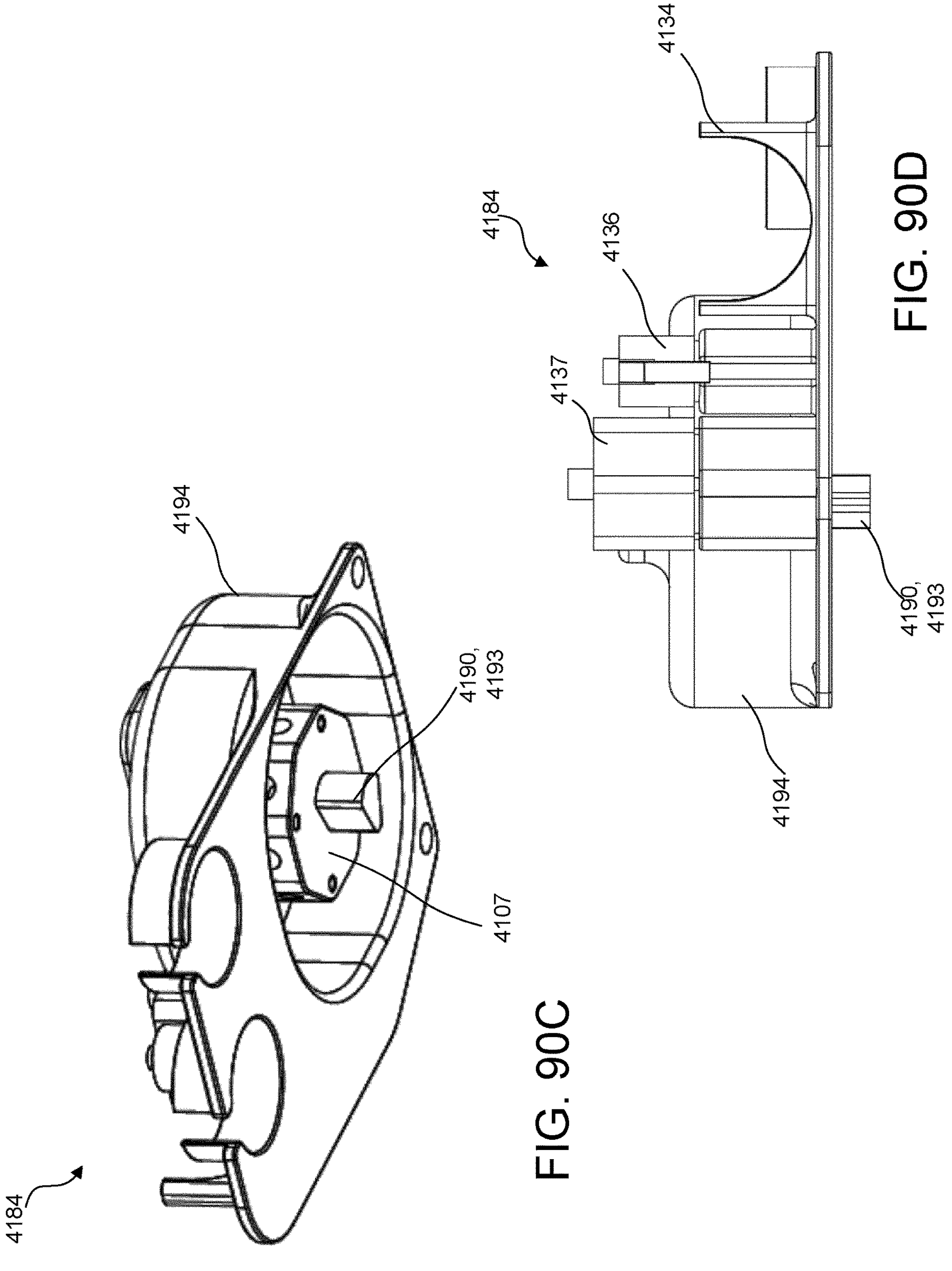
FIG. 90C is a bottom perspective view of the portion of the valve assembly of the tray assembly of FIG. 84.
FIG. 90D is a side view of the portion of the valve assembly of the tray assembly of FIG. 84.

The valve assembly 4184 includes the valve 4107 disposed within a valve housing 4194 (as shown, for example, in FIGS. 90B and 90C). The valve 4107 can be configured the same as or similar to, for example, the valve 2407 described above and include a master port 4188 and multiple selectable ports 4189 (see e.g., FIG. 89) to which the lids 4108 (and/or other lids/containers) can be selectively fluidically and aseptically coupled via a length of tubing (shown in FIG. 84). The valve 4107 also includes a valve rotor 4190 that includes the mechanical coupler 4193. The mechanical coupler 4193 is configured to mechanically couple to a valve actuator of the instrument (described below), which can have a cavity shaped to accept the mechanical coupler 4193 (see, e.g., FIG. 96), and transfer rotational mechanical energy to the valve 4107. The valve housing 4194 can be coupled to the tray 4102 via a mounting bracket 4118 and a pair of posts 4196. The valve housing 4194 matingly couples to and fits within the mounting bracket 4118 of the tray assembly 4101 and includes openings 4123 (only one is visible in FIG. 89) that receive the posts 4196. The bracket 4118 and the posts 4196 position and maintain the valve assembly 4184 on the tray 4102 during storage and transport. In addition, the tray 4102 defines an opening 4197 that receives the coupler 4193 of the valve rotor 4190.

The valve housing 4194 defines two holder portions 4129 that can each hold a tube 4111 (e.g., a Falcon™ tube known in the art), as shown in FIGS. 84 and 90A. The tubes can be capped with a lid 4108. The tray 4102 defines corresponding cut-out portions 4128 (see, e.g., FIG. 88) through which the tubes 4111 can extend when the valve assembly 4184 is coupled to the tray 4102. The tubes 4111 provide a fluid reservoir that can contain, for example, various fluids, seeding cells, fresh media, waste fluids, etc. The tubes 4111 can be fluidically and aseptically coupled to a select port of the valve 4107. The valve assembly 4184 also includes a pump holder portion 4134 that removably holds a pump 4113 during transport and storage of the tray assembly 4101. In this embodiment, the pump 4113 is a peristaltic pump and is fluidically and aseptically coupled to, for example, the master port of the valve 4107 and to one or more of the containers of the tray assembly 4101. The valve assembly 4184 also holds a two quick connect valve couplers 4136 and 4137 (see, FIG. 90D) discussed in more detail below. The valve couplers 4136 and 4137 can be, for example, an aseptic quick connect fitting (e.g., Equashield® fitting). More specifically, the coupler 4136 is a plug connector and the coupler 4137 is a socket connector. The coupler 4136 can be coupled to a corresponding socket connector (4237 described below) of the tray assembly 4281 and the coupler 4137 can be coupled to a corresponding plug connector (4236 described below) of the input tray assembly 4281 as described below.

The cell counting chip 4117 is best shown in FIG. 89. The cell counting chip 4117 includes an interior fluid reservoir 4133, and an inlet port 4132 and an outlet port 4131 each fluidically coupled to the reservoir 4133. The reservoir 4133 is sized (e.g., has a height and width) such that it has a known volume to provide for accurate counting of cells. The cell counting chip 4117 is fluidically and aseptically coupled within the system 4000 between the containers and the valve 4107 such that the cell counting chip 4117 is within the closed system. The cell sample from any of the containers 4147 can be introduced into and out of the cell counting chip 4117 from selected containers as described herein for other embodiments. For example, cells can be pumped from one of the containers of the system 4000 to the cell counting chip 4117 and the cells can be counted within the cell counting chip 4117 and then moved back to the container or to another container within the system 4000. The cell sample is analyzed within the cell counting chip 4117 to produce a cell signal associated with an amount of cells within the cell sample.

Figure 91:
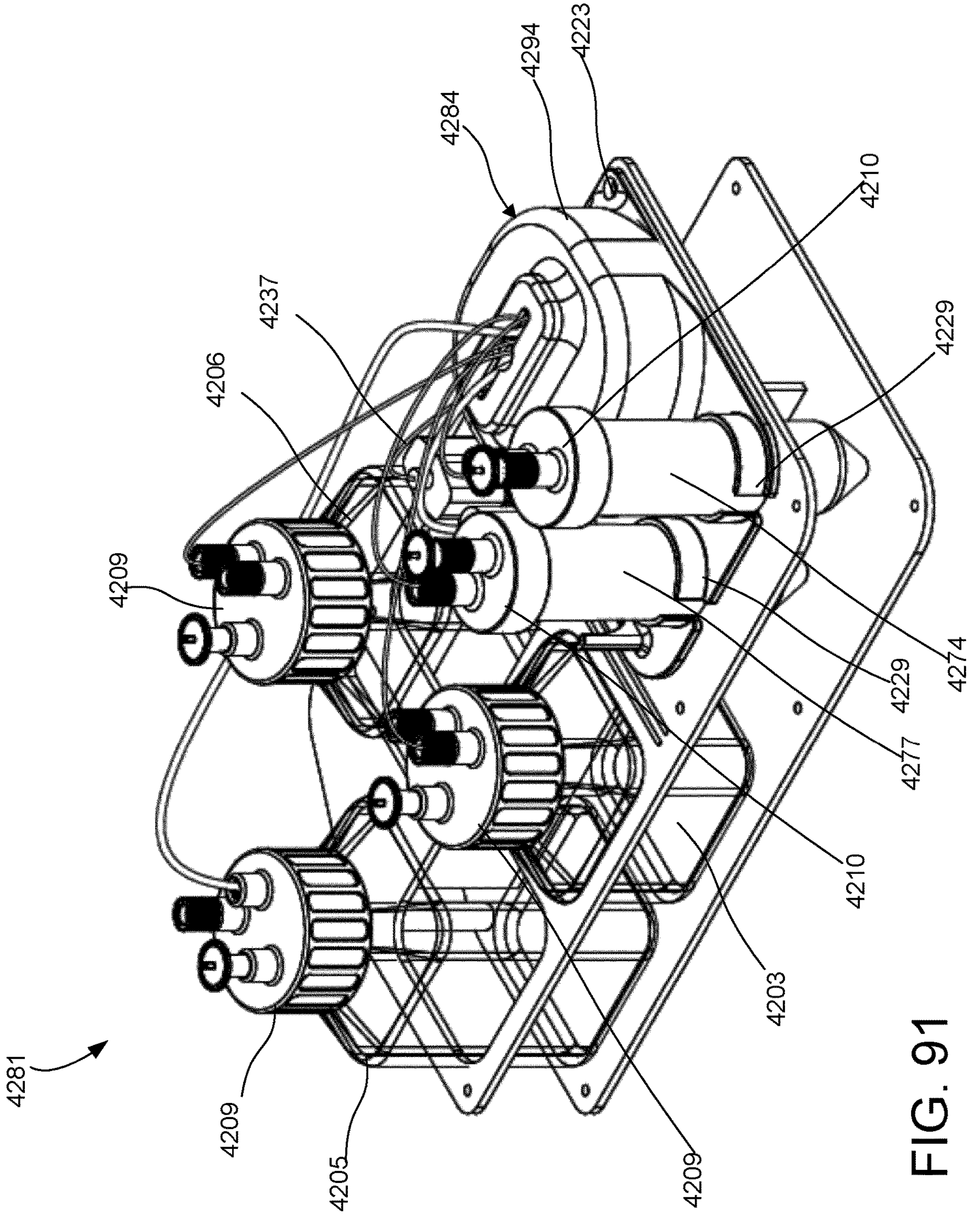
FIG. 91 is a perspective view of an input tray assembly, according to an embodiment.
Figure 92:
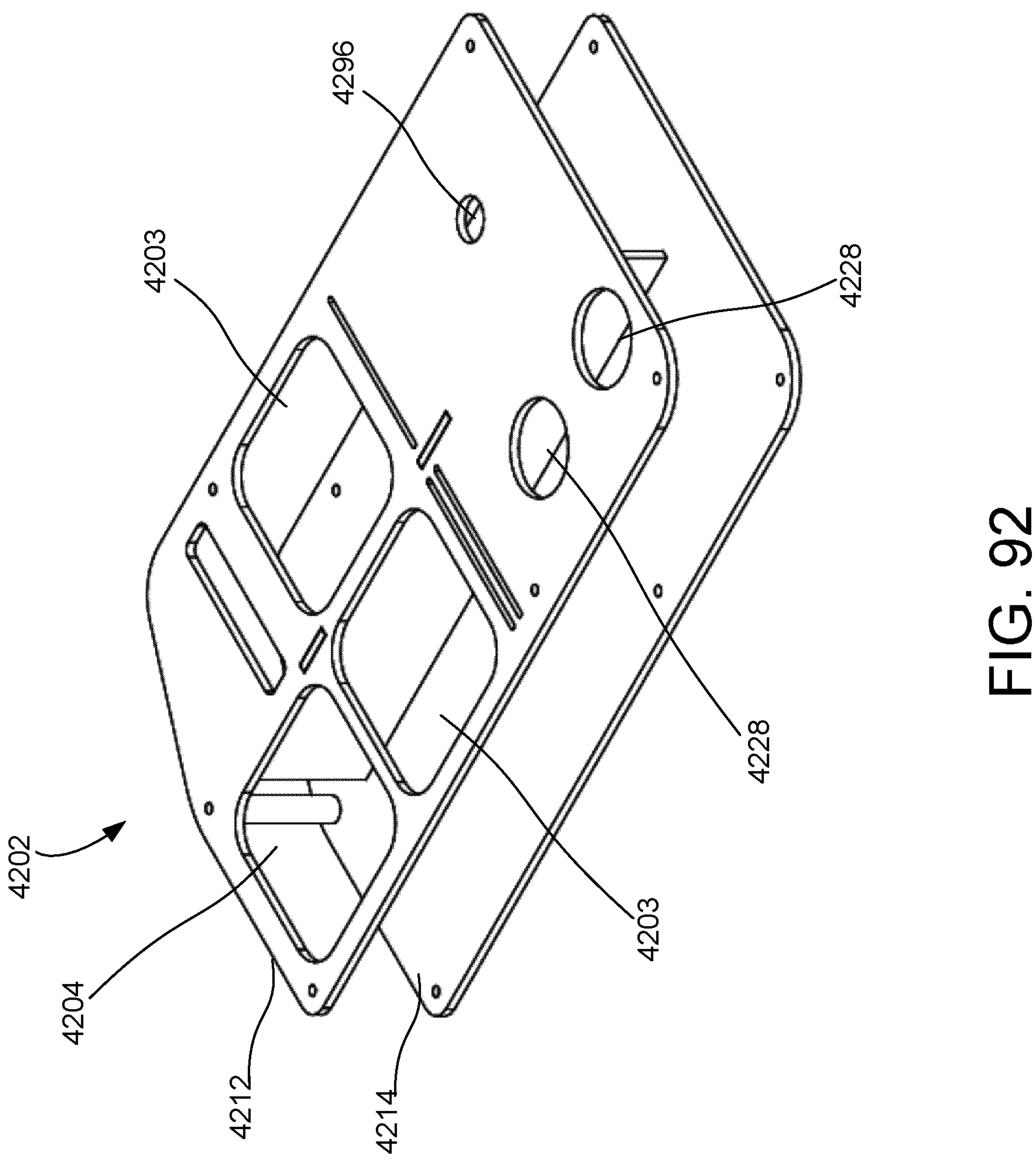
FIG. 92 is a perspective view of the tray of the input tray assembly of FIG. 91.
Figure 93:
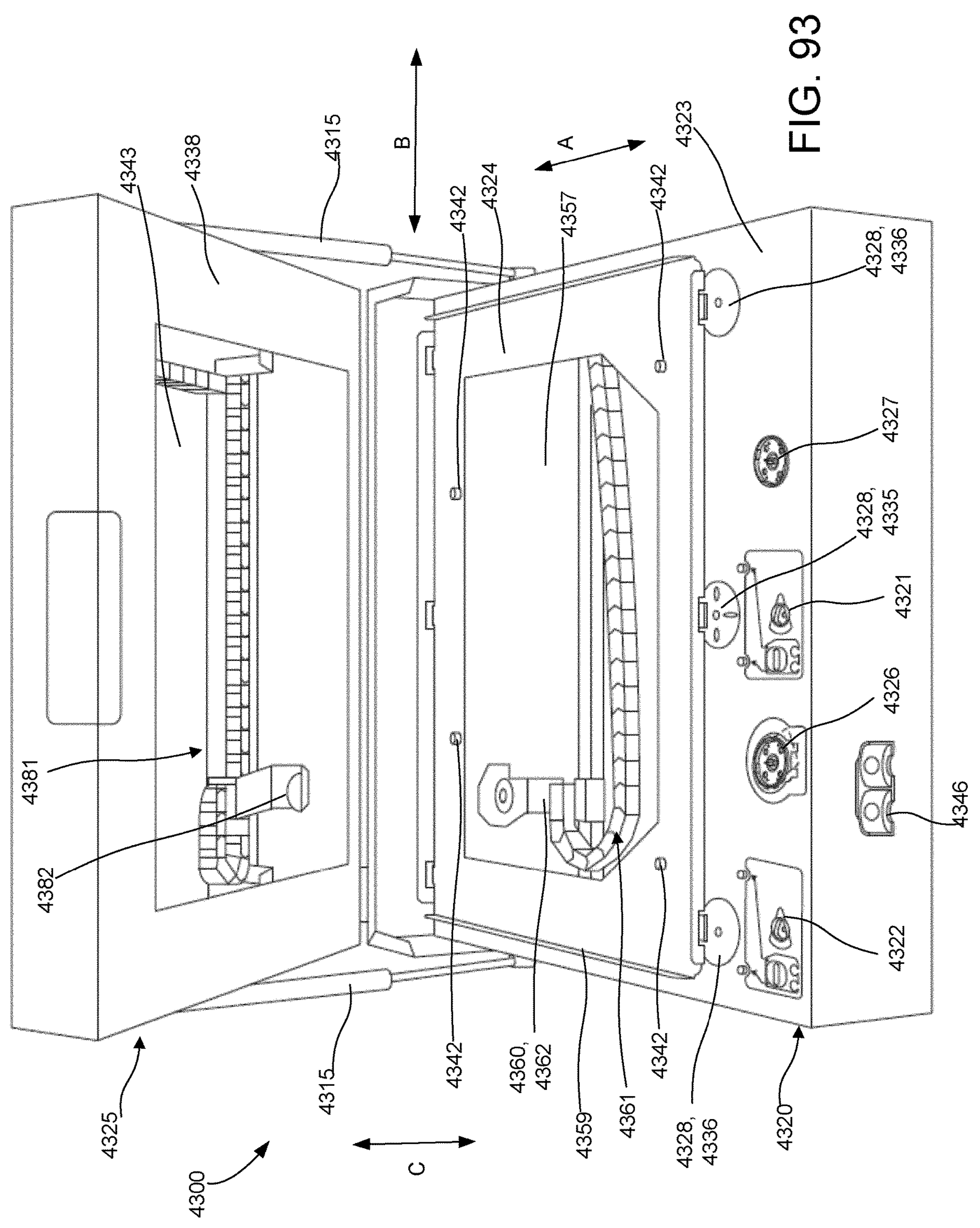
FIG. 93 is a front perspective view of an instrument of a cell culturing system, according to an embodiment.
Figure 94A:
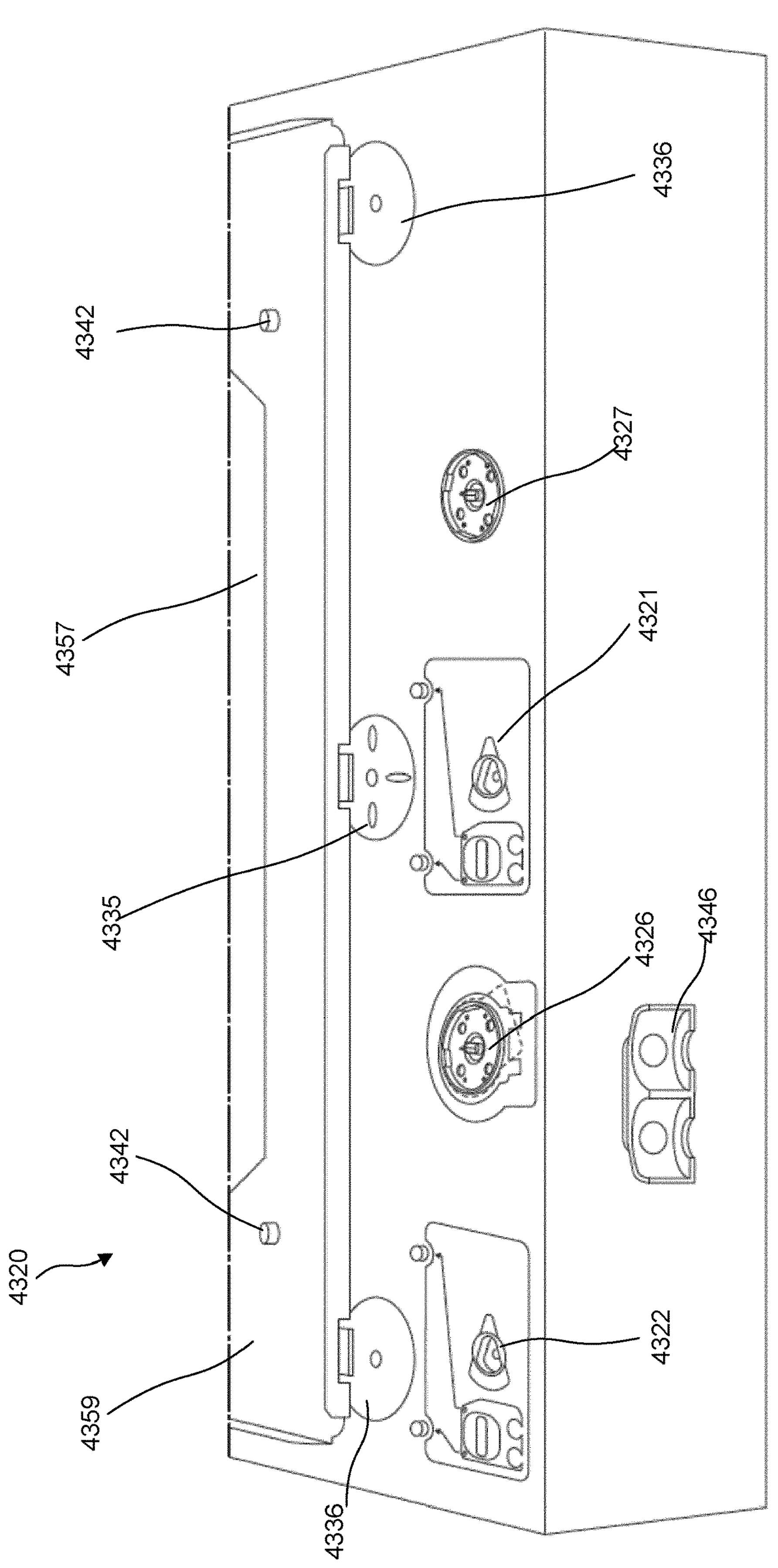
FIG. 94A is an enlarged view of a portion of the instrument of FIG. 93.
Figure 94B:
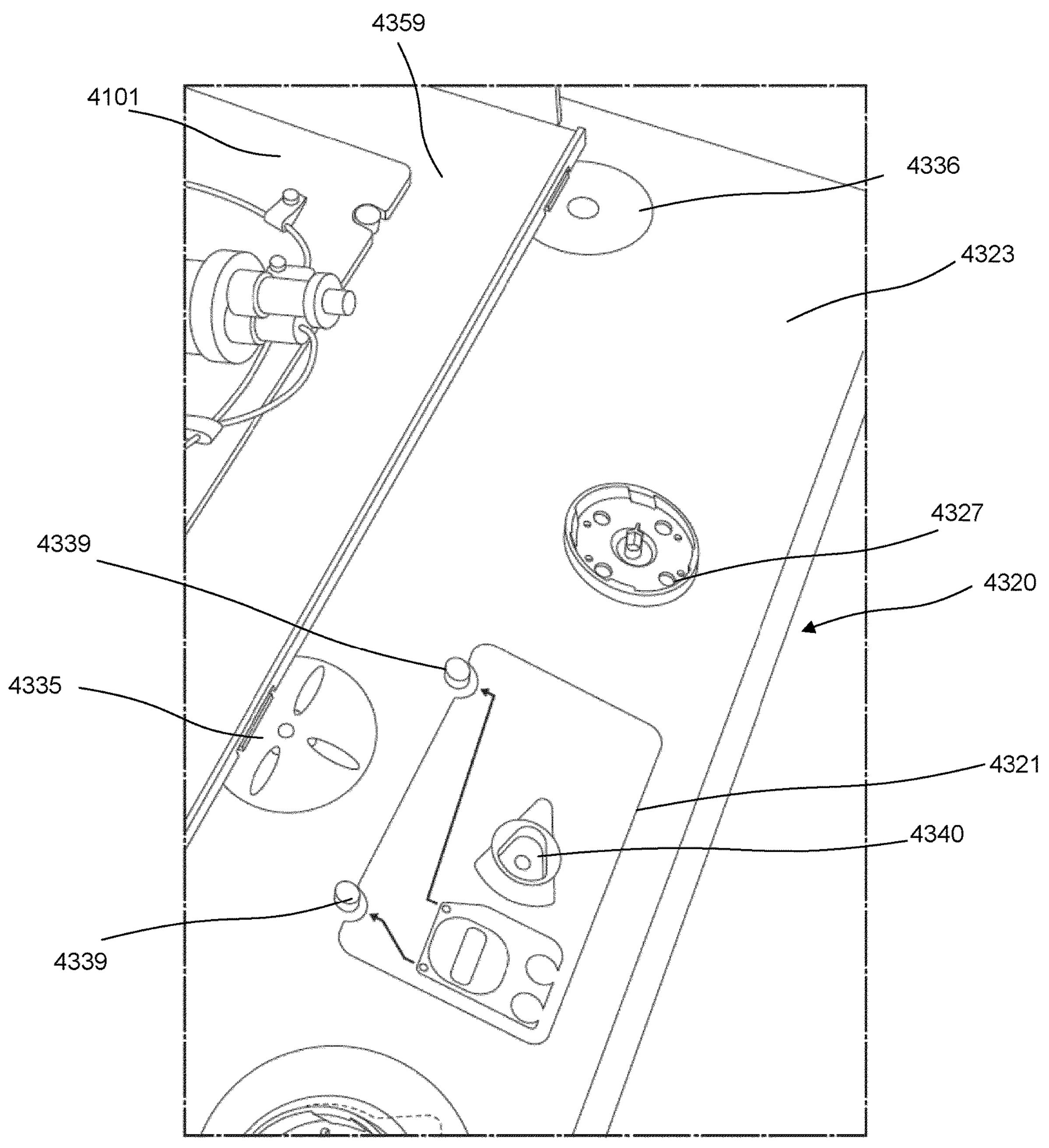
FIG. 94B is an enlarged view of another portion of the instrument of FIG. 93.

As shown in FIGS. 91 and 92, the input tray assembly 4281 includes a holder 4202 that supports a second valve assembly 4284 and multiple containers, 4205, 4203, 4206 and tubes 4277 and 4274. Lids 4209 are coupled to the containers 4205, 4203 and 4206 and lids 4208 are coupled to the tubes 4277 and 4274. The lids 4209 and 4208 can be configured the same as or similar to the lids 4208 described above to provide an aseptic seal between the containers and tubes and the valve of the second valve assembly 4284. For example, the lids 4209 and 4208 can include an aseptic quick connect fitting (e.g., Equashield® fitting). The valve assembly 4284 includes a valve (not shown) disposed within a valve housing 4294. The valve can be constructed the same as the valve 4107 and valve housing 4194 and is not described in detail here. For example, the valve includes a valve rotor (not shown) with a coupler (not shown), a master port and multiple selectable ports. The mechanical coupler of the valve assembly 4284 is configured to mechanically couple to a second valve actuator of the instrument 4300 (described below), which can have a cavity shaped to accept the mechanical coupler in the same manner as described above for valve 4107. The second valve actuator can transfer rotational mechanical energy to the valve of the valve assembly 4284. The valve housing 4294 can be constructed similar to or the same as the valve housing 4194 and includes two holder portions 4229 that can each hold a tube (e.g., Falcon™ tubes 4277 and 4274 described below) and includes openings 4223 (only one is visible in FIG. 91) that are used later to receive locator protrusions of the instrument 4300 described below. The valve assembly 4284 can also hold two quick connect valve couplers 4236 and 4237 (see, e.g., FIG. 100) that can be coupled to the valve couplers 4136 and 4137 of valve assembly 4184 during set-up off the system 4000 in preparation for a cell culturing procedure, as discussed in more detail below. As described above, the coupler 4236 is a plug type connector that can be coupled to the socket connector 4136 of the valve assembly 4184, and the coupler 4237 is a socket type connector that can be coupled to the plug connector 4136 of valve assembly 4184.

The container 4205 can be used, for example, to contain a media or reagent container, the container 4203 can, for example, be used to contain a cell buffer (e.g., PBS), and the container 4206 can be used for example to container waste material and fluids. The containers 4205, 4203 and 4206 can have a lid 4209 couple thereto to aseptically and fluidically couple to the valve of the valve assembly 4284. The tube 4277 can be used, for example, to contain an enzyme (e.g., Trypsin), and the tube 4274 can be used, for example, as a cell seeding or cell collection tube.

As shown in FIG. 92, the holder 4202 includes a top tray portion 4212 and a bottom tray portion 4215. The top portion 4212 defines openings 4204 sized and shaped to receive the containers 4205, 4206, and 4203. The top portion 4212 also defines opening 4228 sized and shaped to receive the tubes 4277 and 4274 when the valve assembly 4284 is coupled to the holder 4202. The bottom portion 4215 supports the containers and tubes when disposed on the holder 4202, as shown in FIG. 91. The top portion 4212 also defines an opening 4296 configured to receive the mechanical coupler of the valve in the same manner as described for tray 4102.

As described above for previous embodiments, the pre-assembled tray assembly 4101 can be removably coupled to the instrument 4300. FIGS. 93-101 illustrate the instrument 4300. The instrument 4300 includes a base unit 4320 and an upper unit 4325 movably coupled to the base unit 4320 with attachments 4315 such that the upper unit 4325 is movable between a closed or partially position and an open position, and the instrument 4300 is movable between an open configuration (see FIGS. 93, 98 and 100) and a closed or partially closed configuration (see FIG. 101). The attachments 4315 can be, for example, a telescoping assembly with an air cylinder that provide shock-absorbing mounting. For example, the shock-absorbing capability can limit the likelihood of components within the upper unit 4325 from being damaged or misaligned through repeated openings and closings. In some embodiments, the attachments 4315 allows the top to be retained in an opened position such that a user can access the interior of the instrument 4300 to prepare the instrument 4300 for a cell culturing procedure. For example, in some embodiments, the attachments 4315 can include a locking feature to lock the upper unit 4325 in the open position. In some embodiments, the instrument 4300 includes one or more lid sensor (not shown) that can detect and provide an indication when the lid is opened or closed.

The base unit 4320 includes a housing 4323 that supports and/or houses various components of the base unit 4320. Similarly, the upper unit 4325 includes a housing 4338 that can support and/or house various components of the upper unit 4325. The base unit 4320 includes a first valve connector portion 4321, a second valve connector portion 4322, a first pump connector 4326, and a second pump connector 4327. The base unit 4320 also includes a holder 4346 on a front surface that can be used to hold valve couplers as described in more detail below. The first valve connector portion 4321 is operatively coupled to a valve actuator (not shown, but which can be similar to the valve actuator 2021 described above) disposed within the housing 4323, and configured to matingly couple to the first valve assembly 4184. The second valve connector 4322 is operatively coupled to a second valve actuator (not shown, but which can be similar to the valve actuator 2021 described above) disposed within the housing 4323 and matingly couple to the second valve assembly 4284. Similarly, the first pump connector 4326 is operatively coupled to a first pump actuator (not shown) and the second pump connector 4327 is operatively coupled to a second pump actuator (not shown) each disposed within the housing 4323. The first pump connector 4326 is configured to be coupled to the pump 4113 described above. The second pump connector 4327 is available for an optional second pump if desired to be added to a particular system. The valve actuators and the pump actuators are collectively configured to be actuated to move fluid into and out of the various components of the system 4000.

Figure 96:
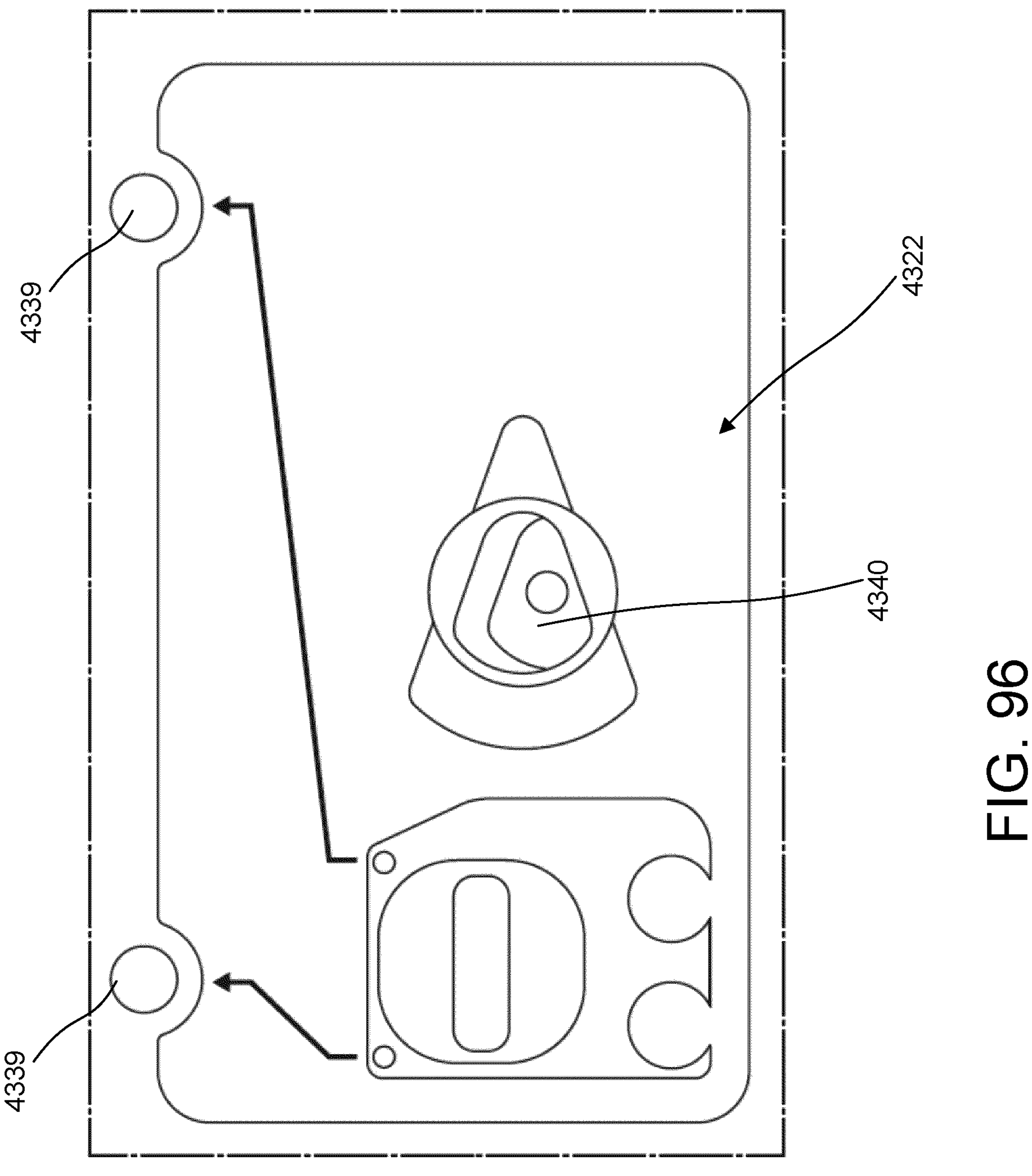
FIG. 96 is an enlarged view of a valve connector and actuator of the instrument of FIG. 93.

The first valve connector portion 4321 and the second valve connector 4322 are configured the same as each other and can each accommodate coupling either the first valve assembly 4184 or the second valve assembly 4322 thereto. As best shown in FIG. 96, which illustrates the second valve connector portion 4322, the valve connector portion 4322 includes locator protrusions 4339 that can be received within the openings 4223 of the valve assembly 4284. The valve connector portion 4322 also includes a mating cavity 4340 that receives the mechanical coupler of the valve of valve assembly 4184 when the valve assembly 4184 is coupled to the base unit 4320. Similarly, the valve connector portion 4321 includes locator protrusions 4339 (see, e.g., FIG. 94B) that can be received within the openings 4123 of the valve assembly 4184. The valve connector portion 4321 also includes a mating cavity 4340 that receives the mechanical coupler 4193 of the valve 4107 of the valve assembly 4184 when the valve assembly 4184 is coupled to base unit 4320.

Figure 99:
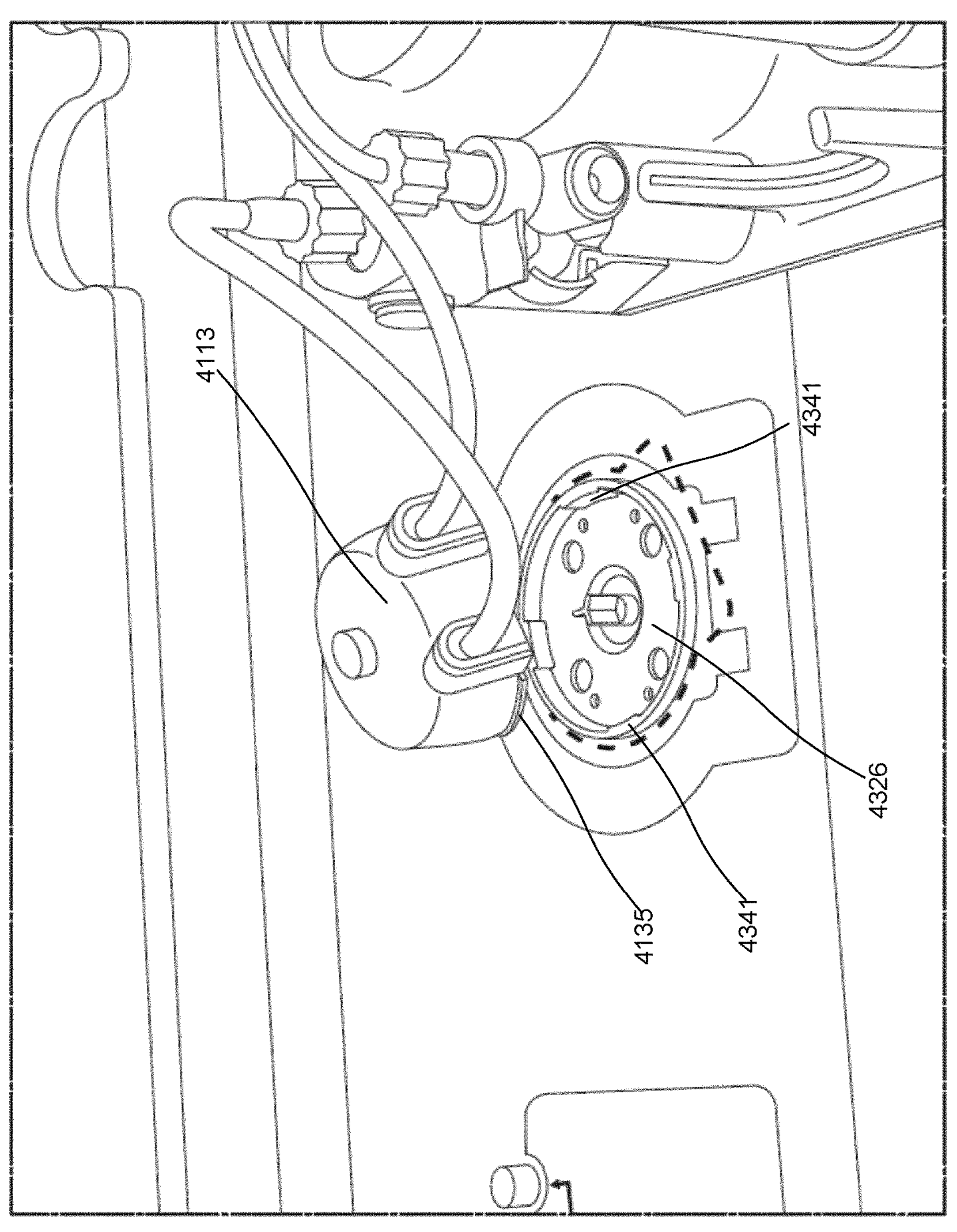
FIG. 99 is an illustration of the assembly of a fluid pump of the tray assembly of FIG. 84 being coupled to a pump actuator of the instrument of FIG. 93.

The first and second pump connectors 4326 and 4327 are configured to be coupled to a peristaltic pump such as the pump 4113. As best shown in FIG. 99, which illustrates an enlarged view of the first pump connector 4326, the first pump connector 4326 includes keyway features 4341 (four in this embodiment) disposed along an inside perimeter edge that matingly receives corresponding locking features 4135 on the pump 4113. For example, the pump 4113 is rotated into locking engagement with the first pump connector 4326 via the keyway features 4341 and locking features 4135. The second pump connector 4327 is similarly configured to matingly couple a pump, such as pump 4113 thereto.

The instrument 4300 also includes an agitator assembly 4328 disposed within the housing 4323 of the base unit 4320. The agitator assembly 4328 can include an agitator actuator (not shown) or be coupled to an agitator actuator. The agitator assembly 4328 (also referred to herein as "agitator") can be, for example, the same as or similar to the agitators 1628, 2038 or 2628 shown and described above and can be configured to agitate or move the removable tray assembly 4101 in relation to the housing 4323 as described above for previous embodiments. For example, the agitator 4328 can include an orbital shaker that moves the tray assembly 4101 when coupled to the instrument 4300 in a circular or half-circular motion. The agitator 4328 may agitate the tray assembly 4101 in an orbital pattern, in a rocking motion, vibrating motion, circular swirling motion, or other motions useful in cell culturing. In some embodiments, the agitator 4328 can be user-programmed to agitate in different patterns such as, for example, a FIG. 8 pattern. Sometimes some agitation patterns may be preferential for some applications. For example, a FIG. 8 pattern may be desirable for providing even distribution of cells (for example when seeding a new cell culture vessel) or mixing of fluids within a container. In some embodiments, the agitator 4328 can be user-programmed to agitate in a windshield wiper (or reciprocating) motion. Such an embodiment may be better for detachment of cells from within the container, e.g., during passaging or harvesting of adherent cells. In some embodiments, individual cell culture vessels/containers may be independently agitated by independent agitators displaced between the cell culture vessel and the removable tray assembly 4101 as previously described. In some embodiments, an agitator may not be included.

Figure 97:
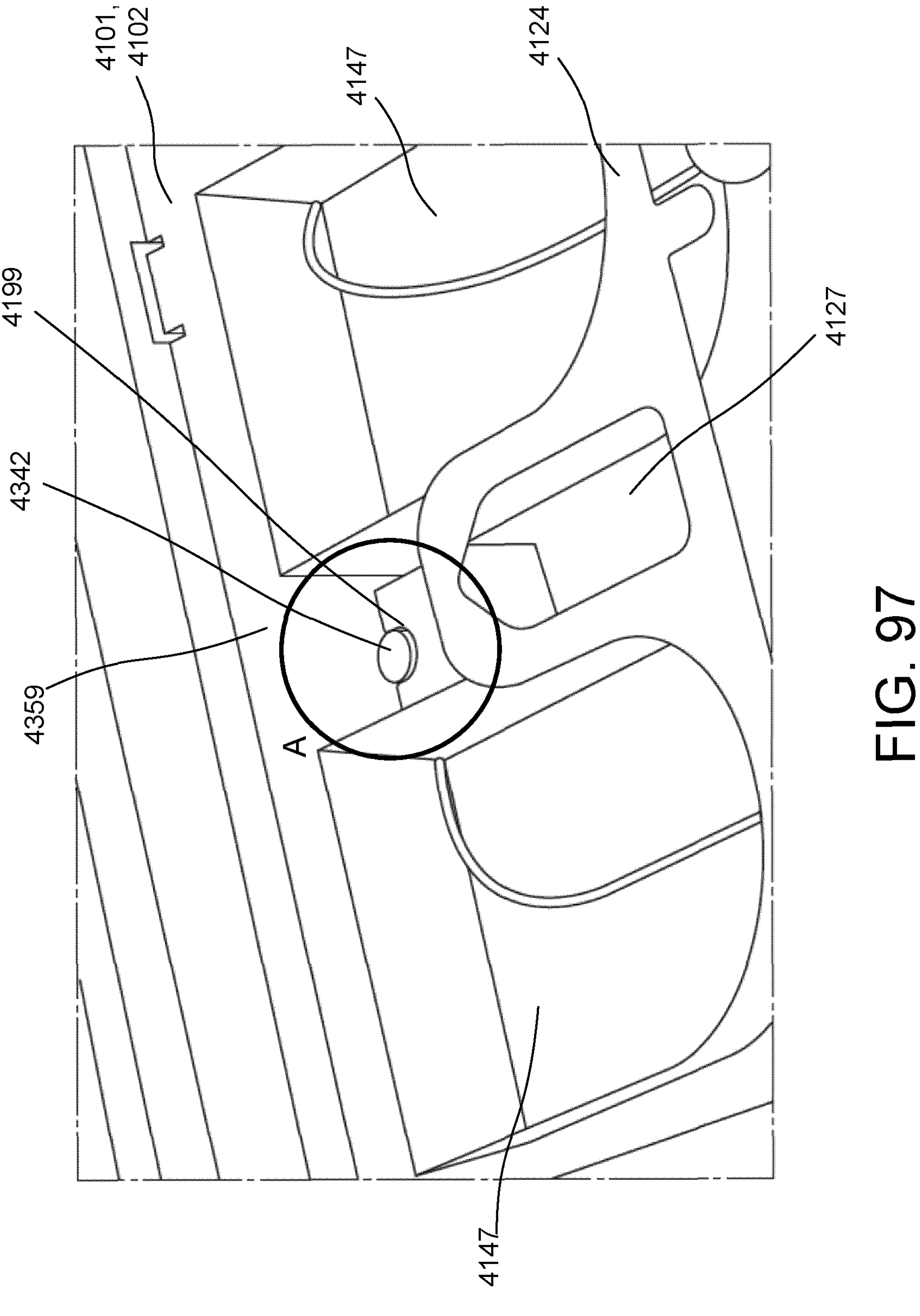
FIG. 97 is an enlarged view of an alignment portion of the tray assembly of FIG. 84 shown aligned with a protrusion on the instrument of FIG. 93.

The base unit 4320 includes a support plate 4359 coupled to the housing 4323 and that provides a receiving portion 4324 on which the tray assembly 4101 can be placed. As shown, for example, in FIG. 93, the receiving portion 4324 includes a transparent portion 4357 that enables viewing through the support plate 4359 such that when the tray assembly 4101 is disposed on the support plate 4359, a sensor, such as a microscope imaging device (described below) can be used to obtain information about the contents of the cell container and/or cell counting chip 4117 through the transparent portion 4357. For example, images and/or other sensor data associated with the contents of the cell culture containers and/or cell counting chip 4117 can be obtained. The support plate 4359 also includes multiple alignment protrusions 4342 (see, e.g., FIGS. 93 and 97) that are received within the alignment portions 4199 of the tray 4102 to assist in positioning the tray assembly 4101 on the support plate 4359 and to help maintain the position of the tray assembly 4101 relative to the support plate 4359 during operation of the system 4000. FIG. 97 illustrates an enlarged portion of the system 4000 illustrating an alignment portion 4199 of the tray 4102 engaged with an alignment protrusion 4323 (in encircled area A).

Figure 95B:
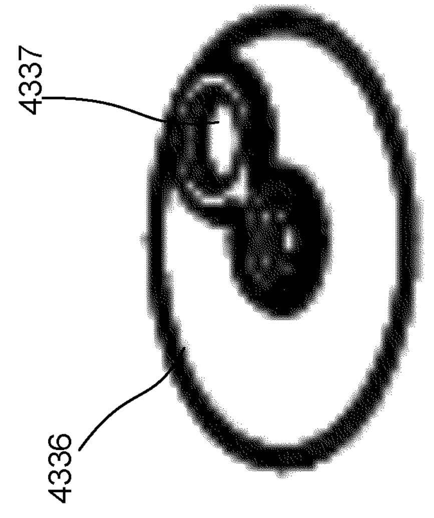
FIGS. 95A and 95B are each a perspective view of a different agitator coupling element of the instrument of FIG. 93.
Figure 95A:
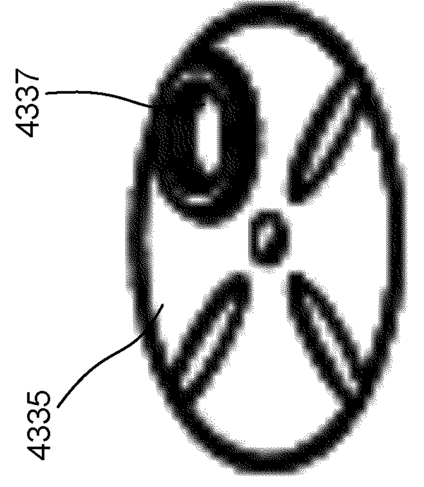

The agitator 4328 is operatively coupled to the support plate 4359 via multiple rotatable coupling elements 4335 and 4336 located about a perimeter of the support plate 4359. Specifically, each of coupling elements 4335, 4336 is coupled to a corresponding attachment location from a set of attachment locations of the support plate 4359 to maintain a position of the support plate 4359 relative to the instrument 4300 in at least two directions. In some embodiments, the rotatable coupling elements 4335 and 4336 include at least one drive element and at least one idler element. In this embodiment, the coupling element 4335 include a drive motor for the agitator 4328 and five of the coupling elements 4336 function as idlers for the agitator 4328. In this embodiment, the coupling element 4335 is disposed at a center location of the housing 4323, but in other embodiments, the coupling element 4335 can be disposed at a different location. Enlarged views of the coupling element 4335 and a coupling element 4336 are shown in FIGS. 95A and 95B, respectively. More specifically, the bottom surface of the support plate 4359 can include magnets that can be magnetically coupled to a ferromagnetic portion of the coupling elements 4335. The magnetic coupling maintains the position of the support plate 4359 relative to the housing 4323 in at least a vertical direction during operation of the cell culturing system 4000. The bottom side of the support plate 4359 also includes protrusions (not shown) that can be received in openings 4337 of the coupling elements 4335 and 4336 as shown in FIGS. 95A and 95B. The protrusion/opening attachment can maintain the position of the support plate 4359 relative to the housing 4323 in at least a front-to-rear direction and side-to-side direction. As described above, the agitator is configured to move the support plate 4359 when actuated to agitate the cell culture tray assembly 4101 when coupled to the support plate 4359.

The instrument also includes a cell sensor assembly that includes a first portion disposed with the housing 4323 of the base unit 4320 and a second portion disposed within the housing 4338 of the upper unit 4325. The cell sensor assembly can be mounted to the instrument 4300 to allow for sensor(s) (e.g., an imaging device, a lighting device) to be movable relative to the housing 4323 of the base unit 4320 as described herein. As shown, for example, in FIG. 93. The housing 4338 includes a transparent portion 4343 (e.g., window) through which the light can pass through during operation of the system 4000.

More specifically, in this embodiment, the first portion of the cell sensor assembly disposed within the housing 4323 of the base unit 4320 includes an imaging device 4360 that includes a microscope 4362 that may be moved relative to the housing 4323 of the base unit 4320 to image the contents of any cell culture container 4147 and/or cell counting chip 4117 disposed on the tray 4101 of the automated cell culture system when coupled to the base unit 4320. The microscope 4362 is mounted on a mechanical system 4361 that is capable of moving the microscope 4362 into alignment with the cell culture containers 4147 and the cell counting chip 4117. The mechanical system 4361 can be any suitable assembly for moving the imaging device 4360, such as a 2-dimensional or 3-dimensional gantry mechanism or a hinged robotic arm mechanism as described above with reference to FIGS. 32-34. In this embodiment, the mechanical system 4361 for moving the microscope 4362 of the imaging device 4360 includes a linkage drive system with a flexible drive chain. The mechanical system includes at least one motor (e.g., belt drive) to move the microscope 4362 in the for-aft direction as shown by arrows A, the left-to-right direction as shown by arrows B, and in a vertical direction (e.g., for focusing) as shown by arrows C relative to the housing 4323 and the support plate 4359. The microscope 4362 can view through the transparent portion 4357 of the support plate 4359 in the top of the base unit 4320 and through the cut outs (or transparent portions) in both the tray 4102 for the cell containers 4347 and the cut-out (or transparent portion) for the cell counting chip 4117 and through the containers 4347 and cell counting chip 4117. As described above, alignment markers 4122 defined by the tray 4102 can be used to align the tray 4102 with the microscope 4360. The microscope 4362 can use the alignment markers 4122 to assist in correctly aligning the microscope 4360 with the location of the cell counting chip 4117 or a container 4147.

As described herein, the imaging device 4360 (i.e., microscope 4362) can be used to collect information related to the contents of a cell culture container 4147 and/or within the cell counting chip 4117 as described herein. For example, in some embodiments, the imaging device 4360 can obtain images of the contents of a cell culture container 4147 and/or the cell counting chip 4117 during a cell culturing procedure, and the images can be used to determine, for example, the density of the contents to determine a quantity of cells within the container (for example, for suspension cells), or a percentage confluence (i.e., percentage of coverage of the container area with cells) in the case of, for example, adherent cells. In some embodiments, the imaging device 4360 can be used to capture images and/or other types of output of a sample portion of the contents of a cell culture container 4147 via the cell counting chip 4117. For example, a sample of the fluid mixture within a cell culture container 4147 can be extracted into the cell counting chip 4117, and the microscope 4362 can be moved to a position in alignment with the cell counting chip 4117 and used to image or otherwise collect information associated with the sample fluid mixture on the cell counting chip 4117.

The second portion of the sensor assembly within the upper unit 4325 includes light system 4382 that can be used with the imaging device 4360. Thus, the light system 4382 is disposed above the support plate 4359 and the tray assembly 4101 when the tray assembly 4101 is coupled to the instrument 4300. As with the imaging device 4360, the light system 4382 is mounted to a mechanical system 4381 to enable the light system 4382 to move with respect to the housing 4338 of the upper unit 4325. For example, the light system 4382 and can move in the same directions as described for the imaging device 4360 (e.g., in the A, B and C directions in FIG. 93). The movement of the light source 4382 can be coordinated with the movement of the microscope 4362 such that light can be provided when the imaging the contents of a container 4147 or the cell counting chip 4117. For example, as described above, the containers 4147 and cell counting chip 4117 can include a transparent portion on a top portion such that light can pass through. In some embodiments, the system 4300 may include one or more cameras or LEDs and/or light sensors to image the contents of cell culture containers.

The imaging device 4360 can be controlled by any of the electronic control systems (e.g., 1630, 1730, 2030) and according to any of the methods described herein. For example, in some embodiments, the microscope imaging device 1960 (and any associated light source) can be controlled to automatically image a cell culture container (e.g., to produce a sensor output associated with the cells within the container). A cell sensor module of an electronic control system (e.g., the electronic control system 1730) or any other electronic control system described herein can receive the sensor output and produce a signal associated with a quantity of cells within the container (e.g., cell density or a percentage confluence). Based on this information the electronic control system can then produce one or more signals (e.g., valve control signals, pump control signals, agitator signals, or the like) to cause the transfer of the cells from within the cell culture container to another container within the system. Similarly stated, in some embodiments, the imaging device 4360 can provide input for automated cell passaging or cell harvesting operations.

In some embodiments, the instrument 4300 can include various sensors as described herein for other embodiments, such as a valve position sensor configured to produce a valve position signal associated with a rotation position of the valve actuator. In this manner the valve position sensor can detect which of the selectable ports is fluidically coupled to the master port. In some embodiments, the sensor(s) can include a pump position sensor configured to produce a pump position signal associated with the movement of the pump. In this manner, the pump position sensor can indicate the travel of the pump and/or the volume of the fluid moved by the pump. As described herein, the electronic control system of system 4300 can determine, based on the pump position signal, an estimated amount of fluid within (or being added to) one of the cell culture containers.

The base unit 4320 can include an electronic control system (not shown) to control the operation of any of the components of the cell culture system 4300 (e.g., the valve actuators (not shown), the pump actuators (not shown), the agitator 4328, the imaging system 4360 and the light system 4382. The electronic control system can be configured the same as or similar to and function the same as or similar to, the electronic control systems 1630 and 2030 described above. The electronic control system can optionally be capable of communicating with other computing devices and/or within a cloud computing environment and can include some or all of the components and features describe above with respect to FIG. 17. For example, as shown in FIG. 17 for electronic control system 1630, the electronic control system of system 4000 can include one or more processor, one or more memory component, a radio and various modules, such as an actuation module, an agitation module, a fluid flow module, a valve module, a pump module, a measurement module (also referred to as a cell sensor module) and/or a network module. The electronic control system of system 4000 can be disposed within the base unit 4320 or the electronic control system or portions thereof can be provided outside of the base unit 4320 (e.g., within a cloud computing environment). The electronic control system can automatically control the fluid flow into and out of the various containers through actuation of, for example, the pump actuator and the valve actuator. The electronic control system can also automatically control the actuation of the agitator 4328, the sensor(s) (e.g., light system 4382 and imaging device 4360), and the valve actuator. Operation and actuation of the fluid pump 4113, valves 4107 and 4207, selection of ports on the valves 4107 and 4207, etc. can be the same as or similar to operation of these components as described above for previous embodiments. As described above for previous embodiments, in operation, the combination of fluid pumps, valves of the multiport valve, containers, and cell culture vessels may be used to transfer liquids to and from the cell culture vessels and the containers.

During preparation for a cell culturing procedure, the instrument 4300 is placed in an incubator with the upper unit 4325 in the open position, and the tray assembly 4101 can be placed in an aseptic environment (e.g., a laminar flow hood) and the overwrap can be removed. While in the aseptic environment (e.g., the laminar flow hood), cell culture containers 4147 can be prepared (e.g., cells and reagent added to the containers). As described above, in this embodiment, the lids 4108 are aseptically coupled to the containers 4147 and tubes 4111, and to the valve 4107, within the overwrap of the tray assembly 4101 such that the cells and reagent can be introduced into the containers directly through the lid couplings without having to remove the lids 4108. The input tray assembly 4201 can also be placed in an aseptic environment (e.g., the laminar flow hood) and the overwrap removed.

Figure 98:
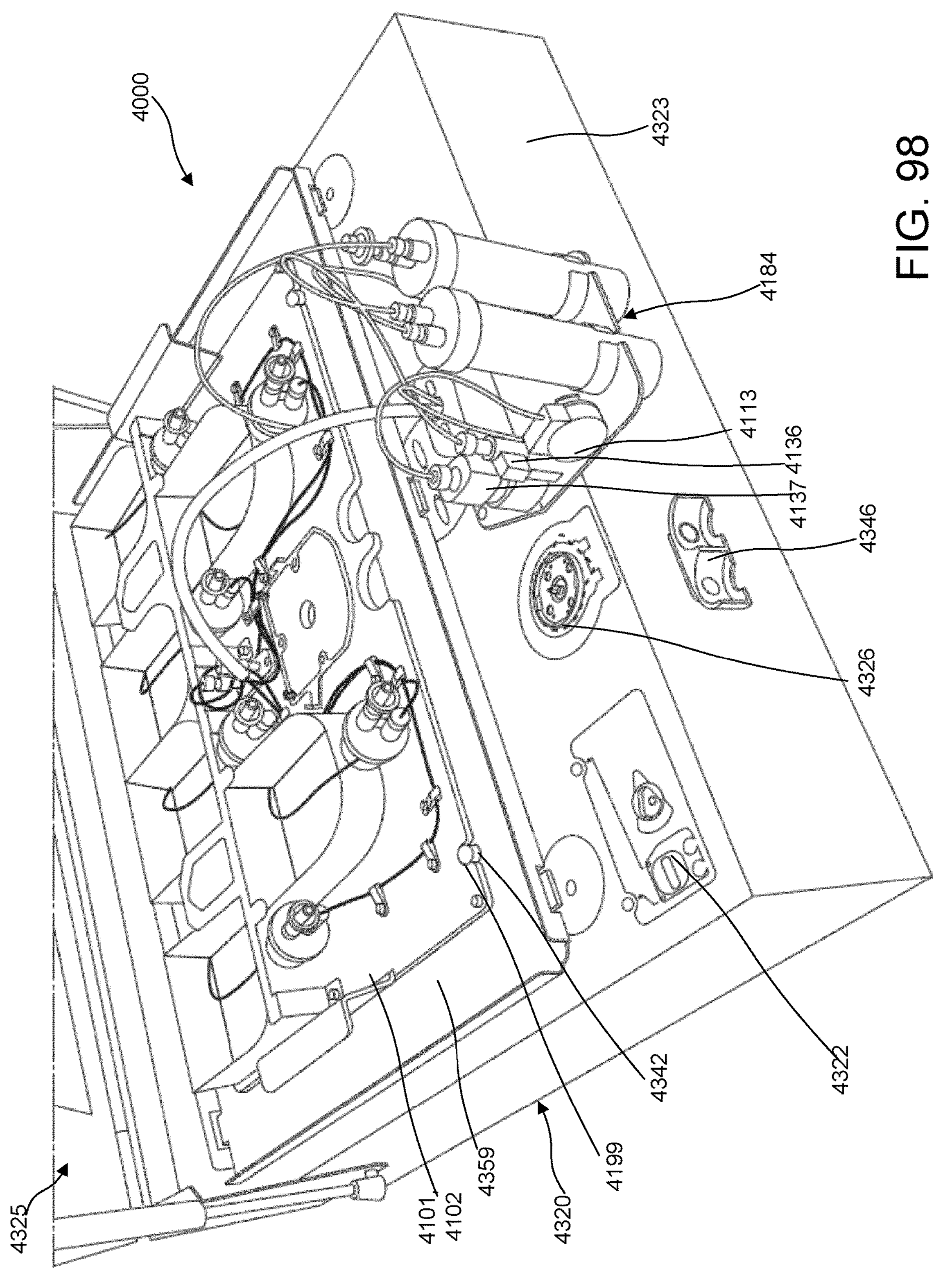
FIG. 98 is a perspective view of a portion of the instrument of FIG. 93 with the tray assembly of FIG. 84 coupled thereto.

The tray assembly 4101 can then be coupled to the base unit 4320 of the instrument 4300, as shown in FIG. 98. More specifically, as described above, the alignment portions 4199 of the tray 4102 are engaged with the protrusions 4342 of the support plate 4359 (see, e.g., FIGS. 97 and 98). The tubes 4111 are removed from the valve assembly 4184 and can be temporarily placed within the openings 4127 of the bracket 4124 in an angled orientation in the for-aft direction (e.g., direction of arrows B in FIG. 93). The tubes 4111 can be moved while remaining aseptically and fluidically coupled to the valve 4107 of the first valve assembly 4184.

Figure 100:
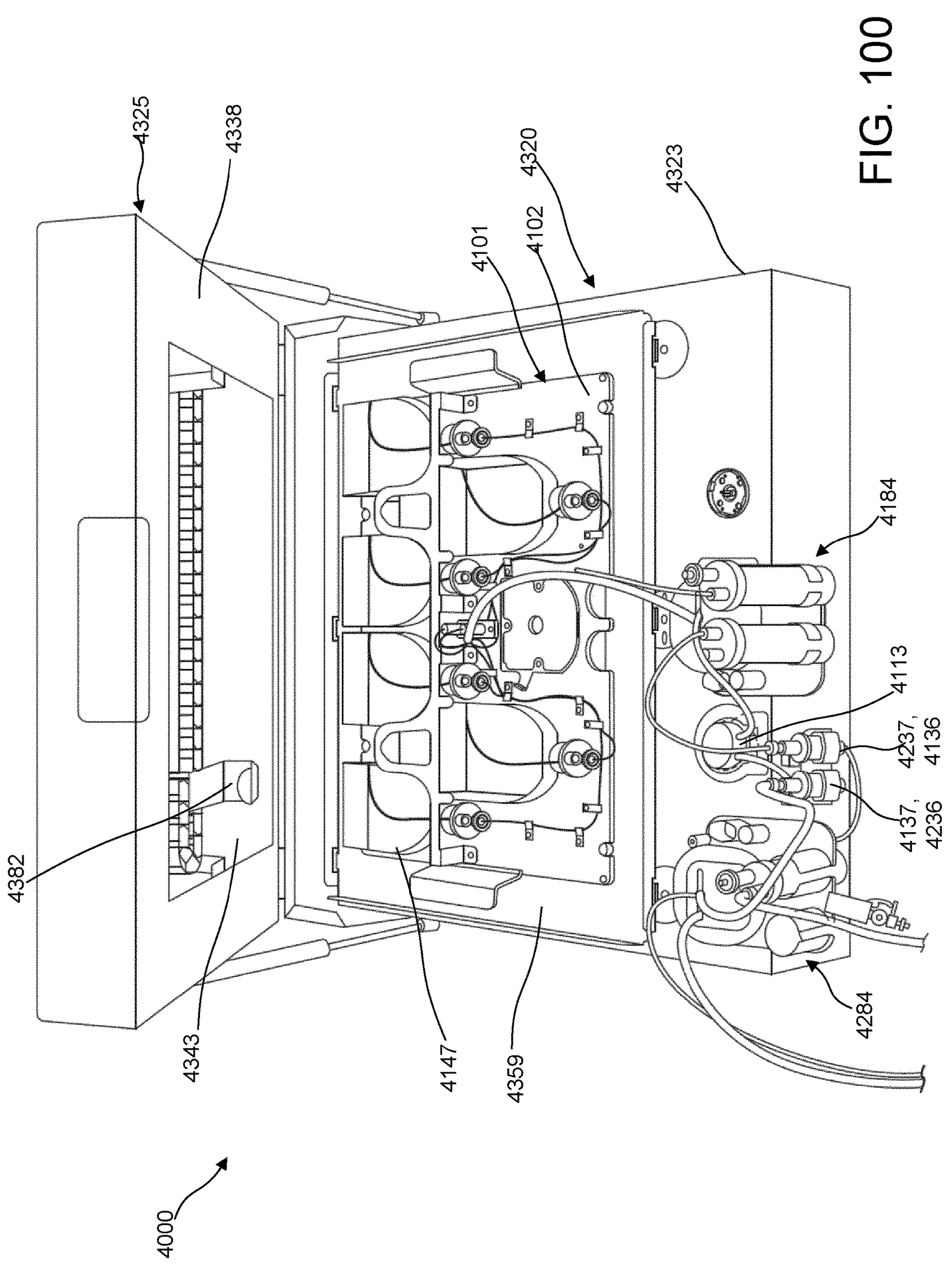
FIG. 100 is a front perspective view of the instrument in an open configuration with the tray assembly of FIG. 84 and the input tray assembly of FIG. 91 coupled thereto.
Figure 101:
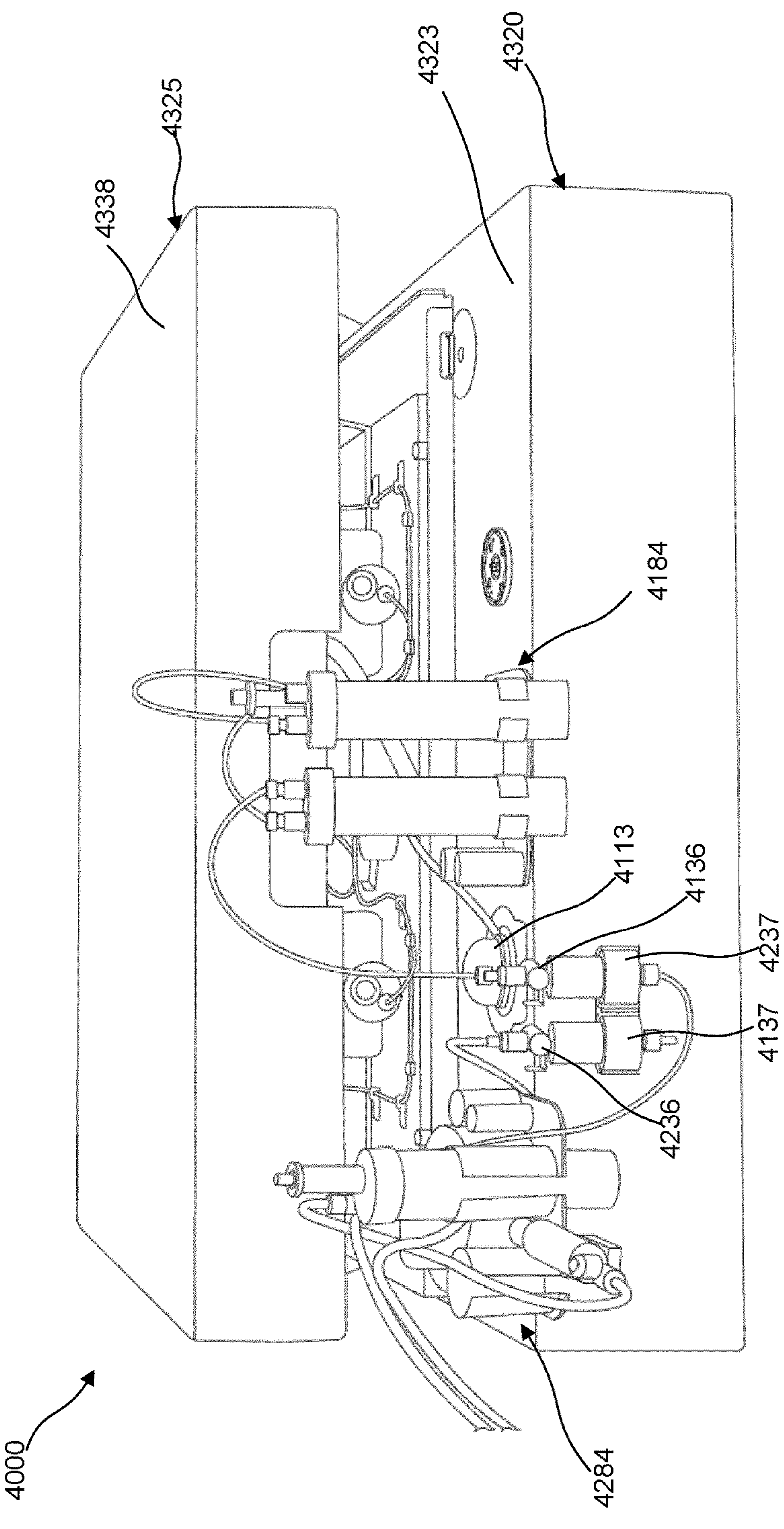
FIG. 101 is a front perspective view of the instrument in a closed configuration with the tray assembly of FIG. 84 and the input tray assembly of FIG. 91 coupled thereto.

The first valve assembly 4184 is then decoupled from the tray assembly 4101 and matingly coupled to the first valve actuator of the instrument 4300 via the first valve coupling portion 4321. As described above, the openings 4123 of the valve housing 4194 can be placed over the locator protrusions 4339 of the first valve coupling portion 4321 in the base unit 4320, and the cavity 4340 of the first valve coupling portion 4321 receives the mechanical coupler 4193 of the first valve 4107 of the first valve assembly 4184. The first valve assembly 4184 can be moved to the base unit 4320 while remaining aseptically and fluidically coupled to the various lids 4108 of the tray assembly 4101 via tubing as described herein. The fluid pump 4113 can then be moved from the valve assembly 4184 to the pump connector 4326 as shown, for example, in FIG. 99. As described above, the pump 4113 is rotated into locking engagement with the first pump connector 4326 via the keyway features 4341 of the pump connector 4326 and the locking features 4135 of the pump 4113. As with the valve assembly 4184, the pump 4113 can be moved while remaining aseptically coupled within the closed system. After the valve assembly 4184 has been coupled to the base unit 4320, the tubes 4111 can be placed back in the holders 4129 of the valve housing 4194, as shown in FIGS. 98, 100 and 101.

To prepare the input tray assembly 4281 for the cell culturing procedure, the media container 4205 can first be removed from the flow hood and placed in a refrigerator near the incubator. The containers 4203, 4206 and 4277 can be placed in holders (not shown) on the side of the incubator while remaining coupled to the valve of the second valve assembly 4284. The second valve assembly 4284 of the input tray assembly 4281 can be removed from the holder 4202 and matingly coupled to the second valve actuator of the instrument 4300 via the second valve coupling portion 4322 as shown in FIG. 100. As described above for first valve assembly 4184, the openings 4223 of the valve housing 4294 can be placed over the locator protrusions 4339 of the second valve coupling portion 4322 in the base unit 4320, and the cavity 4340 of the second valve coupling portion 4322 receives the mechanical coupler of the valve of the second valve assembly 4284. The second valve assembly 4284 can be moved to the base unit 4320 while remaining aseptically and fluidically coupled to the various lids 4208 of the input tray assembly 4281 via tubing as described herein. The holder 4202 can be stored for later use after the cell culture procedure is completed.

With the tray assembly 4101 and the input tray assembly 4281 coupled to the instrument 4300, the first valve 4107 of the first valve assembly 4184 can be coupled to the second valve of the second valve assembly 4284. More specifically, the coupler 4136 of the first valve assembly 4184 is coupled to the coupler 4237 of the second valve assembly 4284, and the coupler 4137 of the first valve assembly 4184 is coupled to the coupler 4236 of the second valve assembly 4284. The valve couplings 4136, 4237 and 4236, 4137 can be supported on the front of the instrument 4300 in the holder 4346 as shown in FIGS. 100 and 101. In some embodiments, the holder 4346 can include one or more magnets that can be used to hold the valve couplings. For example, the valve couplers can include a ferromagnetic portion that can be magnetically coupled to the holder 4346.

After the tray assembly 4101 and the input tray assembly 4281 have been coupled to the instrument 4300, and the seeding tube and other containers have been prepared with the appropriate fluids, medias, reagents, etc., the cell culturing procedure can be performed as described herein. Various methods of automated cell culturing using the system 4000 or any of the systems (110, 1600, 2000, 2100, 2200, 2600) described herein are described below.

The cell culture systems described herein enable many advantageous methods of cell culturing that improve the efficiency, cell viability, and/or minimize potential cell loss or contamination when culturing cells. Specifically, the cell culture systems described herein allow for a variety of cell culture operations (e.g., cell passaging, cell washing, or counting cells within the system) to be performed while maintaining the system as a closed system. Similarly stated, any of the cell culture systems described herein (e.g., the cell culture systems 110, 1600, 2000, 2100, 2200, 2600, and 4000) are systems in which the containers, components (e.g., valves) and fluid paths (e.g., tubing) therebetween are all substantially isolated from an external environment in a manner that limits the ingress of microbes into the system. Thus, as described herein, the containers within the systems can include lids that have a gas exchange port (see, e.g., the lids 803, 2408, and 4108 described herein) that allows gas exchange with the cell culture container in a manner that maintains the sterility of the cell culture environment. Thus, a closed system does not require that the containers, components, and fluid paths be hermetically isolated from the external environment, but rather the closed systems described herein limit the likelihood of contamination within the cell culture environment. Importantly, many of the methods described herein can be performed while maintaining the closed system. Similarly stated, many of the methods described herein include cell culture operations that are performed while the closed system is maintained, thereby limiting likelihood of contamination.

Figure 102:
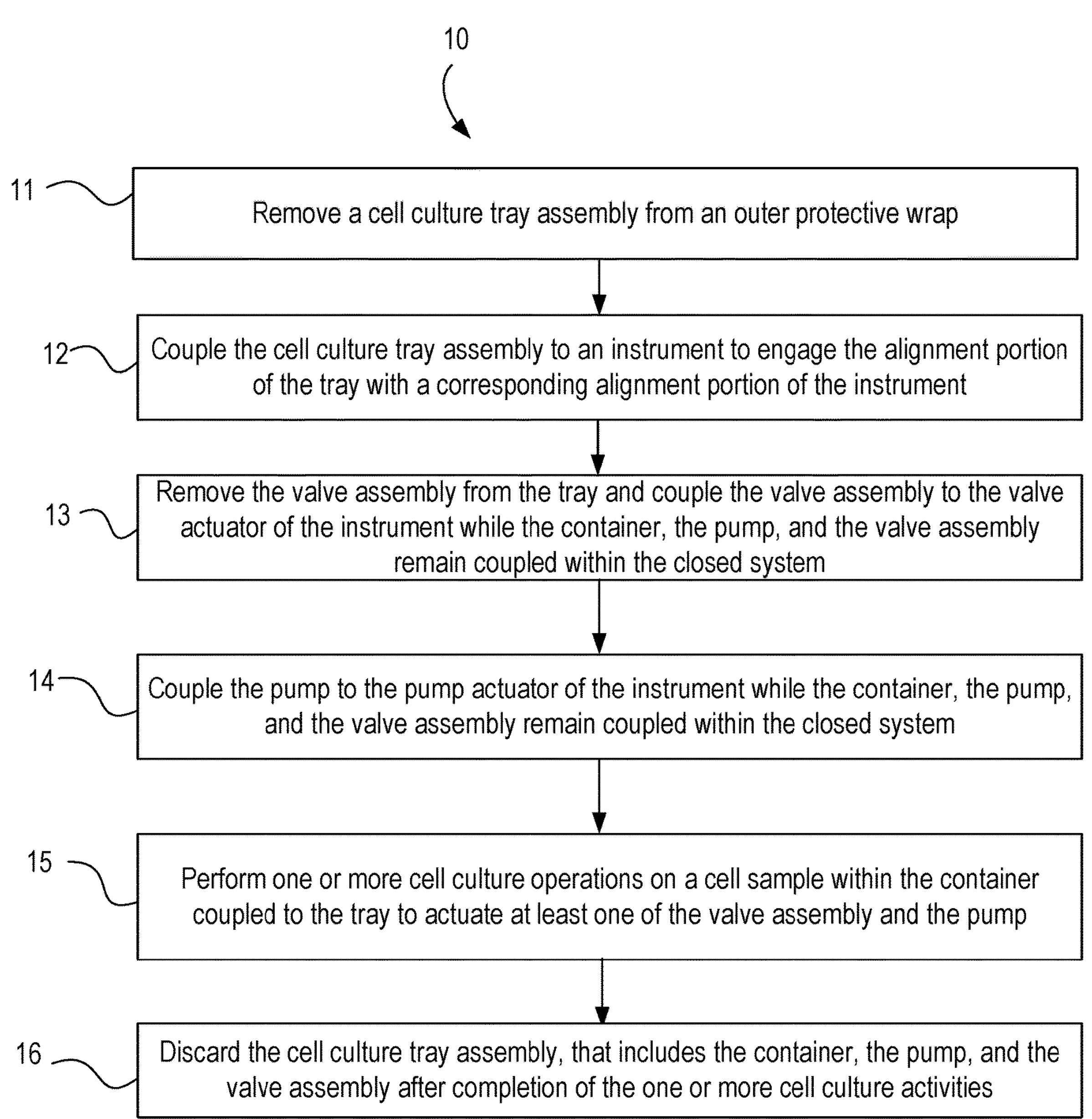
FIG. 102 is a flowchart of a method of cell culturing, according to an embodiment.

The cell culture systems described herein enable methods that are particularly advantageous for culturing cells for therapeutic purposes, where it is often desirable to have smaller quantities of different cell types being cultured at the same time. Specifically, the systems described herein allow for accurate and repeatable control of the cell culture environment. Moreover, the systems described herein limit the setup time for establishing a cell culture, and also reduce the post-culture tasks associated with cleaning and sterilizing equipment. Specifically, the cell culture systems described herein facilitate methods in which all of the components within the closed system environment (e.g., containers, valves, tubing, etc.) are discarded after use. For example, FIG. 102 is a flowchart of a method 10 of cell culturing, according to an embodiment. The method 10 can be performed with any of the cell culture systems described herein, such as, for example, the cell culture systems 110, 1600, 2000, 2100, 2200, 2600, and 4000 described herein. The method includes removing a cell culture tray assembly from an outer protective wrap, at 11. The cell culture tray assembly can be any of the cell culture tray assemblies described herein (e.g., the flask assembly 4101), and includes a tray, a container coupled to the tray, a pump, and a valve assembly removably coupled to the tray. The tray includes an alignment portion (e.g., cut-out portions 4199 described herein). The container is aseptically coupled to the pump and the valve assembly to form a closed system (i.e., a system that is substantially isolated from the external environment in a manner that limits the ingress of microbes into the system). As described herein, the valve assembly and the fluid pump are each configured to be actuated to cause transfer of a fluid into or out of the container.

The cell culture tray assembly is coupled to an instrument by engaging the alignment portion of the tray with a corresponding alignment portion of the instrument, at 12. In some embodiments, the instrument can be the instrument 4300 described herein, and the corresponding alignment portion of the instrument can include a set of protrusions that are matingly engaged with the cut-out portions (or openings) 4199 of the tray. In some embodiments, one of the instrument or the cell culture tray assembly can include a lock member that retains the tray assembly within (or coupled to) the instrument. Such lock members can include, for example, a movable lock arm that slides over a portion of the tray, a deformable member that secures a perimeter edge of the tray to the instrument.

The instrument includes a valve actuator and a pump actuator. The valve actuator and the pump actuator can be similar to those shown and described in connection with the instrument 4300. The valve assembly is removed from the tray and is coupled to the valve actuator of the instrument while the container, the pump, and the valve assembly remain coupled within the closed system, at 13. As described herein, the valve assembly can remain fluidically coupled with the container(s), the pump, and any other cell culturing components that may be present to preserve the closed system while the valve assembly is coupled to the valve actuator of the instrument. In this manner, the valve for controlling flow into and out of the components of the cell culture tray assembly can be quickly coupled to the instrument (i.e., the valve actuator) without opening the cell culture system (i.e., without exposing the cell sample to the external atmosphere). In some embodiments, the valve assembly is coupled to the valve actuator of the instrument in a single motion, thereby making the coupling quick and easy. In some embodiments, the valve assembly includes a valve body and a valve housing, and the valve housing defines a mounting opening. The tray includes a first mounting protrusion that is received within the mounting opening to removably secure the valve assembly to the tray. In such embodiments, the removing the valve assembly from the tray includes lifting the valve housing to remove the first mounting protrusion of the tray from within the mounting opening. In some embodiments, the coupling the valve assembly to the valve actuator includes placing the valve body within a valve actuator opening of the instrument and placing a second mounting protrusion (of the instrument) within the mounting opening.

The pump is coupled to the pump actuator of the instrument, at 14, while the container, the pump, and the valve assembly remain coupled within the closed system. For example, in some embodiments, the instrument (e.g., the instrument 4300) includes a base housing having a pump coupling slot. The coupling the pump to the pump actuator includes locking a portion of the pump within the pump coupling slot.

The method further includes performing one or more cell culture operations on a cell sample within the container coupled to the tray by actuating at least one of the valve assembly and the pump, at 15. Such cell culture operations can include, for example, conveying nutrients into the container to facilitate cell growth, passaging the cells from the container, conveying a dissociation reagent into the container (e.g., to separate adherent cells from the surface of the container), imaging the cells for evaluations, receiving signals associated with the cells (e.g., an image signal, a temperature, a pressure, or the like), counting the cells, actuating at least one of the pump or the valve assembly to convey a portion of the cell sample from the first container into a second container, agitating the cell container, or any of the operations described herein. For example, in some embodiments, the container is a first container and the cell culture tray assembly includes a second container coupled to the tray. The second container is coupled to the first container, the pump, and the valve assembly within the closed system. The cell culture operation can include actuating at least one of the pump or the valve assembly to convey a portion of the cell sample from the first container into the second container.

In some embodiments, the method 10 optionally includes coupling a seeding container within the closed system to the container, the pump, and the valve assembly. The seeding container contains a cell sample. The one or more cell culture operations includes actuating at least one of the pump or the valve assembly to convey a portion of the cell sample from the seeding container to the container to seed the container with the cell sample. In this manner, seeding of the cell sample can be performed without opening the lid of the cell culture container. Rather, the cell sample can be pumped into the container via a fluid path within the closed system, thereby limiting the likelihood of contamination (e.g., the ingress of microbes).

After completing the one or more cell culture activities, the cell culture tray assembly (including the container, the pump, and the valve assembly) is discarded, at 16. This can be performed by removing the pump from the pump actuator of the instrument and removing the valve assembly from the valve actuator of the instrument in a reverse manner as described herein. Because these components, the container(s) and the tubing interconnects therebetween remain in a closed system, the removal of these components does not expose the lab environment to the cell culture components that have been manipulated during the cell culture activities described herein. The tray assembly, along with all of the components of the closed system (e.g., including the valve and the pump) can be securely wrapped or packaged, and discarded in the appropriate waste streams. In some embodiments, the assembly can be returned to a central processing facility for sterilization and later reuse.

In some embodiments, the instrument includes a support plate and an agitator assembly coupled to the support plate. The agitator assembly is outside of the closed system formed by the container, the pump, and the valve assembly. The tray assembly is coupled to the support plate and the one or more cell culture operations includes actuating the agitator assembly to move the support plate and the cell culture tray assembly. In this manner, the container (and cell sample therein) can be agitated to facilitate dissociation from the surface (e.g., for cell passaging), to facilitate washing of the cells (e.g., with fresh reagents/media), and/or to facilitate uniform seeding of the cells within the container. In some embodiments, the agitator assembly can be similar to the agitator assembly 4328 described herein. Specifically, the agitator assembly includes a set of rotatable coupling elements, each of which is coupled to a corresponding attachment location from a set of attachment locations of the support plate to maintain a position of the support plate relative to the instrument in at least two directions. For example, the coupling elements and corresponding attachment location(s) can include mating protrusions and openings that are engaged to maintain the support plate coupled to the agitator assembly in the X-Y directions (i.e., the for-aft direction and the side-by-side direction). In some embodiments, the coupling elements and corresponding attachment location(s) can include magnetic couplings to keep the support plate coupled to the agitator assembly in the Z direction (i.e., the vertical direction). In some embodiments, the rotatable coupling elements include at least one drive element and at least one idler element.

In some embodiments, the instrument includes an electronic control system (similar to any of the electronic control systems described herein, such as the electronic control system 1630) including an actuator module implemented in at least one of a memory or a processing device. In such embodiments, the one or more cell culture operations includes producing, via the actuator module, an actuation signal to actuate at least one of the pump or the valve assembly. In some embodiments, the one or more cell culture operations includes producing, via an actuator module of the electronic control system, an agitator signal to cause a motor to rotate a rotatable coupling element to agitate the support plate and the cell culture tray assembly.

In some embodiments, the electronic control system includes a cell sensor module implemented in at least one of a memory or a processing device. In such embodiments, the one or more cell culture operations includes analyzing the cell sample within the closed system (e.g., within the container). The analyzing can be performed by producing an image of the cell sample and analyzing, via the cell sensor module, the image to produce a cell signal.

Figure 103:
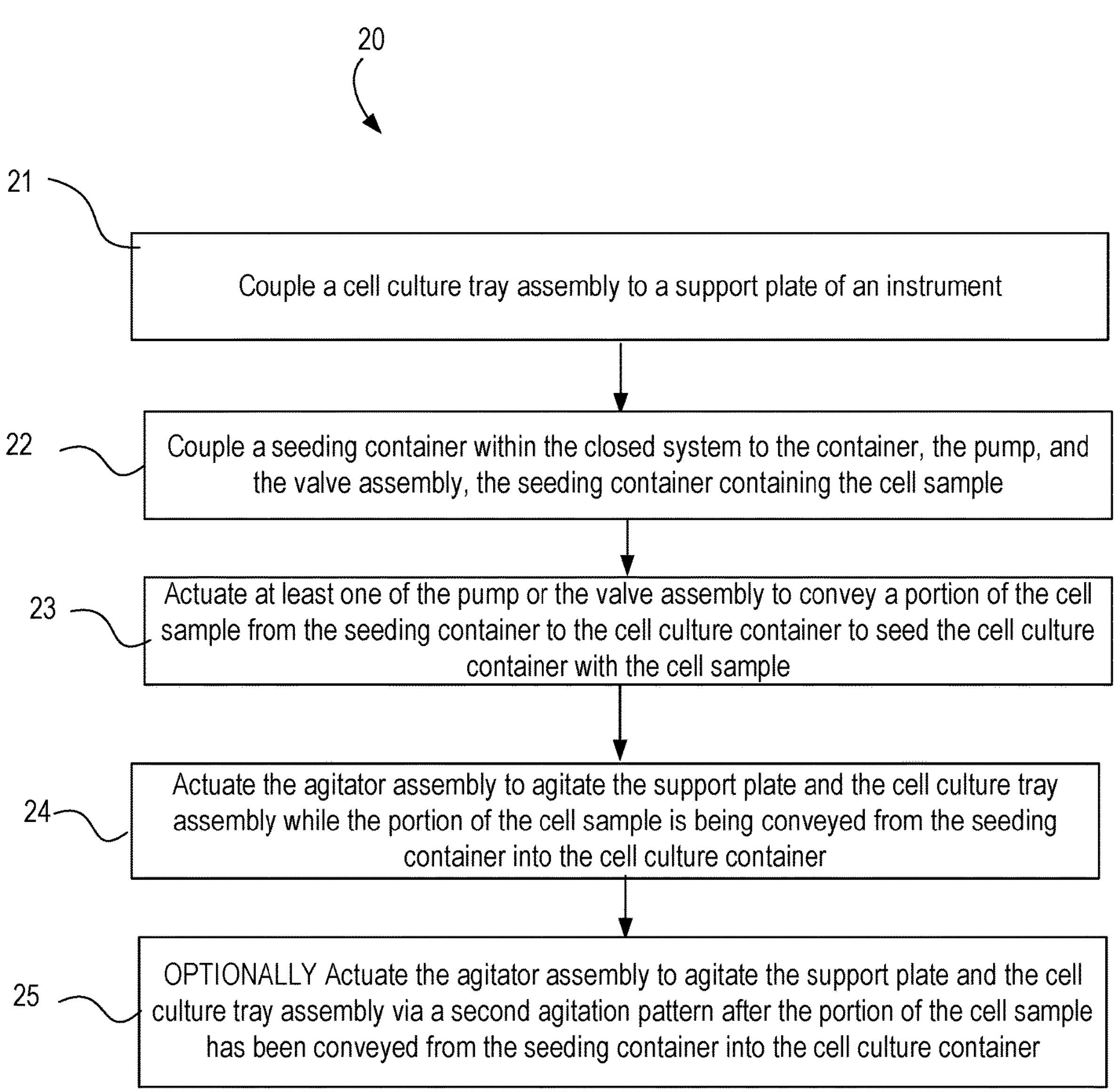
FIG. 103 is a flowchart of a method of seeding a cell sample into a cell culture container, according to an embodiment.

The cell culture systems described herein enable methods of seeding cell culture containers while maintaining a closed system. Additionally, the cell culture systems described herein enable methods of seeding cell culture containers to produce a uniform distribution of cells within the cell culture container. In this manner, the performance and growth of the cells can be enhanced. In particular, the methods of seeding described herein can limit undesired cell differentiation, which can result when cells are seeded in a non-uniform manner (i.e., in a manner that is not substantially spatially homogenous). For example, FIG. 103 is a flowchart of a method 20 of seeding a cell sample into a cell culture container, according to an embodiment. The method 20 can be performed with any of the cell culture systems described herein, such as, for example, the cell culture systems 110, 1600, 2000, 2100, 2200, 2600, and 4000 described herein. The method includes coupling a cell culture tray assembly to a support plate of an instrument, at 21. The cell culture tray assembly can be any of the cell culture tray assemblies described herein (e.g., the flask assembly 4101), and includes a tray (to which the cell culture container is coupled), a pump, and a valve assembly removably coupled to the tray. The cell culture container is aseptically coupled to the pump and the valve assembly to form a closed system (i.e., a system that is substantially isolated from the external environment in a manner that limits the ingress of microbes into the system). As described herein, the valve assembly and the fluid pump are each configured to be actuated to cause transfer of a fluid into or out of the cell culture container. The instrument can be any of the instruments described herein (e.g., the instrument 4300) and includes the support plate, a valve actuator, a pump actuator, and an agitator assembly. The agitator assembly configured to agitate the support plate.

A seeding container is coupled within the closed system, thus being placed in the system in connection to the container, the pump, and the valve assembly, at 22. The seeding container can be in any suitable location and can be coupled within the closed system by any suitable manner. For example, in some embodiments, the seeding container can be a Falcon™ tube that is coupled within the closed system by coupling one or more aseptic quick connect fittings (e.g., Equashield® fittings). In some embodiments, the seeding container can have a cap with a tube, the tube being coupled to a second tube feeding into the valve assembly via an aseptic quick connect fitting.

At least one of the pump or the valve assembly is actuated to convey a portion of the cell sample from the seeding container to the cell culture container to seed the cell culture container with the cell sample, at 23. In this manner, the cell sample can be conveyed into the cell culture chamber while remaining within the closed system. Said another way, the cell sample can be conveyed into the cell culture container without opening the lid of the cell culture container and/or without the need for manually pipetting or transferring the sample into the cell culture container.

The agitator assembly is actuated to agitate the support plate and the cell culture tray assembly while the portion of the cell sample is being conveyed from the seeding container into the cell culture container, at 24. This allows the cells to be distributed within the cell culture container during the process of being loaded into the container, which can produce a more spatially uniform distribution of the cells within the container. By agitating the container at the same time as the cell sample is being conveyed into the container, the likelihood of the cells adhering to the surface of the container (and/or to any nutrient layers or coatings therein) before being distributed within the container.

Figure 104A:
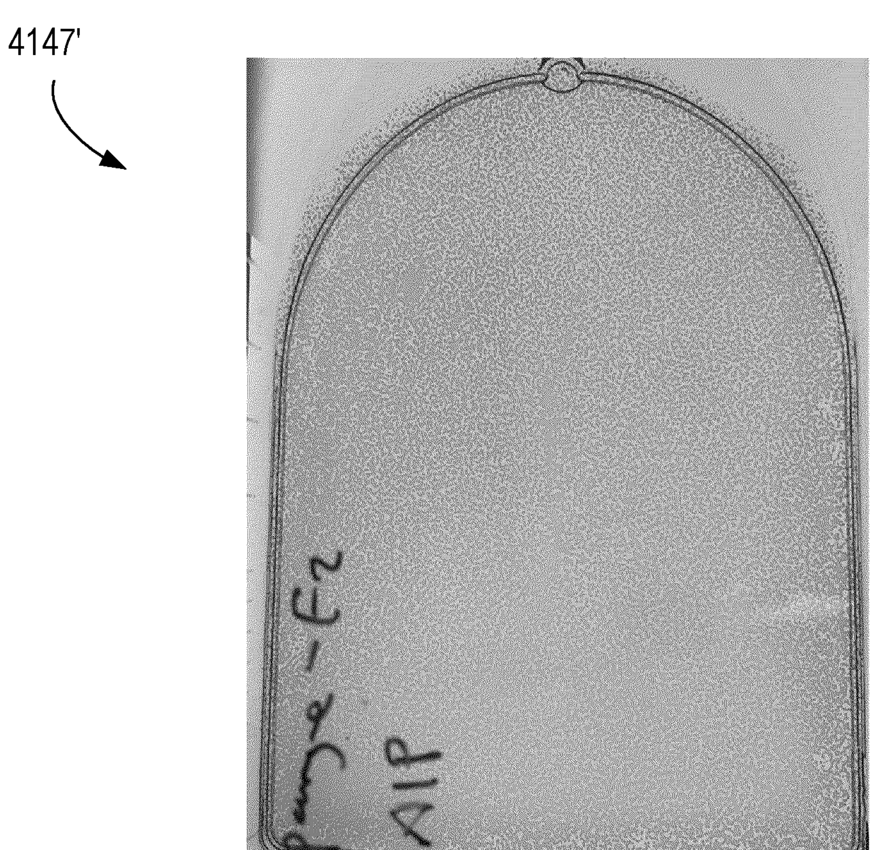
FIG. 104A is an image of a cell culture container containing a cell sample that was seeded according to the method FIG. 103.
Figure 104B:
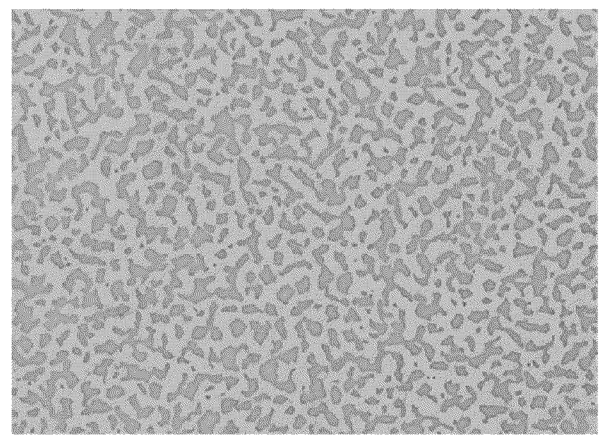
FIG. 104B is an enlarged view of a portion of the image of FIG. 104A.

In some embodiments, the agitator assembly agitates the support plate and the cell culture tray via a first agitation pattern. In such embodiments, the method optionally include actuating the agitator assembly to agitate the support plate and the cell culture tray assembly via a second agitation pattern after the portion of the cell sample has been conveyed from the seeding container into the cell culture container, at 25. By using a "two-stage" agitation, the spatial uniformity of the cells within the cell culture container can be improved. For example, in some embodiments, the first agitation pattern can be an orbital pattern. This rotational pattern will cause the cell sample to be conveyed around the perimeter of the cell culture container, and will limit the likelihood of the cells becoming concentrated in the region where the cell sample enters the container. The second agitation pattern can be a reciprocal (or oscillating) pattern. This reciprocating pattern will cause the cell sample to be conveyed from the perimeter of the cell culture container and throughout the central region of the container, thereby producing a uniform distribution of cells within the cell culture container. FIGS. 104A and 104B show an image of a cell culture container 4147' containing a cell sample that was seeded according to the method 20. As shown, the cell sample is uniformly distributed within the container 4147'.

In some embodiments, the agitator assembly can be similar to the agitator assembly 4328 described herein. Specifically, the agitator assembly includes a set of rotatable coupling elements, each of which is coupled to a corresponding attachment location from a set of attachment locations of the support plate to maintain a position of the support plate relative to the instrument in at least two directions. For example, the coupling elements and corresponding attachment location(s) can include mating protrusions and openings that are engaged to maintain the support plate coupled to the agitator assembly in the X-Y directions (i.e., the for-aft and side-to-side directions). In some embodiments, the coupling elements and corresponding attachment location(s) can include magnetic couplings to keep the support plate coupled to the agitator assembly in the Z direction (i.e., vertical direction). In some embodiments, the rotatable coupling elements include at least one drive element and at least one idler element.

In some embodiments, the instrument includes an electronic control system (similar to any of the electronic control systems described herein, such as the electronic control system 1630) including an actuator module implemented in at least one of a memory or a processing device. In some embodiments, the actuating the agitator assembly includes producing, via an actuator module of the electronic control system, an agitator signal to cause a motor to rotate a rotatable coupling element to agitate the support plate and the cell culture tray assembly.

Figure 105:
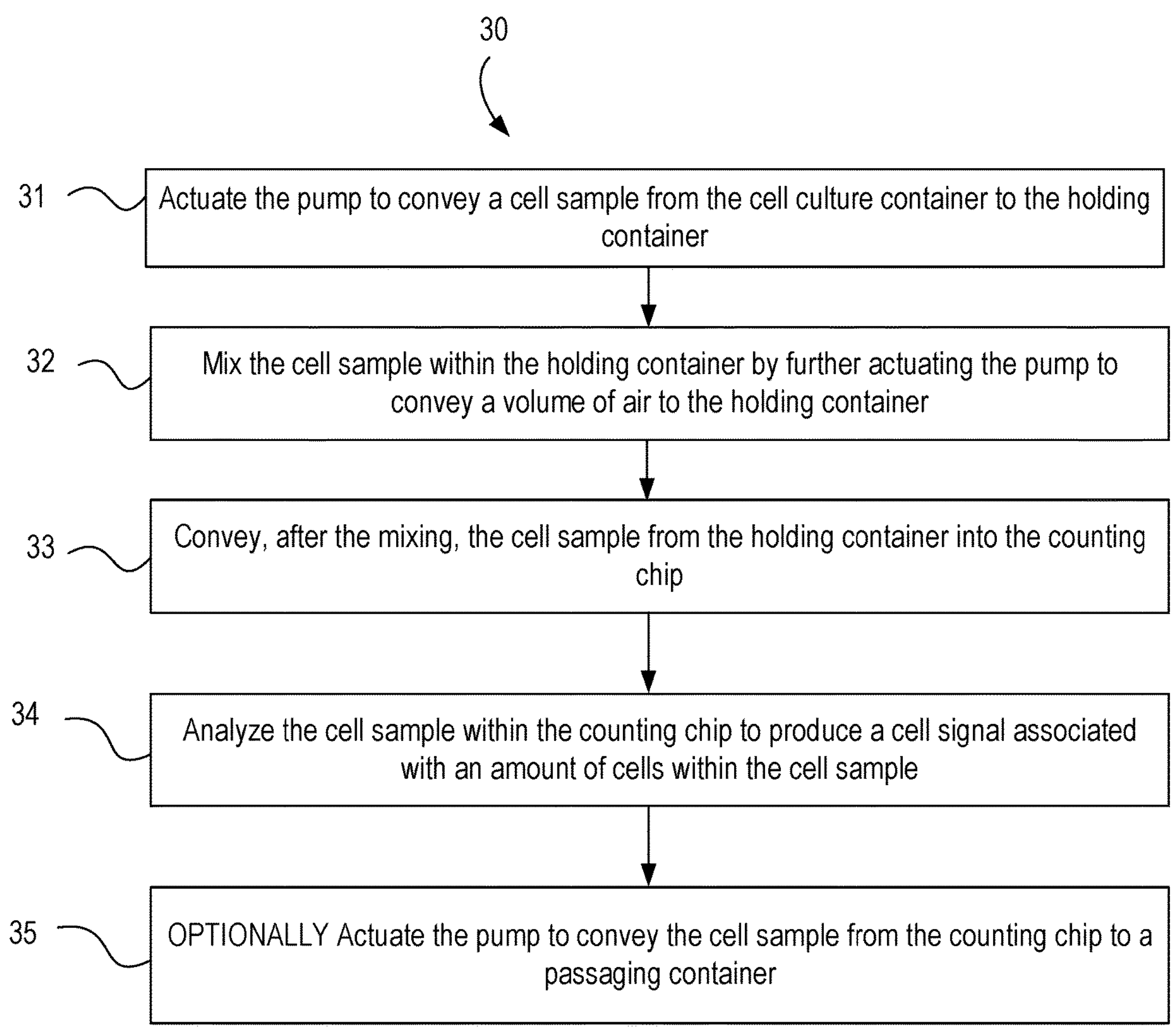
FIG. 105 is a flowchart of a method of counting cells within a cell culture system, according to an embodiment.

The cell culture systems described herein enable methods of counting cells within the closed system (i.e., without opening the system and removing the cells for counting via an external instrument). Similarly stated, the cell culture systems described herein including an integrated counting chip that enable methods of counting cells within the closed system. Moreover, the systems described herein can facilitate recapturing counted cells for later use (e.g., reseeding to a new container, passaging, etc.). In this manner, the systems and methods described herein can facilitate efficient use of cells, which can be particularly advantageous when cell culturing small amounts of cells for therapeutic purposes. For example, FIG. 105 is a flowchart of a method 30 of counting cells within a cell culture system, according to an embodiment. The method 30 can be performed with any of the cell culture systems described herein, such as, for example, the cell culture systems 110, 1600, 2000, 2100, 2200, 2600, and 4000 described herein. In particular, the cell culture system includes a tray, a cell culture container coupled to the tray, a holding container, a counting chip coupled to the tray, and a pump. The system can optionally include a valve assembly, of the types shown and described herein. The cell culture container, the holding container, the counting chip, and the pump are aseptically coupled together to form a closed system (i.e., a system that is substantially isolated from the external environment in a manner that limits the ingress of microbes into the system).

The method includes actuating the pump to convey a cell sample from the cell culture container to the holding container, at 31. The pump can be actuated in response to a user input to initiate a cell counting operation. In other embodiments, the pump can be actuated in response to an automated determination that a cell counting operation is desired. For example, in some embodiments, a cell sensor (e.g., a microscope) can produce an image of the cell sample within the cell culture container and based on the image, the system can determine that a density or confluence of the cell sample is such that a counting operation is appropriate. In some embodiments, the cell sample can be dissociated from a surface of the cell culture container before the pump is actuated to convey the cell sample to the holding container. Any of the cell dissociation methods can be performed along with (or as a part of) the method 30 of counting cells.

The cell sample is mixed within the within the holding container by further actuating the pump to convey a volume of air to the holding container, at 32. In some embodiments, the volume of air can be pumped from the cell culture container and into the holding container. In other embodiments, however, the volume of air is pumped from a separate location and into the holding container. The mixing (e.g., the amount of and characteristics of the air conveyed into the holding container) can be performed in a manner to ensure that the cell sample is substantially homogenous within the solution to be conveyed to the counting chip. By increasing the likelihood that the sample to be counted is a homogenous sample, the accuracy of the cell counting can be improved. Specifically, if the counted sample contains a non-uniform mixture of cells, then the cell count may produce a result that is not reflective of the full cell sample.

In addition to improving the likelihood that the sample will be substantially homogeneous, conveying the volume of air through the tubing and flow paths can assist in purging cells from the flow path, thereby limiting cell waste during a counting operation. Said another way, in some embodiments, the cell sample is conveyed from the cell culture container to the holding container via a flow path within the closed system. The volume of air acts to purge the flow path of residual cells within the flow path.

The method includes conveying, after the mixing, the cell sample from the holding container into the counting chip, at 33. The cell sample is then analyzed within the counting chip to produce a cell signal associated with an amount of cells within the cell sample, at 34.

In some embodiments, the cell culture system includes an instrument to which the tray is mounted. The instrument can be any suitable instruments as described herein, such as the instrument 4300. Specifically, the instrument includes a pump actuator and an electronic control system (similar to any of the electronic control systems described herein, such as the electronic control system 1630). The pump is coupled to the pump actuator of the instrument, and the electronic control system is coupled to the pump actuator and includes an actuator module implemented in at least one of a memory or a processing device. In such embodiments, the actuating the pump includes producing, via the actuator module, a pump signal to cause the pump actuator to actuate the pump.

In some embodiments, the instrument includes a cell sensor assembly, and the electronic control system is operably coupled to the cell sensor assembly. The electronic control system includes a cell sensor module implemented in at least one of a memory or a processing device. In such embodiments, the analyzing is controlled electronically. Specifically, the cell sample can be analyzed within the counting chip by: A) producing an image of the cell sample within counting chip and B) analyzing, via the cell sensor module, the image to produce the cell signal. The cell signal can be at least one of a quantity of cells, a percentage confluence of cells, or density of cells. In some embodiments, the cell sensor assembly includes a microscope that produces the image and the cell sensor module produces the cell signal indicating a quantity of cells within the counting chip based on the image.

In some embodiments, the method can optionally include actuating the pump to convey the cell sample from the counting chip to a passaging container, at 35. In this manner, the counted cells (which have remained within the closed system) can be used for their desired purposes and do not need to be discarded. The passaging container can be any of the containers described herein. The passaging container can be included on the tray or secured in a separate locations (e.g., within the incubator, refrigerator or some other portion of the system).

In some embodiments, any of the systems or methods described herein can transmit information associated with the cell counting or any cell signals described herein from the cell culture system (e.g., the instrument) to a computer or other instrument that is remote from the cell culture system. For example, in some embodiments, the electronic control system includes a radio configured to electronically communicate with a computing device. The radio is configured to send to the computing device a wireless signal associated with the cell signal.

Figure 106:
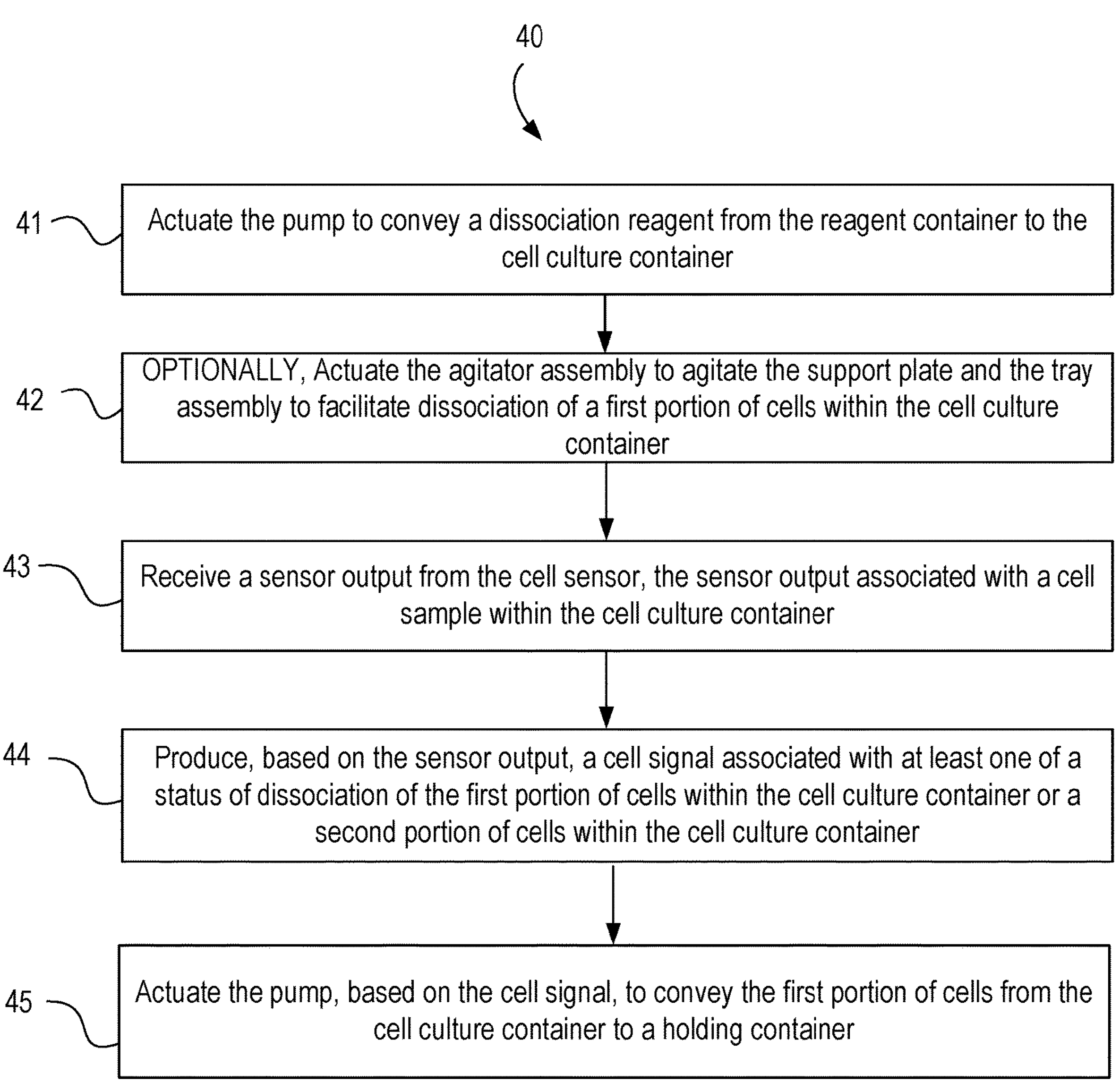
FIG. 106 is a flowchart of a method of selectively removing cells within a cell culture system, according to an embodiment.

The cell culture systems described herein enable methods of selectively detaching cells within a cell culture container while the container remains within the closed system (i.e., without opening the system for selective removing of the cells). Such methods can be advantageous for cell culturing of stem cells for therapeutic purposes. Stem cells can be subject to undesired differentiation during culturing. The systems and methods described herein can allow for the formation of potentially corrupt or undesirable cells to be identified and the desirable cells to be removed. In this manner, the systems and methods described herein can preserve those cells within the cell culture container that are still viable for the desired purposes. Similarly stated, the systems and methods described herein can prevent the entire cell culture container (containing both desirable and undesirable cells) from being discarded when potentially undesirable cells are identified. For example, FIG. 106 is a flowchart of a method 40 of selectively removing cells within a cell culture system, according to an embodiment. The method 40 can be performed with any of the cell culture systems described herein, such as, for example, the cell culture systems 110, 1600, 2000, 2100, 2200, 2600, and 4000 described herein. In particular, the cell culture system includes a tray assembly and an instrument. The tray assembly includes a tray, a cell culture container coupled to the tray, a reagent container, a holding container, and a pump. The system can optionally include a valve assembly, of the types shown and described herein. The cell culture container, the holding container, the reagent container, and the pump are aseptically coupled together to form a closed system (i.e., a system that is substantially isolated from the external environment in a manner that limits the ingress of microbes into the system). The instrument includes a support plate to which the tray is removably coupled, a pump actuator, an agitator assembly configured to agitate the support plate, and a cell sensor (or cell sensor assembly).

The method includes actuating the pump to convey a dissociation reagent from the reagent container to the cell culture container, at 41. The pump can be actuated in response to a user input to initiate a dissociation or selective removal operation. In other embodiments, the pump can be actuated in response to an automated determination that such an operation is desired. For example, in some embodiments, the cell sensor (e.g., a microscope) can produce an image of the cell sample within the cell culture container and based on the image, the system can determine that spontaneous (or undesirable) cell differentiation is occurring within the cell culture container. Similarly stated, the system can perform morphological monitoring to evaluate the likelihood of spontaneous differentiation occurring within the cell culture container. For example, in some embodiments, the instrument includes an electronic control system (similar to any of the electronic control systems described herein, such as the electronic control system 1630) including an actuator module and a cell sensor module, each being implemented in at least one of a memory or a processing device. In such embodiments, method can include analyzing the image (or cell signal) and determining, via the cell sensor module, the likelihood of spontaneous differentiations of the cells. The actuating the pump includes producing, via the actuator module, an actuation signal to actuate at least one of the pump or the optional valve assembly.

The dissociation reagent can be any suitable reagent that can selectively dissociated the desired (i.e., undifferentiated) cells from the surface of the cell culture container. For example, when culturing induced pluripotent stem cells (iPSC) the dissociation reagent can include trypsin. In other embodiments, the dissociation reagent can be an enzyme-free reagent that limits damage to the stem cells and that is formulated to selectively lift undifferentiated stem cells (e.g., EZ-Lift™ reagent produced by Millipore Sigma or ReLeSR™ reagent available from Stemcell Technologies, Inc.). After being conveyed into the cell culture container (and specifically while the cell culture container is maintained within the closed system), the desirable stem cells will be dissociated from the surface in preparation for passaging.

The method includes optionally actuating the agitator assembly to agitate the support plate and the tray assembly to facilitate dissociation of a first portion of cells within the cell culture container, at 42. In some embodiments, the one or more cell culture operations includes producing, via an actuator module of the electronic control system, an agitator signal to cause a motor to rotate a rotatable coupling element to agitate the support plate and the cell culture tray assembly. The agitation can be performed at selected intervals during the course of the method. In other embodiments, however, agitation is not needed.

A sensor output from the cell sensor is received, at 43. The sensor output is associated with a cell sample within the cell culture container and can be, for example, an image from a microscope within the instrument. The sensor output can be received periodically (e.g., at predetermined time intervals) to monitor the progress of dissociation of the first portion of the cells (i.e., those cells that remain undifferentiated). Dissociation can be monitored based on any suitable characteristics of the sensor output. For example, in some embodiments, the sensor output can be associated with a pH, temperature, or other condition of the solution within the cell culture container, and based upon the conditions, the level of selective dissociation can be determined. In other embodiments, the sensor output can be an image, and based upon morphological characteristics of the cells within the image, the level of selective dissociation can be determined.

Figure 107A:
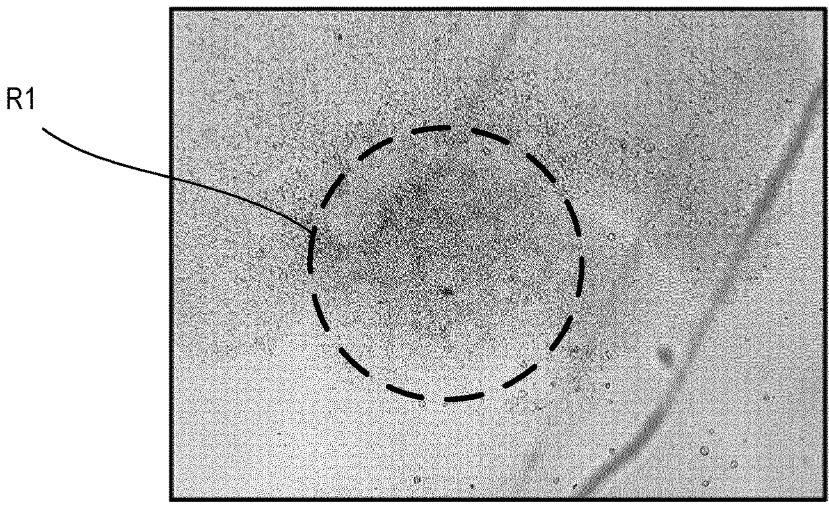
FIG. 107A is an image of cells within a region R1 of the cell culture container that exhibits cells that have undergone spontaneous differentiation.
Figure 107B:
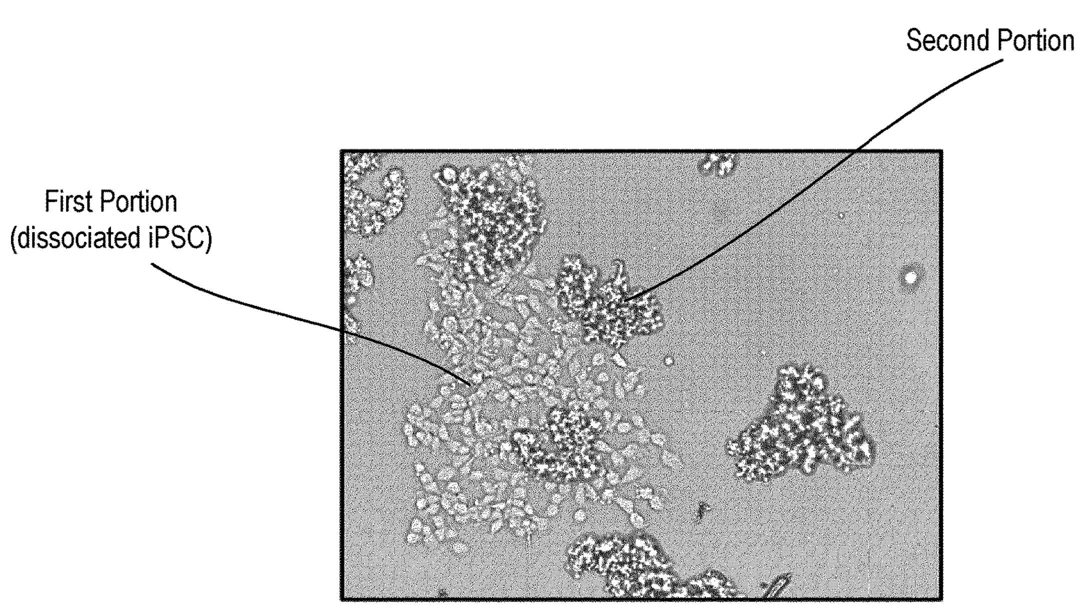
FIG. 107B is an enlarged view of a portion of the region R1 in FIG. 107A, showing a first portion of iPSC's that have been dissociated and a second portion that has remained in place within the cell culture container.

The iPSC morphology and selective dissociation associated with the method 40 are illustrated in FIGS. 107A and 107B, which show images of cells within a cell culture container of a system similar to the system 4000 described herein. FIG. 107A shows a region R1 of the cell culture container that exhibits cells that have undergone spontaneous differentiation. After identification of possible spontaneous differentiation, the reagent is conveyed, and the cell container is optionally agitated to promote dissociation, as described at operations 41 and 42. FIG. 107B shows a zoom view of a portion of the region R1, which is a sensor output as received in operation 43, showing a first portion of iPSC's that have been dissociated and a second portion that has remained in place within the cell culture container.

Based on the sensor output, a cell signal is produced, at 44. The cell signal is associated with at least one of a status of dissociation of the first portion of cells within the cell culture container or a second portion of cells within the cell culture container. The cell signal can be based on morphological analysis of an image (e.g., the image of FIG. 107B) and can provide an indicator of whether the first portion of the cells has been dissociated sufficiently for passaging. In other embodiments, the cell signal can also be based on a user input. In this manner, a user can manually enter a prompt (or signal) to provide additional information regarding the status of the cells.

After determination that the first portion of the cells are in condition for passaging, the method includes actuating the pump, based on the cell signal, to convey the first portion of cells from the cell culture container to a holding container, at 45. In this manner, the undifferentiated (i.e., desirable) cells can be passaged from the cell culture container while the container is maintained in the closed system. Similarly stated, the undifferentiated cells can be recovered from the cell culture container without the need to open the lid of the cell culture container and/or manually scrap and/or remove the desired cells.

In some embodiments, the method includes actuating the pump to convey fresh media into the cell culture container to flush the first portion (i.e., the detached portion) of the cells before the first portion of the cells are removed (in operation 45).

Figure 108:
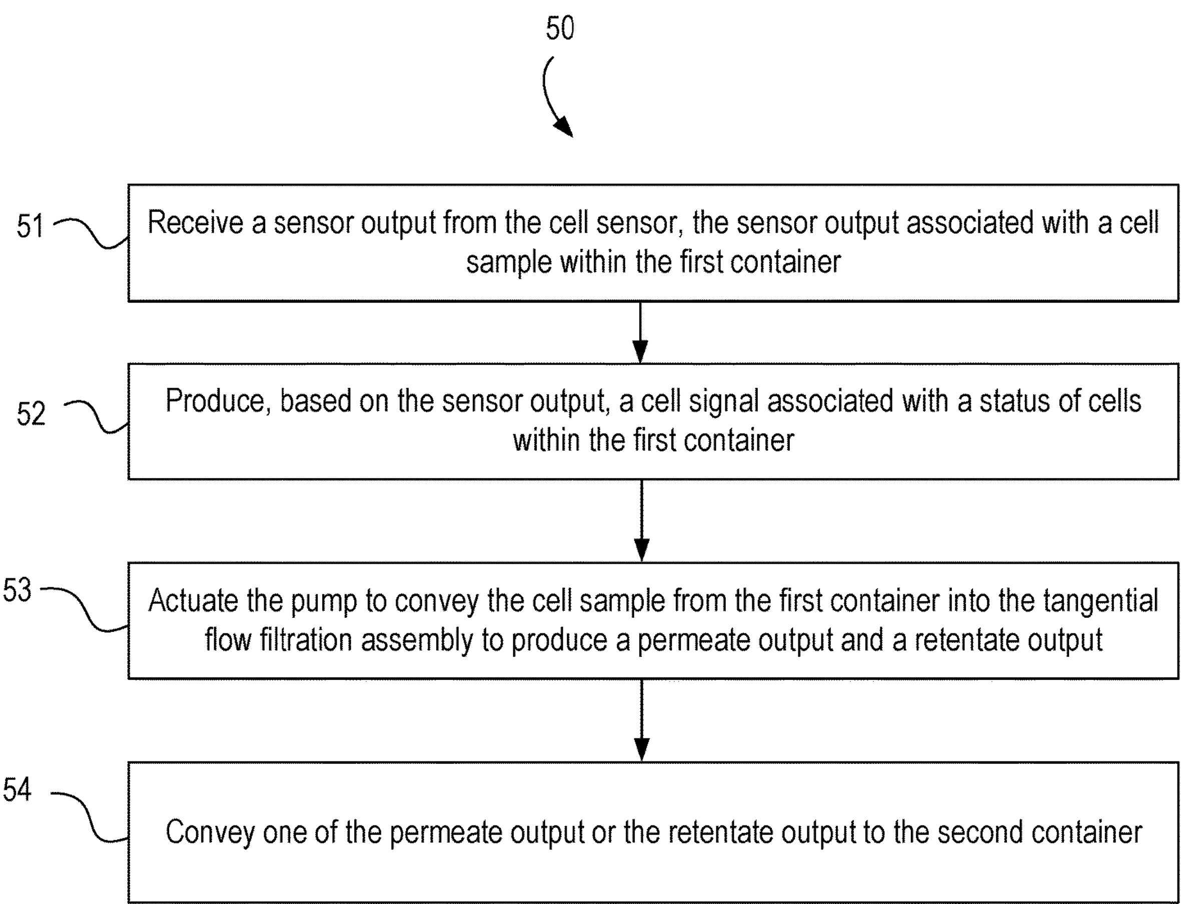
FIG. 108 is a flowchart of a method of selectively removing cells within a cell culture system, according to an embodiment.

The cell culture systems described herein enable methods of washing and/or filtering cells while the cell container (and other components involved in the cell culturing operations) remains within the closed system (i.e., without opening the system for selective removing of the cells). For example, as described herein in some embodiments, a cell culture system can include a tangential flow filter assembly (TFF), such as the types shown and described in FIGS. 74-80, which can allow the cell media and/or reagents to be exchanged. The use of TFF allows the cells to be maintained in a closed system (vs. being removed and placed into a separate centrifuge system for removal of cell media and/or reagents). For example, FIG. 108 is a flowchart of a method 50 of selectively removing cells within a cell culture system, according to an embodiment. The method 50 can be performed with any of the cell culture systems described herein that include TFF, such as, for example, the cell culture systems 2800, 2900, 3000, 3100, 3200, and 3300 described herein. In particular, the cell culture system includes a tray assembly and an instrument. The tray assembly includes a tray, a first container coupled to the tray, a second container coupled to the tray, a tangential flow filtration assembly, and a pump. The system can optionally include a valve assembly, of the types shown and described herein. The first container, the second container, the tangential flow filtration assembly, and the pump are aseptically coupled together to form a closed system (i.e., a system that is substantially isolated from the external environment in a manner that limits the ingress of microbes into the system). The instrument includes a support plate to which the tray is removably coupled, a pump actuator, and a cell sensor (or cell sensor assembly).

The method includes receiving a sensor output from the cell sensor, the sensor output associated with a cell sample within the first container, at 51. A cell signal associated with a status of cells within the first container is produced based on the sensor output, at 52. The sensor output can be, for example, an image from a microscope within the instrument. The sensor output can be received periodically (e.g., at predetermined time intervals) to monitor the status of the cell culture. In some embodiments, the status of the cells can be monitored based on a sensor output associated with a pH, temperature, or other condition of the solution within the cell culture container. For example, in some embodiments, conditions of the solution can indicate that the media and/or reagents within the cell culture container should be exchanged or refreshed. In other embodiments, the status of the cells can be monitored based on an image of the cells (i.e., the sensor output is an image). In such embodiments, the system can evaluate the morphological characteristics of the cells within the image. The cell signal can be any suitable signal associated with the status of the cells. For example, in some embodiments. The cell signal can be an indication that the cells within the cell culture container are sufficiently dissociated from the surface and are ready for passaging.

The method further includes actuating the pump to convey the cell sample from the first container into the tangential flow filtration assembly to produce a permeate output and a retentate output, at 53. One of the permeate output or the retentate output is then conveyed to the second container, at 54. The pump can be actuated in response to the cell signal (i.e., an automated determination that a filtration operation is desired). For example, in some embodiments, the instrument includes an electronic control system (similar to any of the electronic control systems described herein, such as the electronic control system 1630) including an actuator module and a cell sensor module, each being implemented in at least one of a memory or a processing device. In such embodiments, method can include analyzing an image (or other cell signal) and determining, via the cell sensor module, that a filtration operation is desired. The actuating the pump includes producing, via the actuator module, an actuation signal to actuate at least one of the pump or the optional valve assembly. In other embodiments, the pump can be actuated in response to a user input to initiate a filtering operation.

The tangential flow filtration (TFF) assembly can be any suitable assembly as described herein and can perform any suitable filtration operation to produce the permeate output and retentate output. For example, in some embodiments, the retentate output includes the cell sample and the second container is a cell culture container coupled to the tray. In such embodiments, the retentate produced by the TFF operation is conveyed to the second cell culture container as part of a cell splitting operation to seed the second container for continued culture of the cell sample. In other embodiments, the second container is a holding container within which the retentate (including the cell sample) is mixed with fresh reagents, cell media or the like. In this manner, the TFF operation can exchange the initial reagents and/or media with fresh reagents and/or media for continued culturing operations.

In some embodiments, the pump can remain actuated to cause the cell sample (present in the retentate) to cycle through the TFF assembly multiple times. For example, as shown in FIGS. 74 and 76, the permeate (e.g. spent media or reagents) can be conveyed to a waste container, and the retentate (including the cell sample) can be conveyed into a holding container. Further, the system can convey fresh media and/or reagents into the holding container. In this manner, the remaining spent media or reagents is mixed with the fresh media. The mixture is then cycled through the TFF assembly to repeat the process, each time removing a portion of the spent media and/or reagents from the cell sample. This method is advantageous in that it allows the amount of permeate removed to be controlled. Specifically, if too much of the liquid permeate is removed, then cell damage or undesirable cell adherence to the filter media may result. Thus, by removing only a portion of the liquid from the cell sample with each pass through the filter, cell viability can be maintained, and the media can be substantially exchanged over a predetermined number of cycles (and/or time). For example, in some embodiments, each cycle through the TTF assembly can remove between about 50 percent and 75 percent of the existing media and/or reagents. By replenishing the media with each cycle, the spent media and/or reagents can be substantially removed within 3-4 cycles. This procedure allows the media to be exchanged without opening the cell culture system (e.g., to centrifuge the cells), and in a manner that preserves cell viability by limiting the undesirable shear forces, reducing the likelihood of filter plugging, etc.

The TFF methods described herein also allow for the concentration of the cell sample to be increased as desired for therapeutic purposes. For example, in some embodiments, the cell sample is cultured at a first concentration (e.g., 100,000 cells per mL or 1M cells per mL). When the cells are ready for passaging to be removed from the system, it can be desirable to have a higher concentration of cells. Having a higher concentration can facilitate more efficient handling both within the system and after the cell sample has been passaged and removed from the system. For example, reducing the overall volume removed can limit the number of operations and/or external containers used in downstream operations. Additionally, some downstream operations specify that the cell sample should be within a concentration range that differs from the concentration of cell maintained during culturing. Thus, in some embodiments, the TFF methods (including the method 50) can be used to produce a retentate having a second concentration of cells within a desired range. For example, in some embodiments, the retentate can have a second concentration of cells that is greater than 1M cells per mL (e.g., the second concentration can be between 1M cells per mL and 10M cells per mL; between 1M cells per mL and 5M cells per mL; between 2M cells per mL and 5M cells per mL).

The TFF methods described herein also allow for the cell sample to be prepared for collection and storage while remaining within the closed system. For example, in some embodiments, the cell sample can be concentrated (as described above) within a cryopreservation solution. The output solution is then in condition for long term storage (i.e., freezing).

The systems and methods described herein allow for the amount of permeate removed to be carefully controlled to achieve the desired results. For example, as shown in FIG. 76, the inclusion of a positive displacement pump on the inlet line (see pump 2913) and the permeate line (see pump 2913') can allow the flow rates of the inlet solution and the permeate output to be controlled as the TFF filter media becomes diminished (e.g., clogged with waste material, cells, etc.). Because the flow rate is directly related to the pump speed (for a positive displacement pump), the system can change the pump operating characteristics to ensure consistent flow rates throughout each cycle of TFF operation.

As described above, the TFF system and methods can be advantageously used for many different cell culturing operations, including multiple levels of separation (e.g., separation of cells via a first filtration assembly and later separation of a virus via a second filtration assembly).

In some embodiments, replication-competent virus (RCV) assays are used to prove that viruses from a manufactured batch of viruses (for cell editing) do not have the ability to replicate. This is so they can be used for therapeutic applications. Manually, these assays are performed by the following steps: (1) infecting cells (such as HEK cells) with the virus and seeding these cells into a flask, (2) when the cells reach a target confluence, taking a sample of the supernatant and then passaging a portion of the cells to a new flask, (3) analyzing the supernatant sample, and using the acquired information to infer if the virus can replicate, (4) repeat step two for about ten passages, and (5) taking a portion of the final cells to be frozen as a stock.

An automated process for RCV assays can be performed on the systems described herein. First, the system seeds a flask with infected cells, or infects the cells in a flask. When the cells reach a target confluence (as determined, for example, with a microscope), a sample of the supernatant is output for the user to take away, and then a portion of the cells is passaged into a new flask (e.g., dissociation reagent and optional TFF). The above steps are repeated until around ten passages are completed. The system can include enough empty flasks for the system to keep passaging into, or the user can periodically connect a vessel of harvested cells to a new consumable tray to which the machine passages into. A portion of the final cells are harvested for the user to collect.

As described for some of the embodiments herein, holders and/or couplers are provided on the tray assembly (e.g., for waste and/or reagent containers) for example, for transport purposes, then the containers are removed and placed in the incubator (e.g., waste container) or in a refrigerator (e.g., reagent container). In some embodiments, the cell culture containers are provided after the overwrap is removed from a tray during preparation for a cell culturing procedure. In some embodiments, the cell culture containers can be provided with the tray assembly within the overwrap (i.e., preassembled on the tray). For example, a sterilization method (e.g., an ethylene oxide) can be used to sterilize the tray with the cell culture containers connected.

In some embodiments, rather than adding the cells to a cell culture container within an aseptic environment (e.g., laminar flow hood), in some cases, the cells can be added outside of the hood. For example, a lid can be provided with an aseptic connector, such as, a septum-style connector on it. The lid can include a first portion of the aseptic connector, (e.g., the female or male portion), and in a sterile environment (such as the flow hood), cells in suspension are prepared in a vial which can include a second portion of the septum connector (e.g., the other of the male or female portion). The lid can include a first portion of the aseptic connector, (e.g., the female or male portion) and a vial of cells can include a second portion of the septum connector (e.g., the other of the male or female portion). The vial of cells (e.g., defrosted cells) can be, for example, in the flow hood. The second portion of the connector of the vial can then be connected to the first portion of the aseptic connection of the lid, which can be disposed on a tray assembly within an incubator, or at a location outside the flow hood. Thus, the vial of cells can be coupled to the tray assembly outside the aseptic environment. In some embodiments, the lid with the septum could be put on the vial of cells before the cells are frozen. In some situations, a specialized "freezing medium" can be added to the vial before the cells are frozen in order to ensure the cells do not get burst by ice crystals during freezing. In another example, in some embodiments, cells are harvested on the system by transferring the cell suspension from a flask/container into a vial with a lid with a septum connection on it. For example, in some embodiments, the tray assembly can be shipped with a detachable harvesting vessel, which can have a lid with an aseptic connector as described above. After the cells have been harvested, the aseptic connection can then be disconnected and the vial removed from the tray assembly. Although not shown and described above for specific embodiments, lids and containers/vessels with septum-style connectors as described above can be used in any of the embodiments of a cell culturing system described herein.

In some embodiments, a cell culturing system as described herein can be self-incubating. In other words, the base unit can enclose and incubate the tray. For example, the system can include an enclosure with a heater, and appropriate gas and humidity control. Such a system can include temperature sensors, CO2 and/or O2 sensors, a humidity sensor and an electronic control system that includes a temperature module, gas modules, and a humidity module to monitor and control the functions of the incubator.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general-purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Any of the components and sub-components described herein can be included in any of the embodiments unless mutually exclusive. For example, in some embodiments, an agitator, an electronic control system, sensors, lights, various containers, etc. are not shown or described, but it should be understood that any embodiment can include one or more of these components and/or features.

As another example, although the cell culture systems are described above as including a multiport valve, in some embodiments, a cell culture system may not include a multiport valve as described herein, but instead include one or more single port valves. For example, in some embodiments, a cell culture assembly can include a set of single port valves that control the flow into or out of each container and/or lid. The set of single port valves can be connected to a central pump by a manifold or other connected. The single port valves can be, for example, pinch valves (that pinch the tubing coupling a container to another element in the system), a needle valve, or the like.

Any of the embodiments described herein can use any suitable type of pump. For example, as described herein the pump can be a peristaltic pump, a syringe or another type of positive displacement fluid pump. In other embodiments, the pump can be a centrifugal pump (i.e., a non-positive displacement pump). In some embodiments, the pump can include a section of tubing that is placed within a peristaltic pump actuator on the instrument. As described herein, in some embodiments, a cell culture system can include a fluid pump or pump portion on the tray assembly for the system, and the fluid pump can be moved to the instrument (e.g., base unit) and connected to a pump actuator for use during a procedure. In some embodiments, a cell culture system can include a fluid pump or pump portion provided on the instrument rather than on the tray assembly. In such an embodiment, a portion of tubing on the tray assembly within the closed system can be coupled to the fluid pump on the instrument. Thus, it should be understood that any of the embodiments of a cell culture system described herein can be configured with a fluid pump included with the tray assembly or alternatively a fluid pump provided on the instrument (e.g., the base unit).

In some embodiments, any of the pumps described herein can be pre-calibrated to account for the density of the liquid that is being flowed therethrough to ensure that the desired flow rates are attained during use. In this manner, the system can ensure accurate delivery of the desired amounts of the fluids (e.g., delivery of the desired volume of nutrient media to reach a desired cell density). Such calibration can be performed during assembly of the base unit. In other embodiments, any of the base units or systems described herein can include one or more self-calibrating pumps. Such pumps can include a "look up" table in the electronic control system that includes flow amounts for specific pump speeds and loads. Such tables can be used to allow the pump to adjust to changes in the types of fluids (e.g., fluid viscosity, density, or the like) during system use. In some embodiments, a pump can self-calibrate by means of a flow sensor, or other arrangement that can infer liquid flowed through the pump versus intended flow through the pump.

In some embodiments, any of the systems and methods described herein can be used to culture pluripotent stem cells, such as induced pluripotent stem cells (iPSCs), tissue stem cells and embryonic stem cells (ESCs).

Although various embodiments have been described as having particular features and/or combinations of components, other embodiments are possible having a combination of any features and/or components from any of embodiments where appropriate. For example, any of the devices shown and described herein can include a tangential flow filtration (TFF) element similar to the TFF shown in the cell culturing system 2800 as described herein.

What is claimed is:

1. A method of seeding a cell sample into a cell culture container, comprising:

coupling a cell culture tray assembly to a support plate of an instrument, the cell culture tray assembly including a tray, the cell culture container coupled to the tray, a pump, and a valve assembly removably coupled to the tray, the cell culture container aseptically coupled to the pump and the valve assembly to form a closed system, the valve assembly and the pump each configured to be actuated to cause transfer of a fluid into or out of the cell culture container;

the instrument including the support plate, a valve actuator, a pump actuator, and an agitator assembly, the agitator assembly configured to agitate the support plate and includes a plurality of rotatable coupling elements, each of the plurality of rotatable coupling elements coupled to a corresponding attachment location from a plurality of attachment locations on the support plate to maintain a position of the support plate relative to the instrument in at least two directions;

a bottom surface of the support plate includes a magnet at each attachment location from the plurality of attachment locations that are magnetically coupled to a ferromagnetic portion of each rotatable coupling element from the plurality of rotatable coupling elements to maintain the position of the support plate relative to the instrument in at least a vertical direction;

coupling a seeding container within the closed system to the container, the pump, and the valve assembly, the seeding container containing the cell sample;

actuating at least one of the pump or the valve assembly to convey a portion of the cell sample from the seeding container to the cell culture container to seed the cell culture container with the cell sample; and actuating the agitator assembly to agitate the support plate and the cell culture tray assembly while the portion of the cell sample is being conveyed from the seeding container into the cell culture container.

2. The method of claim 1, wherein the actuating the agitator assembly agitates the support plate and the cell culture tray assembly via a first agitation pattern, the method further comprising:

actuating the agitator assembly to agitate the support plate and the cell culture tray assembly via a second agitation pattern after the portion of the cell sample has been conveyed from the seeding container into the cell culture container.

3. The method of claim 2, wherein:

the first agitation pattern is an orbital pattern; and the second agitation pattern is a reciprocal pattern.

4. The method of claim 1, wherein the plurality of rotatable coupling elements includes at least one drive element and at least one idler element.

5. The method of claim 1, wherein:

the instrument includes an electronic control system including an actuator module implemented in at least one of a memory or a processing device; and the actuating the agitator assembly to agitate the support plate and the cell culture tray assembly while the portion of the cell sample is being conveyed from the seeding container into the cell culture container includes producing, via the actuator module, an agitator signal to cause a motor to rotate a rotatable coupling element to agitate the support plate and the cell culture tray assembly.

6. The method of claim 1, wherein the cell culture container is a first cell culture container, the cell culture tray assembly includes a second cell culture container coupled to the tray, the second cell culture container coupled to the first cell culture container, the pump, and the valve assembly within the closed system, the method further comprising:

actuating at least one of the pump or the valve assembly to convey a second portion of the cell sample from the seeding container to the second cell culture container to seed the second cell culture container with the cell sample; and actuating the agitator assembly to agitate the support plate and the cell culture tray assembly while the portion of the cell sample is being conveyed from the seeding container into the second cell culture container.

7. The method of claim 1, wherein:

the valve assembly includes a pinch valve tube, the valve actuator is a pinch valve actuator, the method further comprises coupling the pinch valve tube to the pinch valve actuator.

8. The method of claim 7, wherein the cell sample includes adherent cells.

9. The method of claim 1, wherein:

each of the plurality of attachment locations are located about a perimeter of the support plate.

10. The method of claim 1, wherein:

one of the plurality of rotatable coupling elements includes a drive motor and two of the rotatable coupling elements function as idlers for the agitator assembly.

* * * * *